US010745712B2

(12) United States Patent
Larue et al.

(10) Patent No.: US 10,745,712 B2
(45) Date of Patent: Aug. 18, 2020

(54) METHODS AND COMPOSITIONS FOR GENE EXPRESSION IN PLANTS

(71) Applicant: Monsanto Technology LLC, St. Louis, MO (US)

(72) Inventors: Clayton T. Larue, Chesterfield, MO (US); Joel E. Ream, St. Louis, MO (US); Aabid Shariff, St. Louis, MO (US); Yuanji Zhang, St. Louis, MO (US); Xuefeng Zhou, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 52 days.

(21) Appl. No.: 15/660,660

(22) Filed: Jul. 26, 2017

(65) Prior Publication Data

US 2018/0044690 A1 Feb. 15, 2018

Related U.S. Application Data

(60) Provisional application No. 62/368,840, filed on Jul. 29, 2016.

(51) Int. Cl.
*C12N 15/82* (2006.01)
*C07K 14/415* (2006.01)
*C12N 9/02* (2006.01)

(52) U.S. Cl.
CPC ........ *C12N 15/8274* (2013.01); *C07K 14/415* (2013.01); *C12N 9/001* (2013.01); *C12N 15/8221* (2013.01); *C12Y 103/03004* (2013.01)

(58) Field of Classification Search
None
See application file for complete search history.

(56) References Cited

U.S. PATENT DOCUMENTS

| | | | |
|---|---|---|---|
| 5,767,373 A * | 6/1998 | Ward | C12N 5/04 435/418 |
| 6,023,012 A | 2/2000 | Volrath | |
| 2012/0304336 A1 | 11/2012 | Bourett et al. | |
| 2015/0252379 A1 | 9/2015 | Hutzler et al. | |
| 2016/0029644 A1 | 2/2016 | Tao | |
| 2016/0194655 A1 | 7/2016 | Aponte et al. | |
| 2017/0037427 A1 | 2/2017 | Evdokimov et al. | |
| 2017/0058290 A1 | 3/2017 | Evdokimov et al. | |
| 2017/0175131 A1 | 6/2017 | Ellis et al. | |
| 2019/0185873 A1 | 6/2019 | Larue et al. | |

FOREIGN PATENT DOCUMENTS

| | | |
|---|---|---|
| JP | H1118775 A | 1/1999 |
| WO | 01/68826 A2 | 9/2001 |
| WO | 2015092706 A1 | 6/2015 |
| WO | WO 2016/099153 | 6/2016 |

OTHER PUBLICATIONS

UniProt Accession No. R0H9S5_9BRAS, submitted on Jun. 26, 2013.*
DeMarco et al, Biochem. Biophys. Res. Comm. (2003) 309:873-878.*
UniProt Accession No. A0A085G3K7, submitted on Oct. 29, 2014.*
U.S. Appl. No. 16/218,822, filed Dec. 13, 2018, Larue et al., Publication No. 2019018583A1, publication date: Jun. 20, 2019.
USPTO: Non-Final Office Action regarding U.S. Appl. No. 15/224,276, dated Feb. 15, 2019.
Response to Non-Final Office Action regarding U.S. Appl. No. 15/224,276, dated Apr. 5, 2019.
USPTO: Non-Final Office Action regarding U.S. Appl. No. 15/228,993, dated Feb. 27, 2019.
Response to Non-Final Office Action regarding U.S. Appl. No. 15/228,993, dated Apr. 5, 2019.
International Search Report and Written Opinion regarding International Application No. PCT/US2017/043990, dated Nov. 27, 2017.
Partial Supplementary European Search Report regarding Europe Application No. 17835219.1 dated Dec. 17, 2019.
Emanuelsson et al., "Predicting Subcellular Localization of Proteins Based on their N-Terminal Amino Acid Sequence", J. Mol. Biol. 300(4):1005-1016, 2000.
U.S. Appl. No. 16/452,305, filed Jun. 25, 2019, Evdokimov et al.
U.S. Appl. No. 16/452,327, filed Jun. 25, 2019, Evdokimov et al.
U.S. Appl. No. 16/452,349, filed Jun. 25, 2019, Evdokimov et al.
USPTO: Notice of Allowance regarding U.S. Appl. No. 15/224,276, dated May 1, 2019.
USPTO: Notice of Allowance regarding U.S. Appl. No. 15/228,993, dated May 1, 2019.

* cited by examiner

*Primary Examiner* — Mykola V. Kovalenko
(74) *Attorney, Agent, or Firm* — Dentons US LLP; Lawrence M. Lavin, Jr., Esq.

(57) ABSTRACT

The invention provides recombinant DNA molecules useful for providing efficient expression of proteins in transgenic plants, as well as compositions and methods for using the recombinant DNA molecules. In particular embodiments, the invention provides recombinant DNA molecules and constructs comprising sequences encoding transit peptides and operably linked sequences conferring herbicide tolerance.

20 Claims, No Drawings
Specification includes a Sequence Listing.

METHODS AND COMPOSITIONS FOR GENE EXPRESSION IN PLANTS

REFERENCE TO RELATED APPLICATION

This application claims the benefit of U.S. provisional application No. 62/368,840, filed Jul. 29, 2016 which is herein incorporated by reference in its entirety.

INCORPORATION OF SEQUENCE LISTING

A computer readable form of a sequence listing is filed with this application by electronic submission and is incorporated into this application by reference in its entirety. The sequence listing is contained in the file named MONS397US_ST25, which is 330 kilobytes in size (measured in operating system MS Windows) and was created on Jul. 14, 2017.

BACKGROUND OF THE INVENTION

Field of the Invention

The invention relates generally to the fields of agriculture, plant biotechnology, and molecular biology. More specifically, the invention relates to compositions for recombinant protein expression in transgenic plants and methods of use thereof.

Description of Related Art

Agricultural crop production often utilizes crops with modified genomes, including transgenic traits created using the methods of molecular biology. For example, a heterologous gene, also known as a transgene, can be introduced into a plant genome. Expression of the transgene in the plant confers a trait, such as herbicide-tolerance or insect control, on the plant. Successful expression of a transgene in a plant may be achieved by utilizing heterologous gene expression elements. One example of this is the use of a transit peptide operably linked to a recombinant protein to achieve subcellular localization of the recombinant protein and thus enhanced protein expression or function. A need therefore exists for novel transit peptides capable of effectively localizing recombinant proteins within plant cells.

SUMMARY OF INVENTION

In one aspect, the present invention provides a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266. In one embodiment, the heterologous herbicide-tolerance protein has herbicide-insensitive protoporphyrinogen oxidase activity. In another embodiment, the heterologous herbicide-tolerance protein comprises an amino acid sequence comprising at least 97 percent identity to a sequence selected from the group consisting of SEQ ID NOs:100-119, SEQ ID NOs:163-182, and SEQ ID NOs:224-228. In a further embodiment, the DNA sequence encoding a transit peptide comprises a nucleic acid sequence comprising at least 97 percent identity to a sequence selected from the group consisting of SEQ ID NOs:54-99 and SEQ ID NOs:267-297. In still a further embodiment, the DNA sequence encoding a heterologous herbicide-tolerance protein comprises a nucleic acid sequence comprising at least 97 percent identity to a sequence selected from the group consisting of SEQ ID NOs:121-162 and SEQ ID NOs:183-223, SEQ ID NOs:229-235. In yet a further embodiment, the recombinant DNA molecule further comprises a heterologous promoter operably linked to the DNA sequence encoding a transit peptide.

In another aspect, the present invention provides a DNA construct comprising a DNA molecule provided herein, such as a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266, operably linked to a heterologous promoter. In one embodiment, the heterologous herbicide-tolerance protein has herbicide-insensitive protoporphyrinogen oxidase activity. In another embodiment, the heterologous herbicide-tolerance protein comprises an amino acid sequence selected from the group consisting of SEQ ID NOs:100-119, SEQ ID NOs:163-182, and SEQ ID NOs:224-228. In still another embodiment, the DNA construct is present in the genome of a transgenic plant, seed, or cell.

In a further aspect, the present invention provides a transgenic plant, seed, or cell comprising a recombinant DNA molecule provided herein, such as a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs: 236-266. In one embodiment, the plant, seed, or cell is tolerant to at least one PPO herbicide. In another embodiment, the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100. In a further embodiment, the transgenic plant, seed, or cell is tolerant to at least a second herbicide.

In another aspect, the present invention provides a recombinant protein comprising in operable linkage: a) a transit peptide comprising an amino acid sequence comprising at least 95 percent identity to a sequence selected from the group consisting of SEQ ID NOs:4-49 and SEQ ID NOs: 236-266; and b) a heterologous herbicide-tolerance protein. In one embodiment, the heterologous herbicide-tolerance protein has herbicide-insensitive protoporphyrinogen oxidase activity. In a further aspect, the present invention provides a transgenic plant, seed, or cell comprising the recombinant protein provided herein.

In yet another aspect, the present invention provides, a method for producing an herbicide-tolerant plant comprising the steps of: a) transforming a plant cell with a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs: 236-266; and b) regenerating therefrom an herbicide-tolerant plant that comprises the DNA molecule. In one embodiment, the heterologous herbicide-tolerance protein comprises an amino acid sequence selected from the group consisting of SEQ ID NOs:100-119, SEQ ID NOs:163-182, and SEQ ID NOs:224-228. In another embodiment, the method further comprises the step of crossing the regenerated plant with itself or with a second plant to produce one or more progeny plants. In yet another embodiment, the method may further comprise the step of selecting a progeny plant that is tolerant to at least one PPO herbicide. In certain embodiments, the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

In a further aspect, the present invention provides a method for producing an herbicide-tolerant transgenic plant or seed comprising crossing a plant comprising a recombinant DNA molecule provided herein with itself or a second plant to produce an herbicide-tolerant transgenic plant or seed. In certain embodiments, the recombinant DNA molecule comprises a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266.

In yet a further aspect, the present invention provides a method for expressing a heterologous herbicide-tolerance protein in a plant or cell, the method comprising growing a plant or cell that comprises a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266, wherein the growing results in expression of the heterologous herbicide-tolerance protein. In one embodiment, the heterologous herbicide-tolerance protein has herbicide-insensitive protoporphyrinogen oxidase activity.

In another aspect, the present invention provides a method for controlling or preventing weed growth in a plant growth area comprising applying an effective amount of at least one PPO herbicide to a plant growth area that comprises a transgenic plant or seed as provided herein, such as a transgenic plant or seed comprising a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266, wherein the transgenic plant or seed is tolerant to the PPO herbicide. In certain embodiments, the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

In a further aspect, the present invention provides method for controlling the growth of herbicide tolerant weeds comprising: a) cultivating in a plant growth area a plant or seed provided herein, for instance a plant or seed comprising a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266; and b) applying a PPO herbicide and at least one other herbicide to the plant growth area, wherein the plant or seed is tolerant to the PPO herbicide and the at least one other herbicide. In certain embodiments, the PPO herbicide is selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100. In another embodiment, the other herbicide to which to plant or seed is tolerant is selected from the group consisting of: an ACCase inhibitor, an ALS inhibitor, an EPSPS inhibitor, a synthetic auxin, a photosynthesis inhibitor, a glutamine synthetase inhibitor, a HPPD inhibitor, a PPO inhibitor, and a long-chain fatty acid inhibitor. In further embodiments, the ACCase inhibitor is an aryloxyphenoxy propionate or a cyclohexanedione; the ALS inhibitor is a sulfonylurea, imidazolinone, triazolopyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthetase inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the very long-chain fatty acid inhibitor is a chloroacetamide, an oxyacetamide, or a pyrazole.

In yet a further aspect, the present invention provides a recombinant DNA molecule comprising a DNA sequence encoding a transit peptide operably linked to a DNA sequence encoding a heterologous herbicide-tolerance protein, wherein the transit peptide comprises an amino acid sequence comprising at least 95 percent identity to a sequence selected from the group consisting of SEQ ID NOs:236-266. In one embodiment, the heterologous herbicide-tolerance protein has herbicide-insensitive protoporphyrinogen oxidase activity. In another embodiment, the heterologous herbicide-tolerance protein comprises an amino acid sequence comprising at least 95 percent identity to a sequence selected from the group consisting of SEQ ID NOs:100-119, SEQ ID NOs:163-182, and SEQ ID NOs:224-228. If a further embodiment, the DNA sequence encoding a transit peptide comprises a nucleic acid sequence comprising at least 95 percent identity to a sequence selected from the group consisting of SEQ ID NOs:267-297. In yet another embodiment, the DNA sequence encoding a heterologous herbicide-tolerance protein comprises a nucleic acid sequence comprising at least 95 percent identity to a sequence selected from the group consisting of SEQ ID NOs:121-162 and SEQ ID NOs:183-223, SEQ ID NOs:229-235. In still a further embodiment, the recombinant DNA molecule further comprises a heterologous promoter operably linked to the DNA sequence encoding a transit peptide.

BRIEF DESCRIPTION OF THE SEQUENCES

SEQ ID NOs:1-2 and SEQ ID NO:236 are amino acid sequences of the *Arabidopsis thaliana* albino and pale green (APG6) transit peptide.

SEQ ID NO:3 is the amino acid sequence of the cotton 12G088600TP transit peptide.

SEQ ID NOs:4-49 and SEQ ID NOs:237-266 are amino acid sequences of transit peptides.

SEQ ID NOs:50-52 and SEQ ID NO:267 are nucleic acid sequences encoding the APG6 transit peptide.

SEQ ID NO:53 is the nucleic acid sequence encoding the cotton 12G088600TP transit peptide.

SEQ ID NOs:54-99 and SEQ ID NOs:268-297 are exemplary nucleic acid sequences encoding SEQ ID NOs:4-49 and SEQ ID NOs:237-266, respectively.

SEQ ID NOs:100-119 are amino acid sequences of HemG protoporphyrinogen oxidases.

SEQ ID NO:120 is the amino acid sequence of the wild-type protoporphyrinogen oxidase from *Amaranthus tuberculatus* (waterhemp) (WH).

SEQ ID NOs:121-162 and SEQ ID NO:229 are exemplary nucleic acid sequences encoding SEQ ID NOs:100-119.

SEQ ID NOs:163-182 and SEQ ID NOs:224-228 are amino acid sequences of HemY protoporphyrinogen oxidases.

SEQ ID NOs:183-223 and SEQ ID NOs:230-235 are exemplary nucleic acid sequences encoding SEQ ID NOs:163-182 and SEQ ID NOs:224-228.

DETAILED DESCRIPTION

The following descriptions and definitions are provided to better define the invention and to guide those of ordinary skill in the art in the practice of the invention. Unless otherwise noted, terms are to be understood according to conventional usage by those of ordinary skill in the relevant art.

Operably linking a transit peptide to a heterologous protein utilizes the transgenic plant cell's protein localization system to achieve sub-cellular localization of the heterologous protein. The transit peptide is removed from the heterologous protein in a processing step during translocation of the heterologous protein into an organelle. The properties of the combination of a specific transit peptide with a specific heterologous protein when expressed in a plant can be unpredictable and surprising. For example, the efficiency of sub-cellular localization and the efficiency of processing (removal of the transit peptide from the heterologous protein) varies and may be affected by the amino acid sequence of the transit peptide, the heterologous protein, or both. These variables affect the function and levels of a heterologous protein and thus affect the phenotype of a transgenic cell, plant, or seed comprising the heterologous protein. Various transit peptides are known in the art for use in transgenic plants, but in view of the variability in the efficiencies of sub-cellular localization and processing and the continuing development of new transgenic traits, novel transit peptides are needed.

The invention provides novel, recombinant DNA molecules for effectively targeting heterologous proteins within plant cells. Effective targeting of a heterologous protein involves efficient sub-cellular localization of the transit peptide and heterologous protein combination and processing of the transit peptide from the heterologous protein. Although transit peptides for localizing heterologous proteins within cells are known, the degree of localization and processing for any transit peptide and heterologous protein combination varies. Localization and processing affect the expression level and function of a heterologous protein and thus affect the phenotype of the cell, plant, or seed comprising the heterologous protein. For example, inefficient localization and processing of a transit peptide and herbicide-tolerance protein combination can result in poor herbicide-tolerance for a transgenic plant.

The invention overcomes these obstacles by providing novel recombinant DNA molecules capable of providing efficient targeting of a protein through improved localization and processing. Recombinant DNA molecules of the invention comprise a DNA sequence encoding a transit peptide operably linked to a DNA sequence encoding a heterologous protein. In one example, recombinant DNA molecules of the invention include, but are not limited to, a recombinant DNA molecule comprising a DNA sequence encoding a transit peptide operably linked to a DNA sequence encoding an herbicide-tolerant protoporphyrinogen oxidase. Compositions and methods for using these recombinant DNA molecules are also provided.

Recombinant Molecules

As used herein, the term "recombinant" refers to a non-natural DNA, protein, cell, seed, or organism that is the result of genetic engineering and was created by human intervention. A "recombinant DNA molecule" is a DNA molecule that does not naturally occur and as such is the result of human intervention, such as a DNA molecule comprised of a combination of at least two DNA sequences heterologous to each other. An example of a recombinant DNA molecule is a DNA molecule provided herein encoding a transit peptide of the present invention, such as a transit peptide comprising a sequence selected from the group consisting of SEQ ID NOs:4-49 and SEQ ID NOs:236-266, operably linked to a DNA molecule encoding an herbicide-tolerance protein of the present invention, such as a protoporphyrinogen oxidase comprising a sequence selected from the group consisting of SEQ ID NOs:100-119, 163-182, and 224-228. A "recombinant protein" is a protein produced as a result of human intervention that does not naturally occur. An example of a recombinant protein is a protein provided herein comprising a transit peptide of the present invention, such as a transit peptide comprising a sequence selected from the group consisting of SEQ ID NOs:4-49 and SEQ ID NOs:236-266, operably linked to a heterologous protein, such as an herbicide-tolerance protein of the present invention, for instance, a protoporphyrinogen oxidase comprising a sequence selected from the group consisting of SEQ ID NOs:100-119, 163-182, and 224-228. A recombinant cell, seed, or organism is a cell, seed, or organism comprising transgenic or heterologous DNA or protein, for example a transgenic plant cell, seed, plant, or plant part comprising a heterologous DNA molecule or heterologous protein of the invention.

As used herein, the term "isolated DNA molecule" means that the DNA molecule is present alone or in combination with other compositions but is not within its natural environment. A DNA molecule of the invention is an isolated DNA molecule so long as the DNA molecule is not within the DNA of the organism at the genomic location in which it naturally occurs. For example, a recombinant DNA molecule comprising a protein-coding DNA sequence and heterologous transit peptide DNA sequence is considered isolated when it is found in a context that is not the genome in which both the protein-coding DNA sequence and the heterologous transit peptide DNA sequence are naturally found (such as the genome of a transgenic plant, seed, plant part, or cell).

As used herein, the term "genetic engineering" refers to the creation, modification, or production of a DNA molecule, protein, cell, or organism using the techniques of biotechnology (such as molecular biology, protein biochemistry, bacterial transformation, and plant transformation). Genetic engineering is thus a result of human intervention. For example, genetic engineering may be used to create a recombinant DNA molecule encoding a transit peptide comprising a sequence selected from the group consisting of SEQ ID NOs:4-49 and SEQ ID NOs:236-266 operably linked to a DNA molecule encoding an herbicide-tolerance protein, such as a protoporphyrinogen oxidase comprising a sequence selected from the group consisting of SEQ ID NOs:100-119, 163-182, and 224-228 using one or more of the techniques of molecular biology, such as gene cloning, DNA ligation, and DNA synthesis. Such a recombinant DNA molecule optionally may further comprise a heterologous promoter functional in a plant cell.

As used herein, "herbicide-tolerance" or "herbicide-tolerant" with respect to a protein means the ability to maintain at least some of its activity or function in the presence of an herbicide. For example, a protoporphyrinogen oxidase (PPO) is herbicide-tolerant if it maintains at least some of its enzymatic activity in the presence of one or more PPO herbicide(s). Herbicide-tolerance can be measured by any means known in the art. For example, enzymatic activity of a protoporphyrinogen oxidase can be measured by an enzymatic assay in which the production of the product of protoporphyrinogen oxidase or the consumption of the substrate of protoporphyrinogen oxidase in the presence of one or more PPO herbicide(s) is measured via fluorescence, high performance liquid chromatography (HPLC), or mass spectrometry (MS). Another example of an assay for measuring enzymatic activity of a protoporphyrinogen oxidase is a bacterial assay, such as the growth assays described herein, whereby a recombinant protoporphyrinogen oxidase is expressed in a bacterial cell otherwise lacking PPO activity and the ability of the recombinant protoporphyrinogen oxidase to complement this knockout phenotype is measured. Herbicide-tolerance may be complete or partial insensitivity to an herbicide, and may be expressed as a percent (%) tolerance or insensitivity to a PPO herbicide. As used herein, an "herbicide-tolerant protoporphyrinogen oxidase" exhibits herbicide-tolerance in the presence of one or more PPO herbicide(s).

As used herein, "herbicide-tolerance" or "herbicide-tolerant" with respect to an organism, plant, seed, tissue, part, or cell means the organism, plant, seed, tissue, part, or cell's ability to resist the effects of an herbicide when applied. For example, an herbicide-tolerant plant can survive or continue to grow in the presence of the herbicide. The herbicide-tolerance of a plant, seed, plant tissue, plant part, or cell may be measured by comparing the plant, seed, plant tissue, plant part, or cell to a suitable control. For example, the herbicide-tolerance may be measured or assessed by applying an herbicide to a plant comprising a recombinant DNA molecule encoding a protein capable of conferring herbicide-tolerance (the test plant) and a plant not comprising the recombinant DNA molecule encoding the protein capable of conferring herbicide-tolerance (the control plant) and then comparing the plant injury of the two plants, where herbicide-tolerance of the test plant is indicated by a decreased injury rate as compared to the injury rate of the control plant. An herbicide-tolerant plant, seed, plant tissue, plant part, or cells exhibits a decreased response to the toxic effects of an herbicide when compared to a control plant, seed, plant tissue, plant part, or cell. As used herein, an "herbicide-tolerance trait" is a transgenic trait imparting improved herbicide-tolerance to a plant as compared to the wild-type plant. Contemplated plants which might be produced with an herbicide-tolerance trait of the present invention could include, for instance, any plant including crop plants such as soybean (*Glycine max*), maize (*Zea mays*), cotton (*Gossypium* sp.), wheat (*Triticum* spp.), and *Brassica* plants, among others.

As used herein, a "hemG knockout strain" means an organism or cell of an organism, such as *E. coli*, that lacks HemG activity to the extent that it is unable to grow on heme-free growth medium, or such that its growth is detectably impaired in the absence of heme relative to an otherwise isogenic strain comprising a functional HemG. A hemG knockout strain of, for instance, *E. coli* may be prepared in view of knowledge in the art, for instance in view of the *E. coli* hemG sequence (Ecogene Accession No. EG11485; Sasarman et al., "Nucleotide sequence of the hemG gene involved in the protoporphyrinogen oxidase activity of *Escherichia coli* K12" *Can J Microbiol* 39:1155-1161, 1993).

The term "transgene" refers to a DNA molecule artificially incorporated into an organism's genome as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the invention comprise the recombinant DNA molecules provided by the invention.

As used herein, the term "heterologous" refers to the relationship between two or more things not normally associated in nature, for instance that are derived from different sources or not normally found in nature together in any other manner. For example, a DNA molecule or protein may be heterologous with respect to another DNA molecule, protein, cell, plant, seed, or organism if not normally found in nature together or in the same context. In certain embodiments, a first DNA molecule is heterologous to a second DNA molecule if the two DNA molecules are not normally found in nature together in the same context, and a protein is heterologous with respect to a second operably linked protein, such as a transit peptide, if such combination is not normally found in nature. In another embodiment, a recombinant DNA molecule encoding a transit peptide operably linked to a protoporphyrinogen oxidase is heterologous with respect to an operably linked promoter that is functional in a plant cell if such combination is not normally found in nature. A recombinant DNA molecule also may be heterologous with respect to a cell, seed, or organism into which it is inserted when it would not naturally occur in that cell, seed, or organism. A "heterologous protein" is a protein present in a plant, seed, cell, tissue, or organism in which it does not naturally occur or operably linked to a protein with which it is not naturally linked. An example of a heterologous protein is a protein comprising a sequence selected from the group consisting of SEQ ID NOs:4-49, 236-266, 100-119, 163-182, and 224-228 that is expressed in a plant, seed, cell, tissue, or organism in which it does not naturally occur, or that is operably linked to a second protein, such as a transit peptide or herbicide-tolerant protein, with which it is not naturally linked. In another example, a heterologous protein, such as a heterologous herbicide-tolerance protein, for instance a protoporphyrinogen oxidase may be introduced into a plant cell in which it does not naturally occur using the techniques of molecular biology and plant transformation.

As used herein, the term "protein-coding DNA molecule" refers to a DNA molecule comprising a DNA sequence that encodes a protein. As used herein, a "protein-coding DNA sequence" means a DNA sequence that encodes a protein. A protein-coding DNA sequence may be any DNA sequence that encodes a protein, for example a protein comprising a sequence selected from the group consisting of SEQ ID NOs:4-49, 236-266, 100-119, 163-182, and 224-228. As used herein, the term "protein" refers to a chain of amino acids linked by peptide (amide) bonds and includes both polypeptide chains that are folded or arranged in a biologically functional way and polypeptide chains that are not. A "sequence" means a sequential arrangement of nucleotides or amino acids. The boundaries of a protein-coding sequence are usually determined by a translation start codon at the 5'-terminus and a translation stop codon at the 3'-terminus.

As used herein, the term "herbicide-tolerance protein" means a protein capable of conferring herbicide-tolerance to a cell, tissue, plant part, seed, or organism. Examples of herbicide-tolerance proteins are well known in the art and include, but are not limited to, glyphosate-tolerant 5-enolypyruvyl shikimate 3-phosphate synthases (e.g., CP4-EPSPS, 2mEPSPS), glyphosate oxidoreductases (GOX), glyphosate N-acetyltransferases (GAT), herbicide-tolerant acetolactate synthases (ALS)/acetohydroxyacid synthases (AHAS), herbicide-tolerant 4-hydroxyphenylpyruvate dioxygenases (HPPD), dicamba monooxygenases (DMO), phosphinothricin acetyl transferases (PAT), herbicide-tolerant glutamine synthetases (GS), 2,4-dichlorophenoxyproprionate dioxygenases (TfdA), R-2,4-dichlorophenoxypropionate dioxygenases (RdpA), S-2,4-dichlorophenoxypropionate dioxygenases (SdpA), herbicide-tolerant protoporphyrinogen oxidases (PPO), and cytochrome P450 monooxygenases. For example, a protoporphyrinogen oxidase comprising an amino acid sequence selected from the group consisting of SEQ ID NOs:100-119, SEQ ID NOs:163-182, and SEQ ID NOs:224-228 is an herbicide-tolerant protein.

As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which may or may not be ultimately folded into proteins. A protein-coding DNA molecule may be operably linked to a heterologous promoter in a DNA construct for use in expressing the protein in a cell transformed with, and thus comprising, the recombinant DNA molecule or a portion thereof. As used herein, "operably linked" means two DNA or protein molecules linked in manner so that one may affect the function of the other. Operably-linked DNA molecules may be part of a single contiguous molecule and may or may not be adjacent. For example, a promoter is operably linked with a protein-coding DNA molecule in a DNA construct where the two DNA molecules are so arranged that the promoter may affect the expression of the transgene. In another embodiment, two or more protein molecules may be operably linked. For instance, a transit peptide may be operably linked to a heterologous protein, such as an herbicide-tolerant protein.

In one embodiment, the recombinant DNA molecules of the invention include a DNA sequence encoding a protoporphyrinogen oxidase (PPO) operably linked to a transit peptide sequence. As used herein, "protoporphyrinogen oxidase" or "PPO" means an oxidase capable of converting protoporphyrinogen IX to protoporphyrin IX. Such protoporphyrinogen oxidase are known in the art and include, for instance, the protein sequences provided as SEQ ID NOs: 100-119, SEQ ID NOs:163-182, and SEQ ID NOs:224-228.

In another embodiment, the recombinant DNA molecules of the invention include a DNA sequence encoding a transit peptide sequence operably linked to a heterologous nucleic acid sequence encoding a protein that has herbicide-tolerant protoporphyrinogen oxidase activity, whereby the transit peptide sequence facilitates localizing the protein molecule within the cell. Transit peptides are also known in the art as signal sequences, targeting sequences, targeting peptides, and localization sequences. An example of a transit peptide is a chloroplast transit peptide (CTP), a mitochondrial targeting sequence (MTS), or a dual chloroplast and mitochondrial targeting peptide. By facilitating protein localization within the cell, such as to the mitochondria or chloroplast, the transit peptide ensures localization of a protein to an organelle for optimal enzyme activity and may increase the accumulation of the protein and protect the protein from proteolytic degradation, and/or enhance the level of herbicide-tolerance, and thereby reduce levels of injury in the transgenic cell, seed, or organism after herbicide application. Upon translocation into the organelle, the transit peptide is typically cleaved from the protein, also referred to as processing. Transit peptide processing may be complete (meaning that the complete transit peptide is cleaved from the amino-terminal end of the protein), incomplete (meaning that one or more amino acids of the transit peptide remain on amino-terminal end of the protein), or result in removal one or more amino acids from the amino-terminal end of the protein. Complete processing of the transit peptide from a protoporphyrinogen oxidase increases the level of protein accumulation, thereby increasing PPO herbicide-tolerance and reducing levels of injury in the transgenic cell, seed, or organism after herbicide application. For example, transit peptides may comprise an amino acid sequence of the present invention, such as those provided by SEQ ID NOs: 1-49 and SEQ ID NOs:236-266. Such a transit peptide may be encoded by a nucleic acid sequence of the invention, for instance as provided by SEQ ID NOs:50-99 and SEQ ID NOs:267-297.

Recombinant DNA molecules of the present invention may be synthesized and modified by methods known in the art, either completely or in part, especially where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes DNA molecules and proteins having at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, and at least 99% sequence identity to any of the DNA molecule or protein sequences provided herein as SEQ ID NOs:1-297. As used herein, the term "percent sequence identity" or "% sequence identity" refers to the percentage of identical nucleotides or amino acids in a linear polynucleotide or protein sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar Inc., 1228 S. Park St., Madison, Wis. 53715), and MUSCLE (version 3.6) (Edgar, *Nucleic Acids Research* 32(5):1792-7, 2004) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence, or a portion thereof, or to a longer sequence.

As used herein, a "DNA construct" is a recombinant DNA molecule comprising two or more heterologous DNA sequences. DNA constructs are useful for transgene expression and may be comprised in vectors and plasmids. DNA constructs may be used in vectors for transformation, that is the introduction of heterologous DNA into a host cell, to produce transgenic plants and cells, and as such may also be contained in the plastid DNA or genomic DNA of a transgenic plant, seed, cell, or plant part. As used herein, a "vector" means any recombinant DNA molecule that may be used for plant transformation. DNA molecules as set forth in the sequence listing, can, for example, be inserted into a vector as part of a construct having the DNA molecule operably linked to a gene expression element that functions in a plant to affect expression of the protein encoded by the DNA molecule. Methods for constructing DNA constructs and vectors are well known in the art. The components for a DNA construct, or a vector comprising a DNA construct, generally include one or more gene expression elements operably linked to a transcribable DNA sequence, such as the following: a promoter for the expression of an operably linked DNA, an operably linked protein-coding DNA molecule, and a 3' untranslated region. Gene expression elements useful in practicing the present invention include, but are not limited to, one or more of the following type of elements: promoter, 5' untranslated region, enhancer, leader, cis-acting element, intron, 3' untranslated region, and one or more selectable marker transgenes.

The DNA constructs of the invention may include a promoter operably linked to a protein-coding DNA molecule provided by the invention, whereby the promoter drives expression of the heterologous protein molecule. Promoters useful in practicing the present invention include those that function in a cell for expression of an operably linked polynucleotide, such as a bacterial or plant promoter. Plant promoters are varied and well known in the art and include those that are inducible, viral, synthetic, constitutive, temporally regulated, spatially regulated, and/or spatio-temporally regulated.

In one embodiment of the invention, a DNA construct provided herein includes a DNA sequence encoding a transit peptide that is operably linked to a heterologous DNA sequence encoding a protein that has herbicide-tolerant protoporphyrinogen oxidase activity, whereby the transit peptide sequence facilitates localizing the protein within the cell.

As used herein, "control" means an experimental control designed for comparison purposes. For example, a control plant in a transgenic plant analysis is a plant of the same type as the experimental plant (that is, the plant to be tested) but does not contain the transgenic insert, recombinant DNA molecule, or DNA construct of the experimental plant. Examples of control plants useful for comparison with transgenic plants include: for maize plants, non-transgenic LH244 maize (ATCC deposit number PTA-1173); for comparison with transgenic soybean plants: non-transgenic A3555 soybean (ATCC deposit number PTA-10207); for comparison with transgenic cotton plants: non-transgenic Coker 130 (Plant Variety Protection (PVP) Number 8900252); for comparison with transgenic canola or *Brassica napus* plants: non-transgenic *Brassica napus* variety 65037 Restorer line (Canada Plant Breeders' Rights Application 06-5517); for comparison with transgenic wheat plants: non-transgenic wheat variety Samson germplasm (PVP 1994).

As used herein, "wild-type" means a naturally occurring similar, but not identical, version. A "wild-type DNA molecule" or "wild-type protein" is a naturally occurring version of the DNA molecule or protein, that is, a version of the DNA molecule or protein pre-existing in nature. An example of a wild-type protein useful for comparison with the engineered proteins provided by the invention is the protoporphyrinogen oxidase from *Arabidopsis thaliana*. A "wild-type plant" is a non-transgenic plant of the same type as the transgenic plant, and as such is genetically distinct from the transgenic plant comprising the herbicide-tolerance trait. Examples of wild-type plants useful for comparison include: for transgenic maize plants, non-transgenic LH244 maize (ATCC deposit number PTA-1173); for comparison with transgenic soybean plants, non-transgenic A3555 soybean (ATCC deposit number PTA-10207); for comparison with transgenic cotton plants, non-transgenic Coker 130 (Plant Variety Protection Number 8900252); for comparison with transgenic canola or *Brassica napus* plants, non-transgenic *Brassica napus* variety 65037 Restorer line (Canada Plant Breeders' Rights Application 06-5517); for comparison with transgenic wheat plants, non-transgenic wheat variety Samson germplasm (PVP 1994).

Transgenic Plants & Herbicides

An aspect of the invention includes transgenic plant cells, transgenic plant tissues, transgenic plants, and transgenic seeds that comprise the recombinant DNA molecules provided by the invention. These cells, tissues, plants, and seeds comprising the recombinant DNA molecules exhibit tolerance to one or more PPO herbicide(s), and, optionally, tolerance to one or more additional herbicide(s).

Suitable methods for transformation of host plant cells for use with the current invention include virtually any method by which DNA can be introduced into a cell (for example, where a recombinant DNA construct is stably integrated into a plant chromosome) and are well known in the art. Exemplary methods for introducing a recombinant DNA construct into plants include the *Agrobacterium* transformation system and DNA particle-bombardment, both of which are well known to those of skill in the art. Another exemplary method for introducing a recombinant DNA construct into plants is insertion of a recombinant DNA construct into a plant genome at a pre-determined site by methods of site-directed integration. Site-directed integration may be accomplished by any method known in the art, for example, by use of zinc-finger nucleases, engineered or native meganucleases, TALE-endonucleases, or an RNA-guided endonuclease (for example a CRISPR/Cas9 system). Transgenic plants can be regenerated from a transformed plant cell by the methods of plant cell culture or by taking a cutting from a transgenic plant and rooting the cutting to establish a vegetative clone of the transgenic plant. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, typically using a SNP assay, DNA sequencing, or a thermal amplification assay that allows for the distinction between heterozygotes and homozygotes, referred to as a zygosity assay.

As used herein, "herbicide" is any molecule that is used to control, prevent, or interfere with the growth of one or more plants. Exemplary herbicides include acetyl-CoA carboxylase (ACCase) inhibitors (for example aryloxyphenoxy propionates and cyclohexanediones); acetolactate synthase (ALS) inhibitors (for example sulfonylureas, imidazolinones, triazolopyrimidines, and triazolinones); 5-enolpyruvyl-shikimate-3-phosphate synthase (EPSPS) inhibitors (for example glyphosate), synthetic auxins (for example phenoxys, benzoic acids, carboxylic acids, semicarbazones), photosynthesis (photosystem II) inhibitors (for example triazines, triazinones, nitriles, benzothiadiazoles, and ureas), glutamine synthetase (GS) inhibitors (for example glufosinate and bialaphos), 4-hydroxyphenylpyruvate dioxygenase (HPPD) inhibitors (for example isoxazoles, pyrazolones, and triketones), protoporphyrinogen oxidase (PPO) inhibitors (for example diphenylethers, N-phenylphthalimide, aryl triazinones, and pyrimidinediones), very long-chain fatty acid inhibitors (for example chloroacetamides, oxyacetamides, and pyrazoles), cellulose biosynthesis inhibitors (for example indaziflam), photosystem I inhibitors (for example paraquat), microtubule assembly inhibitors (for example pendimethalin), and phytoene desaturase (PDS) inhibitors (for example norflurazone), among others.

As used herein, a "PPO herbicide" is a chemical that targets and inhibits the enzymatic activity of a protoporphyrinogen oxidase (PPO), which catalyzes the dehydrogenation of protoporphyrinogen IX to form protoporphyrin IX, which is the precursor to heme and chlorophyll. Inhibition of protoporphyrinogen oxidase causes formation of reactive oxygen species, resulting in cell membrane disruption and ultimately the death of susceptible cells. PPO herbicides are well-known in the art and commercially available. Examples of PPO herbicides include, but are not limited to, diphenylethers (such as acifluorfen, its salts and esters, aclonifen, bifenox, its salts and esters, ethoxyfen, its salts and esters, fluoronitrofen, furyloxyfen, halosafen, chlomethoxyfen, fluoroglycofen, its salts and esters, lactofen, its salts and esters, oxyfluorfen, and fomesafen, its salts and esters); thiadiazoles (such as fluthiacet-methyl and thidiazimin); pyrimidinediones or phenyluracils (such as benzfendizone, butafenacil, ethyl [3-2-chloro-4-fluoro-5-(1-methyl-6-trifluoromethyl-2,4-dioxo-1,2,3,4-tetrahydropyrimidin-3-yl) phenoxy]-2-pyridyloxy]acetate (CAS Registry Number 353292-31-6 and referred to herein as S-3100), flupropacil, saflufenacil, and tiafenacil); phenylpyrazoles (such as fluazolate, pyraflufen and pyraflufen-ethyl); oxadiazoles (such as oxadiargyl and oxadiazon); triazolinones (such as azafenidin, bencarbazone, carfentrazone, its salts and esters, and sulfentrazone); oxazolidinediones (such as pentoxazone); N-phenylphthalimides (such as cinidon-ethyl, flumiclorac, flumiclorac-pentyl, and flumioxazin); benzoxazinone derivatives (such as 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione); flufenpyr and flufenpyr-ethyl; pyraclonil; and profluazol. Protoporphyrinogen oxidases and cells, seeds, plants, and plant parts provided by the invention exhibit herbicide-tolerance to one or more PPO herbicide(s).

Plants, seeds, plant parts, plant tissues, and cells provided by the invention exhibit herbicide-tolerance to one or more PPO herbicide(s). PPO herbicide(s) may be applied to a plant growth area comprising the plants and seeds provided by the invention as a method for controlling weeds. Plants and seeds provided by the invention comprise an herbicide-tolerance trait and as such are tolerant to the application of one or more PPO herbicide(s). The herbicide application may be the recommended commercial rate (1×) or any fraction or multiple thereof, such as twice the recommended commercial rate (2×). Herbicide rates may be expressed as grams per hectare (g/h) or pounds per acre (lbs/acre), acid equivalent per pound per acre (lb ae/acre), acid equivalent per gram per hectare (g ae/ha), pounds active ingredient per acre (lb ai/acre), or grams active ingredient per hectare (g ai/ha) depending on the herbicide and the formulation. The herbicide application comprises at least one PPO herbicide. The plant growth area may or may not comprise weed plants at the time of herbicide application. An herbicidally effective dose of PPO herbicide for use in an area for controlling weeds should consist of a range from about 0.1× to about 30× label rate(s) over a growing season. The 1× label rate for some exemplary PPO herbicides is provided in Table 1. One (1) acre is equivalent to 2.47105 hectares and one (1) pound is equivalent to 453.592 grams. Herbicide rates can be converted between English and metric as: (lb ai/ac) multiplied by 1.12=(kg ai/ha) and (kg ai/ha) multiplied by 0.89= (lb ai/ac).

TABLE 1

Exemplary PPO Herbicides

| PPO Herbicide | Chemical Family | 1X Rate |
| --- | --- | --- |
| acifluorfen | Diphenylethers | 420 g ai/ha |
| fomesafen | Diphenylethers | 420 g ai/ha |
| lactofen | Diphenylethers | 70-220 g ai/ha |
| fluoroglycofen-ethyl | Diphenylethers | 15-40 g ai/ha |
| oxyfluorfen | Diphenylethers | 0.28-2.24 kg ai/ha |
| flumioxazin | N-phenylphthalimide | 70-105 g ai/ha |
| azafenidin | Triazolinone | 240 g ai/ha |
| carfentrazone-ethyl | Triazolinone | 4-36 g ai/ha |
| sulfentrazone | Triazolinone | 0.1-0.42 kg ai/ha |
| fluthiacet-methyl | Thiadiazole | 3-15 g ai/ha |
| oxadiargyl | Oxadiazole | 50-150 g ai/ha |
| oxadiazon | Oxadiazole | 2.24-4.48 kg ai/ha |
| pyraflufen-ethyl | Phenylpyrazole | 6-12 g ai/ha |
| saflufenacil | Pyrimidine dione | 25-100 g/ha |
| S-3100 | Pyrimidine dione | 5-80 g/ha |

Herbicide applications may be sequentially or tank mixed with one, two, or a combination of several herbicides or any other compatible herbicide. Multiple applications of one herbicide or of two or more herbicides, in combination or alone, may be used over a growing season to areas comprising transgenic plants of the invention for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, a "weed" is any undesired plant. A plant may be considered generally undesirable for agriculture or horticulture purposes (for example, *Amaranthus* species) or may be considered undesirable in a particular situation (for example, a crop plant of one species in a field of a different species, also known as a volunteer plant).

The transgenic plants, progeny, seeds, plant cells, and plant parts of the invention may also contain one or more additional traits. Additional traits may be introduced by crossing a plant containing a transgene comprising the recombinant DNA molecules provided by the invention with another plant containing one or more additional trait(s). As used herein, "crossing" means breeding two individual plants to produce a progeny plant. Two plants may thus be crossed to produce progeny that contain the desirable traits from each parent. As used herein "progeny" means the offspring of any generation of a parent plant, and transgenic progeny comprise a DNA construct provided by the invention and inherited from at least one parent plant. Additional trait(s) also may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation or genome editing on a transgenic plant or plant cell). Such additional traits include, but are not limited to, increased insect resistance, increased water use efficiency, increased yield performance, increased drought resistance, increased seed quality, improved nutritional quality, hybrid seed production, and herbicide-tolerance, in which the trait is measured with respect to a wild-type plant. Exemplary additional herbicide-tolerance traits may include transgenic or non-transgenic tolerance to one or more herbicides such as ACCase inhibitors (for example aryloxyphenoxy propionates and cyclohexanediones), ALS inhibitors (for example sulfonylureas, imidazolinones, triazolopyrimidines, and triazolinones) EPSPS inhibitors (for example glyphosate), synthetic auxins (for example phenoxys, benzoic acids, carboxylic acids, semicarbazones), photosynthesis inhibitors (for example triazines, triazinones, nitriles, benzothiadiazoles, and ureas), glutamine synthesis inhibitors (for example glufosinate), HPPD inhibitors (for example isoxazoles, pyrazolones, and triketones), PPO inhibitors (for example diphenylethers, N-phenylphthalimide, aryl triazinones, and pyrimidinediones), and long-chain fatty acid inhibitors (for example chloroacetamindes, oxyacetamides, and pyrazoles), among others. Exemplary insect resistance traits may include resistance to one or more insect members within one or more of the orders of Lepidoptera, Coleoptera, Hemiptera, Thysanoptera, Diptera, Hymenoptera, and Orthoptera, among others. Such additional traits are well known to one of skill in the art; for example, and a list of such transgenic traits is provided by the United States Department of Agriculture's (USDA) Animal and Plant Health Inspection Service (APHIS).

A cell transformed with a polynucleotide of the present invention, such as an expression construct, may be selected for the presence of the polynucleotide or its encoded enzymatic activity before or after regenerating such a cell into a transgenic plant. Transgenic plants comprising such a polynucleotide may thus be selected for instance by identifying a transgenic plant that comprises the polynucleotide or the encoded enzymatic activity, and/or displays an altered trait relative to an otherwise isogenic control plant. Such a trait may be, for example, tolerance to a PPO herbicide.

Transgenic plants and progeny that contain a transgenic trait provided by the invention may be used with any breeding methods that are commonly known in the art. In plant lines comprising two or more transgenic traits, the transgenic traits may be independently segregating, linked, or a combination of both in plant lines comprising three or more transgenic traits. Back-crossing to a parental plant and out-crossing with a non-transgenic plant are also contemplated, as is vegetative propagation. Descriptions of breeding methods that are commonly used for different traits and crops are well known to those of skill in the art. To confirm the presence of the transgene(s) in a plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and western blots) or by enzymatic function; plant part assays, such as leaf or root assays; and, by analyzing the phenotype of the whole plant. To analyze transit peptide processing in a transgenic plant or seed, assays such as Edman degradation sequencing or mass spectrometry analysis may be performed on the heterologous protoporphyrinogen oxidase protein obtained from the transgenic cell, plant, or seed and the resulting sequence data compared to that of the protoporphyrinogen oxidase protein.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly, a plant genotype lacking the desired transgenic trait may be referred to as an unconverted genotype, line, inbred, or hybrid.

As used herein, the term "comprising" means "including but not limited to".

Having described the invention in detail, it will be apparent that modifications, variations, and equivalent embodiments are possible without departing the scope of the invention defined in the appended claims. Furthermore, it should be appreciated that the examples in the present disclosure are provided as non-limiting examples.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit, and scope of the invention. More specifically, it will be apparent that certain agents which are both chemically and physiologically related may be substituted for the agents described herein with the same or similar result achieved. All such similar substitutes and modifications apparent to those skilled in the art are deemed to be within the spirit, scope, and concept of the invention as defined by the appended claims.

Example 1: Transit Peptide Discovery

Novel transit peptides were mined from a collection of plant sequence databases. Bioinformatic methods and tools, such as hidden Markov models (HMM), the Pfam database, and basic local alignment search tool (BLAST), were used to identify thousands of EST and genomic sequences predicted to encode proteins known to be localized to the chloroplast and mitochondria in plant cells, such as protoporphyrinogen oxidase and heat shock proteins. These sequences were then analyzed, and the sequence encoding the transit peptide was identified. Thousands of putative transit peptide sequences were identified and assessed for predicted efficacy and comparative sequence diversity. From these, 60 unique transit peptides were selected for cloning and testing in plant cells, with variants produced for some of these (indicated as "_var" herein). Table 2 provides the SEQ ID NO corresponding to the protein and nucleotide sequences of each transit peptide and variants thereof.

Recombinant DNA molecules encoding the transit peptides were synthesized using the sequence for each predicted transit peptide. DNA constructs were produced operably linking each transit peptide to a promoter and protein-coding sequence. These DNA constructs were then used to transform plant protoplasts. A protoplast assay was used with transformed plant protoplasts to test transit peptides for the functional activity of an operably linked herbicide-tolerance protein in the presence of the herbicide. Successful candidates were then advanced for plant transformation to enable transgenic plant testing.

TABLE 2

| Transit Peptides | | |
|---|---|---|
| Transit Peptide | PRT SEQ ID NO | DNA SEQ ID NO |
| ADADI_1600 | 8 | 58 |
| ALLCE_3035 | 16, 37, 46, 47, 237 | 66, 87, 96, 97, 268 |
| AMACR_2643 | 33 | 83 |
| AMAGR_5230 | 29 | 79 |
| AMAPA_1826 | 12 | 62 |
| AMAPA_4787 | 18 | 68 |
| AMBTR_1537 | 30 | 80 |
| ANDGE_6461 | 26 | 76 |
| BRANA_6036 | 31 | 81 |
| BRANA_9788 | 7 | 57 |
| CAMSA_6215 | 21, 41 | 71, 91 |
| CANRO_3271 | 24 | 74 |
| CANRO_3976 | 4, 35 | 54, 85 |
| CONCA_4103 | 11 | 61 |
| CUCME_4756 | 22, 39, 48 | 72, 89, 98 |
| DIGSA_5107 | 17 | 67 |
| DIGSA_5109 | 27 | 77 |
| ERATE_2090 | 25 | 75 |
| ERATE_4149 | 23, 36, 45 | 73, 86, 95 |
| ERATE_4824 | 28 | 78 |
| KOCSC_1672 | 14 | 64 |
| NICBE_5162 | 6 | 56 |
| ROSHY_6783 | 32 | 82 |
| ROSHY_8873 | 9 | 59 |
| SEDAL_8241 | 20 | 70 |
| SENOB_8832 | 5, 44 | 55, 94 |
| SETIT_2080 | 15 | 65 |
| SPIOL_0401 | 19 | 69 |
| SPIOL_0410 | 13 | 63 |
| TAROF_2111 | 34, 42, 38, 43 | 84, 92, 88, 93 |
| XANST_27 | 10, 40, 49 | 60, 90, 99 |
| ERATE_3481 | 238 | 269 |
| SETIT_9796 | 239 | 270 |
| ACAOS_3432 | 240 | 271 |
| ADADI_0544 | 241 | 272 |
| TAROF_9570 | 242 | 273 |
| AMACR_2380 | 243 | 274 |
| AMACR_2381 | 244 | 275 |
| AMAHY_5254 | 245 | 276 |
| AMAPA_22810 | 246 | 277 |
| AMAPA_2811 | 247 | 278 |
| AMAPA_6265_1 | 248 | 279 |

TABLE 2-continued

| Transit Peptides | | |
|---|---|---|
| Transit Peptide | PRT SEQ ID NO | DNA SEQ ID NO |
| AMAPA_6265_2 | 249 | 280 |
| AMAPA_2906 | 250 | 281 |
| AMARU_1762 | 251 | 282 |
| AMARU_1763 | 252 | 283 |
| AMARU_1764 | 253 | 284 |
| AMAVI_1826 | 254 | 285 |
| AMAVI_1827 | 255 | 286 |
| AMBTR_6334 | 256 | 287 |
| CONCA_3910 | 257 | 288 |
| CUCME_3420 | 258 | 289 |
| KOCSC_5431 | 259 | 290 |
| KOCSC_9516 | 260 | 291 |
| KOCSC_0438 | 261 | 292 |
| ROSHY_3269 | 262 | 293 |
| SEDAL_6599 | 263 | 294 |
| SEDAL_6601 | 264 | 295 |
| SPIOL_1551 | 265 | 296 |
| ALLCE_6618 | 266 | 297 |

Example 2: PPO Enzyme Discovery

Novel microbial HemG and HemY protoporphyrinogen oxidases that are tolerant to PPO herbicides were identified from microbial sequence databases using bioinformatic methods and a novel herbicide bacterial screening system. This screening system used a growth assay of the hemG knockout *E. coli* strain in LB liquid medium with a PPO herbicide to confirm protoporphyrinogen oxidase activity for an enzyme and to identify protoporphyrinogen oxidases that were not sensitive to the PPO herbicide. Briefly, a hemG knockout *E. coli* strain was transformed with a bacterial expression vector containing a putative protoporphyrinogen oxidase and cultured in LB liquid medium. Purified crystalline form of one of five different PPO herbicides (acifluorfen (1 mM), flumioxazin (0.5 mM), lactofen (0.5 mM), fomesafen (1 mM), and S-3100 (100 microM), representing three different PPO chemistry subclasses, was added to the medium. Recombinant proteins were expressed and the *E. coli* growth rates were measured. Growth curves (OD600) were measured for the different variants in the presence and absence of the PPO herbicides at selected time-points from time zero to twenty-four hours. The growth of a transformed hemG knockout *E. coli* strain in LB medium in the presence of a PPO herbicide indicated that the gene used to transform the *E. coli* encoded an herbicide-tolerant protoporphyrinogen oxidase. The hemG knockout *E. coli* strain expressing the waterhemp (WH) protoporphyrinogen oxidase (SEQ ID NO:120), which is sensitive to all five PPO herbicides, was used as a control to confirm that the assay could distinguish between sensitive and tolerant protoporphyrinogen oxidases for each of the herbicides.

Protoporphyrinogen oxidases that are herbicide-tolerant proteins are provided as SEQ ID NOs:100-119, SEQ ID NOs:163-182, and SEQ ID NOs:224-228 and shown in Table 3. The DNA sequence encoding a protoporphyrinogen oxidase can include at the 5' end a codon for a methionine, commonly known as a start codon, or this codon (and optionally a few amino-terminal amino acids, for example 2 to 7), can be eliminated to facilitate operable linkage of a transit peptide sequence to the 5' end of the coding sequence. DNA sequences encoding a protoporphyrinogen oxidase can optionally be synthesized that are optimized for expression in a monocot or dicot. Table 3 provides for each protoporphyrinogen oxidase DNA sequences that are optimized for expression in monocots and dicots.

TABLE 3

Protoporphyrinogen oxidases

| Name | Protein SEQ ID NO | Bacterial DNA SEQ ID NO | Dicot optimized DNA SEQ ID NO | Monocot optimized DNA SEQ ID NO |
|---|---|---|---|---|
| H_N10 | 103, 112 | 124 | 134, 143 | 156 |
| H_N20 | 101, 111 | 122 | 132, 142, 151 | 154 |
| H_N30 | 104, 113 | 125 | 135, 144 | 157 |
| H_N40 | 105, 114 | 126 | 136, 145 | 158 |
| H_N50 | 106, 115 | 127 | 137, 146 | 159 |
| H_N60 | 102 | 123 | 133 | 155 |
| H_N70 | 107 | 128 | 138 | 160 |
| H_N90 | 100, 110, 117, 118 | 121 | 131, 141, 148, 149, 150, 229 | 153 |
| H_N100 | 108, 116, 119 | 129 | 139, 147, 152 | 161 |
| H_N110 | 109 | 130 | 140 | 162 |
| WH PPO | 120 | n/a | n/a | n/a |
| R2N30 | 163, 164 | 183 | 189, 190 | 195 |
| R2N40 | 165, 224 | 184 | 191, 230 | 196 |
| R2N40opt | 166, 225 | 185 | 231, 232 | n/a |
| R2N70 | 167, 226 | 186 | 192, 233 | 197 |
| R2N90 | 168, 227 | 187 | 193, 234 | 198 |
| R2N100 | 169, 228 | 188 | 194, 235 | 199 |
| R1N473 | 170, 175, 179 | 200 | 205, 216, 220 | 211 |
| R1N533 | 171, 176, 180 | 201 | 206, 217, 221 | 212 |
| R1N171 | 172, 177, 181 | 202 | 207, 218, 222 | 213 |
| R1N311 | 173 | 203 | 208 | 214 |
| R1N333 | 174, 178, 182 | 204 | 209, 210, 219, 223 | 215 |

Example 3: Transit Peptide and Protoporphyrinogen Oxidase Testing in Protoplasts Transit peptides operably linked to a protoporphyrinogen oxidase were tested in plant protoplasts for PPO herbicide-tolerance. Plant transformation vectors were constructed comprising a recombinant DNA molecule encoding the H_N90 protoporphyrinogen oxidase operably linked to a transit peptide. The vectors were then used to transform plant protoplasts, which were assessed for sensitivity to PPO herbicides.

Plant transformation vectors were produced comprising (i) fixed expression elements (a promoter and 3′UTR) operably linked to a transit peptide operably linked to the H_N90 protoporphyrinogen oxidase. Using this, 68 transit peptides were tested and direct comparisons were made by the use of the same protoporphyrinogen oxidase and other expression elements in each vector. Control vectors with the same fixed expression elements were produced comprising (i) H_N90 protoporphyrinogen oxidase without any transit peptide (H_N90 Control) or (ii) Green Fluorescent Protein (GFP) without a transit peptide (GFP Control).

Soybean protoplasts were transformed using standard methods and grown in the presence of the PPO herbicide S-3100 at 1.0 microM concentration. Protoplasts were then assayed for PPO herbicide tolerance, expressed relative to the GFP control (allowing derivation of a relative tolerance score to enable comparisons between experiments). Assays were done in two batches, indicated as Experiment No. 1 or Experiment No. 2. The assays were done in four replications, relative tolerance scores were averaged for each transit peptide, and standard error was calculated (SE). Any targeting peptide scoring a relative tolerance score of 50 or higher was considered highly efficacious for providing efficient sub-cellular localization and processing when operably linked to an herbicide-tolerance protein and a score of 40-50 indicates very good for providing efficient sub-cellular localization and processing when operably linked to an herbicide-tolerance protein. The GFP Control assays had a tolerance score of 0, confirming that the soybean protoplasts were not tolerant to the PPO herbicide in the absence of an herbicide-tolerance protein. The H_N90 Control assays had a tolerance score of 24 (Experiment 1, SE 4) and 11 (Experiment 2, SE 4), while several of the transit peptides provide higher tolerance scores, indicating that an effective transit peptide can increase the herbicide tolerance of the plant protoplasts. For example, ADADI_0544 and KOCSC_9516 scored as highly efficacious targeting peptides and AMAPA_62652 scored as a very good targeting peptide. Data are provided in Table 4.

TABLE 4

Protoplast Assay Results

| Transit Peptide | Tolerance score | SE | Experiment |
|---|---|---|---|
| ADADI_0544 | 62 | 2 | 1 |
| KOCSC_9516 | 60 | 1 | 1 |
| ALLCE_3035_var | 56 | 4 | 1 |
| CAMSA_6215 | 56 | 3 | 1 |
| AMAPA_2810 | 56 | 3 | 1 |
| ALLCE_6618 | 56 | 2 | 1 |
| AMARU_1764 | 56 | 3 | 1 |
| AMBTR_6334 | 56 | 1 | 1 |
| SETIT_9796 | 55 | 5 | 1 |
| AMACR_2381 | 55 | 2 | 1 |
| AMAVI_1827 | 54 | 4 | 1 |
| CONCA_3910 | 54 | 1 | 1 |
| ERATE_3481 | 53 | 2 | 1 |
| ROSHY_3269 | 53 | 5 | 1 |
| AMAPA_6265_1 | 53 | 2 | 1 |
| AMAHY_5254 | 52 | 4 | 1 |
| SEDAL_6599 | 52 | 2 | 1 |
| AMACR_2380 | 51 | 3 | 1 |
| CUCME_3420 | 51 | 3 | 1 |
| AMARU_1762 | 51 | 5 | 1 |
| SEDAL_6601 | 50 | 5 | 1 |
| KOCSC_5431 | 48 | 4 | 1 |
| AMAPA_6265_2 | 47 | 2 | 1 |
| KOCSC_0438 | 47 | 3 | 1 |
| AMAPA_2811 | 46 | 3 | 1 |
| AMAVI_1826 | 45 | 4 | 1 |
| ACAOS_3432 | 44 | 2 | 1 |
| SPIOL_1551 | 43 | 4 | 1 |
| AMAPA_2906 | 43 | 2 | 1 |
| TAROF_9570 | 41 | 3 | 1 |
| AMARU_1763 | 40 | 8 | 1 |
| None - H_N90 Control | 24 | 4 | 1 |
| None - GFP | 0 | 4 | 1 |
| ADADI_0544 | 60 | 1 | 2 |
| SPIOL_1551 | 53 | 3 | 2 |
| KOCSC_9516 | 51 | 4 | 2 |
| ROSHY_3269 | 49 | 4 | 2 |
| AMACR_2381 | 48 | 3 | 2 |
| CAMSA_6215 | 46 | 2 | 2 |
| CUCME_4756_var | 46 | 1 | 2 |
| CUCME_3420 | 46 | 3 | 2 |
| CONCA_3910 | 45 | 4 | 2 |
| AMAGR_5230 | 43 | 2 | 2 |
| SENOB_8832 | 43 | 1 | 2 |
| KOCSC_1672 | 42 | 3 | 2 |
| CONCA_4103 | 36 | 5 | 2 |
| ADADI_1600 | 36 | 4 | 2 |
| BRANA_9788 | 33 | 1 | 2 |
| CUCME_4756 | 33 | 4 | 2 |
| ANDGE_6461 | 33 | 2 | 2 |
| ALLCE_3035 | 33 | 3 | 2 |
| AMAPA_4787 | 30 | 2 | 2 |
| TAROF_2111 | 28 | 3 | 2 |
| ROSHY_6783 | 26 | 4 | 2 |
| CANRO_3976 | 25 | 4 | 2 |
| TAROF_2111_var | 25 | 5 | 2 |

TABLE 4-continued

Protoplast Assay Results

| Transit Peptide | Tolerance score | SE | Experiment |
|---|---|---|---|
| XANST_27_var | 24 | 2 | 2 |
| NICBE_5162 | 24 | 3 | 2 |
| XANST_27 | 22 | 3 | 2 |
| SPIOL_0401 | 22 | 2 | 2 |
| ERATE_2090 | 22 | 1 | 2 |
| SPIOL_0410 | 21 | 2 | 2 |
| CANRO_3271 | 20 | 2 | 2 |
| AMAPA_1826 | 20 | 2 | 2 |
| DIGSA_5109 | 20 | 2 | 2 |
| DIGSA_5107 | 17 | 2 | 2 |
| ERATE_4149 | 15 | 4 | 2 |
| SETIT_2080 | 14 | 2 | 2 |
| ROSHY_8873 | 12 | 4 | 2 |
| AMBTR_1537 | 12 | 6 | 2 |
| SEDAL_8241 | 11 | 6 | 2 |
| None - H_N90 Control | 11 | 4 | 2 |
| ERATE_4824 | 9 | 5 | 2 |
| ALLCE_3035_var | 8 | 1 | 2 |
| None - GFP | 0 | 4 | 2 |
| AMACR_2643 | 0 | 4 | 2 |

Example 4: Transit Peptide and Protoporphyrinogen Oxidase Testing in Soybean

Transit peptides operably linked to protoporphyrinogen oxidases were tested in transgenic soybean plants for PPO herbicide-tolerance. Plant transformation vectors were constructed comprising a DNA construct comprising a recombinant DNA molecule optimized for dicot expression and encoding a protoporphyrinogen oxidase operably linked to a transit peptide. The plant transformation vectors were then used to transform soybean, and the plants were regenerated and assessed for their sensitivity to a PPO herbicide.

The genes encoding the seven HemG protoporphyrinogen oxidases H_N10, H_N20, H_N30, H_N40, H_N50, H_N90, and H_N100 were operably linked to thirty-seven different transit peptides and cloned into a base plant transformation vector as described in Example 3. This permitted the side-by-side comparison of seven different HemG protoporphyrinogen oxidases with thirty-seven different transit peptides using the same promoter and 3'UTR elements in every DNA construct. These plant transformation vectors were used to transform soybean excised embryos (germplasm A3555) using *A. tumefaciens* and standard methods known in the art. Four hundred explants were inoculated for each construct. A sterile PPO herbicide solution was used for herbicide-tolerance testing. The herbicide solution consisted of 0.3 g of S-3100 in crop oil concentrate (5.0 mL) and 495 mL of deionized water.

At five weeks post-transformation, plants were sprayed with two passes of the sterile PPO herbicide solution at a 20 g/ha rate. For each DNA construct tested, four containers each with 30-40 individually transformed plants were tested. The treated plantlets then received at least 15 hours of light exposure post spray each day for four days. At the end of day four post application of S-3100, the treated plantlets were photographed and scored on a visual scale of green coloration (green coloration was representative of healthy photosynthetic plant tissue as compared to photo-bleached tissue) versus damage. The scoring values were 0 for poor tolerance, high damage, low green coloration; 1 for some tolerance, average damage, moderate green coloration; and 2 for good tolerance, low damage, high green coloration. The scoring for each construct is presented in Table 5, where n.d. indicates the analysis was not conducted. The results indicate that several constructs provided tolerance to the PPO herbicide.

TABLE 5

Tolerance score at 5 weeks in soybean

| Transit Peptide | H_N10 | H_N20 | H_N30 | H_N40 | H_N50 | H_N90 | H_N100 |
|---|---|---|---|---|---|---|---|
| APG6 | n.d. | 0 | 2 | 2 | 1 | 2 | 2 |
| 12G088600TP | n.d. | 0 | 0 | 1 | 1 | 2 | 1 |
| CANRO_3976 | 1 | 1 | n.d. | 1 | 1 | 2 | 1 |
| SENOB_8832 | n.d. | 1 | n.d. | 2 | 1 | 1 | n.d. |
| NICBE_5162 | n.d. | n.d. | n.d. | n.d. | 0 | 1 | n.d. |
| BRANA_9788 | 0 | 1 | 0 | n.d. | 2 | 2 | 2 |
| ADADI_1600 | n.d. | 2 | 1 | 2 | 1 | 2 | 2 |
| ROSHY_8873 | 0 | 1 | 1 | 2 | 1 | 0 | 0 |
| XANST_27 | 1 | 1 | 1 | 0 | 1 | 1 | 0 |
| CONCA_4103 | n.d. | n.d. | 0 | n.d. | 1 | 2 | 1 |
| AMAPA_1826 | n.d. | 1 | 1 | 1 | 0 | 2 | 0 |
| SPIOL_0410 | 1 | 2 | 1 | 1 | 1 | 2 | 2 |
| KOCSC_1672 | 1 | 2 | 1 | 1 | 1 | 2 | 0 |
| SETIT_2080 | 0 | 0 | n.d. | 2 | 1 | 2 | 1 |
| ALLCE_3035 | n.d. | 1 | 1 | 2 | 2 | 2 | 2 |
| DIGSA_5107 | 1 | 1 | n.d. | n.d. | 0 | 1 | 1 |
| AMAPA_4787 | n.d. | 2 | 1 | 1 | 1 | 2 | 1 |
| SPIOL_0401 | 1 | 1 | 0 | 1 | 1 | 2 | 1 |
| SEDAL_8241 | 0 | 1 | 0 | 1 | 0 | 1 | 1 |
| CAMSA_6215 | 0 | 2 | n.d. | n.d. | n.d. | 2 | 2 |
| CUCME_4756 | 0 | 0 | n.d. | 2 | 1 | 1 | 0 |
| ERATE_4149 | 1 | 1 | n.d. | n.d. | 2 | 2 | 2 |
| CANRO_3271 | 1 | 1 | n.d. | 1 | 1 | 1 | 2 |
| ERATE_2090 | 0 | 1 | 1 | 0 | 1 | 1 | 0 |
| ANDGE_6461 | n.d. | 1 | n.d. | 2 | 2 | 1 | 1 |
| DIGSA_5109 | 0 | 1 | 0 | 1 | 1 | 0 | n.d. |
| ERATE_4824 | 1 | 1 | 0 | 1 | 1 | 1 | 1 |
| AMAGR_5230 | n.d. | 1 | 0 | 1 | 1 | 2 | 1 |
| AMBTR_1537 | n.d. | 1 | 1 | 1 | 1 | 1 | 1 |
| BRANA_6036 | n.d. | 1 | n.d. | 1 | 1 | 1 | 1 |
| ROSHY_6783 | 1 | 1 | n.d. | 1 | 0 | 0 | 1 |
| AMACR_2643 | n.d. | 0 | n.d. | 1 | 1 | 0 | 2 |

TABLE 5-continued

Tolerance score at 5 weeks in soybean

| Transit Peptide | H_N10 | H_N20 | H_N30 | H_N40 | H_N50 | H_N90 | H_N100 |
|---|---|---|---|---|---|---|---|
| TAROF_2111 | 1 | 1 | 1 | 0 | 1 | 2 | 1 |
| CANRO_3976_var | n.d. | n.d. | n.d. | n.d. | n.d. | n.d. | n.d. |
| ERATE_4149_var | n.d. | n.d. | n.d. | n.d. | 0 | 2 | 0 |
| ALLCE_3035_var | n.d. | n.d. | n.d. | n.d. | n.d. | 1 | 1 |
| TAROF_2111_var | 0 | n.d. | n.d. | n.d. | 0 | 2 | 1 |
| CUCME_4756_var | n.d. | n.d. | n.d. | n.d. | n.d. | n.d. | n.d. |
| XANST_27_var | n.d. | n.d. | n.d. | n.d. | 0 | n.d. | n.d. |

The plantlets in the non-sprayed containers corresponding to constructs having a score of 2 were then transplanted at approximately seven weeks post-transformation and grown as R0 plants using standard methods known in the art. A selection of plantlets corresponding to non-tolerant scores of 0 and 1 were also grown to serve as negative controls. The R0 plants were grown in a greenhouse under long-day nursery conditions (18 hours of light at 80° F. then 6 hours of dark at 74° F.) for approximately four additional weeks. At eleven weeks post-transformation, the R0 plants were sprayed with two passes of the same herbicide solution described above for a final application rate of 20 g/ha. For each DNA construct tested, 15-30 individually transformed plants were tested. Herbicide injury ratings were visually scored based on the amount of above ground tissue injury with 0% being no visible injury and 100% being complete death of the plant. Non-transgenic control plants scored injury ratings of greater than 30%. Marginal tolerance was 30% injury or less, good tolerance is 20% injury or less, and excellent tolerance was considered 10% injury or less. Scores were collected seven days after treatment and averaged for all plants for each DNA construct.

The results of the herbicide-tolerance application at eleven weeks to the R0 plants confirmed the low percent injury rating scores observed at five weeks. For the eleven-week evaluation, any injury rating of 30% or above was equivalent to non-transgenic soybean injury ratings. Several of the constructs stood out as providing very good tolerance to the herbicide application. For example, APG6 (SEQ ID NO:1) with PPO H_N90 (SEQ ID NO:110) had only 3% injury, APG6 (SEQ ID NO:1) with PPO H_N30 (SEQ ID NO:113) or APG6 (SEQ ID NO:1) with PPO H_N40 (SEQ ID NO:114) each had only 5% injury; transit peptide CAMSA_6215 (SEQ ID NO:21) with PPO H_N90 (SEQ ID NO:110) had only 5% injury. In contrast, transit peptide AMACR_2643 (SEQ ID NO:33) with the PPO H_N90 (SEQ ID NO:110) had an injury score of 50%. Data are provided in Table 6, where n.d. indicates the analysis was not conducted.

TABLE 6

Tolerance score at 11 weeks in soybean

| Transit Peptide | H_N20 | H_N30 | H_N40 | H_N50 | H_N90 | H_N100 |
|---|---|---|---|---|---|---|
| APG6 | n.d. | 5 | 5 | n.d. | 3 | 15 |
| 12G088600TP | n.d. | n.d. | n.d. | n.d. | 35 | n.d. |
| CANRO_3976 | n.d. | n.d. | n.d. | n.d. | 30 | n.d. |
| SENOB_8832 | n.d. | n.d. | 15 | n.d. | n.d. | n.d. |
| NICBE_5162 | n.d. | n.d. | n.d. | n.d. | n.d. | n.d. |
| BRANA_9788 | 25 | n.d. | n.d. | 40 | 25 | 30 |
| ADADI_1600 | 20 | n.d. | 40 | n.d. | 15 | 30 |
| ROSHY_8873 | n.d. | n.d. | 30 | n.d. | 40 | n.d. |
| XANST_27 | n.d. | 35 | n.d. | 40 | 30 | n.d. |
| CONCA_4103 | n.d. | n.d. | n.d. | n.d. | 30 | 35 |
| AMAPA_1826 | n.d. | 35 | n.d. | n.d. | 30 | n.d. |
| SPIOL_0410 | 20 | n.d. | n.d. | n.d. | 30 | 50 |
| KOCSC_1672 | 20 | n.d. | 15 | 40 | 15 | n.d. |
| SETIT_2080 | n.d. | n.d. | 35 | 40 | 25 | n.d. |
| ALLCE_3035 | 30 | 35 | 30 | 40 | 35 | 30 |
| DIGSA_5107 | n.d. | n.d. | n.d. | n.d. | 35 | n.d. |
| AMAPA_4787 | 25 | n.d. | n.d. | 40 | 15 | n.d. |
| SPIOL_0401 | n.d. | n.d. | n.d. | n.d. | 30 | n.d. |
| SEDAL_8241 | n.d. | n.d. | n.d. | n.d. | n.d. | n.d. |
| CAMSA_6215 | 20 | n.d. | n.d. | n.d. | 5 | 35 |
| CUCME_4756 | n.d. | n.d. | 35 | n.d. | 25 | n.d. |
| ERATE_4149 | n.d. | n.d. | n.d. | 40 | 30 | 30 |
| CANRO_3271 | n.d. | n.d. | n.d. | n.d. | 30 | 35 |
| ERATE_2090 | n.d. | n.d. | n.d. | n.d. | n.d. | n.d. |
| ANDGE_6461 | n.d. | n.d. | 15 | 35 | n.d. | n.d. |
| DIGSA_5109 | n.d. | 35 | n.d. | n.d. | 40 | n.d. |
| ERATE_4824 | n.d. | n.d. | n.d. | n.d. | 35 | n.d. |
| AMAGR_5230 | n.d. | n.d. | n.d. | n.d. | 30 | 35 |
| AMBTR_1537 | 30 | n.d. | n.d. | n.d. | n.d. | 40 |
| BRANA_6036 | n.d. | n.d. | n.d. | n.d. | n.d. | n.d. |
| ROSHY_6783 | n.d. | n.d. | n.d. | n.d. | n.d. | n.d. |
| AMACR_2643 | n.d. | n.d. | n.d. | n.d. | 50 | 40 |
| TAROF_2111 | n.d. | n.d. | n.d. | n.d. | 25 | n.d. |
| CANRO_3976_var | n.d. | n.d. | n.d. | n.d. | n.d. | n.d. |

TABLE 6-continued

| | Tolerance score at 11 weeks in soybean | | | | | |
|---|---|---|---|---|---|---|
| Transit Peptide | H_N20 | H_N30 | H_N40 | H_N50 | H_N90 | H_N100 |
| ERATE_4149_var | n.d. | n.d. | n.d. | n.d. | 35 | n.d. |
| ALLCE_3035_var | n.d. | n.d. | n.d. | n.d. | 15 | 35 |
| TAROF_2111_var | n.d. | n.d. | n.d. | n.d. | 15 | n.d. |
| CUCME_4756_var | n.d. | n.d. | n.d. | n.d. | n.d. | n.d. |
| XANST_27_var | n.d. | n.d. | n.d. | n.d. | n.d. | n.d. |

The genes encoding ten HemY protoporphyrinogen oxidases R2N30, R2N40, R2N40opt, R2N70, R2N90, R2N100, R1N473, R1N533, R1N171, R1N311, and R1N33 were operably linked to thirty-nine different transit peptides and cloned into a base plant transformation vector as described in Example 3. This permitted the side-by-side comparison of ten different HemY protoporphyrinogen oxidases with thirty-nine different transit peptides using the same promoter and 3'UTR elements in every DNA construct. These plant transformation vectors were used to transform soybean excised embryos (germplasm A3555) using *A. tumefaciens* and standard methods known in the art. Four hundred explants were inoculated for each construct. A sterile PPO herbicide solution was used for herbicide-tolerance testing. The herbicide solution consisted of 0.3 g of S-3100 in crop oil concentrate (5.0 mL) and 495 mL of deionized water.

At five weeks post-transformation, for each DNA construct four containers (each with 30-40 individually transformed plants) were sprayed with two passes of the sterile PPO herbicide solution for a final application rate of 20 g/ha. The treated plantlets then received at least 15 hours of light exposure post spray each day for four days. At the end of day four post application of S-3100, the treated plantlets were photographed and scored on a visual scale of green coloration (green coloration was representative of healthy photosynthetic plant tissue as compared to photo-bleached tissue) versus damage. The scoring values were 0 for poor tolerance, high damage, low green coloration; 1 for some tolerance, average damage, moderate green coloration; and 2 for good tolerance, low damage, high green coloration. The scoring for each construct is presented in Table 7, where n.d. indicates the analysis was not conducted. The results indicate that several constructs provided tolerance to the PPO herbicide.

TABLE 7

| | Tolerance score at 5 weeks in soybean | | | | | | | | | |
|---|---|---|---|---|---|---|---|---|---|---|
| Transit Peptide | R1N171 | R1N473 | R1N533 | R2N30 | R2N40 | R2N40opt | R2N70 | R2N90 | R2N100 | R1N333 |
| APG6 | 0 | 2 | 0 | 2 | n.d. | 1 | n.d. | n.d. | 0 | n.d. |
| 12G088600TP | 0 | 0 | 2 | n.d. | n.d. | n.d. | 2 | 0 | 0 | 0 |
| CANRO_3976 | 0 | 1 | 0 | 1 | n.d. | n.d. | 1 | n.d. | 0 | 0 |
| SENOB_8832 | n.d. | 1 | 0 | 2 | n.d. | 0 | 0 | n.d. | 0 | 0 |
| NICBE_5162 | 1 | n.d. | n.d. | n.d. | 1 | 1 | n.d. | 0 | 0 | n.d. |
| BRANA_9788 | n.d. | 1 | 1 | n.d. | n.d. | 1 | 0 | n.d. | 0 | 0 |
| ADADI_1600 | 0 | 1 | 0 | 1 | n.d. | 2 | n.d. | n.d. | n.d. | 0 |
| ROSHY_8873 | 1 | 1 | n.d. | 2 | 0 | 1 | 0 | 1 | 1 | 0 |
| XANST_27 | 1 | 1 | n.d. | 2 | 0 | 0 | n.d. | 1 | n.d. | 1 |
| CONCA_4103 | 1 | 1 | 1 | 2 | n.d. | n.d. | n.d. | 0 | 1 | n.d. |
| AMAPA_1826 | 0 | 0 | 0 | 2 | n.d. | 1 | n.d. | n.d. | n.d. | 0 |
| SPIOL_0410 | 0 | 1 | 0 | 1 | n.d. | 2 | n.d. | 1 | 0 | 1 |
| KOCSC_1672 | 0 | 0 | 0 | n.d. | n.d. | 0 | n.d. | 0 | n.d. | 0 |
| SETIT_2080 | n.d. | 1 | 1 | 1 | n.d. | n.d. | n.d. | 0 | 1 | 0 |
| ALLCE_3035 | 1 | 1 | 1 | 2 | n.d. | 1 | n.d. | n.d. | 0 | 0 |
| DIGSA_5107 | 1 | 1 | 2 | 2 | n.d. | 1 | 0 | 0 | n.d. | 0 |
| AMAPA_4787 | 0 | 1 | n.d. | 1 | n.d. | 1 | n.d. | n.d. | 0 | 0 |
| SPIOL_0401 | 0 | 0 | 0 | 1 | n.d. | 0 | n.d. | 1 | 1 | 0 |
| SEDAL_8241 | 1 | 0 | 1 | n.d. | 2 | 1 | n.d. | 1 | 1 | 0 |
| CAMSA_6215 | 0 | 1 | 1 | 2 | n.d. | 1 | n.d. | 0 | n.d. | n.d. |
| CUCME_4756 | 0 | 0 | n.d. | 1 | n.d. | n.d. | 0 | 1 | 0 | 0 |
| ERATE_4149 | n.d. | 1 | 2 | 1 | n.d. | n.d. | n.d. | 0 | 0 | 0 |
| CANRO_3271 | 1 | 1 | 1 | 1 | n.d. | n.d. | n.d. | 1 | 0 | 1 |
| ERATE_2090 | n.d. | 0 | 2 | 2 | n.d. | n.d. | n.d. | 0 | 0 | 0 |
| ANDGE_6461 | 0 | 1 | 0 | 2 | n.d. | 1 | n.d. | n.d. | 0 | 0 |
| DIGSA_5109 | 1 | 0 | 1 | 1 | n.d. | 1 | n.d. | n.d. | 1 | 0 |
| ERATE_4824 | 0 | 1 | 0 | n.d. | n.d. | 2 | n.d. | 0 | 0 | 1 |
| AMAGR_5230 | 0 | 2 | 0 | 2 | n.d. | n.d. | n.d. | 0 | 1 | 0 |
| AMBTR_1537 | 0 | 0 | 1 | 1 | n.d. | 0 | n.d. | 0 | 0 | 1 |
| BRANA_6036 | 1 | 1 | n.d. | 1 | n.d. | 0 | n.d. | 0 | 0 | 0 |
| ROSHY_6783 | 1 | 1 | 1 | 1 | 0 | 0 | 1 | 0 | 1 | 1 |
| AMACR_2643 | 0 | 1 | 1 | 1 | n.d. | 0 | n.d. | 0 | 0 | 0 |
| TAROF_2111 | 0 | 2 | 0 | n.d. | 2 | 1 | 0 | 0 | 0 | 0 |
| CANRO_3976_var | n.d. | n.d. | n.d. | 0 | 1 | n.d. | n.d. | n.d. | n.d. | 1 |
| ERATE_4149_var | 0 | 0 | 1 | 1 | 1 | 1 | n.d. | n.d. | n.d. | n.d. |
| ALLCE_3035_var | n.d. | n.d. | 0 | 1 | 1 | 1 | n.d. | n.d. | 0 | 1 |
| TAROF_2111_var | 0 | 0 | 0 | 1 | 1 | 2 | n.d. | n.d. | 0 | n.d. |
| CUCME_4756_var | n.d. | n.d. | 2 | 2 | 2 | n.d. | n.d. | n.d. | n.d. | n.d. |
| XANST_27_var | 1 | 1 | 2 | 1 | 2 | 1 | n.d. | n.d. | n.d. | n.d. |

The plantlets in the non-sprayed containers corresponding to constructs having a score of 2 were then transplanted at approximately seven weeks post-transformation and grown as R0 plants using standard methods known in the art. A selection of plantlets corresponding to non-tolerant scores of 0 and 1 were also grown to serve as negative controls. The R0 plants were grown in a greenhouse under long-day nursery conditions (18 hours of light at 80° F. then 6 hours of dark at 74° F.) for approximately four additional weeks. At eleven weeks post-transformation, the R0 plants were sprayed with two passes of the same herbicide solution described above for a final application rate of 20 g/ha. For each DNA construct tested, 15-30 individually transformed plants were tested. Herbicide injury ratings were visually scored based on the amount of above ground tissue injury with 0% being no visible injury and 100% being complete death of the plant. Non-transgenic control plants scored injury ratings of greater than 30%. Marginal tolerance was 30% injury or less, good tolerance is 20% injury or less, and excellent tolerance was considered 10% injury or less. Scores were collected seven days after treatment and averaged for all plants for each DNA construct.

The results of the herbicide-tolerance application at eleven weeks confirmed the low percent injury rating scores observed at five weeks. For the eleven-week evaluation, any injury rating of 30% or above was equivalent to non-transgenic soybean injury ratings. A few of the constructs stood out as providing very good tolerance to the herbicide application. For example, transit peptide ANDGE_6461 (SEQ ID NO:26) with R2N30 (SEQ ID NO:163) had only 7% injury. Data are provided in Table 8, where n.d. indicates the analysis was not conducted.

TABLE 8

Tolerance score at 11 weeks in soybean

| Transit Peptide | R1N171 | R1N473 | R1N533 | R2N30 | R2N40 | R2N40opt | R2N70 | R1N333 |
|---|---|---|---|---|---|---|---|---|
| APG6 | n.d. | 30 | n.d. | 17 | n.d. | 20 | n.d. | n.d. |
| 12G088600TP | n.d. | n.d. | 40 | n.d. | n.d. | n.d. | 30 | n.d. |
| CANRO_3976 | n.d. | n.d. | n.d. | n.d. | n.d. | n.d. | n.d. | n.d. |
| SENOB_8832 | n.d. | n.d. | n.d. | 25 | n.d. | n.d. | n.d. | n.d. |
| NICBE_5162 | n.d. | n.d. | n.d. | n.d. | n.d. | n.d. | n.d. | n.d. |
| BRANA_9788 | n.d. | 35 | n.d. | n.d. | n.d. | n.d. | n.d. | n.d. |
| ADADI_1600 | n.d. | n.d. | n.d. | 25 | n.d. | 30 | n.d. | n.d. |
| ROSHY_8873 | n.d. | n.d. | n.d. | 35 | n.d. | 30 | n.d. | 35 |
| XANST_27 | n.d. | n.d. | n.d. | 20 | n.d. | 25 | n.d. | 35 |
| CONCA_4103 | n.d. | n.d. | n.d. | 25 | n.d. | n.d. | n.d. | n.d. |
| AMAPA_1826 | n.d. | n.d. | n.d. | 25 | n.d. | n.d. | n.d. | n.d. |
| SPIOL_0410 | n.d. | n.d. | n.d. | n.d. | n.d. | 35 | n.d. | n.d. |
| KOCSC_1672 | n.d. | n.d. | n.d. | n.d. | n.d. | n.d. | n.d. | n.d. |
| SETIT_2080 | n.d. | n.d. | n.d. | 20 | n.d. | n.d. | n.d. | 35 |
| ALLCE_3035 | n.d. | n.d. | n.d. | 25 | n.d. | n.d. | n.d. | n.d. |
| DIGSA_5107 | 30 | 40 | 35 | 35 | n.d. | n.d. | n.d. | n.d. |
| AMAPA_4787 | n.d. | n.d. | n.d. | 25 | n.d. | n.d. | n.d. | n.d. |
| SPIOL_0401 | n.d. | n.d. | n.d. | 15 | n.d. | n.d. | n.d. | n.d. |
| SEDAL_8241 | n.d. | n.d. | n.d. | n.d. | 20 | n.d. | n.d. | n.d. |
| CAMSA_6215 | n.d. | n.d. | n.d. | 15 | n.d. | 20 | n.d. | n.d. |
| CUCME_4756 | n.d. | n.d. | n.d. | n.d. | n.d. | n.d. | n.d. | n.d. |
| ERATE_4149 | n.d. | n.d. | 35 | 25 | n.d. | n.d. | n.d. | n.d. |
| CANRO_3271 | n.d. | n.d. | n.d. | n.d. | n.d. | n.d. | n.d. | n.d. |
| ERATE_2090 | n.d. | n.d. | 35 | 15 | n.d. | n.d. | n.d. | n.d. |
| ANDGE_6461 | n.d. | n.d. | n.d. | 7 | n.d. | n.d. | n.d. | n.d. |
| DIGSA_5109 | n.d. | n.d. | n.d. | n.d. | n.d. | n.d. | n.d. | n.d. |
| ERATE_4824 | n.d. | n.d. | n.d. | n.d. | n.d. | 25 | n.d. | n.d. |
| AMAGR_5230 | n.d. | 35 | n.d. | 35 | n.d. | n.d. | n.d. | n.d. |
| AMBTR_1537 | n.d. | n.d. | n.d. | n.d. | n.d. | n.d. | n.d. | n.d. |
| BRANA_6036 | n.d. | n.d. | n.d. | 25 | n.d. | n.d. | n.d. | n.d. |
| ROSHY_6783 | n.d. | n.d. | n.d. | n.d. | n.d. | n.d. | n.d. | n.d. |
| AMACR_2643 | n.d. | n.d. | n.d. | n.d. | n.d. | n.d. | n.d. | n.d. |
| TAROF_2111 | n.d. | 40 | n.d. | n.d. | 20 | n.d. | n.d. | n.d. |
| CANRO_3976_var | n.d. | n.d. | n.d. | n.d. | n.d. | n.d. | n.d. | n.d. |
| ERATE_4149_var | n.d. | n.d. | n.d. | n.d. | n.d. | n.d. | n.d. | n.d. |
| ALLCE_3035_var | n.d. | n.d. | n.d. | 25 | n.d. | n.d. | n.d. | n.d. |
| TAROF_2111_var | n.d. | n.d. | n.d. | n.d. | n.d. | 25 | n.d. | n.d. |
| CUCME_4756_var | n.d. | n.d. | 35 | n.d. | 25 | n.d. | n.d. | n.d. |
| XANST_27_var | n.d. | 30 | 35 | n.d. | n.d. | n.d. | n.d. | n.d. |

The genes encoding the HemG protoporphyrinogen oxidase H_N90 was operably linked to 44 different transit peptides and cloned into a base plant transformation vector as described in Example 3. This permitted the side-by-side comparison of different transit peptides using the same promoter, herbicide-tolerance protein, and 3'UTR elements in every DNA construct. These plant transformation vectors were used to transform soybean excised embryos (germplasm AG3555) using A. tumefaciens and standard methods known in the art. Four hundred to 4,5000 individual transgenic plants were tested for each construct. A sterile PPO herbicide solution was used for herbicide-tolerance testing. The herbicide solution consisted of 0.3 g of S-3100 in crop oil concentrate (5.0 mL) and 495 mL of deionized water.

At five weeks post-transformation, plants were sprayed with two passes of the sterile PPO herbicide solution for a final application rate of 20 g/ha. For each DNA construct tested, 400 to 4,5000 replications were done. The treated plantlets then received at least 15 hours of light exposure post spray each day for four days. At the end of day four post-application of S-3100, the treated plantlets were scored for percentage of relative pass frequency (defined as the percentage of all the individual plants for a DNA construct that visually display tolerance to the herbicide application relative to control transgenic plants sprayed with a surfactant only solution). Plantlets in the non-sprayed containers were transplanted at approximately seven weeks post-transformation and grown as R0 plants. The R0 plants were grown in a greenhouse under long-day nursery conditions (18 hours of light at 80° F. then 6 hours of dark at 74° F.) for approximately four additional weeks. At eleven to twelve weeks post-transformation, the R0 plants were sprayed with two passes of the same herbicide solution described above at a 20 g/ha rate. For each DNA construct tested, 15-45 replications were done. Herbicide injury ratings were collected three to seven days after treatment. For the eleven-week evaluation, the percentage of plants at or below 10% injury and at or below 20% injury was recorded. At the herbicide application rates tested, transgenic plants expressing the protoporphyrinogen oxidase H_N90 without any operably linked transit peptide (PPO Control), produced a zero plants with 20% injury or less. Several of the transit peptides operably linked to the H_N90 herbicide tolerance protein stood out as providing excellent or very good tolerance to the herbicide application. For example, at the eleven-week spray over 50% of plants had an injury score at or below 20% when expressing H-N90 operably linked to ALLCE_3035 (57%), KOCSC_9516 (59%), CAMSA_6215 (69%), ROSHY_3269 (70%), ADADI_0544 (75%), CUCME_3420 (80%), SPIOL_1551 (85%), CUCME_4756 (89%), or CONCA_3910 (90%). Data are provided in Table 9.

TABLE 9

Tolerance score at 5 and 11 weeks in soybean

| Transit Peptide | 5 week spray relative pass frequency | 11 week spray % plants at ≤10% | 11 week spray % plants at ≤20% |
|---|---|---|---|
| CUCME_4756 | 27% | 0% | 0% |
| CANRO_3271 | 23% | 0% | 0% |
| DIGSA_5109 | 24% | 0% | 0% |
| CAMSA_6215 | 68% | 62% | 69% |
| AMACR_2381 | 30% | 0% | 0% |
| ROSHY_3269 | 54% | 25% | 70% |
| CUCME_3420 | 51% | 20% | 80% |
| ADADI_0544 | 30% | 20% | 75% |
| SPIOL_1551 | 40% | 70% | 85% |
| NICBE_5162 | 9% | 0% | 0% |
| CUCME_4756 | 28% | 26% | 89% |
| BRANA_9788 | 11% | 0% | 0% |
| SPIOL_0410 | 18% | 0% | 0% |
| XANST_0027 | 22% | 0% | 0% |
| SETIT_2080 | 3% | 0% | 0% |
| ERATE_4149 | 3% | 0% | 0% |
| TAROF_2111 | 3% | 0% | 0% |
| CONCA_4103 | 26% | 0% | 0% |
| CANRO_3976 | 6% | 0% | 0% |
| AMACR_2643 | 3% | 0% | 0% |
| SPIOL_0401 | 6% | 0% | 0% |
| ADADI_1600 | 30% | 0% | 0% |
| ANDGE_6461 | 47% | 0% | 0% |
| ERATE_2090 | 11% | 0% | 0% |
| 12G088600TP | 13% | 0% | 0% |
| ALLCE_3035 | 5% | 0% | 0% |
| SENOB_8832 | 52% | 0% | 0% |
| TAROF_2111 | 66% | 0% | 0% |
| ROSHY_8873 | 10% | 0% | 0% |
| KOCSC_1672 | 25% | 12% | 24% |
| AMBTR_1537 | 2% | 0% | 0% |
| AMAPA_1826 | 7% | 0% | 0% |
| BRANA_6036 | 5% | 0% | 0% |
| CONCA_3910 | 40% | 60% | 90% |
| AMAPA_4787 | 6% | 0% | 0% |
| ROSHY_6783 | 0% | 0% | 0% |

TABLE 9-continued

Tolerance score at 5 and 11 weeks in soybean

| Transit Peptide | 5 week spray relative pass frequency | 11 week spray % plants at ≤10% | 11 week spray % plants at ≤20% |
|---|---|---|---|
| ALLCE_3035 | 26% | 35% | 57% |
| ERATE_4824 | 12% | 0% | 0% |
| AMAGR_5230 | 2% | 0% | 0% |
| SEDAL_8241 | 5% | 0% | 0% |
| DIGSA_5107 | 11% | 0% | 0% |
| KOCSC_9516 | 27% | 16% | 59% |
| XANST_0027_var | 3% | 0% | 0% |
| APG6 | 60% | 30% | 63% |
| None - PPO Control | 1% | 0% | 0% |

Example 5: Transit Peptide and Protoporphyrinogen Oxidase Testing in Corn

Transit peptides operably linked to protoporphyrinogen oxidases were tested in transgenic corn plants for PPO herbicide-tolerance. Plant transformation vectors were constructed comprising a DNA construct comprising a recombinant DNA molecule optimized for monocot expression and encoding a protoporphyrinogen oxidase operably linked to a transit peptide. The plant transformation vectors were then used to transform corn, and the regenerated plants were assessed for their sensitivity to a PPO herbicide.

The genes encoding the protoporphyrinogen oxidase H_N90 was operably linked to fourteen different transit peptides and cloned into base plant transformation vectors with a variety of promoters and 3' UTR elements. The use of the same protoporphyrinogen oxidase in each DNA construct permitted the side-by-side comparison of different transit peptides. A plant transformation vector was also produced with the protoporphyrinogen oxidase H_N90 without any operably linked transit peptide (PPO Control). These plant transformation vectors were used to transform corn using A. tumefaciens and standard methods known in the art. Regenerated R0 plants were grown and then screened to access the degree of tolerance exhibited to applications of S-3100 (40 to 80 g/ha rate) at approximately 10-14 weeks post-transformation. Tolerance was visually accessed 3 to 10 days following application of the herbicide. Sprayed plants are scored on the percent of injury to the entire above-ground part of the plant following herbicide treatment, relative to controls. For each DNA construct tested, 10 to 120 plants were tested and the injury rate was averaged. The percentage of R0 plants passing at a 20% injury or less score was recorded. Any DNA construct producing transgenic plants with 50% or more having 20% or less injury was considered a highly tolerant DNA construct. Any DNA construct producing transgenic plants with 20% or more having 20% or less injury was considered a tolerant DNA construct. At the herbicide application rates tested (S-3100 at 40 to 80 g/ha), transgenic plants expressing the protoporphyrinogen oxidase H_N90 without any operably linked transit peptide (PPO Control), with XANST_27 or with ALLCE_3035 produced zero plants with 20% injury or less. However, several of the transit peptides produced transgenic plants expressing the protoporphyrinogen oxidase H_N90 that were highly tolerant or tolerant: ADADI_0544 (41%), ANDGE_6461 (60%), CAMSA_6215 (60% and 41% pass), CONCA_3910 (36% and 45%), ROSHY_3269 (64% and 74%), SPIOL_1551 (50% and 55%), SETIT_9796 (55%). Data are provided in Table 10.

TABLE 10

Tolerance score in corn

| Promoter | Transit Peptide | 3'UTR | Percent with 20% or less injury |
|---|---|---|---|
| A | SETIT_9796 | E | 55% |
| A | ACAOS_3432 | E | 37% |
| A | ADADI_0544 | E | 41% |
| A | TAROF_9570 | E | 29% |
| A | ALLCE_6618 | E | 31% |
| D | ROSHY_3269 | H | 74% |
| B | ROSHY_3269 | F | 64% |
| D | CONCA_3910 | H | 36% |
| B | CONCA_3910 | F | 45% |
| D | SPIOL_1551 | H | 55% |
| B | SPIOL_1551 | F | 50% |
| D | CAMSA_6215 | H | 41% |
| B | CAMSA_6215 | F | 60% |
| B | ANDGE_6461 | F | 60% |
| B | ADADI_1600 | F | 11% |
| D | XANST_27_var | H | 0% |
| C | XANST_27_var | G | 0% |
| A | ALLCE_3035 | E | 0% |
| B | ALLCE_3035 | F | 0% |
| C | None - PPO Control | G | 0% |

Example 6: Transit Peptide and Protoporphyrinogen Oxidase Testing in Cotton

Transit peptides operably linked to protoporphyrinogen oxidases were tested in transgenic cotton plants for PPO herbicide-tolerance. Plant transformation vectors were constructed comprising a DNA construct comprising a recombinant DNA molecule optimized for dicot expression and encoding a protoporphyrinogen oxidase operably linked to a transit peptide. The plant transformation vectors were then used to transform cotton, and the regenerated plants were assessed for their sensitivity to a PPO herbicide.

The genes encoding the protoporphyrinogen oxidases H_N20 and H_N90 were operably linked to four different transit peptides and cloned into a base plant transformation vector as described in Example 3. This permitted the side-by-side comparison of different transit peptides using the same promoter and 3'UTR elements in every DNA construct. These plant transformation vectors were used to transform cotton using A. tumefaciens and standard methods known in the art. Regenerated plants were grown and then screened to access the degree of tolerance exhibited to applications of S-3100 (20 g/ha rate) at approximately 11 to 12 weeks post-transformation. Tolerance was visually accessed 3 to 10 days following application of the herbicide. Sprayed plants are scored on the percent of injury to the entire above-ground part of the plant following herbicide treatment, relative to controls. For each DNA construct tested, 10-15 replications were tested and the average injury rate was averaged. An average injury score of 50% or less was considered a highly herbicide-tolerant DNA construct, and an average injury score greater than 50% but less than 80% was considered a marginally herbicide-tolerant DNA construct. An average injury score at or above 80% was considered indistinguishable from control plants. Transgenic cotton plants expressing the protoporphyrinogen oxidase H_N90 operably linked to CAMSA_6215 produced plants that were highly herbicide-tolerant with an average injury score of 38%. Transgenic cotton plants expressing the protoporphyrinogen oxidase H_N90 operably linked to AMAPA_4787 produced plants that were marginally herbicide-tolerant with an average injury score of 63%.

What is claimed is:

1. A recombinant DNA molecule comprising a DNA sequence encoding a transit peptide operably linked to a DNA sequence encoding a heterologous protoporphyrinogen oxidase, wherein the transit peptide comprises an amino acid sequence comprising at least 97 percent identity to the sequence of SEQ ID NO:21, and wherein the heterologous protoporphyrinogen oxidase comprises an amino acid sequence selected from the group consisting of SEQ ID NOs:100-119, SEQ ID NOs:163-182, and SEQ ID NOs: 224-228.

2. The recombinant DNA molecule of claim 1, wherein the DNA sequence encoding the transit peptide comprises a nucleic acid sequence comprising at least 97 percent identity to the sequence of SEQ ID NO:71 or SEQ ID NO:91.

3. The recombinant DNA molecule of claim 1, wherein the DNA sequence encoding the heterologous protoporphyrinogen oxidase comprises a nucleic acid sequence selected from the group consisting of SEQ ID NOs:121-162 and SEQ ID NOs:183-223, SEQ ID NOs:229-235.

4. The recombinant DNA molecule of claim 1, further comprising a heterologous promoter operably linked to the DNA sequence encoding the transit peptide.

5. A DNA construct comprising the DNA molecule of claim 1, wherein said DNA molecule is operably linked to a heterologous promoter.

6. The DNA construct of claim 5, wherein the DNA construct is present in the genome of a transgenic plant, seed, or cell.

7. A transgenic plant, seed, or cell comprising the recombinant DNA molecule of claim 1.

8. The transgenic plant, seed, or cell of claim 7, wherein the plant, seed, or cell is tolerant to at least one PPO herbicide.

9. The transgenic plant, seed, or cell of claim 8, wherein the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

10. The transgenic plant, seed, or cell of claim 7, wherein the transgenic plant, seed, or cell is tolerant to at least one additional herbicide.

11. A method for producing an herbicide-tolerant plant comprising the steps of:
    a) transforming a plant cell with the recombinant DNA molecule of claim 1; and
    b) regenerating therefrom an herbicide-tolerant plant that comprises the DNA molecule.

12. The method of claim 11, further comprising the step of crossing the regenerated plant with itself or with a second plant to produce one or more progeny plants.

13. The method of claim 12, further comprising the step of selecting a progeny plant that is tolerant to at least one PPO herbicide.

14. The method of claim 13, wherein the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

15. A method for controlling or preventing weed growth in a plant growth area comprising applying an effective amount of at least one PPO herbicide to a plant growth area that comprises the transgenic plant or seed of claim 8, wherein the transgenic plant or seed is tolerant to the PPO herbicide.

16. The method of claim 15, wherein the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

17. A method for controlling the growth of herbicide tolerant weeds comprising:
    a) cultivating in a plant growth area the plant or seed of claim 10; and
    b) applying a PPO herbicide and at least one other herbicide to the plant growth area, wherein the plant or seed is tolerant to the PPO herbicide and the at least one other herbicide.

18. The method of claim 17, wherein the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

19. The method of claim 17, wherein the at least one additional herbicide is selected from the group consisting of: an ACCase inhibitor, an ALS inhibitor, an EPSPS inhibitor, a synthetic auxin, a photosynthesis inhibitor, a glutamine synthetase inhibitor, a HPPD inhibitor, PPO inhibitor, and a long-chain fatty acid inhibitor.

20. The method of claim 19, wherein the ACCase inhibitor is an aryloxyphenoxy propionate or a cyclohexanedione; the ALS inhibitor is a sulfonylurea, imidazolinone, triazolopyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthetase inhibitor is glufosinate; the HPPD inhibitor is an isoxazole, a pyrazolone, or a triketone; or the very long-chain fatty acid inhibitor is a chloroacetamide, an oxyacetamide, or a pyrazole.

* * * * *

SEQUENCE LISTING

```
<160> NUMBER OF SEQ ID NOS: 297

<210> SEQ ID NO 1
<211> LENGTH: 68
<212> TYPE: PRT
<213> ORGANISM: Arabidopsis thalinana

<400> SEQUENCE: 1

Met Ala Thr Ala Thr Thr Thr Ala Thr Ala Ala Phe Ser Gly Val Val
1               5                   10                  15

Ser Val Gly Thr Glu Thr Arg Arg Ile Tyr Ser Phe Ser His Leu Gln
                20                  25                  30

Pro Ser Ala Ala Phe Pro Ala Lys Pro Ser Ser Phe Lys Ser Leu Lys
            35                  40                  45

Leu Lys Gln Ser Ala Arg Leu Thr Arg Arg Leu Asp His Arg Pro Phe
        50                  55                  60

Val Val Arg Cys
65

<210> SEQ ID NO 2
<211> LENGTH: 68
<212> TYPE: PRT
<213> ORGANISM: Artificial Sequence
<220> FEATURE:
<223> OTHER INFORMATION: Recombinant
```

```
<400> SEQUENCE: 2

Met Ala Ser Ser Thr Thr Thr Ala Thr Ala Ala Phe Ser Gly Val Val
1               5                   10                  15

Ser Val Gly Thr Glu Thr Arg Arg Ile Tyr Ser Phe Ser His Leu Gln
            20                  25                  30

Pro Ser Ala Ala Phe Pro Ala Lys Pro Ser Ser Phe Lys Ser Leu Lys
            35                  40                  45

Leu Lys Gln Ser Ala Arg Leu Thr Arg Arg Leu Asp His Arg Pro Phe
50                  55                  60

Val Val Arg Cys
65

<210> SEQ ID NO 3
<211> LENGTH: 35
<212> TYPE: PRT
<213> ORGANISM: Gossypium raimondii

<400> SEQUENCE: 3

Met Leu Asn Ile Ala Pro Ser Cys Val Leu Ala Ser Gly Ile Ser Lys
1               5                   10                  15

Pro Val Thr Lys Met Ala Ser Thr Glu Asn Lys Asp Asp His Ser Ser
            20                  25                  30

Ala Lys Arg
        35

<210> SEQ ID NO 4
<211> LENGTH: 45
<212> TYPE: PRT
<213> ORGANISM: Canavalia rosea

<400> SEQUENCE: 4

Met Val Ala Val Phe Asn Asp Val Val Phe Pro Pro Ser Gln Thr Leu
1               5                   10                  15

Leu Arg Pro Ser Phe His Ser Pro Thr Phe Phe Phe Ser Ser Pro Thr
            20                  25                  30

Pro Lys Phe Thr Arg Thr Arg Pro Asn Arg Ile Leu Arg
            35                  40                  45

<210> SEQ ID NO 5
<211> LENGTH: 60
<212> TYPE: PRT
<213> ORGANISM: Senna obtusifolia

<400> SEQUENCE: 5

Met Pro Ala Ile Ala Met Ala Ser Leu Thr Asp Leu Pro Ser Leu Ser
1               5                   10                  15

Pro Thr Gln Thr Leu Val His Ser Asn Thr Ser Phe Ile Ser Ser Arg
            20                  25                  30

Thr Cys Phe Val Cys Pro Ile Ile Pro Phe Pro Ser Arg Ser Gln Leu
            35                  40                  45

Asn Arg Arg Ile Ala Cys Ile Arg Ser Asn Val Arg
50                  55                  60

<210> SEQ ID NO 6
<211> LENGTH: 55
<212> TYPE: PRT
<213> ORGANISM: Nicotiana benthamiana

<400> SEQUENCE: 6
```

-continued

Met Thr Thr Thr Pro Val Ala Asn His Pro Asn Ile Phe Thr His Arg
1               5                   10                  15

Ser Pro Pro Ser Ser Ser Ser Pro Ser Ala Phe Leu Thr Arg
            20                  25                  30

Thr Ser Phe Leu Pro Phe Ser Ser Ile Cys Lys Arg Asn Ser Val Asn
            35                  40                  45

Cys Asn Gly Trp Arg Thr Arg
            50              55

<210> SEQ ID NO 7
<211> LENGTH: 34
<212> TYPE: PRT
<213> ORGANISM: Brassica napus

<400> SEQUENCE: 7

Met Asp Phe Ser Leu Leu Arg Pro Ala Ser Thr Gln Pro Phe Leu Ser
1               5                   10                  15

Pro Phe Ser Asn Pro Phe Pro Arg Ser Arg Pro Tyr Lys Pro Leu Asn
            20                  25                  30

Leu Arg

<210> SEQ ID NO 8
<211> LENGTH: 37
<212> TYPE: PRT
<213> ORGANISM: Adansonia digitata

<400> SEQUENCE: 8

Met Ala Ile Leu Ile Asp Leu Ser Leu Leu Arg Ser Pro Ser Val
1               5                   10                  15

Phe Ser Phe Ser Lys Pro Asn His Arg Ile Pro Pro Arg Ile Tyr Lys
            20                  25                  30

Pro Phe Lys Leu Arg
            35

<210> SEQ ID NO 9
<211> LENGTH: 47
<212> TYPE: PRT
<213> ORGANISM: Rosa hybrida osiana

<400> SEQUENCE: 9

Met Thr Thr Leu Ser Arg Leu Ala Asp Leu Pro Ser Phe Ala Ala Pro
1               5                   10                  15

Pro Pro Leu Leu Thr His Arg Pro Pro Ser Val Phe Leu Thr Pro
            20                  25                  30

Lys Pro Thr Lys Pro Ser Pro Pro His His Phe Phe Lys Leu Arg
            35                  40                  45

<210> SEQ ID NO 10
<211> LENGTH: 46
<212> TYPE: PRT
<213> ORGANISM: Xanthium strumarium

<400> SEQUENCE: 10

Met Ser Ser Leu Thr Asp Leu Pro Ser Leu Asn His Tyr Arg Thr Cys
1               5                   10                  15

Ser Pro Arg Pro Phe Pro Ile Ser Arg Gln Thr Ser Ser Ser Ile Asn
            20                  25                  30

Pro Asn Asn Leu Thr Thr Ser Asn Arg Trp Arg Arg Phe Arg
            35                  40                  45

<210> SEQ ID NO 11
<211> LENGTH: 35
<212> TYPE: PRT
<213> ORGANISM: Conyza canadensis

<400> SEQUENCE: 11

Met Thr Ser Leu Thr Asn Phe Thr Pro Leu Lys Leu Thr Asn Pro Asn
1               5                   10                  15

Tyr Leu Asn Thr Thr Thr Thr Tyr Asn His Arg Lys Leu Ser Asn Phe
            20                  25                  30

Arg Phe Arg
        35

<210> SEQ ID NO 12
<211> LENGTH: 45
<212> TYPE: PRT
<213> ORGANISM: Amaranthus palmeri

<400> SEQUENCE: 12

Met Ser Ala Met Ala Leu Ser Ser Ser Ile Leu Gln Cys Pro Pro His
1               5                   10                  15

Ser Asp Ile Ser Phe Arg Phe Ser Ala Tyr Thr Ala Thr Arg Ser Pro
            20                  25                  30

Phe Phe Phe Gly Arg Pro Arg Lys Leu Ser Tyr Ile His
        35                  40                  45

<210> SEQ ID NO 13
<211> LENGTH: 47
<212> TYPE: PRT
<213> ORGANISM: Spinacia oleracea

<400> SEQUENCE: 13

Met Ser Ala Met Ala Leu Ser Ser Thr Met Ala Leu Ser Leu Pro Gln
1               5                   10                  15

Ser Ser Met Ser Leu Ser His Cys Arg His Asn Arg Ile Thr Ile Leu
            20                  25                  30

Ile Pro Ser Ser Leu Arg Arg Arg Gly Gly Ser Ser Ile Arg
        35                  40                  45

<210> SEQ ID NO 14
<211> LENGTH: 61
<212> TYPE: PRT
<213> ORGANISM: Kochia Scoparia

<400> SEQUENCE: 14

Met Ser Ala Met Ala Ser Pro Ser Ile Ile Pro Gln Ser Phe Leu Gln
1               5                   10                  15

Arg Ser Pro Thr Ser Leu Gln Ser Arg Ser Asn Tyr Ser Lys Asn His
            20                  25                  30

Ile Ile Ile Ser Ile Ser Thr Pro Cys Ser His Gly Lys Asn Gln Arg
        35                  40                  45

Arg Phe Leu Arg Lys Thr Thr His Phe Arg Ser Ile His
    50                  55                  60

<210> SEQ ID NO 15
<211> LENGTH: 34
<212> TYPE: PRT
<213> ORGANISM: Setaria italica

<400> SEQUENCE: 15

```
Met Val Ala Ala Ala Met Ala Thr Ala Pro Ser Ala Gly Val Pro Pro
1               5                   10                  15

Leu Arg Gly Thr Arg Gly Pro Ala Arg Phe Arg Ile Arg Gly Val Ser
            20                  25                  30

Val Arg

<210> SEQ ID NO 16
<211> LENGTH: 27
<212> TYPE: PRT
<213> ORGANISM: Allium cepa

<400> SEQUENCE: 16

Met Ala Thr Thr Thr Ala Ala Ala Val Thr Ile Ser Ile Pro Lys
1               5                   10                  15

Lys Pro Val Phe Ile Arg Arg Pro Arg Leu Arg
            20                  25

<210> SEQ ID NO 17
<211> LENGTH: 33
<212> TYPE: PRT
<213> ORGANISM: Digitaria sanguinalis

<400> SEQUENCE: 17

Met Leu Ser Ser Thr Ala Thr Ala Ser Ser Ala Ser Ser His His Pro
1               5                   10                  15

Tyr Arg Ser Ala Ser Ala Arg Ala Ser Ser Thr Arg Leu Arg Pro Val
            20                  25                  30

Leu

<210> SEQ ID NO 18
<211> LENGTH: 49
<212> TYPE: PRT
<213> ORGANISM: Amaranthus palmeri

<400> SEQUENCE: 18

Met Val Ile Gln Ser Ile Thr His Leu Ser Pro Lys Leu Ala Leu Pro
1               5                   10                  15

Ser Pro Leu Ser Ile Ser Ala Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val

<210> SEQ ID NO 19
<211> LENGTH: 48
<212> TYPE: PRT
<213> ORGANISM: Spinacia oleracea

<400> SEQUENCE: 19

Met Val Ile Leu Pro Val Ser Gln Leu Ser Thr Asn Leu Gly Leu Ser
1               5                   10                  15

Leu Val Ser Pro Thr Lys Asn Asn Pro Val Met Gly Asn Val Ser Glu
            20                  25                  30

Arg Asn Gln Val Asn Gln Pro Ile Ser Ala Lys Arg Val Ala Val Val
        35                  40                  45

<210> SEQ ID NO 20
<211> LENGTH: 51
<212> TYPE: PRT
<213> ORGANISM: Sedum album
```

```
<400> SEQUENCE: 20

Met Leu Ser Leu Ser Ser His Ser Ser Ala Thr Thr Tyr Ser Leu
1               5                   10                  15

Arg Gln Arg Tyr Ser Thr Thr Thr Lys Gly Ser Leu Asn Gln Pro Glu
                20                  25                  30

Met Ala Ser Ala Glu Asn Pro Ser Ser Lys Gly Ser Gly Lys Arg Gly
            35                  40                  45

Ala Val Val
        50

<210> SEQ ID NO 21
<211> LENGTH: 38
<212> TYPE: PRT
<213> ORGANISM: Camelina sativa

<400> SEQUENCE: 21

Met Glu Leu Ser Leu Leu Arg Pro Ser Thr Gln Ser Leu Leu Pro Ser
1               5                   10                  15

Phe Ser Lys Pro Asn Leu Arg Leu His Val Tyr Lys Pro Leu Lys Leu
                20                  25                  30

Arg Cys Ser Val Ala Gly
            35

<210> SEQ ID NO 22
<211> LENGTH: 43
<212> TYPE: PRT
<213> ORGANISM: Cucumis melo

<400> SEQUENCE: 22

Met Ala Thr Gly Ala Thr Leu Leu Thr Asp Leu Pro Phe Arg Arg Pro
1               5                   10                  15

His Pro Leu Thr Leu Leu Arg Pro Ser Asp Ile Pro Ser Phe Tyr Pro
                20                  25                  30

Leu His Ile Ser Leu Gln Asn Asn Arg Leu Arg
            35                  40

<210> SEQ ID NO 23
<211> LENGTH: 30
<212> TYPE: PRT
<213> ORGANISM: Eragrostis tef

<400> SEQUENCE: 23

Met Val Ala Ala Ala Thr Met Ala Thr Ala Pro Pro Leu Arg
1               5                   10                  15

Ala Pro Gln Thr Leu Ala Arg Pro Arg Arg Gly Ser Val Arg
                20                  25                  30

<210> SEQ ID NO 24
<211> LENGTH: 32
<212> TYPE: PRT
<213> ORGANISM: Canavalia rosea

<400> SEQUENCE: 24

Met Tyr Val Ser Pro Ala Ser Asn Asn Pro Arg Ala Cys Leu Lys Leu
1               5                   10                  15

Ser Gln Glu Met Ala Ser Ser Ala Ala Asp Gly Asn Pro Arg Ser Val
                20                  25                  30

<210> SEQ ID NO 25
```

```
<211> LENGTH: 42
<212> TYPE: PRT
<213> ORGANISM: Eragrostis tef

<400> SEQUENCE: 25

Met Leu Ser Ser Ala Ala Thr Ala Ser Ser Ala Ser Ala His Pro Tyr
1               5                   10                  15

Arg Pro Ala Ser Ala Arg Ala Ser Arg Ser Val Leu Ala Met Ala Gly
            20                  25                  30

Ser Asp Asp Thr Arg Ala Ala Pro Ala Arg
        35                  40

<210> SEQ ID NO 26
<211> LENGTH: 41
<212> TYPE: PRT
<213> ORGANISM: Andropogon gerardii

<400> SEQUENCE: 26

Met Val Ala Ala Thr Ala Met Ala Thr Ala Ser Ala Ala Ala Ala Pro
1               5                   10                  15

Leu Leu Asn Gly Thr Arg Arg Pro Ala Arg Leu Arg His Arg Gly Leu
            20                  25                  30

Arg Val Arg Cys Ala Ala Val Ala Gly
        35                  40

<210> SEQ ID NO 27
<211> LENGTH: 24
<212> TYPE: PRT
<213> ORGANISM: Digitaria sanguinalis

<400> SEQUENCE: 27

Met Leu Ser Ser Thr Ala Thr Ala Ser Ser Ala Ser Ser His His Pro
1               5                   10                  15

Tyr Arg Ser Ala Ser Ala Arg Ala
            20

<210> SEQ ID NO 28
<211> LENGTH: 23
<212> TYPE: PRT
<213> ORGANISM: Eragrostis tef

<400> SEQUENCE: 28

Met Leu Ser Ser Ala Ala Thr Ala Ser Ser Ala Ser Ala His Pro Tyr
1               5                   10                  15

Arg Pro Ala Ser Ala Arg Ala
            20

<210> SEQ ID NO 29
<211> LENGTH: 28
<212> TYPE: PRT
<213> ORGANISM: Amaranthus graecizans

<400> SEQUENCE: 29

Met Ser Ala Met Ala Leu Ser Ser Ser Ile Leu Gln Cys Pro Pro His
1               5                   10                  15

Ser Asp Ile Ser Phe Arg Phe Phe Ala His Thr Arg
            20                  25

<210> SEQ ID NO 30
<211> LENGTH: 13
<212> TYPE: PRT
<213> ORGANISM: Ambrosia trifida
```

-continued

<400> SEQUENCE: 30

Met Ala Ser Pro Thr Ile Val Asp Asn Gln Lys Pro Ala
1               5                   10

<210> SEQ ID NO 31
<211> LENGTH: 14
<212> TYPE: PRT
<213> ORGANISM: Brassica napus

<400> SEQUENCE: 31

Met Ala Ser Asn Ala Ala Ala Asp His Asp Lys Leu Ser Gly
1               5                   10

<210> SEQ ID NO 32
<211> LENGTH: 13
<212> TYPE: PRT
<213> ORGANISM: Rosa hybrida osiana

<400> SEQUENCE: 32

Met Ala Ser Pro Ser Pro Gly Asp Lys His Ser Ser Val
1               5                   10

<210> SEQ ID NO 33
<211> LENGTH: 55
<212> TYPE: PRT
<213> ORGANISM: Amaranthus cruentus

<400> SEQUENCE: 33

Met Lys Gly Arg Lys Arg Arg Ile Thr Arg Glu Ser Ala Arg Glu Met
1               5                   10                  15

Ser Ala Met Ala Leu Ser Ser Ser Ile Leu Gln Cys Pro Pro His Ser
            20                  25                  30

Asp Ile Ser Phe Arg Phe Ser Ala His Ser Pro Thr His Ser Pro Ile
        35                  40                  45

Phe Phe Gly Arg Pro Arg Lys
    50                  55

<210> SEQ ID NO 34
<211> LENGTH: 45
<212> TYPE: PRT
<213> ORGANISM: Taraxacum officinale

<400> SEQUENCE: 34

Met Thr Tyr Leu Thr Asp Val Gly Ser Leu Asn Cys Tyr Arg Ser Trp
1               5                   10                  15

Pro Ser Leu Pro Ala Pro Gly Thr Val Gly Ala Leu Thr Ser Lys Asn
            20                  25                  30

Pro Arg Tyr Leu Ile Thr Tyr Gly Pro Ala His Arg Lys
        35                  40                  45

<210> SEQ ID NO 35
<211> LENGTH: 67
<212> TYPE: PRT
<213> ORGANISM: Canavalia rosea

<400> SEQUENCE: 35

Met Val Ala Val Phe Asn Asp Val Val Phe Pro Pro Ser Gln Thr Leu
1               5                   10                  15

Leu Arg Pro Ser Phe His Ser Pro Thr Phe Phe Ser Ser Pro Thr
            20                  25                  30

-continued

Pro Lys Phe Thr Arg Thr Arg Pro Asn Arg Ile Leu Arg Cys Ser Ile
                35                  40                  45

Ala Gln Glu Ser Thr Thr Ser Pro Ser Gln Ser Arg Glu Ser Ala Pro
 50                  55                  60

Leu Asp Cys
 65

<210> SEQ ID NO 36
<211> LENGTH: 52
<212> TYPE: PRT
<213> ORGANISM: Eragrostis tef

<400> SEQUENCE: 36

Met Val Ala Ala Ala Thr Met Ala Thr Ala Ala Pro Pro Leu Arg
 1               5                  10                  15

Ala Pro Gln Thr Leu Ala Arg Pro Arg Arg Gly Ser Val Arg Cys Ala
                20                  25                  30

Val Val Ser Asp Ala Ala Glu Ala Pro Ala Ala Pro Gly Ala Arg Leu
            35                  40                  45

Ser Ala Asp Cys
     50

<210> SEQ ID NO 37
<211> LENGTH: 51
<212> TYPE: PRT
<213> ORGANISM: Allium cepa

<400> SEQUENCE: 37

Met Ala Thr Thr Thr Ala Ala Ala Val Thr Ile Ser Ile Pro Lys
 1               5                  10                  15

Lys Pro Val Phe Ile Arg Arg Pro Arg Leu Arg Cys Ser Ala Val Ala
                20                  25                  30

Ser Asp Ala Ile Ile Ser Asn Glu Ala Pro Thr Gly Thr Thr Ile Ser
            35                  40                  45

Ala Asp Cys
     50

<210> SEQ ID NO 38
<211> LENGTH: 77
<212> TYPE: PRT
<213> ORGANISM: Taraxacum officinale

<400> SEQUENCE: 38

Met Thr Tyr Leu Thr Asp Val Gly Ser Leu Asn Cys Tyr Arg Ser Trp
 1               5                  10                  15

Pro Ser Leu Pro Ala Pro Gly Thr Val Gly Ala Leu Thr Ser Lys Asn
                20                  25                  30

Pro Arg Tyr Leu Ile Thr Tyr Gly Pro Ala His Arg Lys Cys Asn Ser
            35                  40                  45

Trp Arg Phe Arg Cys Ser Ile Ala Lys Asp Ser Pro Ile Thr Pro Pro
 50                  55                  60

Ile Ser Asn Glu Ser Asn Ser Gln Pro Leu Leu Asp Cys
 65                  70                  75

<210> SEQ ID NO 39
<211> LENGTH: 71
<212> TYPE: PRT
<213> ORGANISM: Cucumis melo

<400> SEQUENCE: 39

```
Met Ala Thr Gly Ala Thr Leu Leu Thr Asp Leu Pro Phe Arg Arg Pro
1               5                   10                  15

His Pro Leu Thr Leu Leu Arg Pro Ser Asp Ile Pro Ser Phe Tyr Pro
            20                  25                  30

Leu His Ile Ser Leu Gln Asn Asn Arg Leu Arg Ser His Phe Arg Cys
        35                  40                  45

Ser Ile Ala Glu Gly Ser Thr Ala Leu Ser Pro Ser Asn Ala Ser Ser
    50                  55                  60

Gln Ser Ser Ile Leu Asp Cys
65              70
```

<210> SEQ ID NO 40
<211> LENGTH: 71
<212> TYPE: PRT
<213> ORGANISM: Xanthium strumarium

<400> SEQUENCE: 40

```
Met Ser Ser Leu Thr Asp Leu Pro Ser Leu Asn His Tyr Arg Thr Cys
1               5                   10                  15

Ser Pro Arg Pro Phe Pro Ile Ser Arg Gln Thr Ser Ser Ser Ile Asn
            20                  25                  30

Pro Asn Asn Leu Thr Thr Ser Asn Arg Trp Arg Arg Phe Arg Cys Ser
        35                  40                  45

Ile Ala Asn Asp Thr Pro Ile Ser Pro Pro Ile Ser Ser Asp Ser Thr
    50                  55                  60

Ser His Pro Phe Leu Asp Cys
65              70
```

<210> SEQ ID NO 41
<211> LENGTH: 38
<212> TYPE: PRT
<213> ORGANISM: Camelina sativa

<400> SEQUENCE: 41

```
Met Glu Leu Ser Leu Leu Arg Pro Ser Thr Gln Ser Leu Leu Pro Ser
1               5                   10                  15

Phe Ser Lys Pro Asn Leu Arg Leu His Val Tyr Lys Pro Leu Lys Leu
            20                  25                  30

Arg Cys Ser Val Ala Gly
            35
```

<210> SEQ ID NO 42
<211> LENGTH: 45
<212> TYPE: PRT
<213> ORGANISM: Taraxacum officinale

<400> SEQUENCE: 42

```
Met Thr Tyr Leu Thr Asp Val Gly Ser Leu Asn Cys Tyr Arg Ser Trp
1               5                   10                  15

Pro Ser Leu Pro Ala Pro Gly Thr Val Gly Ala Leu Thr Ser Lys Asn
            20                  25                  30

Pro Arg Tyr Leu Ile Thr Tyr Gly Pro Ala His Arg Lys
        35                  40                  45
```

<210> SEQ ID NO 43
<211> LENGTH: 65
<212> TYPE: PRT
<213> ORGANISM: Taraxacum officinale

<400> SEQUENCE: 43

Met Thr Tyr Leu Thr Asp Val Gly Ser Leu Asn Cys Tyr Arg Ser Trp
1               5                   10                  15

Pro Ser Leu Pro Ala Pro Gly Thr Val Gly Ala Leu Thr Ser Lys Asn
            20                  25                  30

Pro Arg Tyr Leu Ile Thr Tyr Gly Pro Ala His Arg Lys Asp Ser Pro
        35                  40                  45

Ile Thr Pro Pro Ile Ser Asn Glu Ser Asn Ser Gln Pro Leu Leu Asp
50                  55                  60

Cys
65

<210> SEQ ID NO 44
<211> LENGTH: 60
<212> TYPE: PRT
<213> ORGANISM: Senna obtusifolia

<400> SEQUENCE: 44

Met Pro Ala Ile Ala Ile Ala Ser Leu Thr Asp Leu Pro Ser Leu Ser
1               5                   10                  15

Pro Thr Gln Thr Leu Val His Ser Asn Thr Ser Phe Ile Ser Ser Arg
            20                  25                  30

Thr Cys Phe Val Cys Pro Ile Ile Pro Phe Pro Ser Arg Ser Gln Leu
        35                  40                  45

Asn Arg Arg Ile Ala Cys Ile Arg Ser Asn Val Arg
50                  55                  60

<210> SEQ ID NO 45
<211> LENGTH: 19
<212> TYPE: PRT
<213> ORGANISM: Eragrostis tef

<400> SEQUENCE: 45

Met Val Ala Ala Ala Glu Ala Pro Ala Ala Pro Gly Ala Arg Leu Ser
1               5                   10                  15

Ala Asp Cys

<210> SEQ ID NO 46
<211> LENGTH: 25
<212> TYPE: PRT
<213> ORGANISM: Allium cepa

<400> SEQUENCE: 46

Met Ala Thr Thr Thr Ala Ser Asp Ala Ile Ile Ser Asn Glu Ala Pro
1               5                   10                  15

Thr Gly Thr Thr Ile Ser Ala Asp Cys
            20                  25

<210> SEQ ID NO 47
<211> LENGTH: 12
<212> TYPE: PRT
<213> ORGANISM: Allium cepa

<400> SEQUENCE: 47

Met Ala Thr Thr Gly Thr Ile Ser Ala Asp Cys
1               5                   10

<210> SEQ ID NO 48
<211> LENGTH: 19
<212> TYPE: PRT

<213> ORGANISM: Cucumis melo

<400> SEQUENCE: 48

Met Ala Thr Ala Leu Ser Pro Ser Asn Ala Ser Ser Gln Ser Ser Ile
1               5                   10                  15

Leu Asp Cys

<210> SEQ ID NO 49
<211> LENGTH: 32
<212> TYPE: PRT
<213> ORGANISM: Xanthium strumarium

<400> SEQUENCE: 49

Met Ser Ser Leu Thr Asp Leu Pro Ser Leu Asn His Tyr Arg Thr Cys
1               5                   10                  15

Ser Pro Pro Ile Ser Ser Asp Ser Thr Ser His Pro Phe Leu Asp Cys
            20                  25                  30

<210> SEQ ID NO 50
<211> LENGTH: 204
<212> TYPE: DNA
<213> ORGANISM: Artificial Sequence
<220> FEATURE:
<223> OTHER INFORMATION: Recombinant

<400> SEQUENCE: 50
atggccaccg ccaccactac cgccaccgct gcgttctccg gcgtggtgag cgtcggcact      60
gagacgcgca ggatctactc cttcagccac ctccagcctt ctgctgcgtt ccccgctaag     120
ccgtcttcgt tcaagagcct gaagctgaaa cagtccgcac gccttacccg cgcgcctggac   180 cataggccat cgttgtcag gtgc                                             204

<210> SEQ ID NO 51
<211> LENGTH: 204
<212> TYPE: DNA
<213> ORGANISM: Artificial Sequence
<220> FEATURE:
<223> OTHER INFORMATION: Recombinant

<400> SEQUENCE: 51
atggcgacgg ctacgacgac tgctacggcg gcgtttagtg gtgtagtcag tgtaggaacg      60
gagactcgaa ggatttattc gttttctcat cttcaacctt ctgcggcttt ccggcgaag     120 cctagttcct tcaaatctct caaattaaag cagagcgcga ggctcacacg gcggcttgat   180
catcggccgt tcgttgtccg atgt                                             204

<210> SEQ ID NO 52
<211> LENGTH: 204
<212> TYPE: DNA
<213> ORGANISM: Artificial Sequence
<220> FEATURE:
<223> OTHER INFORMATION: Recombinant

<400> SEQUENCE: 52
atggcttcct ccacgacgac tgctacggcg gcgtttagtg gtgtagtcag tgtaggaacg      60
gagactcgaa ggatttattc gttttctcat cttcaacctt ctgcggcttt ccggcgaag     120 cctagttcct tcaaatctct caaattaaag cagagcgcga ggctcacacg gcggcttgat   180
catcggccgt tcgttgtccg atgt                                             204

<210> SEQ ID NO 53

```
<211> LENGTH: 105
<212> TYPE: DNA
<213> ORGANISM: Artificial Sequence
<220> FEATURE:
<223> OTHER INFORMATION: Recombinant

<400> SEQUENCE: 53
atgcttaaca ttgcgccgag ttgtgttttg ccagcggga tctctaagcc cgtgaccaag      60
atggctagca cggagaacaa ggacgaccac agcagcgcca agagg                    105

<210> SEQ ID NO 54
<211> LENGTH: 135
<212> TYPE: DNA
<213> ORGANISM: Artificial Sequence
<220> FEATURE:
<223> OTHER INFORMATION: Recombinant

<400> SEQUENCE: 54
atggtggctg tgttcaacga cgtagtgttc cctccttcgc agacccttct tcgcccctcc     60
ttccacagcc cgacgttctt ttttagcagc cccacaccaa agttcacgcg tacgaggccg    120
aatagaatac tgcgg                                                     135

<210> SEQ ID NO 55
<211> LENGTH: 180
<212> TYPE: DNA
<213> ORGANISM: Artificial Sequence
<220> FEATURE:
<223> OTHER INFORMATION: Recombinant

<400> SEQUENCE: 55
atgccggcga tagcaatggc ttctttaact gatctgccgt cgttgagccc cacacagacc     60
ctcgttcact cgaacacgag cttcatttca tcgagaacct gcttcgtctg tccgatcatc    120
cccttcccat cgaggtcgca actgaaccgc cgcatcgcct gcatcaggtc caacgtaagg    180

<210> SEQ ID NO 56
<211> LENGTH: 165
<212> TYPE: DNA
<213> ORGANISM: Artificial Sequence
<220> FEATURE:
<223> OTHER INFORMATION: Recombinant

<400> SEQUENCE: 56
atgaccacaa ccccggtagc aaaccacccc aatatcttca ctcaccgaag ccctccgtca     60
tcttcctcgt cctcacccag cgcgtttctg acccgcacct cctttctgcc cttctctagc    120
atctgcaaaa ggaactctgt gaactgcaat gggtggcgaa cccgg                    165

<210> SEQ ID NO 57
<211> LENGTH: 102
<212> TYPE: DNA
<213> ORGANISM: Artificial Sequence
<220> FEATURE:
<223> OTHER INFORMATION: Recombinant

<400> SEQUENCE: 57
atggacttca gtctccttag gcccgcttcg acgcagccgt tcctctcacc cttctccaat     60
cccttcccac ggagtaggcc atacaagcca cttaatctga gg                       102

<210> SEQ ID NO 58
<211> LENGTH: 111
<212> TYPE: DNA
<213> ORGANISM: Artificial Sequence
```

```
<220> FEATURE:
<223> OTHER INFORMATION: Recombinant

<400> SEQUENCE: 58
atggccatct tgattgacct ctccctcctg aggtcctctc cgtcggtctt ctccttctcc    60
aagccgaacc acaggatacc accgcggatc tacaagccgt tcaagttgag g            111

<210> SEQ ID NO 59
<211> LENGTH: 141
<212> TYPE: DNA
<213> ORGANISM: Artificial Sequence
<220> FEATURE:
<223> OTHER INFORMATION: Recombinant

<400> SEQUENCE: 59
atgaccacgc tttccaggct cgctgacctt ccttcttttg ctgcccctcc tcctctcttg    60
acccaccggc cccctccttc agttttcctg actccgaagc cgacaaagcc gtcacctcca   120
catcacttct ttaaactgcg c                                             141

<210> SEQ ID NO 60
<211> LENGTH: 138
<212> TYPE: DNA
<213> ORGANISM: Artificial Sequence
<220> FEATURE:
<223> OTHER INFORMATION: Recombinant

<400> SEQUENCE: 60
atgtcgtccc taacggacct cccctccctg aatcactata ggacgtgcag cccgcgccca    60
ttccccatct ccaggcagac cagttcatca attaacccaa caacttgac gaccagtaac    120 cgttggcgca ggttcagg                                                 138

<210> SEQ ID NO 61
<211> LENGTH: 105
<212> TYPE: DNA
<213> ORGANISM: Artificial Sequence
<220> FEATURE:
<223> OTHER INFORMATION: Recombinant

<400> SEQUENCE: 61
atgacgagtc tcaccaactt caccccgctc aagctgacga accccaacta cctcaacacg    60
accaccacct acaaccaccg taagctctcc aacttccggt tccgc                   105

<210> SEQ ID NO 62
<211> LENGTH: 135
<212> TYPE: DNA
<213> ORGANISM: Artificial Sequence
<220> FEATURE:
<223> OTHER INFORMATION: Recombinant

<400> SEQUENCE: 62
atgtcggcca tggcgctgtc cagcagcatt ctacagtgcc cgcctcactc agacatatcc    60
ttccgcttct cggcatacac tgccacccgc tcacctttct tcttcgggag gccaaggaaa   120
ctatcttaca tccac                                                    135

<210> SEQ ID NO 63
<211> LENGTH: 141
<212> TYPE: DNA
<213> ORGANISM: Artificial Sequence
<220> FEATURE:
<223> OTHER INFORMATION: Recombinant
```

<400> SEQUENCE: 63

```
atgtcggcca tggcattgag ctccaccatg gccctcagcc tgccacaatc tagcatgtcc      60
ttgagccact gcagacacaa tagaataact attctgatcc cctcgagctc gttacggcga     120
cggggaggtt cctcgatccg c                                                141
```

<210> SEQ ID NO 64
<211> LENGTH: 183
<212> TYPE: DNA
<213> ORGANISM: Artificial Sequence
<220> FEATURE:
<223> OTHER INFORMATION: Recombinant

<400> SEQUENCE: 64

```
atgtctgcta tggcgagccc ctccatcatc ccgcagtcgt tcctccagcg aagcccgacc      60
tccttgcaat ctcgatccaa ctactcgaag aaccacatca tcatctccat cagcaccccg     120
tgctctcatg ggaagaacca gcgacgtttc ttgcgaaaga ccacccactt ccgatccatc     180
cac                                                                    183
```

<210> SEQ ID NO 65
<211> LENGTH: 102
<212> TYPE: DNA
<213> ORGANISM: Artificial Sequence
<220> FEATURE:
<223> OTHER INFORMATION: Recombinant

<400> SEQUENCE: 65

```
atggtcgccg ctgcaatggc tacagcccct tccgctggag tccctcctct tagagggaca      60
aggggtccag caaggtttag aatccgggga gtgtcagtgc gt                        102
```

<210> SEQ ID NO 66
<211> LENGTH: 81
<212> TYPE: DNA
<213> ORGANISM: Artificial Sequence
<220> FEATURE:
<223> OTHER INFORMATION: Recombinant

<400> SEQUENCE: 66

```
atggccacta ccacagcagc cgcggcggtc accatcagca ttcctaaaaa gcctgttttt      60
atccgccgcc cacgacttcg t                                                81
```

<210> SEQ ID NO 67
<211> LENGTH: 99
<212> TYPE: DNA
<213> ORGANISM: Artificial Sequence
<220> FEATURE:
<223> OTHER INFORMATION: Recombinant

<400> SEQUENCE: 67

```
atgttgtcta gcactgctac tgcaagttct gcatcctcac accaccccta ccgttcagct      60
tctgcaaggg cttcgtcgac acgtctccgc ccggtcctt                             99
```

<210> SEQ ID NO 68
<211> LENGTH: 147
<212> TYPE: DNA
<213> ORGANISM: Artificial Sequence
<220> FEATURE:
<223> OTHER INFORMATION: Recombinant

<400> SEQUENCE: 68

```
atggtcattc agtcaattac gcatctttct cccaagctcg cactgccctc tccgctgtcg      60
```

| | |
|---|---|
| atctcggcta agaactaccc ggtggccgtg atggggaata tcagcgagag ggaggagcca | 120 |
| acttctgcta aaagggtggc cgtggtg | 147 |

<210> SEQ ID NO 69
<211> LENGTH: 144
<212> TYPE: DNA
<213> ORGANISM: Artificial Sequence
<220> FEATURE:
<223> OTHER INFORMATION: Recombinant

<400> SEQUENCE: 69

| | |
|---|---|
| atggtcattc tacccgtgtc ccagctctcg actaatttgg ggctttccct tgttagtcca | 60 |
| acgaagaaca acccggtgat gggcaacgtg tccgagagga accaggtgaa ccagccaatc | 120 |
| tccgccaagc gcgttgctgt cgtg | 144 |

<210> SEQ ID NO 70
<211> LENGTH: 153
<212> TYPE: DNA
<213> ORGANISM: Artificial Sequence
<220> FEATURE:
<223> OTHER INFORMATION: Recombinant

<400> SEQUENCE: 70

| | |
|---|---|
| atgctctcac tgagcagctc ccactcatcc gcgacaacgt attctctccg gcaacggtac | 60 |
| tctacaacga ccaaaggttc gttgaaccag cctgagatgg ccagcgccga aaacccttcc | 120 |
| agcaagggat caggtaagag aggagcagtg gtg | 153 |

<210> SEQ ID NO 71
<211> LENGTH: 114
<212> TYPE: DNA
<213> ORGANISM: Artificial Sequence
<220> FEATURE:
<223> OTHER INFORMATION: Recombinant

<400> SEQUENCE: 71

| | |
|---|---|
| atggagctga gcctcctaag accgtctact cagtcattgc tcccctcgtt cagcaagcct | 60 |
| aatttgcggc tccacgtgta caagccccctt aagctccgat gcagcgtagc cggt | 114 |

<210> SEQ ID NO 72
<211> LENGTH: 129
<212> TYPE: DNA
<213> ORGANISM: Artificial Sequence
<220> FEATURE:
<223> OTHER INFORMATION: Recombinant

<400> SEQUENCE: 72

| | |
|---|---|
| atggcgacag gagccaccct gctaacagac ctgccgttcc gtaggccgca cccgcttacg | 60 |
| ctcttacgtc cgagcgatat cccgtccttt tacccactac acataagcct acagaacaat | 120 |
| cgtttgagg | 129 |

<210> SEQ ID NO 73
<211> LENGTH: 90
<212> TYPE: DNA
<213> ORGANISM: Artificial Sequence
<220> FEATURE:
<223> OTHER INFORMATION: Recombinant

<400> SEQUENCE: 73

| | |
|---|---|
| atggtggctg ctgcggcaac gatggctacc gccgcaccac cattaagagc gcctcaaact | 60 | cttgcacgac cgcgaagagg tagtgtgaga                                    90

<210> SEQ ID NO 74
<211> LENGTH: 96
<212> TYPE: DNA
<213> ORGANISM: Artificial Sequence
<220> FEATURE:
<223> OTHER INFORMATION: Recombinant

<400> SEQUENCE: 74
atgtatgtgt cgcccgcctc gaacaaccca cgagcatgcc tcaagctgtc acaggaaatg    60
gcgtcttcag cagcagacgg caacccaaga tccgtt                             96

<210> SEQ ID NO 75
<211> LENGTH: 126
<212> TYPE: DNA
<213> ORGANISM: Artificial Sequence
<220> FEATURE:
<223> OTHER INFORMATION: Recombinant

<400> SEQUENCE: 75
atgttgtcta gcgcagcgac agctagcagc gcaagtgctc atccttatcg acctgcttct    60
gcccgggcga gtaggagcgt gttggctatg gctggatcag acgatactag ggcagctcct   120
gcccgg                                                             126

<210> SEQ ID NO 76
<211> LENGTH: 123
<212> TYPE: DNA
<213> ORGANISM: Artificial Sequence
<220> FEATURE:
<223> OTHER INFORMATION: Recombinant

<400> SEQUENCE: 76
atggtggctg cgaccgcaat ggccaccgct gcttcggctg ctgcgcctct cctaaacgga    60
acgagacgac cggcacgatt gagacataga ggtttacgtg ttaggtgtgc tgcagtagca   120
gga                                                                123

<210> SEQ ID NO 77
<211> LENGTH: 72
<212> TYPE: DNA
<213> ORGANISM: Artificial Sequence
<220> FEATURE:
<223> OTHER INFORMATION: Recombinant

<400> SEQUENCE: 77
atgctttcta gcactgccac agcttcctca gcttctagcc accaccgta tcgttcagct    60 tcggcacgtg cc                                                       72

<210> SEQ ID NO 78
<211> LENGTH: 69
<212> TYPE: DNA
<213> ORGANISM: Artificial Sequence
<220> FEATURE:
<223> OTHER INFORMATION: Recombinant

<400> SEQUENCE: 78
atgcttagct cagcagctac ggcctctagt gcttctgccc atccataccg tcccgcatct    60
gctcgagca                                                           69

<210> SEQ ID NO 79
<211> LENGTH: 84

```
<212> TYPE: DNA
<213> ORGANISM: Artificial Sequence
<220> FEATURE:
<223> OTHER INFORMATION: Recombinant

<400> SEQUENCE: 79
atgagcgcga tggcgctttc ttctagcatc ttgcaatgcc cccccactc tgacatttct      60 ttccgcttct tcgcccacac tcgc                                            84

<210> SEQ ID NO 80
<211> LENGTH: 39
<212> TYPE: DNA
<213> ORGANISM: Artificial Sequence
<220> FEATURE:
<223> OTHER INFORMATION: Recombinant

<400> SEQUENCE: 80
atggcgagtc ccacgatcgt tgacaaccag aagccagcg                            39

<210> SEQ ID NO 81
<211> LENGTH: 42
<212> TYPE: DNA
<213> ORGANISM: Artificial Sequence
<220> FEATURE:
<223> OTHER INFORMATION: Recombinant

<400> SEQUENCE: 81
atggctagta acgccgctgc tgaccacgat aagctctcgg gt                        42

<210> SEQ ID NO 82
<211> LENGTH: 39
<212> TYPE: DNA
<213> ORGANISM: Artificial Sequence
<220> FEATURE:
<223> OTHER INFORMATION: Recombinant

<400> SEQUENCE: 82
atggcgtcgc cgtccccagg cgacaaacat tcgtctgta                            39

<210> SEQ ID NO 83
<211> LENGTH: 165
<212> TYPE: DNA
<213> ORGANISM: Artificial Sequence
<220> FEATURE:
<223> OTHER INFORMATION: Recombinant

<400> SEQUENCE: 83
atgaaggggc ggaagagacg gatcacgcgg gagtctgcaa gggagatgtc agcgatggca      60
ttgtcttcga gcatactcca gtgccctcct cactccgaca tctctttccg ttttagcgct     120
cactcaccga cacacagccc tatcttcttt gggcgtccca ggaaa                    165

<210> SEQ ID NO 84
<211> LENGTH: 135
<212> TYPE: DNA
<213> ORGANISM: Artificial Sequence
<220> FEATURE:
<223> OTHER INFORMATION: Recombinant

<400> SEQUENCE: 84
atgacctacc tcactgatgt gggtagtctc aattgctaca ggtcctggcc tagcctaccg      60
gcccctggga cggtcggagc attgacttct aagaaccccc gctacttgat cacatacggt     120
ccggctcacc gaaag                                                     135
```

<210> SEQ ID NO 85
<211> LENGTH: 201
<212> TYPE: DNA
<213> ORGANISM: Artificial Sequence
<220> FEATURE:
<223> OTHER INFORMATION: Recombinant

<400> SEQUENCE: 85

```
atggtggctg tgttcaacga cgtagtgttc cctccttcgc agacccttct tcgcccctcc      60
ttccacagcc cgacgttctt ttttagcagc cccacaccaa agttcacgcg tacgaggccg     120
aatagaatac tgcggtgctc gattgcgcag gagtctacaa catcgccgtc gcagtcgcga     180
gagtcagctc cactcgattg t                                               201
```

<210> SEQ ID NO 86
<211> LENGTH: 156
<212> TYPE: DNA
<213> ORGANISM: Artificial Sequence
<220> FEATURE:
<223> OTHER INFORMATION: Recombinant

<400> SEQUENCE: 86

```
atggtggctg ctgcggcaac gatggctacc gccgcaccac cattaagagc gcctcaaact      60
cttgcacgac cgcgaagagg tagtgtgaga tgtgccgtcg ttagcgatgc tgcagaagct     120
ccggctgctc ctggcgctag actctctgca gattgc                               156
```

<210> SEQ ID NO 87
<211> LENGTH: 153
<212> TYPE: DNA
<213> ORGANISM: Artificial Sequence
<220> FEATURE:
<223> OTHER INFORMATION: Recombinant

<400> SEQUENCE: 87

```
atggccacta ccacagcagc cgcggcggtc accatcagca ttcctaaaaa gcctgttttt      60
atccgccgcc cacgacttcg ttgctcggca gttgcatccg acgcaatcat ctccaacgag     120
gcccctacag ggacgacaat ctcggctgac tgt                                  153
```

<210> SEQ ID NO 88
<211> LENGTH: 231
<212> TYPE: DNA
<213> ORGANISM: Artificial Sequence
<220> FEATURE:
<223> OTHER INFORMATION: Recombinant

<400> SEQUENCE: 88

```
atgacctacc tcactgatgt gggtagtctc aattgctaca ggtcctggcc tagcctaccg      60
gcccctggga cggtcggagc attgacttct aagaaccccc gctacttgat cacatacggt     120
ccggctcacc gaaagtgcaa cagctggcgc ttccggtgct ctattgcaaa ggactccccc     180
atcacgcccc aatttcgaa cgagagcaat tcacagcccc tgctagactg c               231
```

<210> SEQ ID NO 89
<211> LENGTH: 213
<212> TYPE: DNA
<213> ORGANISM: Artificial Sequence
<220> FEATURE:
<223> OTHER INFORMATION: Recombinant

<400> SEQUENCE: 89

```
atggcgacag gagccaccct gctaacagac ctgccgttcc gtaggccgca cccgcttacg      60
```

```
ctcttacgtc cgagcgatat cccgtcctttt tacccactac acataagcct acagaacaat    120
cgtttgagga gtcatttcag gtgctcaatc gccgagggct cgacggcact gagcccatct    180
aacgcatcgt cgcaatcgag tatcttggac tgc                                 213
```

<210> SEQ ID NO 90
<211> LENGTH: 213
<212> TYPE: DNA
<213> ORGANISM: Artificial Sequence
<220> FEATURE:
<223> OTHER INFORMATION: Recombinant

<400> SEQUENCE: 90

```
atgtcgtccc taacggacct ccctccctg aatcactata ggacgtgcag cccgcgccca      60
ttccccatct ccaggcagac cagttcatca attaacccaa acaacttgac gaccagtaac   120
cgttggcgca ggttcaggtg ctctattgcg aacgacaccc cgatcagccc gccgatttcc   180
agcgactcta cttcccaccc tttcttggac tgt                                 213
```

<210> SEQ ID NO 91
<211> LENGTH: 114
<212> TYPE: DNA
<213> ORGANISM: Artificial Sequence
<220> FEATURE:
<223> OTHER INFORMATION: Recombinant

<400> SEQUENCE: 91

```
atggagctaa gcctcctaag accgtctact cagtcattgc tccctcgtt cagcaagcct     60 aatttgcggc tccacgtgta caagccccttt aagctccgat gcagcgtagc cggt         114
```

<210> SEQ ID NO 92
<211> LENGTH: 135
<212> TYPE: DNA
<213> ORGANISM: Artificial Sequence
<220> FEATURE:
<223> OTHER INFORMATION: Recombinant

<400> SEQUENCE: 92

```
atgacctacc tcactgatgt gggtagtctc aattgctaca ggtcttggcc tagcctaccg     60 gccctggga cggtcggagc attgacttct aagaaccccc gctacttgat cacatacggt   120
ccggctcacc gaaag                                                     135
```

<210> SEQ ID NO 93
<211> LENGTH: 195
<212> TYPE: DNA
<213> ORGANISM: Artificial Sequence
<220> FEATURE:
<223> OTHER INFORMATION: Recombinant

<400> SEQUENCE: 93

```
atgacctacc tcactgatgt gggtagtctc aattgctaca ggtcctggcc tagcctaccg     60 gccctggga cggtcggagc attgacttct aagaaccccc gctacttgat cacatacggt   120
ccggctcacc gaaaggactc ccccatcacg cccccaattt cgaacgagag caattcacag   180
cccctgctag actgc                                                     195
```

<210> SEQ ID NO 94
<211> LENGTH: 180
<212> TYPE: DNA
<213> ORGANISM: Artificial Sequence
<220> FEATURE:

<223> OTHER INFORMATION: Recombinant

<400> SEQUENCE: 94

```
atgccggcga tagcaatagc ttctttaact gatctgccgt cgttgagccc cacacagacc    60
ctcgttcact cgaacacgag cttcatttca tcgagaacct gcttcgtctg tccgatcatc   120
cccttcccat cgaggtcgca actgaaccgc cgcatcgcct gcatcaggtc caacgtaagg   180
```

<210> SEQ ID NO 95
<211> LENGTH: 57
<212> TYPE: DNA
<213> ORGANISM: Artificial Sequence
<220> FEATURE:
<223> OTHER INFORMATION: Recombinant

<400> SEQUENCE: 95

```
atggtggctg ctgcggaagc tccggctgct cctggcgcta gactctctgc agattgc      57
```

<210> SEQ ID NO 96
<211> LENGTH: 75
<212> TYPE: DNA
<213> ORGANISM: Artificial Sequence
<220> FEATURE:
<223> OTHER INFORMATION: Recombinant

<400> SEQUENCE: 96

```
atggccacta ccacagcatc cgacgcaatc atctccaacg aggcccctac agggacgaca    60
atctcggctg actgt                                                    75
```

<210> SEQ ID NO 97
<211> LENGTH: 36
<212> TYPE: DNA
<213> ORGANISM: Artificial Sequence
<220> FEATURE:
<223> OTHER INFORMATION: Recombinant

<400> SEQUENCE: 97

```
atggccacta cagggacgac aatctcggct gactgt                              36
```

<210> SEQ ID NO 98
<211> LENGTH: 57
<212> TYPE: DNA
<213> ORGANISM: Artificial Sequence
<220> FEATURE:
<223> OTHER INFORMATION: Recombinant

<400> SEQUENCE: 98

```
atggcgacgg cactgagccc atctaacgca tcgtcgcaat cgagtatctt ggactgc       57
```

<210> SEQ ID NO 99
<211> LENGTH: 96
<212> TYPE: DNA
<213> ORGANISM: Artificial Sequence
<220> FEATURE:
<223> OTHER INFORMATION: Recombinant

<400> SEQUENCE: 99

```
atgtcgtccc taacggacct cccctccctg aatcactata ggacgtgcag cccgccgatt    60
tccagcgact ctacttccca ccctttcttg gactgt                              96
```

<210> SEQ ID NO 100
<211> LENGTH: 179
<212> TYPE: PRT
<213> ORGANISM: Enterobacter cloacae

<400> SEQUENCE: 100

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 101
<211> LENGTH: 178
<212> TYPE: PRT
<213> ORGANISM: Pantoea ananatis

<400> SEQUENCE: 101

```
Met Lys Ala Leu Ile Leu Phe Ser Thr Arg Asp Gly Gln Thr Gln Lys
1               5                   10                  15

Ile Ala Ser Ala Ile Ala Asp Glu Ile Lys Gly Gln Gln Ser Cys Asp
            20                  25                  30

Val Ile Asn Ile Gln Asp Ala Lys Thr Leu Asp Trp Gln Gln Tyr Asp
        35                  40                  45

Arg Val Leu Ile Gly Ala Ser Ile Arg Tyr Gly His Phe Gln Pro Val
    50                  55                  60

Val Asn Glu Phe Val Lys His Asn Leu Leu Ala Leu Gln Arg Val
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Val Lys Phe Leu Ala Gln Ser Pro
            100                 105                 110

Trp Gln Pro Asp Cys Cys Ala Val Phe Ala Gly Ala Leu Tyr Tyr Pro
        115                 120                 125

Arg Tyr Arg Trp Phe Asp Arg Val Met Ile Gln Phe Ile Met Arg Met
    130                 135                 140

Thr Gly Gly Glu Thr Asp Ala Ser Lys Glu Val Glu Tyr Thr Asp Trp
145                 150                 155                 160

Gln Gln Val Gln Arg Phe Ala Arg Asp Phe Ala Gln Leu Pro Gly Lys
                165                 170                 175
```

Ser Tyr

<210> SEQ ID NO 102
<211> LENGTH: 177
<212> TYPE: PRT
<213> ORGANISM: Pantoea stewardii

<400> SEQUENCE: 102

```
Met Lys Ala Leu Ile Leu Tyr Ser Thr Arg Asp Gly Gln Thr Arg Lys
1               5                   10                  15
Ile Ala Ser Ser Ile Ala Asp Val Ile Arg Gln Gln Gln Cys Asp
            20                  25                  30
Val Leu Asn Ile Lys Asp Ala Ser Leu Pro Asp Trp Ala Gln Tyr Asp
        35                  40                  45
Arg Val Leu Ile Gly Ala Ser Ile Arg Tyr Gly His Phe Gln Pro Val
    50                  55                  60
Val Asp Lys Phe Val Lys Gln His Leu His Glu Leu Gln Gln Arg Thr
65                  70                  75                  80
Ser Gly Phe Phe Ser Val Asn Leu Thr Ala Arg Lys Pro Glu Lys Arg
                85                  90                  95
Ser Pro Glu Thr Asn Ala Tyr Thr Gln Lys Phe Leu Ala His Ser Pro
            100                 105                 110
Trp Gln Pro Asp Cys Cys Ala Val Phe Ala Gly Ala Leu Tyr Tyr Pro
        115                 120                 125
Arg Tyr Arg Trp Phe Asp Arg Val Met Ile Gln Leu Ile Met Arg Met
    130                 135                 140
Thr Gly Gly Glu Thr Asp Ser Thr Lys Glu Val Glu Tyr Thr Asp Trp
145                 150                 155                 160
Gln Gln Val Ser Thr Phe Ala Asn Asp Phe Ala Gln Leu Pro Gly Lys
                165                 170                 175
Ser
```

<210> SEQ ID NO 103
<211> LENGTH: 181
<212> TYPE: PRT
<213> ORGANISM: Escherichia coli

<400> SEQUENCE: 103

```
Met Lys Thr Leu Ile Leu Phe Ser Thr Arg Asp Gly Gln Thr Arg Glu
1               5                   10                  15
Ile Ala Ser Tyr Leu Ala Ser Glu Leu Lys Glu Leu Gly Ile Gln Ala
            20                  25                  30
Asp Val Ala Asn Val His Arg Ile Glu Glu Pro Gln Trp Glu Asn Tyr
        35                  40                  45
Asp Arg Val Val Ile Gly Ala Ser Ile Arg Tyr Gly His Tyr His Ser
    50                  55                  60
Ala Phe Gln Glu Phe Val Lys Lys His Ala Thr Arg Leu Asn Ser Met
65                  70                  75                  80
Pro Ser Ala Phe Tyr Ser Val Asn Leu Val Ala Arg Lys Pro Glu Lys
                85                  90                  95
Arg Thr Pro Gln Thr Asn Ser Tyr Ala Arg Lys Phe Leu Met Asn Ser
            100                 105                 110
Gln Trp Arg Pro Asp Arg Cys Ala Val Ile Ala Gly Ala Leu Arg Tyr
        115                 120                 125
Pro Arg Tyr Arg Trp Tyr Asp Arg Phe Met Ile Lys Leu Ile Met Lys
    130                 135                 140
```

```
Met Ser Gly Gly Glu Thr Asp Thr Arg Lys Glu Val Val Tyr Thr Asp
145                 150                 155                 160

Trp Glu Gln Val Ala Asn Phe Ala Arg Glu Ile Ala His Leu Thr Asp
            165                 170                 175

Lys Pro Thr Leu Lys
            180
```

<210> SEQ ID NO 104
<211> LENGTH: 178
<212> TYPE: PRT
<213> ORGANISM: Erwinia toletana

<400> SEQUENCE: 104

```
Met Lys Ala Leu Ile Leu Phe Ser Ser Arg Glu Gly Gln Thr Arg Glu
1               5                   10                  15

Ile Ala Ser Tyr Ile Ala Asn Ser Ile Lys Glu Glu Met Glu Cys Asp
            20                  25                  30

Val Phe Asn Ile Leu Arg Val Glu Gln Ile Asp Trp Ser Gln Tyr Asp
        35                  40                  45

Arg Val Leu Ile Gly Gly Ser Ile His Tyr Gly His Phe His Pro Ala
    50                  55                  60

Val Ala Lys Phe Val Lys Arg His Leu His Glu Leu Gln Gln Arg Ser
65                  70                  75                  80

Ser Gly Phe Phe Cys Val Asn Leu Thr Ala Arg Lys Ala Asp Lys Arg
                85                  90                  95

Thr Pro Gln Thr Asn Ala Tyr Met Arg Lys Phe Leu Leu Gln Ser Pro
            100                 105                 110

Trp Gln Pro Asp Cys Cys Ala Val Phe Ala Gly Ala Leu Arg Tyr Thr
        115                 120                 125

Arg Tyr Arg Trp Phe Asp Arg Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Thr Gln Val Ala Arg Phe Ala Gln Glu Phe Ala His Leu Pro Gly Lys
                165                 170                 175

Thr Gln
```

<210> SEQ ID NO 105
<211> LENGTH: 179
<212> TYPE: PRT
<213> ORGANISM: Pectobacterium carotovorum

<400> SEQUENCE: 105

```
Met Lys Ala Leu Ile Val Phe Ser Ser Arg Asp Gly Gln Thr Arg Ala
1               5                   10                  15

Ile Ala Ser Tyr Ile Ala Asn Thr Leu Lys Gly Thr Leu Glu Cys Asp
            20                  25                  30

Val Val Asn Val Leu Asn Ala Asn Asp Ile Asp Leu Ser Gln Tyr Asp
        35                  40                  45

Arg Val Ala Ile Gly Ala Ser Ile Arg Tyr Gly Arg Phe His Pro Ala
    50                  55                  60

Val Asn Gln Phe Ile Arg Lys His Leu Thr Ser Leu Gln Gln Leu Pro
65                  70                  75                  80

Ser Ala Phe Phe Ser Val Asn Leu Thr Ala Arg Lys Pro Glu Lys Arg
                85                  90                  95
```

```
Thr Ile Gln Thr Asn Ala Tyr Thr Arg Lys Phe Leu Leu Asn Ser Pro
            100                 105                 110

Trp Gln Pro Asp Leu Cys Cys Val Phe Ala Gly Ala Leu Arg Tyr Pro
        115                 120                 125

Arg Tyr Arg Trp Phe Asp Arg Val Met Ile Gln Leu Ile Met Arg Ile
    130                 135                 140

Thr Gly Gly Glu Thr Asp Ser Thr Lys Glu Ile Glu Tyr Thr Asp Trp
145                 150                 155                 160

Gln Gln Val Ala Arg Phe Ala Gln Asp Phe Ala Gln Leu Ala Ala Lys
                165                 170                 175

Asn Pro Ala

<210> SEQ ID NO 106
<211> LENGTH: 179
<212> TYPE: PRT
<213> ORGANISM: Shimwellia blattae

<400> SEQUENCE: 106

Met Lys Thr Leu Ile Leu Phe Ser Thr Arg Asp Gly Gln Thr His Lys
1               5                   10                  15

Ile Ala Arg His Ile Ala Gly Val Leu Glu Glu Gln Gly Lys Ala Cys
            20                  25                  30

Glu Leu Val Asp Leu Leu Gln Pro Gly Glu Pro Asp Trp Ser Thr Val
        35                  40                  45

Glu Cys Val Val Leu Gly Ala Ser Ile Arg Tyr Gly His Phe His Lys
    50                  55                  60

Ser Phe Ile Arg Phe Val Asn Thr His Ala Gln Arg Leu Asn Asn Met
65                  70                  75                  80

Pro Gly Ala Leu Phe Thr Val Asn Leu Val Ala Arg Lys Pro Glu Lys
                85                  90                  95

Gln Ser Pro Gln Thr Asn Ser Tyr Thr Arg Lys Phe Leu Ala Ala Ser
            100                 105                 110

Pro Trp Gln Pro Gln Arg Cys Gln Val Phe Ala Gly Ala Leu Arg Tyr
        115                 120                 125

Pro Arg Tyr Ser Trp Tyr Asp Arg Met Met Ile Arg Leu Ile Met Lys
    130                 135                 140

Met Ala Gly Gly Glu Thr Asp Thr Arg Lys Glu Val Glu Tyr Thr Asp
145                 150                 155                 160

Trp Gln Ser Val Thr Arg Phe Ala Arg Glu Ile Ala Gln Leu Pro Gly
                165                 170                 175

Glu Thr Arg

<210> SEQ ID NO 107
<211> LENGTH: 178
<212> TYPE: PRT
<213> ORGANISM: Pantoea stewardii

<400> SEQUENCE: 107

Met Lys Ala Leu Ile Leu Phe Ser Ser Arg Asp Gly Gln Thr Gln Leu
1               5                   10                  15

Ile Ala Ser Ser Ile Ala Lys Glu Leu Glu Gly Lys Gln Ala Cys Asp
            20                  25                  30

Val Leu Asn Ile Leu Asp Thr Thr Asn Val Glu Trp Thr Gln Tyr Asp
        35                  40                  45

Arg Val Leu Ile Gly Ala Ser Ile Arg Tyr Gly His Phe His Pro Ala
    50                  55                  60
```

Val Ala Glu Phe Val Lys Arg His Gln Arg Glu Leu Gln Gln Arg Ser
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Ala Lys Phe Leu Asn Gln Ser Pro
                100                 105                 110

Trp Gln Pro Asp Cys Cys Ala Val Phe Ala Gly Ala Leu Arg Tyr Pro
            115                 120                 125

Arg Tyr Arg Trp Phe Asp Arg Ile Met Ile Gln Leu Ile Met Arg Met
        130                 135                 140

Thr Gly Gly Glu Thr Asp Ser Ser Lys Glu Val Glu Tyr Thr Asp Trp
145                 150                 155                 160

Gln Gln Val Thr Arg Phe Ala Gln Glu Phe Ala Arg Leu Pro Gly Lys
                165                 170                 175

Thr Ser

<210> SEQ ID NO 108
<211> LENGTH: 180
<212> TYPE: PRT
<213> ORGANISM: Enterobacter cloacae

<400> SEQUENCE: 108

Met Lys Thr Leu Ile Leu Phe Ser Thr Arg Asp Gly Gln Thr Arg Glu
1               5                   10                  15

Ile Ala Ala Phe Leu Ala Ser Glu Leu Lys Glu Gln Gly Ile Tyr Ala
                20                  25                  30

Asp Val Ile Asn Leu Asn Arg Thr Glu Glu Ile Ala Trp Gln Glu Tyr
                35                  40                  45

Asp Arg Val Val Ile Gly Ala Ser Ile Arg Tyr Gly His Phe His Pro
            50                  55                  60

Ala Val Asp Arg Phe Val Lys Lys His Thr Glu Thr Leu Asn Ser Leu
65                  70                  75                  80

Pro Gly Ala Phe Phe Ser Val Asn Leu Val Ala Arg Lys Ala Glu Lys
                85                  90                  95

Arg Thr Pro Gln Thr Asn Ser Tyr Thr Arg Lys Phe Leu Leu Asn Ser
                100                 105                 110

Pro Trp Lys Pro Ala Ala Cys Ala Val Phe Ala Gly Ala Leu Arg Tyr
            115                 120                 125

Pro Arg Tyr Arg Trp Tyr Asp Arg Phe Met Ile Arg Leu Ile Met Lys
        130                 135                 140

Met Thr Gly Gly Glu Thr Asp Thr Arg Lys Glu Val Val Tyr Thr Asp
145                 150                 155                 160

Trp Ser Gln Val Ala Ser Phe Ala Arg Glu Ile Val Gln Leu Thr Arg
                165                 170                 175

Ser Ser Arg Leu
            180

<210> SEQ ID NO 109
<211> LENGTH: 177
<212> TYPE: PRT
<213> ORGANISM: Enterobacter mori

<400> SEQUENCE: 109

Met Lys Ile Leu Ile Leu Phe Ser Thr Arg Asp Gly Gln Thr Arg Glu
1               5                   10                  15

-continued

```
Ile Ala Ala Ser Leu Ala Ser Glu Leu Lys Glu Gln Ala Phe Asp Val
            20                  25                  30

Asp Val Asn Leu His Arg Ala Glu Asn Ile Ala Trp Glu Glu Tyr
        35                  40                  45

Asp Gly Val Val Ile Gly Ala Ser Ile Arg Tyr Gly His Phe His Ser
    50                  55                  60

Thr Leu Asn Ser Phe Val Lys Lys His Gln Gln Ala Leu Lys Lys Leu
65                  70                  75                  80

Pro Gly Ala Phe Tyr Ser Val Asn Leu Val Ala Arg Lys Pro Glu Lys
                85                  90                  95

Arg Thr Pro Gln Thr Asn Ser Tyr Thr Arg Lys Phe Leu Leu Asp Ser
            100                 105                 110

Pro Trp Gln Pro Asp Leu Ser Ala Val Phe Ala Gly Ala Leu Arg Tyr
        115                 120                 125

Pro Arg Tyr Asn Trp Tyr Asp Arg Ile Met Ile Arg Leu Ile Met Lys
    130                 135                 140

Ile Thr Gly Gly Glu Thr Asp Thr Arg Lys Glu Val Val Tyr Thr Asp
145                 150                 155                 160

Trp Gln Gln Val Thr His Phe Ala His Glu Ile Val Gln Leu Val Arg
                165                 170                 175

Lys
```

<210> SEQ ID NO 110
<211> LENGTH: 178
<212> TYPE: PRT
<213> ORGANISM: Enterobacter cloacae

<400> SEQUENCE: 110

```
Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
            20                  25                  30

Ile Asp Leu Thr His Gly Glu His Val Asn Leu Thr Gln Tyr Asp Gln
        35                  40                  45

Val Leu Ile Gly Ala Ser Ile Arg Tyr Gly His Phe Asn Ala Val Leu
    50                  55                  60

Asp Lys Phe Ile Lys Arg Asn Val Asp Gln Leu Asn Asn Met Pro Ser
65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
            100                 105                 110

Gln Pro Ala Leu Cys Gly Val Phe Ala Gly Ala Leu Arg Tyr Pro Arg
        115                 120                 125

Tyr Arg Trp Ile Asp Lys Val Met Ile Gln Leu Ile Met Arg Met Thr
    130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu Ser Tyr Lys Lys
                165                 170                 175

Ala Leu
```

<210> SEQ ID NO 111
<211> LENGTH: 177
<212> TYPE: PRT

<213> ORGANISM: Pantoea ananatis

<400> SEQUENCE: 111

Lys Ala Leu Ile Leu Phe Ser Thr Arg Asp Gly Gln Thr Gln Lys Ile
1               5                   10                  15

Ala Ser Ala Ile Ala Asp Glu Ile Lys Gly Gln Gln Ser Cys Asp Val
            20                  25                  30

Ile Asn Ile Gln Asp Ala Lys Thr Leu Asp Trp Gln Gln Tyr Asp Arg
        35                  40                  45

Val Leu Ile Gly Ala Ser Ile Arg Tyr Gly His Phe Gln Pro Val Val
    50                  55                  60

Asn Glu Phe Val Lys His Asn Leu Leu Ala Leu Gln Arg Val Ser
65                  70                  75                  80

Gly Phe Phe Ser Val Asn Leu Thr Ala Arg Lys Pro Glu Lys Arg Ser
                85                  90                  95

Pro Glu Thr Asn Ala Tyr Thr Val Lys Phe Leu Ala Gln Ser Pro Trp
            100                 105                 110

Gln Pro Asp Cys Cys Ala Val Phe Ala Gly Ala Leu Tyr Tyr Pro Arg
        115                 120                 125

Tyr Arg Trp Phe Asp Arg Val Met Ile Gln Phe Ile Met Arg Met Thr
    130                 135                 140

Gly Gly Glu Thr Asp Ala Ser Lys Glu Val Glu Tyr Thr Asp Trp Gln
145                 150                 155                 160

Gln Val Gln Arg Phe Ala Arg Asp Phe Ala Gln Leu Pro Gly Lys Ser
                165                 170                 175

Tyr

<210> SEQ ID NO 112
<211> LENGTH: 180
<212> TYPE: PRT
<213> ORGANISM: Escherichia coli

<400> SEQUENCE: 112

Lys Thr Leu Ile Leu Phe Ser Thr Arg Asp Gly Gln Thr Arg Glu Ile
1               5                   10                  15

Ala Ser Tyr Leu Ala Ser Glu Leu Lys Glu Leu Gly Ile Gln Ala Asp
            20                  25                  30

Val Ala Asn Val His Arg Ile Glu Glu Pro Gln Trp Glu Asn Tyr Asp
        35                  40                  45

Arg Val Val Ile Gly Ala Ser Ile Arg Tyr Gly His Tyr His Ser Ala
    50                  55                  60

Phe Gln Glu Phe Val Lys Lys His Ala Thr Arg Leu Asn Ser Met Pro
65                  70                  75                  80

Ser Ala Phe Tyr Ser Val Asn Leu Val Ala Arg Lys Pro Glu Lys Arg
                85                  90                  95

Thr Pro Gln Thr Asn Ser Tyr Ala Arg Lys Phe Leu Met Asn Ser Gln
            100                 105                 110

Trp Arg Pro Asp Arg Cys Ala Val Ile Ala Gly Ala Leu Arg Tyr Pro
        115                 120                 125

Arg Tyr Arg Trp Tyr Asp Arg Phe Met Ile Lys Leu Ile Met Lys Met
    130                 135                 140

Ser Gly Gly Glu Thr Asp Thr Arg Lys Glu Val Val Tyr Thr Asp Trp
145                 150                 155                 160

Glu Gln Val Ala Asn Phe Ala Arg Glu Ile Ala His Leu Thr Asp Lys
                165                 170                 175

```
Pro Thr Leu Lys
        180

<210> SEQ ID NO 113
<211> LENGTH: 177
<212> TYPE: PRT
<213> ORGANISM: Erwinia toletana

<400> SEQUENCE: 113

Lys Ala Leu Ile Leu Phe Ser Ser Arg Glu Gly Gln Thr Arg Glu Ile
1               5                   10                  15

Ala Ser Tyr Ile Ala Asn Ser Ile Lys Glu Glu Met Glu Cys Asp Val
            20                  25                  30

Phe Asn Ile Leu Arg Val Glu Gln Ile Asp Trp Ser Gln Tyr Asp Arg
        35                  40                  45

Val Leu Ile Gly Gly Ser Ile His Tyr Gly His Phe His Pro Ala Val
    50                  55                  60

Ala Lys Phe Val Lys Arg His Leu His Glu Leu Gln Gln Arg Ser Ser
65                  70                  75                  80

Gly Phe Phe Cys Val Asn Leu Thr Ala Arg Lys Ala Asp Lys Arg Thr
                85                  90                  95

Pro Gln Thr Asn Ala Tyr Met Arg Lys Phe Leu Leu Gln Ser Pro Trp
            100                 105                 110

Gln Pro Asp Cys Cys Ala Val Phe Ala Gly Ala Leu Arg Tyr Thr Arg
        115                 120                 125

Tyr Arg Trp Phe Asp Arg Val Met Ile Gln Leu Ile Met Arg Met Thr
130                 135                 140

Gly Gly Glu Thr Asp Thr Ser Lys Glu Val Glu Tyr Thr Asp Trp Thr
145                 150                 155                 160

Gln Val Ala Arg Phe Ala Gln Glu Phe Ala His Leu Pro Gly Lys Thr
                165                 170                 175

Gln

<210> SEQ ID NO 114
<211> LENGTH: 178
<212> TYPE: PRT
<213> ORGANISM: Pectobacterium carotovorum

<400> SEQUENCE: 114

Lys Ala Leu Ile Val Phe Ser Ser Arg Asp Gly Gln Thr Arg Ala Ile
1               5                   10                  15

Ala Ser Tyr Ile Ala Asn Thr Leu Lys Gly Thr Leu Glu Cys Asp Val
            20                  25                  30

Val Asn Val Leu Asn Ala Asn Asp Ile Asp Leu Ser Gln Tyr Asp Arg
        35                  40                  45

Val Ala Ile Gly Ala Ser Ile Arg Tyr Gly Arg Phe His Pro Ala Val
    50                  55                  60

Asn Gln Phe Ile Arg Lys His Leu Thr Ser Leu Gln Gln Leu Pro Ser
65                  70                  75                  80

Ala Phe Phe Ser Val Asn Leu Thr Ala Arg Lys Pro Glu Lys Arg Thr
                85                  90                  95

Ile Gln Thr Asn Ala Tyr Thr Arg Lys Phe Leu Leu Asn Ser Pro Trp
            100                 105                 110

Gln Pro Asp Leu Cys Cys Val Phe Ala Gly Ala Leu Arg Tyr Pro Arg
        115                 120                 125
```

Tyr Arg Trp Phe Asp Arg Val Met Ile Gln Leu Ile Met Arg Ile Thr
            130                 135                 140

Gly Gly Glu Thr Asp Ser Thr Lys Glu Ile Glu Tyr Thr Asp Trp Gln
145                 150                 155                 160

Gln Val Ala Arg Phe Ala Gln Asp Phe Ala Gln Leu Ala Ala Lys Asn
                165                 170                 175

Pro Ala

<210> SEQ ID NO 115
<211> LENGTH: 178
<212> TYPE: PRT
<213> ORGANISM: Shimwellia blattae

<400> SEQUENCE: 115

Lys Thr Leu Ile Leu Phe Ser Thr Arg Asp Gly Gln Thr His Lys Ile
1               5                   10                  15

Ala Arg His Ile Ala Gly Val Leu Glu Glu Gln Gly Lys Ala Cys Glu
                20                  25                  30

Leu Val Asp Leu Leu Gln Pro Gly Glu Pro Asp Trp Ser Thr Val Glu
            35                  40                  45

Cys Val Val Leu Gly Ala Ser Ile Arg Tyr Gly His Phe His Lys Ser
        50                  55                  60

Phe Ile Arg Phe Val Asn Thr His Ala Gln Arg Leu Asn Asn Met Pro
65                  70                  75                  80

Gly Ala Leu Phe Thr Val Asn Leu Val Ala Arg Lys Pro Glu Lys Gln
                85                  90                  95

Ser Pro Gln Thr Asn Ser Tyr Thr Arg Lys Phe Leu Ala Ala Ser Pro
            100                 105                 110

Trp Gln Pro Gln Arg Cys Gln Val Phe Ala Gly Ala Leu Arg Tyr Pro
        115                 120                 125

Arg Tyr Ser Trp Tyr Asp Arg Met Met Ile Arg Leu Ile Met Lys Met
    130                 135                 140

Ala Gly Gly Glu Thr Asp Thr Arg Lys Glu Val Glu Tyr Thr Asp Trp
145                 150                 155                 160

Gln Ser Val Thr Arg Phe Ala Arg Glu Ile Ala Gln Leu Pro Gly Glu
                165                 170                 175

Thr Arg

<210> SEQ ID NO 116
<211> LENGTH: 179
<212> TYPE: PRT
<213> ORGANISM: Enterobacter cloacae

<400> SEQUENCE: 116

Lys Thr Leu Ile Leu Phe Ser Thr Arg Asp Gly Gln Thr Arg Glu Ile
1               5                   10                  15

Ala Ala Phe Leu Ala Ser Glu Leu Lys Glu Gln Gly Ile Tyr Ala Asp
                20                  25                  30

Val Ile Asn Leu Asn Arg Thr Glu Glu Ile Ala Trp Gln Glu Tyr Asp
            35                  40                  45

Arg Val Val Ile Gly Ala Ser Ile Arg Tyr Gly His Phe His Pro Ala
        50                  55                  60

Val Asp Arg Phe Val Lys Lys His Thr Glu Thr Leu Asn Ser Leu Pro
65                  70                  75                  80

Gly Ala Phe Phe Ser Val Asn Leu Val Ala Arg Lys Ala Glu Lys Arg
                85                  90                  95

Thr Pro Gln Thr Asn Ser Tyr Thr Arg Lys Phe Leu Leu Asn Ser Pro
            100                 105                 110

Trp Lys Pro Ala Ala Cys Ala Val Phe Ala Gly Ala Leu Arg Tyr Pro
        115                 120                 125

Arg Tyr Arg Trp Tyr Asp Arg Phe Met Ile Arg Leu Ile Met Lys Met
    130                 135                 140

Thr Gly Gly Glu Thr Asp Thr Arg Lys Glu Val Val Tyr Thr Asp Trp
145                 150                 155                 160

Ser Gln Val Ala Ser Phe Ala Arg Glu Ile Val Gln Leu Thr Arg Ser
                165                 170                 175

Ser Arg Leu

<210> SEQ ID NO 117
<211> LENGTH: 178
<212> TYPE: PRT
<213> ORGANISM: Artificial Sequence
<220> FEATURE:
<223> OTHER INFORMATION: Recombinant

<400> SEQUENCE: 117

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
            20                  25                  30

Ile Asp Leu Thr His Gly Glu His Val Asn Leu Thr Gln Tyr Asp Gln
        35                  40                  45

Val Leu Ile Gly Ala Asn Ile Arg Tyr Gly His Phe Asn Ala Val Leu
    50                  55                  60

Asp Lys Phe Ile Lys Arg Asn Val Asp Gln Leu Asn Asn Met Pro Ser
65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
            100                 105                 110

Gln Pro Ala Leu Cys Gly Val Phe Ala Gly Ala Leu Arg Tyr Pro Arg
        115                 120                 125

Tyr Arg Trp Ile Asp Lys Val Met Ile Gln Leu Ile Met Arg Met Thr
    130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu Ser Tyr Lys Lys
                165                 170                 175

Ala Leu

<210> SEQ ID NO 118
<211> LENGTH: 172
<212> TYPE: PRT
<213> ORGANISM: Artificial Sequence
<220> FEATURE:
<223> OTHER INFORMATION: Recombinant

<400> SEQUENCE: 118

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
            20                  25                  30

```
Ile Asp Leu Thr His Gly Glu His Val Asn Leu Thr Gln Tyr Asp Gln
             35                  40                  45

Val Leu Ile Gly Ala Ser Ile Arg Tyr Gly His Phe Asn Ala Val Leu
 50                  55                  60

Asp Lys Phe Ile Lys Arg Asn Val Asp Gln Leu Asn Asn Met Pro Ser
 65                  70                  75                  80

Ala Phe Phe Cys Val Asn Leu Thr Ala Arg Lys Pro Glu Lys Arg Thr
                 85                  90                  95

Pro Gln Thr Asn Pro Tyr Val Arg Lys Phe Leu Leu Ala Thr Pro Trp
                100                 105                 110

Gln Pro Ala Leu Cys Gly Val Phe Ala Gly Ala Leu Arg Tyr Pro Arg
            115                 120                 125

Tyr Arg Trp Ile Asp Lys Val Met Ile Gln Leu Ile Met Arg Met Thr
        130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu
                165                 170
```

<210> SEQ ID NO 119
<211> LENGTH: 179
<212> TYPE: PRT
<213> ORGANISM: Artificial Sequence
<220> FEATURE:
<223> OTHER INFORMATION: Recombinant

<400> SEQUENCE: 119

```
Lys Thr Leu Ile Leu Phe Ser Thr Arg Asp Gly Gln Thr Arg Glu Ile
 1               5                  10                  15

Ala Ala Phe Leu Ala Ser Glu Leu Lys Glu Gln Gly Ile Tyr Ala Asp
                 20                  25                  30

Val Ile Asn Leu Asn Arg Thr Glu Glu Ile Ala Trp Gln Glu Tyr Asp
                 35                  40                  45

Arg Val Val Ile Gly Ala Ser Ile Arg Tyr Gly His Phe His Pro Ala
 50                  55                  60

Val Asp Arg Phe Val Lys Lys His Thr Glu Thr Leu Asn Ser Leu Pro
 65                  70                  75                  80

Gly Ala Phe Phe Ser Val Asn Leu Val Ala Arg Lys Ala Glu Lys Arg
                 85                  90                  95

Thr Pro Gln Thr Asn Ser Tyr Thr Arg Lys Phe Leu Leu Asn Ser Pro
                100                 105                 110

Trp Lys Pro Ala Ala Cys Ala Val Phe Ala Gly Ala Leu Arg Tyr Pro
            115                 120                 125

Arg Tyr Arg Trp Tyr Asp Arg Phe Met Ile Arg Leu Ile Met Lys Met
        130                 135                 140

Thr Gly Gly Glu Thr Asp Thr Arg Lys Glu Val Val Tyr Thr Asp Trp
145                 150                 155                 160

Ser Gln Ile Ala Ser Phe Ala Arg Glu Ile Val Gln Leu Thr Arg Ser
                165                 170                 175

Ser Arg Leu
```

<210> SEQ ID NO 120
<211> LENGTH: 504
<212> TYPE: PRT
<213> ORGANISM: Amaranthus tuberculatus

<400> SEQUENCE: 120

```
Met Gly Asn Ile Ser Glu Arg Glu Pro Thr Ser Ala Lys Arg Val
1               5                   10                  15

Ala Val Val Gly Ala Val Ser Gly Leu Ala Ala Tyr Lys Leu
            20                  25                  30

Lys Ser His Gly Leu Ser Val Thr Leu Phe Glu Ala Asp Ser Arg Ala
        35                  40                  45

Gly Gly Lys Leu Lys Thr Val Lys Lys Asp Gly Phe Ile Trp Asp Glu
    50                  55                  60

Gly Ala Asn Thr Met Thr Glu Ser Glu Ala Glu Val Ser Ser Leu Ile
65                  70                  75                  80

Asp Asp Leu Gly Leu Arg Glu Lys Gln Gln Leu Pro Ile Ser Gln Asn
                85                  90                  95

Lys Arg Tyr Ile Ala Arg Asp Gly Leu Pro Val Leu Leu Pro Ser Asn
                100                 105                 110

Pro Ala Ala Leu Leu Thr Ser Asn Ile Leu Ser Ala Lys Ser Lys Leu
            115                 120                 125

Gln Ile Met Leu Glu Pro Phe Leu Trp Arg Lys His Asn Ala Thr Glu
        130                 135                 140

Leu Ser Asp Glu His Val Gln Glu Ser Val Gly Glu Phe Phe Glu Arg
145                 150                 155                 160

His Phe Gly Lys Glu Phe Val Asp Tyr Val Ile Asp Pro Phe Val Ala
                165                 170                 175

Gly Thr Cys Gly Gly Asp Pro Gln Ser Leu Ser Met His His Thr Phe
                180                 185                 190

Pro Glu Val Trp Asn Ile Glu Lys Arg Phe Gly Ser Val Phe Ala Gly
                195                 200                 205

Leu Ile Gln Ser Thr Leu Leu Ser Lys Lys Glu Lys Gly Gly Glu Asn
            210                 215                 220

Ala Ser Ile Lys Lys Pro Arg Val Arg Gly Ser Phe Ser Phe Gln Gly
225                 230                 235                 240

Gly Met Gln Thr Leu Val Asp Thr Met Cys Lys Gln Leu Gly Glu Asp
                245                 250                 255

Glu Leu Lys Leu Gln Cys Glu Val Leu Ser Leu Ser Tyr Asn Gln Lys
                260                 265                 270

Gly Ile Pro Ser Leu Gly Asn Trp Ser Val Ser Ser Met Ser Asn Asn
            275                 280                 285

Thr Ser Glu Asp Gln Ser Tyr Asp Ala Val Val Thr Ala Pro Ile
        290                 295                 300

Arg Asn Val Lys Glu Met Lys Ile Met Lys Phe Gly Asn Pro Phe Ser
305                 310                 315                 320

Leu Asp Phe Ile Pro Glu Val Thr Tyr Val Pro Leu Ser Val Met Ile
                325                 330                 335

Thr Ala Phe Lys Lys Asp Lys Val Lys Arg Pro Leu Glu Gly Phe Gly
                340                 345                 350

Val Leu Ile Pro Ser Lys Glu Gln His Asn Gly Leu Lys Thr Leu Gly
            355                 360                 365

Thr Leu Phe Ser Ser Met Met Phe Pro Asp Arg Ala Pro Ser Asp Met
        370                 375                 380

Cys Leu Phe Thr Thr Phe Val Gly Gly Ser Arg Asn Arg Lys Leu Ala
385                 390                 395                 400

Asn Ala Ser Thr Asp Glu Leu Lys Gln Ile Val Ser Ser Asp Leu Gln
                405                 410                 415
```

Gln Leu Leu Gly Thr Glu Asp Glu Pro Ser Phe Val Asn His Leu Phe
            420                 425                 430

Trp Ser Asn Ala Phe Pro Leu Tyr Gly His Asn Tyr Asp Ser Val Leu
            435                 440                 445

Arg Ala Ile Asp Lys Met Glu Lys Asp Leu Pro Gly Phe Phe Tyr Ala
        450                 455                 460

Gly Asn His Lys Gly Gly Leu Ser Val Gly Lys Ala Met Ala Ser Gly
465                 470                 475                 480

Cys Lys Ala Ala Glu Leu Val Ile Ser Tyr Leu Asp Ser His Ile Tyr
                485                 490                 495

Val Lys Met Asp Glu Lys Thr Ala
            500

<210> SEQ ID NO 121
<211> LENGTH: 537
<212> TYPE: DNA
<213> ORGANISM: Artificial Sequence
<220> FEATURE:
<223> OTHER INFORMATION: Recombinant

<400> SEQUENCE: 121
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcagctg     420
attatgcgca tgaccggcgg cgaaaccgat accagcaaag aagtggaata taccgattgg     480
gaacaggtga aaaatttgc ggaagatttt gcgaaactga gctataaaaa agcgctg        537

<210> SEQ ID NO 122
<211> LENGTH: 534
<212> TYPE: DNA
<213> ORGANISM: Artificial Sequence
<220> FEATURE:
<223> OTHER INFORMATION: Recombinant

<400> SEQUENCE: 122
atgaaagcgc tgattctgtt tagcacccgc gatggccaga cccagaaaat tgcgagcgcg      60
attgcggatg aaattaaagg ccagcagagc tgcgatgtga ttaacattca ggatgcgaaa     120
accctggatt ggcagcagta tgatcgcgtg ctgattggcg cgagcattcg ctatggccat     180
tttcagccgg tggtgaacga atttgtgaaa cataacctgc tggcgctgca gcagcgcgtg     240
agcggctttt ttagcgtgaa cctgaccgcg cgcaaaccgg aaaaacgcag cccggaaacc     300
aacgcgtata ccgtgaaatt tctggcgcag agcccgtggc agccggattg ctgcgcggtg     360
tttgcgggcg cgctgtatta tccgcgctat cgctggtttg atcgcgtgat gattcagttt     420
attatgcgca tgaccggcgg cgaaaccgat gcgagcaaag aagtggaata taccgattgg     480
cagcaggtgc agcgctttgc gcgcgatttt gcgcagctgc cgggcaaaag ctat          534

<210> SEQ ID NO 123
<211> LENGTH: 531
<212> TYPE: DNA
<213> ORGANISM: Artificial Sequence
<220> FEATURE:
<223> OTHER INFORMATION: Recombinant

<400> SEQUENCE: 123

```
atgaaagcgc tgattctgta tagcacccgc gatggccaga cccgcaaaat tgcgagcagc    60
attgcggatg tgattcgcca gcagcagcag tgcgatgtgc tgaacattaa agatgcgagc   120
ctgccggatt gggcgcagta tgatcgcgtg ctgattggcg cgagcattcg ctatggccat   180
tttcagccgg tggtggataa atttgtgaaa cagcatctgc atgaactgca gcagcgcacc   240
agcggctttt ttagcgtgaa cctgaccgcg cgcaaaccgg aaaaacgcag cccggaaacc   300
aacgcgtata cccagaaatt tctggcgcat agcccgtggc agccggattg ctgcgcggtg   360
tttgcgggcg cgctgtatta tccgcgctat cgctggtttg atcgcgtgat gattcagctg   420
attatgcgca tgaccggcgg cgaaaccgat agcaccaaag aagtggaata taccgattgg   480
cagcaggtga gcacctttgc gaacgatttt gcgcagctgc cgggcaaaag c            531
```

<210> SEQ ID NO 124
<211> LENGTH: 546
<212> TYPE: DNA
<213> ORGANISM: Escherichia coli

<400> SEQUENCE: 124

```
gtgaaaacat taattctttt ctcaacaagg gacggacaaa cgcgcgagat tgcctcctac    60
ctggcttcgg aactgaaaga actggggatc caggcggatg tcgccaatgt gcaccgcatt   120
gaagaaccac agtgggaaaa ctatgaccgt gtggtcattg gtgcttctat tcgctatggt   180
cactaccatt cagcgttcca ggaatttgtc aaaaaacatg cgacgcggct gaattcgatg   240
ccgagcgcct tttactccgt gaatctggtg gcgcgcaaac cggagaagcg tactccacag   300
accaacagct acgcgcgcaa gtttctgatg aactcgcaat ggcgtcccga tcgctgcgcg   360
gtcattgccg gggcgctgcg ttacccacgt tatcgctggt acgaccgttt tatgatcaag   420
ctgattatga agatgtcagg cggtgaaacg gatacgcgca agaagttgt ctataccgat    480
tgggagcagg tggcgaattt cgcccgagaa atcgcccatt taaccgacaa accgacgctg   540
aaataa                                                              546
```

<210> SEQ ID NO 125
<211> LENGTH: 534
<212> TYPE: DNA
<213> ORGANISM: Artificial Sequence
<220> FEATURE:
<223> OTHER INFORMATION: Recombinant

<400> SEQUENCE: 125

```
atgaaagcgc tgattctgtt tagcagccgc gaaggccaga cccgcgaaat tgcgagctat    60
attgcgaaca gcattaaaga agaaatggaa tgcgatgtgt taacattct gcgcgtggaa    120
cagattgatt ggagccagta tgatcgcgtg ctgattggcg cagcattca ttatggccat    180
tttcatccgg cggtggcgaa atttgtgaaa cgccatctgc atgaactgca gcagcgcagc   240
agcggctttt tttgcgtgaa cctgaccgcg cgcaaagcgg ataaacgcac cccgcagacc   300
aacgcgtata tgcgcaaatt tctgctgcag agcccgtggc agccggattg ctgcgcggtg   360
tttgcgggcg cgctgcgcta taccgcgtat cgctggtttg atcgcgtgat gattcagctg   420
attatgcgca tgaccggcgg cgaaaccgat accagcaaag aagtggaata taccgattgg   480
acccaggtgg cgcgctttgc gcaggaattt gcgcatctgc cgggcaaaac ccag         534
```

-continued

<210> SEQ ID NO 126
<211> LENGTH: 537
<212> TYPE: DNA
<213> ORGANISM: Artificial Sequence
<220> FEATURE:
<223> OTHER INFORMATION: Recombinant

<400> SEQUENCE: 126

| | | | | | |
|---|---|---|---|---|---|
| atgaaagcgc | tgattgtgtt | tagcagccgc | gatggccaga | cccgcgcgat | tgcgagctat | 60 |
| attgcgaaca | ccctgaaagg | caccctggaa | tgcgatgtgg | tgaacgtgct | gaacgcgaac | 120 |
| gatattgatc | tgagccagta | tgatcgcgtg | gcgattggcg | cgagcattcg | ctatggccgc | 180 |
| tttcatccgg | cggtgaacca | gtttattcgc | aaacatctga | ccagcctgca | gcagctgccg | 240 |
| agcgcgtttt | ttagcgtgaa | cctgaccgcg | cgcaaaccgg | aaaaacgcac | cattcagacc | 300 |
| aacgcgtata | cccgcaaatt | tctgctgaac | agcccgtggc | agccggatct | gtgctgcgtg | 360 |
| tttgcgggcg | cgctgcgcta | tccgcgctat | cgctggtttg | atcgcgtgat | gattcagctg | 420 |
| attatgcgca | ttaccggcgg | cgaaaccgat | agcaccaaag | aaattgaata | taccgattgg | 480 |
| cagcaggtgg | cgcgctttgc | gcaggatttt | gcgcagctgg | cggcgaaaaa | cccggcg | 537 |

<210> SEQ ID NO 127
<211> LENGTH: 537
<212> TYPE: DNA
<213> ORGANISM: Artificial Sequence
<220> FEATURE:
<223> OTHER INFORMATION: Recombinant

<400> SEQUENCE: 127

| | | | | | |
|---|---|---|---|---|---|
| atgaagacct | tgatcctatt | ctccaccagg | gacggccaaa | cacacaagat | cgcaaggcac | 60 |
| atcgcaggag | tcctcgaaga | gcaggggaag | gcctgcgagt | tggtcgatct | gttacagccc | 120 |
| ggcgaaccag | actggagtac | cgttgaatgc | gtcgttctag | ggccagcat | tagatatggt | 180 |
| cacttccata | agtctttcat | caggttcgta | aacactcacg | cgcagcgctt | gaataatatg | 240 |
| ccaggcgccc | ttttcacagt | taacttagtc | gcccgaaagc | ccgagaagca | gagtccacag | 300 |
| acgaactctt | acacccgcaa | gtttctcgcc | gcctcccctt | ggcagccaca | gcgatgccaa | 360 |
| gttttcgcgg | gcgctttgag | gtaccctagg | tactcgtggt | acgacagaat | gatgatacgt | 420 |
| tgataatga | agatggccgg | gggcgagact | gacacaagga | aggaggttga | gtacactgac | 480 |
| tggcagtcgg | tgactcggtt | cgcgagggag | atcgctcagc | tgccgggaga | gacgcgg | 537 |

<210> SEQ ID NO 128
<211> LENGTH: 534
<212> TYPE: DNA
<213> ORGANISM: Artificial Sequence
<220> FEATURE:
<223> OTHER INFORMATION: Recombinant

<400> SEQUENCE: 128

| | | | | | |
|---|---|---|---|---|---|
| atgaaagcgc | tgattctgtt | tagcagccgc | gatggccaga | cccagctgat | tgcgagcagc | 60 |
| attgcgaaag | aactggaagg | caaacaggcg | tgcgatgtgc | tgaacattct | ggataccacc | 120 |
| aacgtggaat | ggaccagta | tgatcgcgtg | ctgattggcg | cgagcattcg | ctatggccat | 180 |
| tttcatccgg | cggtggcgga | atttgtgaaa | cgccatcagc | gcgaactgca | gcagcgcagc | 240 |
| agcggcttt | ttagcgtgaa | cctgaccgcg | cgcaaaccgg | aaaaacgcag | cccggaaacc | 300 |
| aacgcgtata | ccgcgaaatt | tctgaaccag | agcccgtggc | agccggattg | ctgcgcggtg | 360 |
| tttgcgggcg | cgctgcgcta | tccgcgctat | cgctggtttg | atcgcattat | gattcagctg | 420 |

```
attatgcgca tgaccggcgg cgaaaccgat agcagcaaag aagtggaata taccgattgg    480
cagcaggtga cccgctttgc gcaggaattt gcgcgcctgc cgggcaaaac cagc          534

<210> SEQ ID NO 129
<211> LENGTH: 540
<212> TYPE: DNA
<213> ORGANISM: Artificial Sequence
<220> FEATURE:
<223> OTHER INFORMATION: Recombinant

<400> SEQUENCE: 129 atgaaaccc tgattctgtt tagcacccgc gatggccaga cccgcgaaat tgcggcgttt    60
ctggcgagcg aactgaaaga cagggcatt tatgcggatg tgattaacct gaaccgcacc    120
gaagaaattg cgtggcagga atatgatcgc gtggtgattg gcgcgagcat cgctatggc    180 cattttcatc cggcggtgga tcgctttgtg aaaaaacata ccgaaaccct gaacagcctg    240
ccgggcgcgt tttttagcgt gaacctggtg gcgcgcaaag cggaaaaacg caccccgcag    300
accaacagct atacccgcaa atttctgctg aacagcccgt ggaaaccggc ggcgtgcgcg    360
gtgtttgcgg gcgcgctgcg ctatccgcgc tatcgctggt atgatcgctt tatgattcgc    420
ctgattatga aaatgaccgg cggcgaaacc gatacccgca agaagtggt gtataccgat    480 tggagccagg tggcgagctt tgcgcgcgaa attgtgcagc tgacccgcag cagccgcctg    540

<210> SEQ ID NO 130
<211> LENGTH: 531
<212> TYPE: DNA
<213> ORGANISM: Artificial Sequence
<220> FEATURE:
<223> OTHER INFORMATION: Recombinant

<400> SEQUENCE: 130
atgaaaattc tgattctgtt tagcacccgc gatggccaga cccgcgaaat tgcggcgagc    60
ctggcgagcg aactgaaaga acaggcgttt gatgtggatg tggtgaacct gcatcgcgcg    120
gaaaacattg cgtgggaaga atatgatggc gtggtgattg gcgcgagcat tcgctatggc    180
cattttcata gcaccctgaa cagctttgtg aaaaaacatc agcaggcgct gaaaaaactg    240
ccgggcgcgt tttatagcgt gaacctggtg gcgcgcaaac cggaaaaacg caccccgcag    300
accaacagct atacccgcaa atttctgctg gatagcccgt ggcagccgga tctgagcgcg    360
gtgtttgcgg gcgcgctgcg ctatccgcgc tataactggt atgatcgcat tatgattcgc    420
ctgattatga aaattaccgg cggcgaaacc gatacccgca agaagtggt gtataccgat    480 tggcagcagg tgacccattt tgcgcatgaa attgtgcagc tggtgcgcaa a             531

<210> SEQ ID NO 131
<211> LENGTH: 540
<212> TYPE: DNA
<213> ORGANISM: Artificial Sequence
<220> FEATURE:
<223> OTHER INFORMATION: Recombinant

<400> SEQUENCE: 131
atgaaggcct tggtactgta ctcgacgcgg gacggccaga cccacgcaat tgcttcatac    60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
```

```
agcgcgttct tctgcgtaaa cctcacagca aggaagcccg agaagcgtac tccccagaca      300
aacccttatg tccgaaaatt cttgcttgct accccctggc agcccgcgtt gtgcggagtg      360
ttcgcagggg cccttcggta cccgcgatac cggtggatcg acaaggtgat gatccagcta      420
ataatgcgga tgactggggg agagacagac acgagcaagg aggtcgagta cacggattgg      480
gagcaggtta agaagttcgc ggaggatttt gcaaagctat cgtacaagaa ggccctctag      540
```

<210> SEQ ID NO 132
<211> LENGTH: 537
<212> TYPE: DNA
<213> ORGANISM: Artificial Sequence
<220> FEATURE:
<223> OTHER INFORMATION: Recombinant

<400> SEQUENCE: 132

```
atgaaggcct tgatcctgtt ctctacacgc gacggacaga cacagaagat cgcatctgcc       60
atcgctgatg agataaaggg gcagcaatcg tgcgacgtga ttaacataca ggatgccaaa      120
accctcgact ggcagcagta cgaccgggta ctcatcggcg cctccattcg ttacgggcat      180
ttccagcccg ttgtgaatga gtttgtcaag cacaacctct ggccctaca gcagagagtt       240 tccggattct tctccgtgaa cttgacagcc cgaaagccag agaagcggag ccccgagact      300
aacgcttata cagtcaaatt cttggcgcag tcaccctggc aaccggactg ctgcgctgtt      360
tttgcggggg ccctgtacta cccacggtac cggtggttcg ataggagtgat gatacagttc      420 ataatgcgaa tgacgggggg agagaccgac gcatcgaaag aggtggagta cactgactgg      480
cagcaggtgc agcggttcgc gcgagacttc gcgcagttac cgggtaagtc ctactga       537
```

<210> SEQ ID NO 133
<211> LENGTH: 534
<212> TYPE: DNA
<213> ORGANISM: Artificial Sequence
<220> FEATURE:
<223> OTHER INFORMATION: Recombinant

<400> SEQUENCE: 133

```
atgaaggcgc tgatcttgta ctcaaccagg gacggtcaga ctcgcaagat tgcaagtagc       60
attgcggacg tcatcaggca gcagcagcag tgcgacgtct taaacattaa agacgcatca      120
cttcctgact gggcccaata tgaccgagtg ctcatcggag ctagcatccg ttacgggcat      180
ttccagcccg ttgtagacaa gttcgtgaag cagcacttgc acgagcttca gcagcggacc      240
tccggcttct tctccgtgaa cctgacgcg aggaagcctg aaaaaaggag ccctgagacc      300
aatgcctaca cccagaaatt cttggcgcac tccccttggc agcccgattg ctgtgccgtt      360
ttcgcggggg cccttttacta ccccaggtac cgttggttcg accgggtgat gatccagttg      420
attatgcgca tgactggtgg agagaccgac tctaccaagg aagtggagta cactgactgg      480
cagcaggtga gtaccttcgc caacgatttt gcccagcttc aggcaagag ctaa           534
```

<210> SEQ ID NO 134
<211> LENGTH: 546
<212> TYPE: DNA
<213> ORGANISM: Artificial Sequence
<220> FEATURE:
<223> OTHER INFORMATION: Recombinant

<400> SEQUENCE: 134

```
atgaagacct tgattctatt ctccacaagg gacggccaga ctagggagat cgcttcctac       60
ctggccagcg agctaaagga gcttggcatt caggcagacg tggctaacgt gcaccgaatt      120
```

```
gaggagccgc agtgggagaa ctacgatcgg gtcgtgatcg gcgccagcat ccggtatgga      180
cactaccaca gcgcgttcca ggagttcgtg aaaaagcacg cgacccgtct gaatagcatg      240
ccatcagcgt tctactcggt caacctcgtg gctcgtaagc ccgagaagcg gacaccccag      300
accaactcgt atgccaggaa gttccttatg aactcgcagt ggcgaccgga ccgctgcgcg      360
gtgatcgccg gtgcgctcag gtaccctcgt tataggtggt acgacaggtt tatgattaaa      420
cttataatga aaatgagcgg cggagagacc gacaccagaa aagaggtggt ttacacagac      480
tgggagcagg tagcaaactt cgctagggag attgctcacc tcaccgacaa gccgaccttg      540
aagtaa                                                                 546
```

<210> SEQ ID NO 135
<211> LENGTH: 537
<212> TYPE: DNA
<213> ORGANISM: Artificial Sequence
<220> FEATURE:
<223> OTHER INFORMATION: Recombinant

<400> SEQUENCE: 135

```
atgaaggccc ttatactgtt cagttccaga gaaggccaga cgagggagat agcgagttac       60
attgccaact cgataaagga ggaaatggaa tgcgacgtgt tcaacatcct tcgtgtggag      120
cagatcgact ggtctcaata cgaccgcgtc ctgatcgggg gctcgataca ctacggccat      180
ttccacccag cggtggcaaa atttgtcaag aggcacctcc atgagttgca acagaggtct      240
tccggctttt tctgcgtcaa cctgacggcc aggaaggccg acaagcggac tccccagacc      300
aatgcctaca tgagaaagtt cttgttgcag tccccatggc aacccgattg ctgcgccgtg      360
tttgcggggg cccttaggta caccgttac aggtggttcg acagggtaat gattcagctg      420
```

(Note: line 420 may read: tttgcggggg cccttaggta cacccgttac aggtggttcg acagggtaat gattcagctg)

```
atcatgagga tgacgggcgg agagactgac acatcgaagg aggtggagta cacagactgg      480
acgcaggtcg cccgcttcgc gcaggagttc gcccatttgc ccggcaaaac tcagtga        537
```

<210> SEQ ID NO 136
<211> LENGTH: 540
<212> TYPE: DNA
<213> ORGANISM: Artificial Sequence
<220> FEATURE:
<223> OTHER INFORMATION: Recombinant

<400> SEQUENCE: 136

```
atgaaggctc ttatcgtatt ctcttcgagg gatggccaaa cccgagcgat cgcgtcttat       60
attgctaata ccctcaaagg gaccctagag tgcgacgtcg tcaacgtcct caatgctaac      120
gacattgatt tgagccagta cgaccgtgtg gccattggcg cctccattcg ctacgggagg      180
ttccacccag ctgttaacca gtttatccgg aagcacctta cgagcctcca gcagctacca      240
tctgcgttct ctccgtgaa cctcacagct cggaagcccg agaagaggac tatacaaacc      300
aacgcgtaca ctaggaagtt tctactgaac tcgccgtggc agccggacct gtgctgcgtg      360
ttcgcgggag cccttcgcta tccccgttac aggtggtttg accgagtgat gattcaactc      420
ataatgcgca taacgggggg cgagacagac tccaccaagg agatcgagta caccgactgg      480
cagcaggtcg cgcgattcgc ccaggatttt gcacagcttg ccgcaaagaa cccggcatga      540
```

<210> SEQ ID NO 137
<211> LENGTH: 540
<212> TYPE: DNA
<213> ORGANISM: Artificial Sequence
<220> FEATURE:

<223> OTHER INFORMATION: Recombinant

<400> SEQUENCE: 137

```
atgaagacct tgatcctatt ctccaccagg gacggccaaa cacacaagat cgcaaggcac      60
atcgcaggag tcctcgaaga gcaggggaag gcctgcgagt tggtcgatct gttacagccc     120
ggcgaaccag actggagtac cgttgaatgc gtcgttctag gggccagcat tagatatggt     180
cacttccata agtctttcat caggttcgta aacactcacg cgcagcgctt gaataatatg     240
ccaggcgccc ttttcacagt taacttagtc gcccgaaagc ccgagaagca gagtccacag     300
acgaactctt acacccgcaa gtttctcgcc gcctcccctt ggcagccaca gcgatgccaa     360
gttttcgcgg gcgctttgag gtaccctagg tactcgtggt acgacagaat gatgatacgt     420
ttgataatga agatggccgg gggcgagact gacacaagga aggaggttga gtacactgac     480
tggcagtcgg tgactcggtt cgcgagggag atcgctcagc tgccgggaga gacgcggtag     540
```

<210> SEQ ID NO 138
<211> LENGTH: 537
<212> TYPE: DNA
<213> ORGANISM: Artificial Sequence
<220> FEATURE:
<223> OTHER INFORMATION: Recombinant

<400> SEQUENCE: 138

```
atgaaggccc taattttatt cagtagtagg gacggccaga cccagcttat agcatcgtct      60
atcgccaagg agctcgaagg gaagcaggcg tgcgacgtgt tgaatatcct cgacacgact     120
aatgtggagt ggacccagta cgaccgcgtg ctgattggag catccatccg gtacgggcac     180
tttcaccctg cggtcgccga gttcgtaaag cgtcaccagc gagagctaca gcagagaagt     240
agtggctttt tctctgtgaa cttgacggcc cgtaagccgg aaaagaggtc ccccgagact     300
aacgcctata ccgccaagtt ccttaaccaa gtccatggc agcctgactg ttgcgctgtg     360
ttcgctgggg ctttgcgata ccctcggtac cgctggttcg acagaattat gatccagcta     420
atcatgcgga tgactggggg tgagacagat tcttcaaagg aggtcgagta caccgactgg     480
cagcaggtga cccgcttcgc gcaagagttc gccaggcttc cgggaaagac cagttga       537
```

<210> SEQ ID NO 139
<211> LENGTH: 543
<212> TYPE: DNA
<213> ORGANISM: Artificial Sequence
<220> FEATURE:
<223> OTHER INFORMATION: Recombinant

<400> SEQUENCE: 139

```
atgaagaccc taatactgtt ctctacccgc gacgggcaga caagggagat cgccgcgttc      60
cttgcctcgg agctgaagga gcaggggatt tacgctgacg tcataaacct taaccggacg     120
gaggagatag cttggcagga gtatgataga gtcgtaatcg gggcgtcgat ccgatacggg     180
catttccacc ctgctgtcga ccgcttcgtg aagaagcaca cagagacact caactcactg     240
cccggcgcct ttttctctgt aaaccttgtt gcccggaaag ccgagaagag aacgccgcag     300
acgaactcat acaccaggaa gttcctatta aacagcccgt ggaagccagc ggcctgcgcg     360
gtctttgctg gggccctccg ctaccctaga taccgctggt acgacaggtt catgatacga     420
ctgattatga aaatgacagg cggggagacg gatacccgaa aggaggtagt ctacactgac     480
tggtcgcagg tcgcgtcgtt tgccagagag atagtccagt tgaccaggtc atcgcgcttg     540
tga                                                                    543
```

<210> SEQ ID NO 140
<211> LENGTH: 534
<212> TYPE: DNA
<213> ORGANISM: Artificial Sequence
<220> FEATURE:
<223> OTHER INFORMATION: Recombinant

<400> SEQUENCE: 140

```
atgaagatat taatcctttt ctccacccgt gacggccaaa cccgtgagat tgcggcgtcc      60
ttggcgtccg aactcaagga gcaggcattc gacgtggacg tcgtcaacct tcaccgggcc     120
gagaacatcg catgggagga gtacgacggt gttgtcatcg gagcgtccat caggtacggc     180
cactttcata gtaccctgaa ctcatttgtc aagaagcatc agcaggctct taagaagctt     240
cccggggctt tctacagcgt gaacctcgtc gcccggaagc ctgagaagcg cacaccgcag     300
accaatagct acacccgcaa gttcctcttg gattccccgt ggcagcccga cctttcagcc     360
gtgttcgccg gggcactcag gtaccctcgg tacaattggt acgaccgtat catgattaga     420
cttatcatga agattacagg cggcgagact gataccagga aggaagtagt ctacacagac     480
tggcagcagg tcactcactt tgctcacgag atcgtccagc tcgtgcggaa gtag           534
```

<210> SEQ ID NO 141
<211> LENGTH: 537
<212> TYPE: DNA
<213> ORGANISM: Artificial Sequence
<220> FEATURE:
<223> OTHER INFORMATION: Recombinant

<400> SEQUENCE: 141

```
aaggccttgg tactgtactc gacgcgggac ggccagaccc acgcaattgc ttcatacatc      60
gcctcctgca tgaaggagaa ggccgaatgc gacgtgatcg acctcaccca cggggagcac     120
gtgaacctca cccaatacga tcaggtgcta atcggtgcga gtattcgtta cggccacttc     180
aacgccgtgc ttgacaagtt catcaagaga aacgtggatc agctgaacaa catgccaagc     240
gcgttcttct gcgtaaacct cacagcaagg aagcccgaga gcgtactccc cagacaaac     300 ccttatgtcc gaaaattctt gcttgctacc ccctggcagc ccgcgttgtg cggagtgttc     360
gcagggggcc ttcggtaccc gcgataccgg tggatcgaca aggtgatgat ccagctaata     420
atgcggatga ctgggggaga gacagacacg agcaaggagg tcgagtacac ggattgggag     480
caggttaaga agttcgcgga ggattttgca aagctatcgt acaagaaggc cctctag        537
```

<210> SEQ ID NO 142
<211> LENGTH: 534
<212> TYPE: DNA
<213> ORGANISM: Artificial Sequence
<220> FEATURE:
<223> OTHER INFORMATION: Recombinant

<400> SEQUENCE: 142

```
aaggccttga tcctgttctc tacacgcgac ggacagacac agaagatcgc atctgccatc      60
gctgatgaga taaaggggca gcaatcgtgc gacgtgatta acatacagga tgccaaaacc     120
ctcgactggc agcagtacga ccgggtactc atcggcgcct ccattcgtta cgggcatttc     180
cagcccgttg tgaatgagtt tgtcaagcac aacctcttgg ccctacagca gagagtttcc     240
ggattcttct ccgtgaactt gacagcccga aagccagaga gcggagccc cgagactaac     300 gcttatacag tcaaattctt ggcgcagtca ccctggcaac cggactgctg cgctgttttt     360
```

```
gcgggggccc tgtactaccc acggtaccgg tggttcgata gggtgatgat acagttcata    420
atgcgaatga cggggggaga gaccgacgca tcgaaagagg tggagtacac tgactggcag    480
caggtgcagc ggttcgcgcg agacttcgcg cagttaccgg gtaagtccta ctga          534
```

<210> SEQ ID NO 143
<211> LENGTH: 543
<212> TYPE: DNA
<213> ORGANISM: Artificial Sequence
<220> FEATURE:
<223> OTHER INFORMATION: Recombinant

<400> SEQUENCE: 143

```
aagaccttga ttctattctc cacaagggac ggccagacta gggagatcgc ttcctacctg    60
gccagcgagc taaaggagct tggcattcag gcagacgtgg ctaacgtgca ccgaattgag   120
gagccgcagt gggagaacta cgatcgggtc gtgatcggcg ccagcatccg gtatggacac   180
taccacagcg cgttccagga gttcgtgaaa aagcacgcga cccgtctgaa tagcatgcca   240
tcagcgttct actcggtcaa cctcgtggct cgtaagcccg agaagcggac accccagacc   300
aactcgtatg ccaggaagtt ccttatgaac tcgcagtggc gaccggaccg ctgcgcggtg   360
atcgccggtc gctcaggta ccctcgttat aggtggtacg acaggtttat gattaaactt    420
ataatgaaaa tgagcggcgg agagaccgac accagaaaag aggtggttta cacagactgg   480
gagcaggtag caaacttcgc tagggagatt gctcacctca ccgacaagcc gaccttgaag   540
taa                                                                 543
```

<210> SEQ ID NO 144
<211> LENGTH: 534
<212> TYPE: DNA
<213> ORGANISM: Artificial Sequence
<220> FEATURE:
<223> OTHER INFORMATION: Recombinant

<400> SEQUENCE: 144

```
aaggcccta tactgttcag ttccagagaa ggccagacga gggagatagc gagttacatt     60
gccaactcga taaaggagga aatggaatgc gacgtgttca acatccttcg tgtggagcag   120
atcgactggt ctcaatacga ccgcgtcctg atcgggggct cgatacacta cggccatttc   180
cacccagcgg tggcaaaatt tgtcaagagg cacctccatg agttgcaaca gaggtcttcc   240 ggcttttttct gcgtcaacct gacggccagg aaggccgaca agcggactcc ccagaccaat   300
gcctacatga gaaagttctt gttgcagtcc ccatggcaac ccgattgctg cgccgtgttt   360
gcgggggccc ttaggtacac ccgttacagg tggttcgaca gggtaatgat tcagctgatc   420
atgaggatga cgggcggaga gactgacaca tcgaaggagg tggagtacac agactggacg   480
caggtcgccc gcttcgcgca ggagttcgcc catttgcccg gcaaaactca gtga          534
```

<210> SEQ ID NO 145
<211> LENGTH: 537
<212> TYPE: DNA
<213> ORGANISM: Artificial Sequence
<220> FEATURE:
<223> OTHER INFORMATION: Recombinant

<400> SEQUENCE: 145

```
aaggctctta tcgtattctc ttcgagggat ggccaaaccc gagcgatcgc gtcttatatt     60
gctaataccc tcaaagggac cctagagtgc gacgtcgtca acgtcctcaa tgctaacgac   120
attgatttga gccagtacga ccgtgtggcc attggcgcct ccattcgcta cgggaggttc   180
```

-continued

```
cacccagctg ttaaccagtt tatccggaag caccttacga gcctccagca gctaccatct    240
gcgttcttct ccgtgaacct cacagctcgg aagcccgaga agaggactat acaaaccaac    300
gcgtacacta ggaagtttct actgaactcg ccgtggcagc cggacctgtg ctgcgtgttc    360
gcgggagccc ttcgctatcc ccgttacagg tggtttgacc gagtgatgat tcaactcata    420
atgcgcataa cggggggcga gacagactcc accaaggaga tcgagtacac cgactggcag    480
caggtcgcgc gattcgccca ggattttgca cagcttgccg caaagaaccc ggcatga      537
```

<210> SEQ ID NO 146
<211> LENGTH: 537
<212> TYPE: DNA
<213> ORGANISM: Artificial Sequence
<220> FEATURE:
<223> OTHER INFORMATION: Recombinant

<400> SEQUENCE: 146

```
aagaccttga tcctattctc caccagggac ggccaaacac acaagatcgc aaggcacatc     60
gcaggagtcc tcgaagagca ggggaaggcc tgcgagttgg tcgatctgtt acagcccggc    120
gaaccagact ggagtaccgt tgaatgcgtc gttctagggg ccagcattag atatggtcac    180
ttccataagt ctttcatcag gttcgtaaac actcacgcgc agcgcttgaa taatatgcca    240
ggcgcccttt tcacagttaa cttagtcgcc cgaaagcccg agaagcagag tccacagacg    300
aactcttaca cccgcaagtt tctcgccgcc tcccttggc agccacagcg atgccaagtt     360
ttcgcgggcg ctttgaggta ccctaggtac tcgtggtacg acagaatgat gatacgtttg    420
ataatgaaga tggccggggg cgagactgac acaaggaagg aggttgagta cactgactgg    480
cagtcggtga ctcggttcgc gagggagatc gctcagctgc cgggagagac gcggtag       537
```

<210> SEQ ID NO 147
<211> LENGTH: 540
<212> TYPE: DNA
<213> ORGANISM: Artificial Sequence
<220> FEATURE:
<223> OTHER INFORMATION: Recombinant

<400> SEQUENCE: 147

```
aagaccctaa tactgttctc tacccgcgac gggcagacaa gggagatcgc cgcgttcctt     60
gcctcggagc tgaaggagca ggggatttac gctgacgtca taaaccttaa ccggacggag    120
gagatagctt ggcaggagta tgatagagtc gtaatcgggg cgtcgatccg atacgggcat    180
ttccaccctg ctgtcgaccg cttcgtgaag aagcacacag agacactcaa ctcactgccc    240
ggcgcctttt tctctgtaaa ccttgttgcc cggaaagccg agaagagaac gccgcagacg    300
aactcataca ccaggaagtt cctattaaac agcccgtgga agccagcggc ctgcgcggtc    360
tttgctgggg ccctccgcta ccctagatac cgctggtacg acaggttcat gatacgactg    420
attatgaaaa tgacaggcgg ggagacggat acccgaaagg aggtagtcta cactgactgg    480
tcgcaggtcg cgtcgtttgc cagagagata gtccagttga ccaggtcatc gcgcttgtga    540
```

<210> SEQ ID NO 148
<211> LENGTH: 537
<212> TYPE: DNA
<213> ORGANISM: Artificial Sequence
<220> FEATURE:
<223> OTHER INFORMATION: Recombinant

<400> SEQUENCE: 148

```
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga gtattcgtta cggccacttc   180
aacgccgtgc ttgacaagtt catcaagaga aacgtggatc agctgaacaa catgccaagc   240
gcgttcttct gcgtaaacct cacggcaagg aagcccgaga agcgtactcc ccagacaaac   300
ccttatgtcc gaaaattctt gcttgctacc ccctggcagc ccgcgttgtg cggagtgttc   360 gcagggggccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatcgt acaagaaggc cctctag      537
```

<210> SEQ ID NO 149
<211> LENGTH: 537
<212> TYPE: DNA
<213> ORGANISM: Artificial Sequence
<220> FEATURE:
<223> OTHER INFORMATION: Recombinant

<400> SEQUENCE: 149

```
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga atattcgtta cggccacttc   180
aacgccgtgc ttgacaagtt catcaagaga aacgtggatc agctgaacaa catgccaagc   240
gcgttcttct gcgtaaacct cacagcaagg aagcccgaga agcgtactcc ccagacaaac   300
ccttatgtcc gaaaattctt gcttgctacc ccctggcagc ccgcgttgtg cggagtgttc   360 gcagggggccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatcgt acaagaaggc cctctag      537
```

<210> SEQ ID NO 150
<211> LENGTH: 537
<212> TYPE: DNA
<213> ORGANISM: Artificial Sequence
<220> FEATURE:
<223> OTHER INFORMATION: Recombinant

<400> SEQUENCE: 150

```
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga gtattcgtta cggccacttc   180
aacgccgtgc ttgacaagtt catcaagaga aacgtggatc agctgaacaa catgccaagc   240
gcgttcttct gcgtaaacct cacagcaagg aagcccgaga agcgtactcc ccagacaaac   300
ccttatgtcc gaaaattctt gcttgctacc ccctggcagc ccgcgttgtg cggagtgttc   360 gcagggggccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatagt acaagaaggc cctctag      537
```

<210> SEQ ID NO 151
<211> LENGTH: 534
<212> TYPE: DNA
<213> ORGANISM: Artificial Sequence

```
<220> FEATURE:
<223> OTHER INFORMATION: Recombinant

<400> SEQUENCE: 151
aaggccttga tcctgttctc tacacgcgac ggacagacac agaagatcgc atctgccatc        60
gctgatgaga taaaggggca gcaatcgtgc gacgtgatta acatacagga tgccaaaacc       120
ctcgactggc agcagtacga ccgggtactc atcggcgcct ccattcgtta cgggcatttc       180
cagcccgttg tgaatgagtt tgtcaagcac aacctcttgg ccctacagca gagagtttcc       240
ggattcttct ccgtgaactt gacagcccga agccagaga agcggagccc cgagactaac        300
gcttatacag tcaaattctt ggcgcagtca ccctggcaac cggactgctg cgctgttttt       360
gcgggggccc tgtactaccc acggtaccgg tggttcgata gggtgatgat acagttcata       420
atgcgaatga cggggggggga gaccgacgca tcgaaagagg tggagtacac tgactggcag       480
caggtgcagc ggttcgcgcg agacttcgcg cagttaccgg gtaagtccta ctga            534

<210> SEQ ID NO 152
<211> LENGTH: 540
<212> TYPE: DNA
<213> ORGANISM: Artificial Sequence
<220> FEATURE:
<223> OTHER INFORMATION: Recombinant

<400> SEQUENCE: 152
aagaccctaa tactgttctc tacccgcgac gggcagacaa gggagatcgc cgcgttcctt        60
gcctcggagc tgaaggagca ggggatttac gctgacgtca taaaccttaa ccggacggag       120
gagatagctt ggcaggagta tgatagagtc gtaatcgggg cgtcgatccg atacgggcat       180
ttccaccctg ctgtcgaccg cttcgtgaag aagcacacag agacactcaa ctcactgccc       240
ggcgcctttt tctctgtaaa ccttgttgcc cggaaagccg agaagagaac gccgcagacg       300
aactcataca ccaggaagtt cctattaaac agcccgtgga agccagcggc ctgcgcggtc       360
tttgctgggg ccctccgcta ccctagatac cgctggtacg acaggttcat gatacgactg       420
attatgaaaa tgacaggcgg ggagacggat acccgaaagg aggtagtcta cactgactgg       480
tcgcagatcg cgtcgtttgc cagagagata gtccagttga ccaggtcatc gcgcttgtga       540

<210> SEQ ID NO 153
<211> LENGTH: 540
<212> TYPE: DNA
<213> ORGANISM: Artificial Sequence
<220> FEATURE:
<223> OTHER INFORMATION: Recombinant

<400> SEQUENCE: 153
atgaaggcgc tcgtgctcta cagcacacgc gacggccaga ctcatgcgat cgcctcttac        60
atcgcgtcct gtatgaagga gaaggccgag tgcgacgtca tcgatctcac gcacggggag       120
cacgtgaatc ttacgcagta cgaccaagtg ctgataggcg cctctatccg ttacggccat       180
tttaacgccg tcctcgacaa attcatcaag cgcaatgtag accagctgaa caacatgccc       240
tccgcgttct tttgcgtgaa cctgacggct cggaagcctg agaagcgaac acctcagacc       300
aacccatacg tgcggaaatt cctactcgca acgccatggc agcccgccct gtgcggggtt       360
ttcgcagggg cgctacgcta tccgcgttac cgctggatcg ataaggtgat gatccagcta       420
ataatgcgca tgaccggcgg cgagacagac acatcgaagg aagtcgaata cacagactgg       480
gaacaggtga agaagtttgc agaggatttc gccaagctct catacaaaaa ggcattgtga       540
```

<210> SEQ ID NO 154
<211> LENGTH: 537
<212> TYPE: DNA
<213> ORGANISM: Artificial Sequence
<220> FEATURE:
<223> OTHER INFORMATION: Recombinant

<400> SEQUENCE: 154

```
atgaaggcgc ttatactgtt ctcgacacgc gacggtcaga cgcagaaaat cgcctcagcc    60
atcgccgacg agatcaaggg ccagcagagc tgcgatgtga tcaatattca ggacgccaaa   120
actctcgact ggcagcagta tgaccgcgtg ctcattggcg catcaatccg ctacgggcat   180
ttccagccag tcgtcaatga gtttgtgaaa cataacctct ggcattgca gcagcgggtg    240
tctggcttct tctccgtgaa ccttacagct agaaaaccag agaagcgtc gcccgagact    300
aacgcctaca ccgttaagtt ccttgcgcag tcaccgtggc agcctgattg ctgcgcggtc   360
ttcgccgggg cactgtacta ccctcgatac cggtggtttg atagggtaat gatccagttc   420
ataatgcgca tgaccggtgg ggagaccgac gcaagtaaaa aagttgagta cacggattgg   480
cagcaggtgc aaaggttcgc acgcgacttc gcgcagctcc cgggcaagtc ttactga      537
```

<210> SEQ ID NO 155
<211> LENGTH: 534
<212> TYPE: DNA
<213> ORGANISM: Artificial Sequence
<220> FEATURE:
<223> OTHER INFORMATION: Recombinant

<400> SEQUENCE: 155

```
atgaaagccc tgatcctcta ttccaccagg gacggccaga cccgcaagat agcctcctcc    60
atcgctgatg tcatccgcca gcagcagcag tgcgacgttt taaacattaa ggacgcttca   120
ctgcctgatt gggcccagta tgaccgcgtc ctgatcggcg cgtcgattcg gtacggccac   180
ttccagcctg tggttgacaa gttcgtcaag cagcacctgc atgagctgca gcagcgaact   240
agcgggttct tcagtgtgaa cctgacagct agaaagcccg aaaagagatc cccagaaacc   300
aacgcctata cgcagaaatt ccttgctcac tcacctggc agcctgactg ttgtgccgtc    360
ttcgcgggcg ccttgtacta tccccgctac cgctggttcg atagggtgat gatccagctg   420
attatgagaa tgacgggagg ggagaccgat cgaccaagg aggtagagta cactgactgg    480
caacaggtgt caactttcgc aaacgacttc gcacaactac ccggtaagtc ttga         534
```

<210> SEQ ID NO 156
<211> LENGTH: 546
<212> TYPE: DNA
<213> ORGANISM: Artificial Sequence
<220> FEATURE:
<223> OTHER INFORMATION: Recombinant

<400> SEQUENCE: 156

```
atgaaaaccc taatactgtt ctcgacccgc gacggccaga cgcgtgagat tgcgagctac    60
ctggcctccg agctcaagga gctggggatc caagccgatg tcgcgaacgt gcaccgcatt   120
gaggagccgc agtgggagaa ttacgatcgc gttgtgatag ggccagcat ccgctatggc     180
cactaccact cggcctttca ggagtttgta aagaaacacg ccacaagatt aaactccatg   240
cctagcgcct tctactccgt caaccttgtc gcgcgcaagc cggagaagcg gacacctcag   300
acgaactcct acgcgcggaa gttcctgatg aacagccagt ggcggccgga cagatgtgct   360
gttattgcgg gagccctgag ataccccgagg taccggtggt acgataggtt tatgattaaa   420
```

| | |
|---|---|
| cttattatga agatgtctgg tggggagact gacaccagga aggaggtggt atatacagac | 480 |
| tgggagcagg tcgccaattt cgctcgggaa atcgcgcatc tgacagacaa gcctacactg | 540 |
| aagtag | 546 |

<210> SEQ ID NO 157
<211> LENGTH: 537
<212> TYPE: DNA
<213> ORGANISM: Artificial Sequence
<220> FEATURE:
<223> OTHER INFORMATION: Recombinant

<400> SEQUENCE: 157

| | |
|---|---|
| atgaaggccc tgatcctctt tagctctagg gagggccaga cccgcgagat cgcgtcatat | 60 |
| atcgcgaatt ccataaagga ggagatggag tgcgatgtgt taacatcct tagggtggag | 120 |
| caaatagact ggtctcagta tgaccgtgtg ctcataggg ggagcatcca ctacggccac | 180 |
| tttcacccgg ccgtggcgaa attcgtcaag cgacacctcc acgagcttca gcagcgctcc | 240 |
| tcagggttct tctgcgtcaa cctgacagca agaaaggcag ataaacgcac cccgcagacg | 300 |
| aacgcctaca tgaggaagtt ccttctgcag tctccttggc agcccgattg ctgcgcggtg | 360 |
| ttcgccggtg cactgcgcta tacgcgctat agatggtttg atagagtcat gattcagctc | 420 |
| atcatgcgga tgaccggcgg ggaaacggat actagtaagg aggtggagta cacggactgg | 480 |
| acccaggtgg cacgtttcgc ccaggagttt gcacatcttc ctgggaagac ccaatga | 537 |

<210> SEQ ID NO 158
<211> LENGTH: 540
<212> TYPE: DNA
<213> ORGANISM: Artificial Sequence
<220> FEATURE:
<223> OTHER INFORMATION: Recombinant

<400> SEQUENCE: 158

| | |
|---|---|
| atgaaggcgc taattgtgtt cagctccagg gatggccaga cgagggctat agcatcctat | 60 |
| atcgccaata ccttgaaagg aacgctcgag tgtgacgtgg tcaacgtctt gaacgccaat | 120 |
| gacattgacc tttcccagta cgaccgagtt gccataggcg cgtcgatccg ctacgggcga | 180 |
| tttcaccctg cagtcaacca gtttatacgg aagcatttga cctcgctgca gcagctcccg | 240 |
| tcagccttct tctctgtgaa tttaaccgcg cggaagcctg agaaacggac gatccaaaca | 300 |
| aacgcctata cccgaaagtt cctcctgaac agcccatggc agccagacct gtgctgtgtc | 360 |
| ttcgccggcg cgttgcggta tccccgctac aggtggttcg atagagtgat gatccagctc | 420 |
| atcatgagga tcaccggggg agagaccgat agtaccaagg agatcgagta cacggactgg | 480 |
| cagcaggtgg ctcgcttcgc ccaggacttc gctcagttgg ccgcaaagaa tccagcataa | 540 |

<210> SEQ ID NO 159
<211> LENGTH: 540
<212> TYPE: DNA
<213> ORGANISM: Artificial Sequence
<220> FEATURE:
<223> OTHER INFORMATION: Recombinant

<400> SEQUENCE: 159

| | |
|---|---|
| atgaagacac tgatcctgtt ctcgactcga gatggccaga ctcataaaat tgcgcgccac | 60 |
| attgcggggg tcctggagga gcagggcaaa gcgtgcgagc tcgtggactt actccagccc | 120 |
| ggggagccgg actggagcac ggtggagtgc gtcgttctgg gcgcttccat acgttacggg | 180 |

```
catttccaca aaagtttcat ccggttcgtc aacacccacg ctcaacggct gaacaacatg        240
cctggcgcgc tattcactgt taacttagtg gctcgtaagc ccgagaagca gtctccgcag        300
actaactcct acacaaggaa atttctagca gcaagcccat ggcaaccgca gcggtgccag        360
gtgttcgctg gagctctgcg ctatcctagg tacagttggt acgacagaat gatgatacgg        420
ttgattatga agatggcagg cggggagacg gacaccagga aagaggtcga atacactgac        480
tggcaatcag tcactcggtt tgctagagag atcgcgcaat taccaggtga gacgcggtaa        540
```

<210> SEQ ID NO 160
<211> LENGTH: 537
<212> TYPE: DNA
<213> ORGANISM: Artificial Sequence
<220> FEATURE:
<223> OTHER INFORMATION: Recombinant

<400> SEQUENCE: 160

```
atgaaggctc tcatactgtt cagctcgaga gacgggcaga cccagctgat cgcctcctcc         60
atagcaaagg agctagaggg caagcaagcc tgcgacgtgc tcaatattct cgacacaacc        120
aacgtggagt ggactcagta cgacagagtc ctaatcggcg cgtccatcag atacggccac        180
ttccatcccg ccgtcgctga attcgtgaaa cgccaccagc gtgagctcca gcagcgcagc        240
agcggcttct tcagcgtgaa tcttactgcg agaaagccgg aaaagcggag tcccgagact        300
aacgcttata cggcaaagtt cctcaaccaa tctccctggc aaccagactg ctgtgccgtg        360
ttcgctgggg cactgaggta tccgcgctat cggtggttcg atagaatcat gatacagctg        420
ataatgcgta tgactggtgg ggagacggat tccagtaaag aggtagagta tactgattgg        480
cagcaggtca ctaggttcgc gcaggagttt gctaggctgc cgggcaagac atcctga           537
```

<210> SEQ ID NO 161
<211> LENGTH: 543
<212> TYPE: DNA
<213> ORGANISM: Artificial Sequence
<220> FEATURE:
<223> OTHER INFORMATION: Recombinant

<400> SEQUENCE: 161

```
atgaaaacct taatcttgtt cagcacccgc gacggccaga cgcgtgaaat cgcagcgttc         60
ctcgcttcgg agctcaagga acagggaatt tacgccgacg tcattaacct aaaccgtacc        120
gaagagattg cgtggcagga gtatgaccgc gtggtgattg gcgcttctat ccgctatggc        180
cacttccacc cggctgttga ccggttcgtg aagaagcaca cggagacctt gaactcactg        240
ccgggggcat tctttagcgt aaatctggtg gcgcgcaagg ccgagaagcg cacccccag        300 acgaacagct acacccgcaa attttactt aactccccat ggaaacctgc ggcctgcgca        360
gtgttcgcag gagctctccg ctatcctcgc tatcgatggt acgatcggtt catgattcgg        420
ctgattatga aaatgacggg cggcgagacg gatacgcgaa aggaagttgt ctacactgac        480
tggtcccagg tggcctcgtt tgcaagggag atcgtacagc tcactcgatc tagtaggctc        540
tga                                                                      543
```

<210> SEQ ID NO 162
<211> LENGTH: 534
<212> TYPE: DNA
<213> ORGANISM: Artificial Sequence
<220> FEATURE:
<223> OTHER INFORMATION: Recombinant

<400> SEQUENCE: 162

```
atgaagattc tcatcttatt ttccacccga gacggccaaa cccgcgagat tgcggcgtcc     60
ctcgcctccg agttgaagga gcaggcgttt gatgtggatg tggtcaacct ccaccgcgca    120
gaaaacatag cgtgggagga gtacgatggg gtcgtcatcg gagcgtcaat ccgctacgga    180
catttccact caacgctgaa ttcatttgtg aagaagcacc aacaagcgct caagaagctg    240
cccggagcat tctacagcgt caacctcgtg gctcggaagc cggaaaagcg caccccgcaa    300
acaaacagct acacacgcaa gtttctgctc gactcgccct ggcaacccga cctgagtgcc    360
gttttcgccg gggcactgcg ctatccccgt tacaactggt acgatcgcat aatgattcga    420
ctgatcatga agattacagg cggggaaacc gatactcgga aggaggtggt gtatacagac    480
tggcagcagg ttacccactt cgcccacgag atcgtccagc tcgttcgtaa gtga          534
```

```

<210> SEQ ID NO 163
<211> LENGTH: 442
<212> TYPE: PRT
<213> ORGANISM: Xanthomonas campestris
<400> SEQUENCE: 163

Met Gln Thr Gln Pro Val Ile Ile Ala Gly Ala Gly Ile Ala Gly Leu
1               5                   10                  15

Ser Ile Ala Tyr Glu Leu Gln Gln Lys Gly Ile Pro Tyr Glu Ile Met
            20                  25                  30

Glu Ala Ser Ser Tyr Ala Gly Gly Val Val Lys Ser Leu His Ile Asp
        35                  40                  45

Gly Tyr Glu Leu Asp Ala Gly Pro Asn Ser Leu Ala Ala Ser Ala Ala
    50                  55                  60

Phe Met Ala Tyr Ile Asp Gln Leu Gly Leu Gln Asp Gln Val Leu Glu
65                  70                  75                  80

Ala Ala Ala Ala Ser Lys Asn Arg Phe Leu Val Arg Asn Asp Lys Leu
                85                  90                  95

His Ala Val Ser Pro His Pro Phe Lys Ile Leu Gln Ser Ala Tyr Ile
            100                 105                 110

Ser Gly Gly Ala Lys Trp Arg Leu Phe Thr Glu Arg Phe Arg Lys Ala
        115                 120                 125

Ala Ala Pro Glu Gly Glu Glu Thr Val Ser Ser Phe Val Thr Arg Arg
    130                 135                 140

Phe Gly Lys Glu Ile Asn Asp Tyr Leu Phe Glu Pro Val Leu Ser Gly
145                 150                 155                 160

Ile Tyr Ala Gly Asn Pro Asp Leu Met Ser Val Gly Glu Val Leu Pro
                165                 170                 175

Met Leu Pro Gln Trp Glu Gln Lys Tyr Gly Ser Val Thr Gln Gly Leu
            180                 185                 190

Leu Lys Asn Lys Gly Ala Met Gly Gly Arg Lys Ile Ile Ala Phe Lys
        195                 200                 205

Gly Gly Asn Ala Thr Leu Thr Asn Arg Leu Gln Ser Leu Leu Ser Gly
    210                 215                 220

Lys Ile Arg Phe Asn Cys Ala Val Thr Gly Val Thr Arg Gly Ala Asp
225                 230                 235                 240

Asp Tyr Ile Val Gln Tyr Thr Glu Asn Gly Asn Thr Ala Met Leu Asn
                245                 250                 255

Ala Ser Arg Val Ile Phe Thr Thr Pro Ala Tyr Ser Thr Ala Val Ala
            260                 265                 270

Ile Gln Ala Leu Asp Ala Ser Leu Ala Thr His Leu Ser Asp Val Pro
```

```
            275                 280                 285
Tyr Pro Arg Met Gly Val Leu His Leu Gly Phe Gly Ala Glu Ala Arg
290                 295                 300

Gln Lys Ala Pro Ala Gly Phe Gly Phe Leu Val Pro His Ala Ala Gly
305                 310                 315                 320

Lys His Phe Leu Gly Ala Ile Cys Asn Ser Ala Ile Phe Pro Ser Arg
                325                 330                 335

Val Pro Thr Gly Lys Val Leu Phe Thr Val Phe Leu Gly Gly Ala Arg
                340                 345                 350

Gln Glu Gln Leu Phe Asp Gln Leu Gly Pro Glu Lys Leu Gln Gln Thr
                355                 360                 365

Val Val Lys Glu Leu Met Glu Leu Leu Gly Leu Thr Thr Pro Pro Glu
370                 375                 380

Met Gln Arg Phe Ser Glu Trp Asn Arg Ala Ile Pro Gln Leu Asn Val
385                 390                 395                 400

Gly Tyr Ala Gln Thr Arg Gln Gln Ile Gly Val Phe Glu Gln Arg Tyr
                405                 410                 415

Pro Gly Ile Arg Leu Ala Gly Asn Tyr Val Thr Gly Val Ala Val Pro
                420                 425                 430

Ala Ile Ile Gln Ala Ala Lys Gly Tyr Cys
                435                 440
```

<210> SEQ ID NO 164
<211> LENGTH: 439
<212> TYPE: PRT
<213> ORGANISM: Xanthomonas campestris

<400> SEQUENCE: 164

```
Gln Pro Val Ile Ile Ala Gly Ala Gly Ile Ala Gly Leu Ser Ile Ala
1               5                   10                  15

Tyr Glu Leu Gln Gln Lys Gly Ile Pro Tyr Glu Ile Met Glu Ala Ser
                20                  25                  30

Ser Tyr Ala Gly Gly Val Val Lys Ser Leu His Ile Asp Gly Tyr Glu
            35                  40                  45

Leu Asp Ala Gly Pro Asn Ser Leu Ala Ala Ser Ala Ala Phe Met Ala
    50                  55                  60

Tyr Ile Asp Gln Leu Gly Leu Gln Asp Gln Val Leu Glu Ala Ala Ala
65                  70                  75                  80

Ala Ser Lys Asn Arg Phe Leu Val Arg Asn Asp Lys Leu His Ala Val
                85                  90                  95

Ser Pro His Pro Phe Lys Ile Leu Gln Ser Ala Tyr Ile Ser Gly Gly
            100                 105                 110

Ala Lys Trp Arg Leu Phe Thr Glu Arg Phe Arg Lys Ala Ala Ala Pro
        115                 120                 125

Glu Gly Glu Glu Thr Val Ser Ser Phe Val Thr Arg Arg Phe Gly Lys
    130                 135                 140

Glu Ile Asn Asp Tyr Leu Phe Glu Pro Val Leu Ser Gly Ile Tyr Ala
145                 150                 155                 160

Gly Asn Pro Asp Leu Met Ser Val Gly Glu Val Leu Pro Met Leu Pro
                165                 170                 175

Gln Trp Glu Gln Lys Tyr Gly Ser Val Thr Gln Gly Leu Leu Lys Asn
            180                 185                 190

Lys Gly Ala Met Gly Gly Arg Lys Ile Ile Ala Phe Lys Gly Gly Asn
        195                 200                 205
```

```
Ala Thr Leu Thr Asn Arg Leu Gln Ser Leu Leu Ser Gly Lys Ile Arg
    210                 215                 220

Phe Asn Cys Ala Val Thr Gly Val Thr Arg Gly Ala Asp Asp Tyr Ile
225                 230                 235                 240

Val Gln Tyr Thr Glu Asn Gly Asn Thr Ala Met Leu Asn Ala Ser Arg
                245                 250                 255

Val Ile Phe Thr Thr Pro Ala Tyr Ser Thr Ala Val Ala Ile Gln Ala
                260                 265                 270

Leu Asp Ala Ser Leu Ala Thr His Leu Ser Asp Val Pro Tyr Pro Arg
                275                 280                 285

Met Gly Val Leu His Leu Gly Phe Gly Ala Glu Ala Arg Gln Lys Ala
    290                 295                 300

Pro Ala Gly Phe Gly Phe Leu Val Pro His Ala Ala Gly Lys His Phe
305                 310                 315                 320

Leu Gly Ala Ile Cys Asn Ser Ala Ile Phe Pro Ser Arg Val Pro Thr
                325                 330                 335

Gly Lys Val Leu Phe Thr Val Phe Leu Gly Gly Ala Arg Gln Glu Gln
                340                 345                 350

Leu Phe Asp Gln Leu Gly Pro Glu Lys Leu Gln Gln Thr Val Val Lys
                355                 360                 365

Glu Leu Met Glu Leu Leu Gly Leu Thr Thr Pro Pro Glu Met Gln Arg
    370                 375                 380

Phe Ser Glu Trp Asn Arg Ala Ile Pro Gln Leu Asn Val Gly Tyr Ala
385                 390                 395                 400

Gln Thr Arg Gln Gln Ile Gly Val Phe Glu Gln Arg Tyr Pro Gly Ile
                405                 410                 415

Arg Leu Ala Gly Asn Tyr Val Thr Gly Val Ala Val Pro Ala Ile Ile
                420                 425                 430

Gln Ala Ala Lys Gly Tyr Cys
                435

<210> SEQ ID NO 165
<211> LENGTH: 448
<212> TYPE: PRT
<213> ORGANISM: Chitinophaga pinensis

<400> SEQUENCE: 165

Met Ser Asp Gln Pro Val Leu Ile Val Gly Ala Gly Leu Ser Gly Leu
1               5                   10                  15

Ser Ile Ala Tyr Glu Leu Gln Lys Leu Gln Val Pro Tyr Gln Val Leu
                20                  25                  30

Glu Val Ser Gly His Ser Gly Gly Val Met Lys Ser Leu Arg Lys Asp
            35                  40                  45

Gly Phe Glu Leu Asp Ala Gly Ala Asn Thr Ile Ala Ala Ser Pro Glu
        50                  55                  60

Ile Leu Ala Tyr Phe Thr Ser Leu Gly Leu Glu Asn Glu Ile Leu Gln
65                  70                  75                  80

Ala Thr Ala Ala Ser Lys His Arg Phe Leu Val Arg Arg Gln Leu
                85                  90                  95

His Ala Val Ser Pro His Pro Phe Lys Ile Met Ser Ser Pro Tyr Leu
                100                 105                 110

Ser Arg Gly Ser Lys Trp Arg Leu Phe Thr Glu Arg Phe Arg Lys Pro
            115                 120                 125

Val Val Ala Ser Gly Glu Glu Thr Val Thr Asp Phe Ile Thr Arg Arg
        130                 135                 140
```

```
Phe Asn Arg Glu Ile Ala Glu Tyr Val Phe Asp Pro Val Leu Ser Gly
145                 150                 155                 160

Ile Tyr Ala Gly Asn Pro Asp Gln Met Ser Ile Ala Glu Val Leu Pro
            165                 170                 175

Ala Leu Pro Arg Trp Glu Arg Glu Tyr Gly Ser Val Thr Lys Gly Leu
        180                 185                 190

Met Lys Asp Lys Gly Ala Met Gly Gly Arg Lys Ile Ile Ser Phe Lys
            195                 200                 205

Gly Gly Asn Gln Leu Leu Thr Asn Arg Leu Gln Gln Leu Leu Thr Thr
        210                 215                 220

Pro Val Arg Phe Asn Cys Lys Val Thr Gly Ile Thr Ala Ser Asn Gly
225                 230                 235                 240

Gly Tyr Ile Val Ser Ala Val Glu Asp Gly Val Ser Glu Ser Tyr Thr
            245                 250                 255

Ala Ser Arg Val Ile Leu Thr Thr Pro Ala Tyr Ser Ala Ala Ala Thr
        260                 265                 270

Ile Thr Asn Leu Asp Ala Ala Thr Ala Ala Leu Leu Asn Glu Ile His
            275                 280                 285

Tyr Pro Arg Met Gly Val Leu His Leu Gly Phe Asp Ala Thr Ala Leu
        290                 295                 300

Pro Gln Pro Leu Asp Gly Phe Gly Phe Leu Val Pro Asn Ala Glu Asn
305                 310                 315                 320

Met His Phe Leu Gly Ala Ile Cys Asn Ala Ala Ile Phe Pro Asp Lys
            325                 330                 335

Ala Pro Pro Gly Lys Ile Leu Phe Thr Val Phe Leu Gly Gly Ala Arg
        340                 345                 350

Gln Glu Ser Leu Phe Asp Gln Met Thr Pro Glu Ala Leu Gln Gln Gln
        355                 360                 365

Val Val Ser Glu Val Met Ser Leu Leu His Leu Ser Ala Pro Pro Val
        370                 375                 380

Met Gln His Phe Ser Ser Trp Asn Lys Ala Ile Pro Gln Leu Asn Val
385                 390                 395                 400

Gly His Val Lys Leu Arg Arg Ala Val Glu Ala Phe Glu Lys Lys Tyr
            405                 410                 415

Pro Gly Ile His Leu Ser Gly Asn Tyr Leu Gln Gly Val Ala Ile Pro
        420                 425                 430

Ala Leu Leu Gln His Ala Ala Ala Leu Ala Ala Ser Leu Lys Lys Asn
        435                 440                 445

<210> SEQ ID NO 166
<211> LENGTH: 445
<212> TYPE: PRT
<213> ORGANISM: Artificial Sequence
<220> FEATURE:
<223> OTHER INFORMATION: Recombinant

<400> SEQUENCE: 166

Gln Pro Val Leu Ile Val Gly Ala Gly Leu Ser Gly Leu Ser Ile Ala
1               5                   10                  15

Tyr Glu Leu Gln Lys Leu Gln Val Pro Tyr Gln Val Leu Glu Val Ser
            20                  25                  30

Gly His Ser Gly Gly Val Met Lys Ser Leu Arg Lys Asp Gly Phe Glu
        35                  40                  45

Leu Asp Ala Gly Ala Asn Thr Ile Ala Thr Ser Pro Glu Ile Leu Ala
    50                  55                  60
```

```
Tyr Phe Thr Ser Leu Gly Leu Glu Asn Glu Ile Leu Gln Ala Thr Ala
 65                  70                  75                  80

Thr Ser Lys His Arg Phe Leu Val Arg Arg Gln Leu His Ala Val
             85                  90                  95

Ser Pro His Pro Phe Lys Ile Met Ser Ser Pro Tyr Leu Cys Arg Gly
            100                 105                 110

Ser Lys Trp Arg Leu Phe Thr Glu Arg Phe Lys Pro Val Val Ala
        115                 120                 125

Ser Gly Glu Glu Thr Val Thr Asp Phe Ile Thr Arg Arg Phe Asn Arg
130                 135                 140

Glu Ile Ala Glu Tyr Val Phe Pro Val Leu Ser Gly Ile Tyr Ala
145                 150                 155                 160

Gly Asn Pro Asp Gln Met Ser Ile Ala Glu Val Leu Pro Ala Leu Pro
                165                 170                 175

Arg Trp Glu Arg Glu Tyr Gly Ser Val Thr Lys Gly Leu Met Lys Asp
            180                 185                 190

Lys Gly Ala Met Gly Gly Arg Lys Ile Ile Ser Phe Lys Gly Gly Asn
        195                 200                 205

Gln Leu Leu Thr Asn Arg Leu Gln Gln Leu Leu Thr Thr Pro Val Arg
210                 215                 220

Phe Asn Cys Lys Val Thr Gly Ile Thr Ala Ser Asn Gly Gly Tyr Ile
225                 230                 235                 240

Val Ser Ala Val Glu Asp Gly Val Ser Glu Ser Tyr Thr Ala Ser Arg
                245                 250                 255

Val Ile Leu Thr Thr Pro Ala Tyr Ser Ala Ala Thr Ile Thr Asn
                260                 265                 270

Leu Asp Ala Ala Thr Ala Ala Leu Leu Asn Glu Ile His Tyr Pro Arg
            275                 280                 285

Met Gly Val Leu His Leu Gly Phe Asp Ala Thr Ala Leu Pro Gln Pro
290                 295                 300

Leu Asp Gly Phe Gly Phe Leu Val Pro Asn Ala Glu Asn Met His Phe
305                 310                 315                 320

Leu Gly Ala Ile Cys Asn Ala Ala Ile Phe Pro Asp Lys Ala Pro Pro
                325                 330                 335

Gly Lys Ile Leu Phe Thr Val Phe Leu Gly Gly Ala Arg Gln Glu Ser
            340                 345                 350

Leu Phe Asp Gln Met Thr Pro Glu Ala Leu Gln Gln Val Val Ser
        355                 360                 365

Glu Val Met Ser Leu Leu His Leu Ser Ala Pro Pro Val Met Gln His
        370                 375                 380

Phe Ser Ser Trp Asn Lys Ala Ile Pro Gln Leu Asn Val Gly His Val
385                 390                 395                 400

Lys Leu Arg Arg Ala Val Glu Ala Phe Glu Lys Tyr Pro Gly Ile
                405                 410                 415

His Leu Ser Gly Asn Tyr Leu Gln Gly Val Ala Ile Pro Ala Leu Leu
                420                 425                 430

Gln His Ala Ala Ala Leu Ala Ala Ser Leu Lys Lys Asn
        435                 440                 445

<210> SEQ ID NO 167
<211> LENGTH: 470
<212> TYPE: PRT
<213> ORGANISM: Bacillus subtilis
```

```
<400> SEQUENCE: 167

Met Ser Asp Gly Lys Lys His Val Val Ile Ile Gly Gly Ile Thr
 1               5                  10                 15

Gly Leu Ala Ala Ala Phe Tyr Met Glu Lys Glu Ile Lys Glu Lys Asn
             20                  25                  30

Leu Pro Leu Glu Leu Thr Leu Val Glu Ala Ser Pro Arg Val Gly Gly
         35                  40                  45

Lys Ile Gln Thr Val Lys Lys Asp Gly Tyr Ile Ile Glu Arg Gly Pro
     50                  55                  60

Asp Ser Phe Leu Glu Arg Lys Lys Ser Ala Pro Gln Leu Val Lys Asp
 65                  70                  75                  80

Leu Gly Leu Glu His Leu Leu Val Asn Asn Ala Thr Gly Gln Ser Tyr
                 85                  90                  95

Val Leu Val Asn Arg Thr Leu His Pro Met Pro Lys Gly Ala Val Met
            100                 105                 110

Gly Ile Pro Thr Lys Ile Ala Pro Phe Val Ser Thr Gly Leu Phe Ser
        115                 120                 125

Leu Ser Gly Lys Ala Arg Ala Ala Met Asp Phe Ile Leu Pro Ala Ser
    130                 135                 140

Lys Thr Lys Asp Asp Gln Ser Leu Gly Glu Phe Arg Arg Arg Val
145                 150                 155                 160

Gly Asp Glu Val Val Glu Asn Leu Ile Glu Pro Leu Leu Ser Gly Ile
                165                 170                 175

Tyr Ala Gly Asp Ile Asp Lys Leu Ser Leu Met Ser Thr Phe Pro Gln
            180                 185                 190

Phe Tyr Gln Thr Glu Gln Lys His Arg Ser Leu Ile Leu Gly Met Lys
        195                 200                 205

Lys Thr Arg Pro Gln Gly Ser Gly Gln Gln Leu Thr Ala Lys Lys Gln
    210                 215                 220

Gly Gln Phe Gln Thr Leu Ser Thr Gly Leu Gln Thr Leu Val Glu Glu
225                 230                 235                 240

Ile Glu Lys Gln Leu Lys Leu Thr Lys Val Tyr Lys Gly Thr Lys Val
                245                 250                 255

Thr Lys Leu Ser His Ser Gly Ser Gly Tyr Ser Leu Glu Leu Asp Asn
            260                 265                 270

Gly Val Thr Leu Asp Ala Asp Ser Val Ile Val Thr Ala Pro His Lys
        275                 280                 285

Ala Ala Ala Gly Met Leu Ser Glu Leu Pro Ala Ile Ser His Leu Lys
    290                 295                 300

Asn Met His Ser Thr Ser Val Ala Asn Val Ala Leu Gly Phe Pro Glu
305                 310                 315                 320

Gly Ser Val Gln Met Glu His Glu Gly Thr Gly Phe Val Ile Ser Arg
                325                 330                 335

Asn Ser Asp Phe Ala Ile Thr Ala Cys Thr Trp Thr Asn Lys Lys Trp
            340                 345                 350

Pro His Ala Ala Pro Glu Gly Lys Thr Leu Leu Arg Ala Tyr Val Gly
        355                 360                 365

Lys Ala Gly Asp Glu Ser Ile Val Asp Leu Ser Asp Asn Asp Ile Ile
    370                 375                 380

Asn Ile Val Leu Glu Asp Leu Lys Lys Val Met Asn Ile Asn Gly Glu
385                 390                 395                 400

Pro Glu Met Thr Cys Val Thr Arg Trp His Glu Ser Met Pro Gln Tyr
                405                 410                 415
```

```
His Val Gly His Lys Gln Arg Ile Lys Glu Leu Arg Glu Ala Leu Ala
            420                 425                 430

Ser Ala Tyr Pro Gly Val Tyr Met Thr Gly Ala Ser Phe Glu Gly Val
            435                 440                 445

Gly Ile Pro Asp Cys Ile Asp Gln Gly Lys Ala Ala Val Ser Asp Ala
450                 455                 460

Leu Thr Tyr Leu Phe Ser
465                 470

<210> SEQ ID NO 168
<211> LENGTH: 470
<212> TYPE: PRT
<213> ORGANISM: Bacillus pumilus

<400> SEQUENCE: 168

Met His Asp Asn Gln Lys His Leu Val Ile Gly Gly Gly Ile Thr
1               5                   10                  15

Gly Leu Ala Ala Ala Phe Tyr Leu Glu Lys Glu Val Glu Glu Lys Gly
            20                  25                  30

Leu Pro Ile Gln Ile Ser Leu Ile Glu Ala Ser Pro Arg Leu Gly Gly
            35                  40                  45

Lys Ile Gln Thr Leu Tyr Lys Asp Gly Tyr Ile Ile Glu Arg Gly Pro
50                  55                  60

Asp Ser Phe Leu Glu Arg Lys Val Ser Gly Pro Gln Leu Ala Lys Asp
65                  70                  75                  80

Val Gly Leu Ser Asp Gln Leu Val Asn Asn Glu Thr Gly Gln Ala Tyr
            85                  90                  95

Val Leu Val Asn Glu Lys Leu His Pro Met Pro Lys Gly Ala Val Met
            100                 105                 110

Gly Ile Pro Thr Gln Ile Ser Pro Phe Ile Thr Thr Gly Leu Phe Ser
            115                 120                 125

Val Ala Gly Lys Ala Arg Ala Ala Met Asp Phe Val Leu Pro Lys Ser
            130                 135                 140

Lys Gln Thr Glu Asp Gln Ser Leu Gly Glu Phe Phe Arg Arg Arg Val
145                 150                 155                 160

Gly Asp Glu Val Val Glu Asn Leu Ile Glu Pro Leu Leu Ser Gly Ile
                165                 170                 175

Tyr Ala Gly Asp Ile Asp Arg Leu Ser Leu Met Ser Thr Phe Pro Gln
            180                 185                 190

Phe Tyr Gln Thr Glu Gln Gln His Arg Ser Leu Ile Leu Gly Met Lys
            195                 200                 205

Lys Ser Gln Gln His Ala Lys Ala Gln Gln Val Thr Ala Lys Lys Gln
            210                 215                 220

Gly Gln Phe Gln Thr Ile Asn Gln Gly Leu Gln Ser Leu Val Glu Ala
225                 230                 235                 240

Val Glu Gly Lys Leu Lys Leu Thr Thr Val Tyr Lys Gly Thr Lys Val
            245                 250                 255

Lys Gln Ile Glu Lys Thr Asp Gly Gly Tyr Gly Leu Gln Leu Asp Ser
            260                 265                 270

Gly Gln Thr Leu Phe Ala Asp Ser Ala Ile Val Thr Thr Pro His Gln
            275                 280                 285

Ser Ile Tyr Ser Met Phe Pro Lys Glu Ala Gly Leu Glu Tyr Leu His
            290                 295                 300

Asp Met Thr Ser Thr Ser Val Ala Thr Val Ala Leu Gly Phe Lys Asp
```

```
             305                 310                 315                 320
         Glu Asp Val His Asn Glu Tyr Asp Gly Thr Gly Phe Val Ile Ser Arg
                         325                 330                 335
         Asn Ser Asp Phe Ser Ile Thr Ala Cys Thr Trp Thr Asn Lys Lys Trp
                         340                 345                 350
         Pro His Thr Ala Pro Lys Gly Lys Thr Leu Leu Arg Ala Tyr Val Gly
                         355                 360                 365
         Lys Ala Gly Asp Glu Ser Ile Val Glu Gln Ser Asp Ser Gln Ile Val
                         370                 375                 380
         Ser Ile Val Leu Glu Asp Leu Lys Lys Ile Met Asp Ile Lys Ala Asp
         385                 390                 395                 400
         Pro Glu Leu Thr Thr Val Thr Arg Trp Lys Thr Ser Met Pro Gln Tyr
                         405                 410                 415
         His Val Gly His Gln Lys Ala Ile Ser Asn Met Arg Glu Thr Phe Lys
                         420                 425                 430
         Gln Ser Tyr Pro Gly Val Tyr Ile Thr Gly Ala Ala Phe Glu Gly Val
                         435                 440                 445
         Gly Ile Pro Asp Cys Ile Asp Gln Gly Lys Ala Ala Ile Ser Glu Ala
                         450                 455                 460
         Val Ser Tyr Leu Phe Ser
         465                 470

<210> SEQ ID NO 169
<211> LENGTH: 470
<212> TYPE: PRT
<213> ORGANISM: Bacillus pumilus

<400> SEQUENCE: 169

Met His Asp Asn Gln Lys His Leu Val Ile Gly Gly Ile Thr
         1               5                   10                  15
         Gly Leu Ala Ala Ala Phe Tyr Leu Glu Lys Glu Val Glu Lys Gly
                         20                  25                  30
         Leu Pro Ile Gln Ile Ser Leu Ile Glu Ala Ser Pro Arg Leu Gly Gly
                         35                  40                  45
         Lys Ile Gln Thr Leu Tyr Lys Asp Gly Tyr Ile Ile Glu Arg Gly Pro
         50                  55                  60
         Asp Ser Phe Leu Glu Arg Lys Val Ser Gly Pro Gln Leu Ala Lys Asp
         65                  70                  75                  80
         Val Gly Leu Ser Asp Gln Leu Val Asn Asn Glu Thr Gly Gln Ala Tyr
                         85                  90                  95
         Val Leu Val Asn Glu Thr Leu His Pro Met Pro Lys Gly Ala Val Met
                         100                 105                 110
         Gly Ile Pro Thr Gln Ile Ser Pro Phe Ile Thr Thr Gly Leu Phe Ser
                         115                 120                 125
         Val Ala Gly Lys Ala Arg Ala Ala Met Asp Phe Val Leu Pro Lys Ser
                         130                 135                 140
         Lys Gln Thr Glu Asp Gln Ser Leu Gly Glu Phe Arg Arg Arg Val
         145                 150                 155                 160
         Gly Asp Glu Val Val Glu Asn Leu Ile Glu Pro Leu Ser Gly Ile
                         165                 170                 175
         Tyr Ala Gly Asp Ile Asp Arg Leu Ser Leu Met Ser Thr Phe Pro Gln
                         180                 185                 190
         Phe Tyr Gln Thr Glu Gln Lys His Arg Ser Leu Ile Leu Gly Met Lys
                         195                 200                 205
```

-continued

Lys Ser Gln Gln His Ala Lys Ala Gln Val Thr Ala Lys Lys Gln
    210                 215                 220

Gly Gln Phe Gln Thr Ile Asn Gln Gly Leu Gln Ala Leu Val Glu Ala
225                 230                 235                 240

Val Glu Ser Lys Leu Lys Leu Thr Thr Ile Tyr Lys Gly Thr Lys Val
                245                 250                 255

Lys Gln Ile Glu Lys Thr Asp Gly Gly Tyr Gly Val Gln Leu Asp Ser
            260                 265                 270

Gly Gln Thr Leu Leu Ala Asp Ser Ala Ile Val Thr Thr Pro His Gln
        275                 280                 285

Ser Ile Tyr Ser Met Phe Pro Lys Glu Ala Gly Leu Glu Tyr Leu His
    290                 295                 300

Asp Met Thr Ser Thr Ser Val Ala Thr Val Ala Leu Gly Phe Lys Glu
305                 310                 315                 320

Glu Asp Val His Asn Glu Tyr Asp Gly Thr Gly Phe Val Ile Ser Arg
                325                 330                 335

Asn Ser Asp Phe Ser Ile Thr Ala Cys Thr Trp Thr Asn Lys Lys Trp
            340                 345                 350

Pro His Thr Ala Pro Lys Gly Lys Thr Leu Leu Arg Ala Tyr Val Gly
        355                 360                 365

Lys Ala Gly Asp Glu Ser Ile Val Glu Gln Ser Asp His Gln Ile Val
    370                 375                 380

Ser Ile Val Leu Glu Asp Leu Lys Lys Ile Met Asp Ile Lys Ala Asp
385                 390                 395                 400

Pro Glu Leu Thr Thr Val Thr Arg Trp Lys Thr Ser Met Pro Gln Tyr
                405                 410                 415

His Val Gly His Gln Lys Ala Ile Ser Asn Met Arg Glu Thr Phe Lys
            420                 425                 430

Gln Ser Tyr Pro Gly Val Tyr Ile Thr Gly Ala Ala Phe Glu Gly Val
        435                 440                 445

Gly Ile Pro Asp Cys Ile Asp Gln Gly Lys Ala Ala Ile Ser Glu Ala
    450                 455                 460

Val Ser Tyr Leu Phe Ser
465                 470

<210> SEQ ID NO 170
<211> LENGTH: 477
<212> TYPE: PRT
<213> ORGANISM: Paenibacillus macerans

<400> SEQUENCE: 170

Met Ser Lys Lys Ile Ala Val Ile Gly Gly Gly Ile Thr Gly Leu Ser
1               5                   10                  15

Val Ala Tyr Tyr Val Arg Lys Leu Leu Arg Glu Gln Gly Val Asn Ala
                20                  25                  30

Gly Val Thr Leu Val Glu Gln Ser Asp Arg Leu Gly Gly Lys Ile Arg
            35                  40                  45

Ser Leu Arg Arg Asp Gly Phe Thr Ile Glu Gln Gly Pro Asp Ser Met
    50                  55                  60

Ile Ala Arg Lys Pro Ala Ala Leu Glu Leu Ile Arg Glu Leu Gly Leu
65                  70                  75                  80

Glu Asp Lys Leu Ala Gly Thr Asn Pro Gln Ala Lys Arg Ser Tyr Ile
                85                  90                  95

Leu His Arg Gly Lys Phe His Pro Met Pro Pro Gly Leu Met Leu Gly
            100                 105                 110

Ile Pro Thr Gln Met Trp Pro Met Val Lys Thr Gly Leu Leu Ser Pro
            115                 120                 125

Ala Gly Lys Leu Arg Ala Ala Met Asp Leu Leu Pro Ala Arg Arg
130                 135                 140

Gly Gly Gly Asp Glu Ser Leu Gly Gly Phe Ile Arg Arg Leu Gly
145                 150                 155                 160

Arg Glu Val Leu Glu Gln Met Thr Glu Pro Leu Leu Ala Gly Ile Tyr
                165                 170                 175

Ala Gly Asp Thr Glu Gln Leu Ser Leu Lys Ala Thr Phe Pro Gln Phe
            180                 185                 190

Met Glu Met Glu Arg Lys His Arg Ser Leu Ile Leu Gly Leu Leu Ala
            195                 200                 205

Gly Lys Lys Gln Pro Pro Arg Pro Gly Gly Ser Gln Val Pro Leu Pro
210                 215                 220

Lys Ala Ala Gln Thr Ser Met Phe Leu Thr Leu Thr Gly Gly Leu Glu
225                 230                 235                 240

Gly Leu Thr Glu Ala Leu Glu Glu Ser Leu Ser Glu Lys Ile Ile
                245                 250                 255

Thr Gly Gln Ala Val Thr Gly Leu Ser Gln Gln Glu Ala Gly Tyr Glu
            260                 265                 270

Leu Asn Leu Ser Gly Gly Glu Arg Leu Asn Ala Asp Gly Val Ile Leu
            275                 280                 285

Ala Val Pro Ala Phe Ala Ala Ala Arg Leu Leu Asp Gly Val Pro Glu
            290                 295                 300

Ala Ala Tyr Leu Glu Arg Ile Arg Tyr Val Ser Val Ala Asn Leu Ala
305                 310                 315                 320

Phe Ala Tyr Arg Arg Glu Asp Val Pro His Asp Leu Asn Gly Ser Gly
                325                 330                 335

Val Leu Ile Pro Arg Gly Glu Gly Arg Met Ile Thr Ala Ile Thr Trp
            340                 345                 350

Val Ser Ser Lys Trp Leu His Ser Ala Pro Gly Asp Lys Ala Leu Leu
            355                 360                 365

Arg Ala Tyr Ile Gly Arg Leu Gly Asp Glu Ala Trp Thr Ala Met Cys
            370                 375                 380

Arg Ala Asp Ile Glu Arg Arg Val Ala Ala Glu Leu Arg Asp Leu Leu
385                 390                 395                 400

Gly Ile Ala Ala Ser Pro Leu Phe Cys Glu Leu Ala Ala Leu Pro Glu
                405                 410                 415

Ser Met Pro Gln Tyr Pro Val Gly His Val Glu Arg Leu Glu Ala Leu
            420                 425                 430

Arg Gly Ala Leu Cys Arg Ala Lys Pro Gly Leu Leu Leu Cys Gly Ala
            435                 440                 445

Gly Tyr Ala Gly Val Gly Ile Pro Asp Cys Ile Arg Gln Gly Lys Glu
450                 455                 460

Ala Ala Glu Ser Met Ala Ala Tyr Leu Arg Asp Gly Arg
465                 470                 475

<210> SEQ ID NO 171
<211> LENGTH: 493
<212> TYPE: PRT
<213> ORGANISM: Paenibacillus thiaminolyticus

<400> SEQUENCE: 171

Met Lys Ala Leu Arg Lys Leu Val Val Ile Gly Gly Gly Ile Thr Gly

-continued

```
1               5                   10                  15
Leu Ser Ala Ala Phe Tyr Ala Leu Lys Gln Ala Asp Glu Glu Gly Gln
            20                  25                  30

Pro Ile Ser Val Thr Ile Ile Glu Gln Ser Asp Arg Leu Gly Gly Lys
            35                  40                  45

Ile Gln Thr Leu Arg Lys Glu Gly Cys Val Ile Glu Lys Gly Pro Asp
 50                  55                  60

Ser Phe Leu Ala Arg Lys Leu Pro Met Ile Asp Leu Ala Arg Asp Leu
 65                  70                  75                  80

Gly Met Asp Ser Glu Leu Val Ala Thr Asn Pro His Ala Lys Lys Thr
                85                  90                  95

Tyr Ile Leu Arg Arg Gly Lys Leu Tyr Arg Met Pro Pro Gly Leu Val
                100                 105                 110

Leu Gly Ile Pro Thr Glu Leu Gly Pro Phe Ala Lys Thr Gly Leu Ile
                115                 120                 125

Ser Pro Trp Gly Lys Leu Arg Ala Ala Met Asp Leu Phe Ile Lys Pro
            130                 135                 140

His Pro Ala Asp Glu Asp Ser Val Gly Ala Phe Leu Asp Arg Arg
145                 150                 155                 160

Leu Gly Arg Glu Val Thr Glu His Ile Ala Glu Pro Leu Leu Ala Gly
                165                 170                 175

Ile Tyr Ala Gly Asp Leu Gln Ala Leu Ser Leu Gln Ala Thr Phe Pro
            180                 185                 190

Gln Phe Ala Gln Val Glu Arg Lys His Gly Gly Leu Ile Arg Gly Met
            195                 200                 205

Lys Ala Ser Arg Gln Ala Gly Gln Ser Val Pro Gly Leu Pro Asp Val
210                 215                 220

Ala Lys Gly Thr Met Phe Leu Thr Phe Arg Asn Gly Leu Thr Ser Leu
225                 230                 235                 240

Val Glu Arg Leu Glu Glu Thr Leu Arg Asp Arg Ala Glu Leu Cys Leu
                245                 250                 255

Gly Ile Gly Ala Glu Gly Phe Glu Lys Arg Glu Asp Gly Thr Tyr Leu
            260                 265                 270

Val Arg Leu Ser Asp Gly Ser Arg Leu Gln Ala Asp Ala Val Ile Val
            275                 280                 285

Thr Thr Pro Ser Tyr His Ala Ala Ser Leu Leu Glu Glu His Val Asp
            290                 295                 300

Ala Ser Ala Leu Gln Ala Ile Arg His Val Ser Val Ala Asn Val Val
305                 310                 315                 320

Ser Val Phe Asp Arg Lys Gln Val Asn Asn Gln Phe Asp Gly Thr Gly
                325                 330                 335

Phe Val Ile Ser Arg Arg Glu Gly Arg Ala Ile Thr Ala Cys Thr Trp
                340                 345                 350

Thr Ser Val Lys Trp Pro His Thr Ser Arg Gly Asp Lys Leu Ile Ile
            355                 360                 365

Arg Cys Tyr Ile Gly Arg Ala Gly Asp Glu Glu Arg Val Asp Trp Pro
370                 375                 380

Asp Glu Ala Leu Lys Arg Thr Val Arg Ser Glu Leu Arg Glu Leu Leu
385                 390                 395                 400

Asp Ile Asp Ile Asp Pro Glu Phe Val Glu Ile Thr Arg Leu Arg His
                405                 410                 415

Ser Met Pro Gln Tyr Pro Val Gly His Val Gln Ala Ile Arg Ser Leu
                420                 425                 430
```

Arg Asp Glu Val Gly Arg Thr Leu Pro Gly Val Phe Leu Ala Gly Gln
    435                 440                 445

Pro Tyr Glu Gly Val Gly Met Pro Asp Cys Val Arg Ser Gly Arg Asp
    450                 455                 460

Ala Ala Glu Ala Ala Val Ser Ala Met Gln Ala Met Ser Thr Glu Pro
465                 470                 475                 480

Glu Ala Pro Ala Glu Asp Ala Ala Thr Gly Thr Ala Gly
                485                 490

<210> SEQ ID NO 172
<211> LENGTH: 474
<212> TYPE: PRT
<213> ORGANISM: Paenibacillus polymyxa

<400> SEQUENCE: 172

Met Gly Asp Lys Lys Arg Arg Val Val Val Gly Gly Gly Leu Thr
1               5                   10                  15

Gly Leu Ser Ala Ala Phe Tyr Ile Arg Lys His Tyr Arg Glu Ala Gly
                20                  25                  30

Val Glu Pro Val Ile Thr Leu Val Glu Lys Ser Ser Met Gly Gly
            35                  40                  45

Met Ile Glu Thr Leu His Arg Asp Gly Phe Val Ile Glu Lys Gly Pro
    50                  55                  60

Asp Ser Phe Leu Ala Arg Lys Thr Ala Met Ile Asp Leu Ala Lys Glu
65                  70                  75                  80

Leu Glu Ile Asp His Glu Leu Val Ser Gln Asn Pro Glu Ser Lys Lys
                85                  90                  95

Thr Tyr Ile Met Gln Arg Gly Lys Leu His Pro Met Pro Ala Gly Leu
                100                 105                 110

Val Leu Gly Ile Pro Thr Glu Leu Arg Pro Phe Leu Arg Ser Gly Leu
            115                 120                 125

Val Ser Pro Ala Gly Lys Leu Arg Ala Leu Met Asp Phe Val Ile Pro
130                 135                 140

Pro Arg Arg Thr Thr Glu Asp Glu Ser Leu Gly Tyr Met Ile Glu Arg
145                 150                 155                 160

Arg Leu Gly Ala Glu Val Leu Glu Asn Leu Thr Glu Pro Leu Leu Ala
                165                 170                 175

Gly Ile Tyr Ala Gly Asp Met Arg Arg Leu Ser Leu Gln Ala Thr Phe
            180                 185                 190

Pro Gln Phe Gly Glu Val Glu Arg Asp Tyr Gly Ser Leu Ile Arg Gly
        195                 200                 205

Met Met Thr Gly Arg Lys Pro Ala Glu Thr His Thr Gly Thr Lys Arg
    210                 215                 220

Ser Ala Phe Leu Asn Phe Arg Gln Gly Leu Gln Ser Leu Val His Ala
225                 230                 235                 240

Leu Val His Glu Leu Gln Asp Val Asp Gln Arg Leu Asn Thr Ala Val
                245                 250                 255

Lys Ser Leu Gln Arg Leu Asp Gly Ala Gln Thr Arg Tyr Arg Val Glu
            260                 265                 270

Leu Gly Asn Gly Glu Met Leu Glu Ala Asp Val Val Thr Val
        275                 280                 285

Pro Thr Tyr Val Ala Ser Glu Leu Leu Lys Pro His Val Asp Thr Ala
    290                 295                 300

Ala Leu Asp Ala Ile Asn Tyr Val Ser Val Ala Asn Val Val Leu Ala

```
            305                 310                 315                 320
        Phe Glu Lys Lys Glu Val Glu His Val Phe Asp Gly Ser Gly Phe Leu
                        325                 330                 335

Val Pro Arg Lys Glu Gly Arg Asn Ile Thr Ala Cys Thr Trp Thr Ser
                        340                 345                 350

Thr Lys Trp Leu His Thr Ser Pro Asp Asp Lys Val Leu Leu Arg Cys
                        355                 360                 365

Tyr Val Gly Arg Ser Gly Asp Glu Gln Asn Val Glu Leu Pro Asp Glu
                        370                 375                 380

Ala Leu Thr Asn Leu Val Leu Lys Asp Leu Arg Glu Thr Met Gly Ile
        385                 390                 395                 400

Glu Ala Val Pro Ile Phe Ser Glu Ile Thr Arg Leu Arg Lys Ser Met
                        405                 410                 415

Pro Gln Tyr Pro Val Gly His Leu Gln His Ile Ala Ala Leu Arg Glu
                        420                 425                 430

Glu Leu Gly Ser Lys Leu Pro Gly Val Tyr Ile Ala Gly Ala Gly Tyr
                        435                 440                 445

Glu Gly Val Gly Leu Pro Asp Cys Ile Arg Gln Ala Lys Glu Met Ser
                        450                 455                 460

Val Gln Ala Thr Gln Glu Leu Ala Ala Asp
        465                 470

<210> SEQ ID NO 173
<211> LENGTH: 470
<212> TYPE: PRT
<213> ORGANISM: Bacillus atrophaeus

<400> SEQUENCE: 173

Met Ser Asp Gly Lys Lys His Leu Val Ile Ile Gly Gly Gly Ile Thr
        1               5                   10                  15

Gly Leu Ala Ser Ala Phe Tyr Met Glu Lys Glu Ile Arg Glu Lys Asn
                        20                  25                  30

Leu Pro Leu Ser Val Thr Leu Val Glu Ala Ser Pro Arg Val Gly Gly
                        35                  40                  45

Lys Ile Gln Thr Ala Arg Lys Asp Gly Tyr Ile Ile Glu Arg Gly Pro
                        50                  55                  60

Asp Ser Phe Leu Glu Arg Lys Lys Ser Ala Pro Glu Leu Val Glu Asp
        65                  70                  75                  80

Leu Gly Leu Glu His Leu Leu Val Asn Asn Ala Thr Gly Gln Ser Tyr
                        85                  90                  95

Val Leu Val Asn Glu Thr Leu His Pro Met Pro Lys Gly Ala Val Met
                        100                 105                 110

Gly Ile Pro Thr Lys Ile Ala Pro Phe Met Ser Thr Gly Leu Phe Ser
                        115                 120                 125

Phe Ser Gly Lys Ala Arg Ala Ala Met Asp Phe Val Leu Pro Ala Ser
                        130                 135                 140

Lys Pro Lys Glu Asp Gln Ser Leu Gly Glu Phe Arg Arg Arg Val
        145                 150                 155                 160

Gly Asp Glu Val Val Glu Asn Leu Ile Glu Pro Leu Leu Ser Gly Ile
                        165                 170                 175

Tyr Ala Gly Asp Ile Asp Arg Leu Ser Leu Met Ser Thr Phe Pro Gln
                        180                 185                 190

Phe Tyr Gln Thr Glu Gln Lys His Arg Ser Leu Ile Leu Gly Met Lys
                        195                 200                 205
```

-continued

Lys Thr Arg Pro Gln Gly Ser Gly Gln Arg Leu Thr Ala Lys Lys Gln
    210                 215                 220

Gly Gln Phe Gln Thr Leu Lys Thr Gly Leu Gln Thr Leu Val Glu Glu
225                 230                 235                 240

Leu Glu Asn Gln Leu Lys Leu Thr Lys Val Tyr Lys Gly Thr Lys Val
            245                 250                 255

Thr Asn Ile Ser Arg Gly Glu Lys Gly Cys Ser Ile Ala Leu Asp Asn
        260                 265                 270

Gly Met Thr Leu Asp Ala Asp Ala Ile Val Thr Ser Pro His Lys
    275                 280                 285

Ser Ala Ala Gly Met Phe Pro Asp Leu Pro Ala Val Ser Gln Leu Lys
290                 295                 300

Asp Met His Ser Thr Ser Val Ala Asn Val Ala Leu Gly Phe Pro Gln
305                 310                 315                 320

Glu Ala Val Gln Met Glu His Glu Gly Thr Gly Phe Val Ile Ser Arg
                325                 330                 335

Asn Ser Asp Phe Ser Ile Thr Ala Cys Thr Trp Thr Asn Lys Lys Trp
            340                 345                 350

Pro His Ser Ala Pro Glu Gly Lys Thr Leu Leu Arg Ala Tyr Val Gly
        355                 360                 365

Lys Ala Gly Asp Glu Ser Ile Val Glu Leu Ser Asp Asn Glu Ile Ile
370                 375                 380

Lys Ile Val Leu Glu Asp Leu Lys Val Met Lys Ile Lys Gly Glu
385                 390                 395                 400

Pro Glu Met Thr Cys Val Thr Arg Trp Asn Glu Ser Met Pro Gln Tyr
                405                 410                 415

His Val Gly His Lys Gln Arg Ile Lys Lys Val Arg Glu Ala Leu Ala
            420                 425                 430

Ala Ser Tyr Pro Gly Val Tyr Met Thr Gly Ala Ser Phe Glu Gly Val
        435                 440                 445

Gly Ile Pro Asp Cys Ile Asp Gln Gly Lys Ser Ala Val Ser Asp Val
    450                 455                 460

Leu Ala Tyr Leu Phe Gly
465                 470

<210> SEQ ID NO 174
<211> LENGTH: 470
<212> TYPE: PRT
<213> ORGANISM: Bacillus atrophaeus

<400> SEQUENCE: 174

Met Ser Asp Gly Lys Lys His Leu Val Ile Ile Gly Gly Gly Ile Thr
1               5                   10                  15

Gly Leu Ala Ser Ala Phe Tyr Met Glu Lys Glu Ile Arg Glu Lys Asn
            20                  25                  30

Leu Pro Leu Ser Val Thr Leu Val Glu Ala Ser Pro Arg Val Gly Gly
        35                  40                  45

Lys Ile Gln Thr Ala Arg Lys Asp Gly Tyr Ile Ile Glu Arg Gly Pro
    50                  55                  60

Asp Ser Phe Leu Glu Arg Lys Lys Ser Ala Pro Glu Leu Val Glu Asp
65                  70                  75                  80

Leu Gly Leu Glu His Leu Leu Val Asn Asn Ala Thr Gly Gln Ser Tyr
                85                  90                  95

Val Leu Val Asn Glu Thr Leu His Pro Met Pro Lys Gly Ala Val Met
            100                 105                 110

Gly Ile Pro Thr Lys Ile Ala Pro Phe Met Ser Thr Arg Leu Phe Ser
            115                 120                 125

Phe Ser Gly Lys Ala Arg Ala Met Asp Phe Val Leu Pro Ala Ser
        130                 135                 140

Lys Pro Lys Glu Asp Gln Ser Leu Gly Glu Phe Phe Arg Arg Arg Val
145                 150                 155                 160

Gly Asp Glu Val Val Glu Asn Leu Ile Glu Pro Leu Leu Ser Gly Ile
                165                 170                 175

Tyr Ala Gly Asp Ile Asp Arg Leu Ser Leu Met Ser Thr Phe Pro Gln
            180                 185                 190

Phe Tyr Gln Thr Glu Gln Lys His Arg Ser Leu Ile Leu Gly Met Lys
        195                 200                 205

Lys Thr Arg Pro Gln Gly Ser Gly Gln Gln Leu Thr Ala Lys Lys Gln
210                 215                 220

Gly Gln Phe Gln Thr Leu Lys Thr Gly Leu Gln Thr Leu Val Glu Glu
225                 230                 235                 240

Leu Glu Asn Gln Leu Lys Leu Thr Lys Val Tyr Lys Gly Thr Lys Val
                245                 250                 255

Thr Asn Ile Ser Arg Gly Glu Lys Gly Cys Ser Ile Ala Leu Asp Asn
            260                 265                 270

Gly Met Thr Leu Asp Ala Asp Ala Ile Val Thr Ser Pro His Lys
        275                 280                 285

Ser Ala Ala Gly Met Phe Pro Asp Leu Pro Ala Val Ser Gln Leu Lys
290                 295                 300

Asp Met His Ser Thr Ser Val Ala Asn Val Ala Leu Gly Phe Pro Gln
305                 310                 315                 320

Glu Ala Val Gln Met Glu His Glu Gly Thr Gly Phe Val Ile Ser Arg
                325                 330                 335

Asn Ser Asp Phe Ser Ile Thr Ala Cys Thr Trp Thr Asn Lys Lys Trp
            340                 345                 350

Pro His Ser Ala Pro Glu Gly Lys Thr Leu Leu Arg Ala Tyr Val Gly
        355                 360                 365

Lys Ala Gly Asp Glu Ser Ile Val Glu Leu Ser Asp Asn Glu Ile Ile
370                 375                 380

Lys Ile Val Leu Glu Asp Leu Lys Lys Val Met Lys Ile Lys Gly Glu
385                 390                 395                 400

Pro Glu Met Thr Cys Val Thr Arg Trp Asn Glu Ser Met Pro Gln Tyr
                405                 410                 415

His Val Gly His Lys Gln Arg Ile Lys Lys Val Arg Glu Ala Leu Ala
            420                 425                 430

Ala Ser Tyr Pro Gly Val Tyr Met Thr Gly Ala Ser Phe Glu Gly Val
        435                 440                 445

Gly Ile Pro Asp Cys Ile Asp Gln Gly Lys Ser Ala Val Ser Asp Val
450                 455                 460

Leu Ala Tyr Leu Phe Glu
465                 470

<210> SEQ ID NO 175
<211> LENGTH: 475
<212> TYPE: PRT
<213> ORGANISM: Artificial Sequence
<220> FEATURE:
<223> OTHER INFORMATION: Recombinant

<400> SEQUENCE: 175

```
Lys Ile Ala Val Ile Gly Gly Ile Thr Gly Leu Ser Val Ala
1               5                   10                  15

Tyr Tyr Val Arg Lys Leu Leu Arg Glu Gln Gly Val Asn Ala Gly Val
            20                  25                  30

Thr Leu Val Glu Gln Ser Asp Arg Leu Gly Gly Lys Ile Arg Ser Leu
            35                  40                  45

Arg Arg Asp Gly Phe Thr Ile Glu Gln Gly Pro Asp Ser Met Ile Ala
50                      55                  60

Arg Lys Pro Ala Ala Leu Glu Leu Ile Arg Glu Leu Gly Leu Glu Asp
65                      70                  75                  80

Lys Leu Ala Gly Thr Asn Pro Gln Ala Lys Arg Ser Tyr Ile Leu His
                85                  90                  95

Arg Gly Lys Phe His Pro Met Pro Pro Gly Leu Met Leu Gly Ile Pro
                100                 105                 110

Thr Gln Met Trp Pro Met Val Lys Thr Gly Leu Leu Ser Pro Ala Gly
                115                 120                 125

Lys Leu Arg Ala Ala Met Asp Leu Leu Leu Pro Ala Arg Arg Gly Gly
                130                 135                 140

Gly Asp Glu Ser Leu Gly Gly Phe Ile Arg Arg Arg Leu Gly Arg Glu
145                 150                 155                 160

Val Leu Glu Gln Met Thr Glu Pro Leu Leu Ala Gly Ile Tyr Ala Gly
                165                 170                 175

Asp Thr Glu Gln Leu Ser Leu Lys Ala Thr Phe Pro Gln Phe Met Glu
                180                 185                 190

Met Glu Arg Lys His Arg Ser Leu Ile Leu Gly Leu Leu Ala Gly Lys
                195                 200                 205

Lys Gln Pro Pro Arg Pro Gly Gly Ser Gln Val Pro Leu Pro Lys Ala
                210                 215                 220

Ala Gln Thr Ser Met Phe Leu Thr Leu Thr Gly Gly Leu Glu Gly Leu
225                 230                 235                 240

Thr Glu Ala Leu Glu Glu Ser Leu Ser Glu Glu Lys Ile Ile Thr Gly
                245                 250                 255

Gln Ala Val Thr Gly Leu Ser Gln Gln Glu Ala Gly Tyr Glu Leu Asn
                260                 265                 270

Leu Ser Gly Gly Glu Arg Leu Asn Ala Asp Gly Val Ile Leu Ala Val
                275                 280                 285

Pro Ala Phe Ala Ala Ala Arg Leu Leu Asp Gly Val Pro Glu Ala Ala
                290                 295                 300

Tyr Leu Glu Arg Ile Arg Tyr Val Ser Val Ala Asn Leu Ala Phe Ala
305                 310                 315                 320

Tyr Arg Arg Glu Asp Val Pro His Asp Leu Asn Gly Ser Gly Val Leu
                325                 330                 335

Ile Pro Arg Gly Glu Gly Arg Met Ile Thr Ala Ile Thr Trp Val Ser
                340                 345                 350

Ser Lys Trp Leu His Ser Ala Pro Gly Asp Lys Ala Leu Leu Arg Ala
                355                 360                 365

Tyr Ile Gly Arg Leu Gly Asp Glu Ala Trp Thr Ala Met Cys Arg Ala
                370                 375                 380

Asp Ile Glu Arg Arg Val Ala Ala Glu Leu Arg Asp Leu Leu Gly Ile
385                 390                 395                 400

Ala Ala Ser Pro Leu Phe Cys Glu Leu Ala Ala Leu Pro Glu Ser Met
                405                 410                 415
```

```
Pro Gln Tyr Pro Val Gly His Val Glu Arg Leu Glu Ala Leu Arg Gly
                420                 425                 430

Ala Leu Cys Arg Ala Lys Pro Gly Leu Leu Cys Gly Ala Gly Tyr
        435                 440                 445

Ala Gly Val Gly Ile Pro Asp Cys Ile Arg Gln Gly Lys Glu Ala Ala
    450                 455                 460

Glu Ser Met Ala Ala Tyr Leu Arg Asp Gly Arg
465                 470                 475

<210> SEQ ID NO 176
<211> LENGTH: 489
<212> TYPE: PRT
<213> ORGANISM: Artificial Sequence
<220> FEATURE:
<223> OTHER INFORMATION: Recombinant

<400> SEQUENCE: 176

Arg Lys Leu Val Val Ile Gly Gly Ile Thr Gly Leu Ser Ala Ala
1               5                   10                  15

Phe Tyr Ala Leu Lys Gln Ala Asp Glu Gly Gln Pro Ile Ser Val
            20                  25                  30

Thr Ile Ile Glu Gln Ser Asp Arg Leu Gly Gly Lys Ile Gln Thr Leu
        35                  40                  45

Arg Lys Glu Gly Cys Val Ile Glu Lys Gly Pro Asp Ser Phe Leu Ala
50                  55                  60

Arg Lys Leu Pro Met Ile Asp Leu Ala Arg Asp Leu Gly Met Asp Ser
65                  70                  75                  80

Glu Leu Val Ala Thr Asn Pro His Ala Lys Lys Thr Tyr Ile Leu Arg
                85                  90                  95

Arg Gly Lys Leu Tyr Arg Met Pro Pro Gly Leu Val Leu Gly Ile Pro
            100                 105                 110

Thr Glu Leu Gly Pro Phe Ala Lys Thr Gly Leu Ile Ser Pro Trp Gly
        115                 120                 125

Lys Leu Arg Ala Ala Met Asp Leu Phe Ile Lys Pro His Pro Ala Asp
130                 135                 140

Glu Asp Glu Ser Val Gly Ala Phe Leu Asp Arg Arg Leu Gly Arg Glu
145                 150                 155                 160

Val Thr Glu His Ile Ala Glu Pro Leu Leu Ala Gly Ile Tyr Ala Gly
                165                 170                 175

Asp Leu Gln Ala Leu Ser Leu Gln Ala Thr Phe Pro Gln Phe Ala Gln
            180                 185                 190

Val Glu Arg Lys His Gly Gly Leu Ile Arg Gly Met Lys Ala Ser Arg
        195                 200                 205

Gln Ala Gly Gln Ser Val Pro Gly Leu Pro Asp Val Ala Lys Gly Thr
210                 215                 220

Met Phe Leu Thr Phe Arg Asn Gly Leu Thr Ser Leu Val Glu Arg Leu
225                 230                 235                 240

Glu Glu Thr Leu Arg Asp Arg Ala Glu Leu Cys Leu Gly Ile Gly Ala
                245                 250                 255

Glu Gly Phe Glu Lys Arg Glu Asp Gly Thr Tyr Leu Val Arg Leu Ser
            260                 265                 270

Asp Gly Ser Arg Leu Gln Ala Asp Ala Val Ile Val Thr Thr Pro Ser
        275                 280                 285

Tyr His Ala Ala Ser Leu Leu Glu Glu His Val Asp Ala Ser Ala Leu
    290                 295                 300
```

-continued

```
Gln Ala Ile Arg His Val Ser Val Ala Asn Val Ser Val Phe Asp
305                 310                 315                 320

Arg Lys Gln Val Asn Asn Gln Phe Asp Gly Thr Gly Phe Val Ile Ser
            325                 330                 335

Arg Arg Glu Gly Arg Ala Ile Thr Ala Cys Thr Trp Thr Ser Val Lys
        340                 345                 350

Trp Pro His Thr Ser Arg Gly Asp Lys Leu Ile Ile Arg Cys Tyr Ile
            355                 360                 365

Gly Arg Ala Gly Asp Glu Glu Arg Val Asp Trp Pro Asp Glu Ala Leu
    370                 375                 380

Lys Arg Thr Val Arg Ser Glu Leu Arg Glu Leu Leu Asp Ile Asp Ile
385                 390                 395                 400

Asp Pro Glu Phe Val Glu Ile Thr Arg Leu Arg His Ser Met Pro Gln
                405                 410                 415

Tyr Pro Val Gly His Val Gln Ala Ile Arg Ser Leu Arg Asp Glu Val
            420                 425                 430

Gly Arg Thr Leu Pro Gly Val Phe Leu Ala Gly Gln Pro Tyr Glu Gly
        435                 440                 445

Val Gly Met Pro Asp Cys Val Arg Ser Gly Arg Asp Ala Ala Glu Ala
    450                 455                 460

Ala Val Ser Ala Met Gln Ala Met Ser Thr Glu Pro Glu Ala Pro Ala
465                 470                 475                 480

Glu Asp Ala Ala Thr Gly Thr Ala Gly
                485

<210> SEQ ID NO 177
<211> LENGTH: 469
<212> TYPE: PRT
<213> ORGANISM: Artificial Sequence
<220> FEATURE:
<223> OTHER INFORMATION: Recombinant

<400> SEQUENCE: 177

Arg Arg Val Val Val Gly Gly Gly Leu Thr Gly Leu Ser Ala Ala
1               5                   10                  15

Phe Tyr Ile Arg Lys His Tyr Arg Glu Ala Gly Val Glu Pro Val Ile
            20                  25                  30

Thr Leu Val Glu Lys Ser Ser Met Gly Gly Met Ile Glu Thr Leu
        35                  40                  45

His Arg Asp Gly Phe Val Ile Glu Lys Gly Pro Asp Ser Phe Leu Ala
    50                  55                  60

Arg Lys Thr Ala Met Ile Asp Leu Ala Lys Glu Leu Glu Ile Asp His
65                  70                  75                  80

Glu Leu Val Ser Gln Asn Pro Glu Ser Lys Lys Thr Tyr Ile Met Gln
                85                  90                  95

Arg Gly Lys Leu His Pro Met Pro Ala Gly Leu Val Leu Gly Ile Pro
            100                 105                 110

Thr Glu Leu Arg Pro Phe Leu Arg Ser Gly Leu Val Ser Pro Ala Gly
        115                 120                 125

Lys Leu Arg Ala Leu Met Asp Phe Val Ile Pro Pro Arg Arg Thr Thr
130                 135                 140

Glu Asp Glu Ser Leu Gly Tyr Met Ile Glu Arg Arg Leu Gly Ala Glu
145                 150                 155                 160

Val Leu Glu Asn Leu Thr Glu Pro Leu Leu Ala Gly Ile Tyr Ala Gly
                165                 170                 175
```

Asp Met Arg Arg Leu Ser Leu Gln Ala Thr Phe Pro Gln Phe Gly Glu
            180                 185                 190

Val Glu Arg Asp Tyr Gly Ser Leu Ile Arg Gly Met Thr Gly Arg
        195                 200                 205

Lys Pro Ala Glu Thr His Thr Gly Thr Lys Arg Ser Ala Phe Leu Asn
    210                 215                 220

Phe Arg Gln Gly Leu Gln Ser Leu Val His Ala Leu Val His Glu Leu
225                 230                 235                 240

Gln Asp Val Asp Gln Arg Leu Asn Thr Ala Val Lys Ser Leu Gln Arg
                245                 250                 255

Leu Asp Gly Ala Gln Thr Arg Tyr Arg Val Glu Leu Gly Asn Gly Glu
            260                 265                 270

Met Leu Glu Ala Asp Asp Val Val Thr Val Pro Thr Tyr Val Ala
    275                 280                 285

Ser Glu Leu Leu Lys Pro His Val Asp Thr Ala Ala Leu Asp Ala Ile
290                 295                 300

Asn Tyr Val Ser Val Ala Asn Val Leu Ala Phe Glu Lys Lys Glu
305                 310                 315                 320

Val Glu His Val Phe Asp Gly Ser Gly Phe Leu Val Pro Arg Lys Glu
                325                 330                 335

Gly Arg Asn Ile Thr Ala Cys Thr Trp Thr Ser Thr Lys Trp Leu His
            340                 345                 350

Thr Ser Pro Asp Asp Lys Val Leu Arg Cys Tyr Val Gly Arg Ser
    355                 360                 365

Gly Asp Glu Gln Asn Val Glu Leu Pro Asp Gly Ala Leu Thr Asn Leu
370                 375                 380

Val Leu Lys Asp Leu Arg Glu Thr Met Gly Ile Glu Ala Val Pro Ile
385                 390                 395                 400

Phe Ser Glu Ile Thr Arg Leu Arg Lys Ser Met Pro Gln Tyr Pro Val
                405                 410                 415

Gly His Leu Gln His Ile Ala Ala Leu Arg Glu Glu Leu Gly Ser Lys
            420                 425                 430

Leu Pro Gly Val Tyr Ile Ala Gly Ala Gly Tyr Glu Gly Val Gly Leu
    435                 440                 445

Pro Asp Cys Ile Arg Gln Ala Lys Glu Met Ser Val Gln Ala Thr Gln
    450                 455                 460

Glu Leu Ala Ala Asp
465

<210> SEQ ID NO 178
<211> LENGTH: 465
<212> TYPE: PRT
<213> ORGANISM: Artificial Sequence
<220> FEATURE:
<223> OTHER INFORMATION: Recombinant

<400> SEQUENCE: 178

Lys His Leu Val Ile Ile Gly Gly Gly Ile Thr Gly Leu Ala Ser Ala
1               5                   10                  15

Phe Tyr Met Glu Lys Glu Ile Arg Glu Lys Asn Leu Pro Leu Ser Val
            20                  25                  30

Thr Leu Val Glu Ala Ser Pro Arg Val Gly Gly Lys Ile Gln Thr Ala
        35                  40                  45

Arg Lys Asp Gly Tyr Ile Ile Glu Arg Gly Pro Asp Ser Phe Leu Glu
50                  55                  60

```
Arg Lys Lys Ser Ala Pro Glu Leu Val Glu Asp Leu Gly Leu Glu His
 65                  70                  75                  80

Leu Leu Val Asn Asn Ala Thr Gly Gln Ser Tyr Val Leu Val Asn Glu
                 85                  90                  95

Thr Leu His Pro Met Pro Lys Gly Ala Val Met Gly Ile Pro Thr Lys
            100                 105                 110

Ile Ala Pro Phe Met Ser Thr Arg Leu Phe Ser Phe Ser Gly Lys Ala
            115                 120                 125

Arg Ala Ala Met Asp Phe Val Leu Pro Ala Ser Lys Pro Lys Glu Asp
130                 135                 140

Gln Ser Leu Gly Glu Phe Phe Arg Arg Val Gly Asp Glu Val Val
145                 150                 155                 160

Glu Asn Leu Ile Glu Pro Leu Leu Ser Gly Ile Tyr Ala Gly Asp Ile
                165                 170                 175

Asp Arg Leu Ser Leu Met Ser Thr Phe Pro Gln Phe Tyr Gln Thr Glu
                180                 185                 190

Gln Lys His Arg Ser Leu Ile Leu Gly Met Lys Lys Thr Arg Pro Gln
                195                 200                 205

Gly Ser Gly Gln Gln Leu Thr Ala Lys Lys Gln Gly Gln Phe Gln Thr
210                 215                 220

Leu Lys Thr Gly Leu Gln Thr Leu Val Glu Glu Leu Glu Asn Gln Leu
225                 230                 235                 240

Lys Leu Thr Lys Val Tyr Lys Gly Thr Lys Val Thr Asn Ile Ser Arg
                245                 250                 255

Gly Glu Lys Gly Cys Ser Ile Ala Leu Asp Asn Gly Met Thr Leu Asp
                260                 265                 270

Ala Asp Ala Ala Ile Val Thr Ser Pro His Lys Ser Ala Ala Gly Met
275                 280                 285

Phe Pro Asp Leu Pro Ala Val Ser Gln Leu Lys Asp Met His Ser Thr
290                 295                 300

Ser Val Ala Asn Val Ala Leu Gly Phe Pro Gln Glu Ala Val Gln Met
305                 310                 315                 320

Glu His Glu Gly Thr Gly Phe Val Ile Ser Arg Asn Ser Asp Phe Ser
                325                 330                 335

Ile Thr Ala Cys Thr Trp Thr Asn Lys Lys Trp Pro His Ser Ala Pro
                340                 345                 350

Glu Gly Lys Thr Leu Leu Arg Ala Tyr Val Gly Lys Ala Gly Asp Glu
                355                 360                 365

Ser Ile Val Glu Leu Ser Asp Asn Glu Ile Ile Lys Ile Val Leu Glu
                370                 375                 380

Asp Leu Lys Lys Val Met Lys Ile Lys Gly Glu Pro Glu Met Thr Cys
385                 390                 395                 400

Val Thr Arg Trp Asn Glu Ser Met Pro Gln Tyr His Val Gly His Lys
                405                 410                 415

Gln Arg Ile Lys Lys Val Arg Glu Ala Leu Ala Ala Ser Tyr Pro Gly
                420                 425                 430

Val Tyr Met Thr Gly Ala Ser Phe Glu Gly Val Gly Ile Pro Asp Cys
                435                 440                 445

Ile Asp Gln Gly Lys Ser Ala Val Ser Asp Val Leu Ala Tyr Leu Phe
                450                 455                 460

Glu
465
```

-continued

```
<210> SEQ ID NO 179
<211> LENGTH: 473
<212> TYPE: PRT
<213> ORGANISM: Artificial Sequence
<220> FEATURE:
<223> OTHER INFORMATION: Recombinant

<400> SEQUENCE: 179
```

Ile Ala Val Ile Gly Gly Ile Thr Gly Leu Ser Val Ala Tyr Tyr
1               5                   10                  15

Val Arg Lys Leu Leu Arg Glu Gln Val Asn Ala Gly Val Thr Leu
            20                  25                  30

Val Glu Gln Ser Asp Arg Leu Gly Gly Lys Ile Arg Ser Leu Arg Arg
        35                  40                  45

Asp Gly Phe Thr Ile Glu Gln Gly Pro Asp Ser Met Ile Ala Arg Lys
    50                  55                  60

Pro Ala Ala Leu Glu Leu Ile Arg Glu Leu Gly Leu Glu Asp Lys Leu
65                  70                  75                  80

Ala Gly Thr Asn Pro Gln Ala Lys Arg Ser Tyr Ile Leu His Arg Gly
                85                  90                  95

Lys Phe His Pro Met Pro Pro Gly Leu Met Leu Gly Ile Pro Thr Gln
            100                 105                 110

Met Trp Pro Met Val Lys Thr Gly Leu Leu Ser Pro Ala Gly Lys Leu
        115                 120                 125

Arg Ala Ala Met Asp Leu Leu Leu Pro Ala Arg Arg Gly Gly Gly Asp
    130                 135                 140

Glu Ser Leu Gly Gly Phe Ile Arg Arg Arg Leu Gly Arg Glu Val Leu
145                 150                 155                 160

Glu Gln Met Thr Glu Pro Leu Leu Ala Gly Ile Tyr Ala Gly Asp Thr
                165                 170                 175

Glu Gln Leu Ser Leu Lys Ala Thr Phe Pro Gln Phe Met Glu Met Glu
            180                 185                 190

Arg Lys His Arg Ser Leu Ile Leu Gly Leu Leu Ala Gly Lys Lys Gln
        195                 200                 205

Pro Pro Arg Pro Gly Gly Ser Gln Val Pro Leu Pro Lys Ala Ala Gln
    210                 215                 220

Thr Ser Met Phe Leu Thr Leu Thr Gly Gly Leu Glu Gly Leu Thr Glu
225                 230                 235                 240

Ala Leu Glu Glu Ser Leu Ser Glu Glu Lys Ile Ile Thr Gly Gln Ala
                245                 250                 255

Val Thr Gly Leu Ser Gln Gln Glu Ala Gly Tyr Glu Leu Asn Leu Ser
            260                 265                 270

Gly Gly Glu Arg Leu Asn Ala Asp Gly Val Ile Leu Ala Val Pro Ala
        275                 280                 285

Phe Ala Ala Ala Arg Leu Leu Asp Gly Val Pro Glu Ala Ala Tyr Leu
    290                 295                 300

Glu Arg Ile Arg Tyr Val Ser Val Ala Asn Leu Ala Phe Ala Tyr Arg
305                 310                 315                 320

Arg Glu Asp Val Pro His Asp Leu Asn Gly Ser Gly Val Leu Ile Pro
                325                 330                 335

Arg Gly Glu Gly Arg Met Ile Thr Ala Ile Thr Trp Val Ser Ser Lys
            340                 345                 350

Trp Leu His Ser Ala Pro Gly Asp Lys Ala Leu Leu Arg Ala Tyr Ile
        355                 360                 365

Gly Arg Leu Gly Asp Glu Ala Trp Thr Ala Met Cys Arg Ala Asp Ile

```
                370                 375                 380
Glu Arg Arg Val Ala Ala Glu Leu Arg Asp Leu Leu Gly Ile Ala Ala
385                 390                 395                 400

Ser Pro Leu Phe Cys Glu Leu Ala Ala Leu Pro Glu Ser Met Pro Gln
                405                 410                 415

Tyr Pro Val Gly His Val Glu Arg Leu Glu Ala Leu Arg Gly Ala Leu
                420                 425                 430

Cys Arg Ala Lys Pro Gly Leu Leu Leu Cys Gly Ala Gly Tyr Ala Gly
                435                 440                 445

Val Gly Ile Pro Asp Cys Ile Arg Gln Gly Lys Glu Ala Ala Glu Ser
450                 455                 460

Met Ala Ala Tyr Leu Arg Asp Gly Arg
465                 470

<210> SEQ ID NO 180
<211> LENGTH: 487
<212> TYPE: PRT
<213> ORGANISM: Artificial Sequence
<220> FEATURE:
<223> OTHER INFORMATION: Recombinant

<400> SEQUENCE: 180

Leu Val Val Ile Gly Gly Ile Thr Gly Leu Ser Ala Ala Phe Tyr
1               5                   10                  15

Ala Leu Lys Gln Ala Asp Glu Gly Gln Pro Ile Ser Val Thr Ile
                20                  25                  30

Ile Glu Gln Ser Asp Arg Leu Gly Gly Lys Ile Gln Thr Leu Arg Lys
                35                  40                  45

Glu Gly Cys Val Ile Glu Lys Gly Pro Asp Ser Phe Leu Ala Arg Lys
50                  55                  60

Leu Pro Met Ile Asp Leu Ala Arg Asp Leu Gly Met Asp Ser Glu Leu
65                  70                  75                  80

Val Ala Thr Asn Pro His Ala Lys Lys Thr Tyr Ile Leu Arg Arg Gly
                85                  90                  95

Lys Leu Tyr Arg Met Pro Pro Gly Leu Val Leu Gly Ile Pro Thr Glu
                100                 105                 110

Leu Gly Pro Phe Ala Lys Thr Gly Leu Ile Ser Pro Trp Gly Lys Leu
                115                 120                 125

Arg Ala Ala Met Asp Leu Phe Ile Lys Pro His Pro Ala Asp Glu Asp
                130                 135                 140

Glu Ser Val Gly Ala Phe Leu Asp Arg Arg Leu Gly Arg Glu Val Thr
145                 150                 155                 160

Glu His Ile Ala Glu Pro Leu Leu Ala Gly Ile Tyr Ala Gly Asp Leu
                165                 170                 175

Gln Ala Leu Ser Leu Gln Ala Thr Phe Pro Gln Phe Ala Gln Val Glu
                180                 185                 190

Arg Lys His Gly Gly Leu Ile Arg Gly Met Lys Ala Ser Arg Gln Ala
                195                 200                 205

Gly Gln Ser Val Pro Gly Leu Pro Asp Val Ala Lys Gly Thr Met Phe
                210                 215                 220

Leu Thr Phe Arg Asn Gly Leu Thr Ser Leu Val Glu Arg Leu Glu Glu
225                 230                 235                 240

Thr Leu Arg Asp Arg Ala Glu Leu Cys Leu Gly Ile Gly Ala Glu Gly
                245                 250                 255

Phe Glu Lys Arg Glu Asp Gly Thr Tyr Leu Val Arg Leu Ser Asp Gly
```

```
                260                 265                 270
Ser Arg Leu Gln Ala Asp Ala Val Ile Val Thr Thr Pro Ser Tyr His
            275                 280                 285
Ala Ala Ser Leu Leu Glu Glu His Val Asp Ala Ser Ala Leu Gln Ala
        290                 295                 300
Ile Arg His Val Ser Val Ala Asn Val Val Ser Val Phe Asp Arg Lys
305                 310                 315                 320
Gln Val Asn Asn Gln Phe Asp Gly Thr Gly Phe Val Ile Ser Arg Arg
            325                 330                 335
Glu Gly Arg Ala Ile Thr Ala Cys Thr Trp Thr Ser Val Lys Trp Pro
        340                 345                 350
His Thr Ser Arg Gly Asp Lys Leu Ile Ile Arg Cys Tyr Ile Gly Arg
            355                 360                 365
Ala Gly Asp Glu Glu Arg Val Asp Trp Pro Asp Glu Ala Leu Lys Arg
        370                 375                 380
Thr Val Arg Ser Glu Leu Arg Glu Leu Leu Asp Ile Asp Ile Asp Pro
385                 390                 395                 400
Glu Phe Val Glu Ile Thr Arg Leu Arg His Ser Met Pro Gln Tyr Pro
            405                 410                 415
Val Gly His Val Gln Ala Ile Arg Ser Leu Arg Asp Glu Val Gly Arg
            420                 425                 430
Thr Leu Pro Gly Val Phe Leu Ala Gly Gln Pro Tyr Glu Gly Val Gly
            435                 440                 445
Met Pro Asp Cys Val Arg Ser Gly Arg Asp Ala Ala Glu Ala Ala Val
        450                 455                 460
Ser Ala Met Gln Ala Met Ser Thr Glu Pro Glu Ala Pro Ala Glu Asp
465                 470                 475                 480
Ala Ala Thr Gly Thr Ala Gly
                485

<210> SEQ ID NO 181
<211> LENGTH: 467
<212> TYPE: PRT
<213> ORGANISM: Artificial Sequence
<220> FEATURE:
<223> OTHER INFORMATION: Recombinant

<400> SEQUENCE: 181

Val Val Val Val Gly Gly Gly Leu Thr Gly Leu Ser Ala Ala Phe Tyr
1               5                   10                  15
Ile Arg Lys His Tyr Arg Glu Ala Gly Val Glu Pro Val Ile Thr Leu
            20                  25                  30
Val Glu Lys Ser Ser Ser Met Gly Gly Met Ile Glu Thr Leu His Arg
        35                  40                  45
Asp Gly Phe Val Ile Glu Lys Gly Pro Asp Ser Phe Leu Ala Arg Lys
    50                  55                  60
Thr Ala Met Ile Asp Leu Ala Lys Glu Leu Glu Ile Asp His Glu Leu
65                  70                  75                  80
Val Ser Gln Asn Pro Glu Ser Lys Lys Thr Tyr Ile Met Gln Arg Gly
            85                  90                  95
Lys Leu His Pro Met Pro Ala Gly Leu Val Leu Gly Ile Pro Thr Glu
            100                 105                 110
Leu Arg Pro Phe Leu Arg Ser Gly Leu Val Ser Pro Ala Gly Lys Leu
        115                 120                 125
Arg Ala Leu Met Asp Phe Val Ile Pro Pro Arg Arg Thr Thr Glu Asp
```

```
        130                 135                 140
Glu Ser Leu Gly Tyr Met Ile Glu Arg Arg Leu Gly Ala Glu Val Leu
145                 150                 155                 160

Glu Asn Leu Thr Glu Pro Leu Leu Ala Gly Ile Tyr Ala Gly Asp Met
                165                 170                 175

Arg Arg Leu Ser Leu Gln Ala Thr Phe Pro Gln Phe Gly Glu Val Glu
            180                 185                 190

Arg Asp Tyr Gly Ser Leu Ile Arg Gly Met Met Thr Gly Arg Lys Pro
        195                 200                 205

Ala Glu Thr His Thr Gly Thr Lys Arg Ser Ala Phe Leu Asn Phe Arg
    210                 215                 220

Gln Gly Leu Gln Ser Leu Val His Ala Leu Val His Glu Leu Gln Asp
225                 230                 235                 240

Val Asp Gln Arg Leu Asn Thr Ala Val Lys Ser Leu Gln Arg Leu Asp
                245                 250                 255

Gly Ala Gln Thr Arg Tyr Arg Val Glu Leu Gly Asn Gly Glu Met Leu
            260                 265                 270

Glu Ala Asp Asp Val Val Val Thr Val Pro Thr Tyr Val Ala Ser Glu
        275                 280                 285

Leu Leu Lys Pro His Val Asp Thr Ala Ala Leu Asp Ala Ile Asn Tyr
    290                 295                 300

Val Ser Val Ala Asn Val Val Leu Ala Phe Glu Lys Lys Glu Val Glu
305                 310                 315                 320

His Val Phe Asp Gly Ser Gly Phe Leu Val Pro Arg Lys Glu Gly Arg
                325                 330                 335

Asn Ile Thr Ala Cys Thr Trp Thr Ser Thr Lys Trp Leu His Thr Ser
            340                 345                 350

Pro Asp Asp Lys Val Leu Leu Arg Cys Tyr Val Gly Arg Ser Gly Asp
        355                 360                 365

Glu Gln Asn Val Glu Leu Pro Asp Glu Ala Leu Thr Asn Leu Val Leu
    370                 375                 380

Lys Asp Leu Arg Glu Thr Met Gly Ile Glu Ala Val Pro Ile Phe Ser
385                 390                 395                 400

Glu Ile Thr Arg Leu Arg Lys Ser Met Pro Gln Tyr Pro Val Gly His
                405                 410                 415

Leu Gln His Ile Ala Ala Leu Arg Glu Glu Leu Gly Ser Lys Leu Pro
            420                 425                 430

Gly Val Tyr Ile Ala Gly Ala Gly Tyr Glu Gly Val Gly Leu Pro Asp
        435                 440                 445

Cys Ile Arg Gln Ala Lys Glu Met Ser Val Gln Ala Thr Gln Glu Leu
    450                 455                 460

Ala Ala Asp
465

<210> SEQ ID NO 182
<211> LENGTH: 463
<212> TYPE: PRT
<213> ORGANISM: Artificial Sequence
<220> FEATURE:
<223> OTHER INFORMATION: Recombinant

<400> SEQUENCE: 182

Leu Val Ile Ile Gly Gly Gly Ile Thr Gly Leu Ala Ser Ala Phe Tyr
1               5                   10                  15

Met Glu Lys Glu Ile Arg Glu Lys Asn Leu Pro Leu Ser Val Thr Leu
```

```
                20                  25                  30
Val Glu Ala Ser Pro Arg Val Gly Gly Lys Ile Gln Thr Ala Arg Lys
            35                  40                  45

Asp Gly Tyr Ile Ile Glu Arg Gly Pro Asp Ser Phe Leu Glu Arg Lys
        50                  55                  60

Lys Ser Ala Pro Glu Leu Val Glu Asp Leu Gly Leu Glu His Leu Leu
65                  70                  75                  80

Val Asn Asn Ala Thr Gly Gln Ser Tyr Val Leu Val Asn Glu Thr Leu
                85                  90                  95

His Pro Met Pro Lys Gly Ala Val Met Gly Ile Pro Thr Lys Ile Ala
            100                 105                 110

Pro Phe Met Ser Thr Arg Leu Phe Ser Phe Ser Gly Lys Ala Arg Ala
        115                 120                 125

Ala Met Asp Phe Val Leu Pro Ala Ser Lys Pro Lys Glu Asp Gln Ser
    130                 135                 140

Leu Gly Glu Phe Phe Arg Arg Val Gly Asp Glu Val Val Glu Asn
145                 150                 155                 160

Leu Ile Glu Pro Leu Leu Ser Gly Ile Tyr Ala Gly Asp Ile Asp Arg
                165                 170                 175

Leu Ser Leu Met Ser Thr Phe Pro Gln Phe Tyr Gln Thr Glu Gln Lys
            180                 185                 190

His Arg Ser Leu Ile Leu Gly Met Lys Lys Thr Arg Pro Gln Gly Ser
        195                 200                 205

Gly Gln Gln Leu Thr Ala Lys Lys Gln Gly Gln Phe Gln Thr Leu Lys
    210                 215                 220

Thr Gly Leu Gln Thr Leu Val Glu Glu Leu Glu Asn Gln Leu Lys Leu
225                 230                 235                 240

Thr Lys Val Tyr Lys Gly Thr Lys Val Thr Asn Ile Ser Arg Gly Glu
                245                 250                 255

Lys Gly Cys Ser Ile Ala Leu Asp Asn Gly Met Thr Leu Asp Ala Asp
            260                 265                 270

Ala Ala Ile Val Thr Ser Pro His Lys Ser Ala Ala Gly Met Phe Pro
        275                 280                 285

Asp Leu Pro Ala Val Ser Gln Leu Lys Asp Met His Ser Thr Ser Val
    290                 295                 300

Ala Asn Val Ala Leu Gly Phe Pro Gln Glu Ala Val Gln Met Glu His
305                 310                 315                 320

Glu Gly Thr Gly Phe Val Ile Ser Arg Asn Ser Asp Phe Ser Ile Thr
                325                 330                 335

Ala Cys Thr Trp Thr Asn Lys Lys Trp Pro His Ser Ala Pro Glu Gly
            340                 345                 350

Lys Thr Leu Leu Arg Ala Tyr Val Gly Lys Ala Gly Asp Glu Ser Ile
        355                 360                 365

Val Glu Leu Ser Asp Asn Glu Ile Ile Lys Ile Val Leu Glu Asp Leu
    370                 375                 380

Lys Lys Val Met Lys Ile Lys Gly Glu Pro Glu Met Thr Cys Val Thr
385                 390                 395                 400

Arg Trp Asn Glu Ser Met Pro Gln Tyr His Val Gly His Lys Gln Arg
                405                 410                 415

Ile Lys Lys Val Arg Glu Ala Leu Ala Ala Ser Tyr Pro Gly Val Tyr
            420                 425                 430

Met Thr Gly Ala Ser Phe Glu Gly Val Gly Ile Pro Asp Cys Ile Asp
        435                 440                 445
```

Gln Gly Lys Ser Ala Val Ser Asp Val Leu Ala Tyr Leu Phe Glu
            450             455             460

<210> SEQ ID NO 183
<211> LENGTH: 1329
<212> TYPE: DNA
<213> ORGANISM: Xanthomonas campestris

<400> SEQUENCE: 183

| | |
|---|---:|
| atgcaaacac agcccgttat cattgccggc gccggtattg ccggactaag tatagcttac | 60 |
| gaattacagc agaaaggcat tccctatgaa atcatggagg cctcttccta tgcaggaggc | 120 |
| gttgtgaaat cattacatat tgatggttat gaactggatg ctggcccfaa ttcgctggcc | 180 |
| gcatctgcag cattcatggc ttatatcgat caactgggtt tgcaggacca ggtattggaa | 240 |
| gctgcggctg ccagtaagaa ccgctttctg gtcagaaatg ataaattgca tgcagtatcg | 300 |
| ccacatccct ttaagatact gcagtcagca tatatcagtg gtggcgccaa gtggcgtctg | 360 |
| ttcacagaaa gatttcgaaa agcggccgct ccggagggga aggaaacagt atcttccttt | 420 |
| gtgacccgcc gttttggaaa ggagatcaat gactaccttt ttgaacccgt gctttctggt | 480 |
| atatatgcag gtaatcctga tctgatgtca gttggtgaag tactgccfat gctgccacaa | 540 |
| tgggagcaaa aatacggtag tgttacgcag ggactcctga gaataaagg agctatgggt | 600 |
| ggacgtaaga tcattgcctt taaggaggt aatgcgacac tgacaaacag attgcaatcc | 660 |
| ctgcttagcg gtaagataag atttaactgt gccgtaacgg gtgtaacccg tggggcggac | 720 |
| gactatattg tacaatatac cgagaatggt aatacagcta tgctgaatgc atcccgtgtg | 780 |
| atattcacca cccctgcata cagtacagcc gtagctatac aggcacttga cgcttcccft | 840 |
| gctacacatc tcagcgatgt tccctatccc cgtatgggcg tactgcacct ggggtttgga | 900 |
| gcggaagccc ggcagaaagc accggcaggt tttggtttcc tggtgccgca tgctgcagga | 960 |
| aagcatttcc tgggcgctat ctgtaacagc gctatattcc cttcccgcgt accgacaggt | 1020 |
| aaagtgctgt ttacggtgtt cctgggtggc gcgagacaag aacagctgtt tgatcagctg | 1080 |
| gggcctgaaa agctacagca gacagtagtg aaagaactga tggaactgct gggcctgact | 1140 |
| acaccaccag aaatgcagcg ttttagtgaa tggaacagag cgattccgca actaaatgta | 1200 |
| ggttatgcac agacgaggca gcagataggc gttttttgaac agcgttaccc gggcatcaga | 1260 |
| ttagcgggta actatgtgac cggagtggct gtaccgcta tcatacaggc cgcaaaaggg | 1320 |
| tactgttga | 1329 |

<210> SEQ ID NO 184
<211> LENGTH: 1347
<212> TYPE: DNA
<213> ORGANISM: Chitinophaga pinensis

<400> SEQUENCE: 184

| | |
|---|---:|
| atgtctgatc aacccgtatt gattgtcggc gccggcttat ccggattgag cattgcgtat | 60 |
| gaattgcaga aactgcaggt gccttaccag gtactggaag tttcgggtca tagcggcggc | 120 |
| gtgatgaaat cattacggaa agatggattt gaactggatg caggcgctaa tacaatcgca | 180 |
| gcttctcctg aaatactggc atacttcaca tcactgggac tggaaaatga gatattgcag | 240 |
| gccaccgctg ccagcaagca ccggttcctg gtaagacggc ggcagttgca cgctgtttct | 300 |
| ccccatcctt tcaagatcat gtcgtctcct tacctgagca ggggcagtaa atggcggttg | 360 |
| tttaccgaac gttttcgcaa acctgttgtg gcaagcggag aagaaaccgt caccgatttt | 420 |

```
ataacaagaa ggtttaaccg ggagatagca gaatatgtgt ttgacccggt attatccggc       480
atatatgccg gcaatcccga ccagatgagc atagcggaag tattacctgc gttgccgcgc       540
tgggagcggg aatatgggag tgttaccaaa gggctgatga agataaagg cgcaatgggc        600 ggccggaaga ttatcagttt taaaggtggt aaccagttgc tcacaaaccg tttgcagcaa       660
ttgctcacta ccccggtgcg ctttaattgt aaggtaaccg gtatcaccgc atccaatggc       720
ggctatattg taagcgctgt agaagatggc gtatcagaaa gttatactgc ttcaagggtg       780
atattaacca cacctgctta cagcgcggca gcaactatta cgaatcttga tgctgctacc       840
gctgccttgt taaatgaaat tcattatccc cgtatgggcg tgctgcacct gggttttgac       900
gctactgcgt tgccgcagcc cctggatgga tttggtttcc tggtaccgaa tgctgaaaat       960
atgcatttcc tgggagcaat ctgcaacgct gcaattttcc cggataaggc gcctccggga      1020
aaaatcctct ttacggtatt cctgggagga gcaagacagg aaagtttgtt tgaccagatg      1080
acgcccgaag ctctgcaaca gcaggtagtt tcagaggtca tgtctttact gcatttatct      1140
gcgccgccgg taatgcagca tttcagtagc tggaataaag cgattccgca gttaaatgtg      1200
ggtcatgtta agttacggcg tgccgtggaa gcttttgaaa aaaaatatcc cggtattcac      1260
ctcagcggga attacctgca aggcgtagct atcccggctt tactgcaaca tgccgccgct      1320
ttggcggctt ccctgaagaa aaattaa                                          1347
```

<210> SEQ ID NO 185
<211> LENGTH: 1335
<212> TYPE: DNA
<213> ORGANISM: Artificial Sequence
<220> FEATURE:
<223> OTHER INFORMATION: Recombinant

<400> SEQUENCE: 185

```
caacccgtcc tcatcgttgg agctggtctc tccgggctct caatcgctta cgaactacag        60
aagctgcaag tcccttacca agtgctggag gtttctggac attctggtgg agtcatgaag       120
tcactccgga aggacggatt tgaactcgac gctggtgcca acaccatagc cacgtctccc       180
gagattcttg cgtactttac ctcactaggt cttgagaatg agatcctcca ggcgactgct       240
acttctaaac accgcttctt ggtgcggcga aggcaactgc acgccgtgag cccgcacccg       300
ttcaagatca tgtcatcgcc gtacctctgc cgtggctcca aatggaggct ctttactgag       360
cggtttcgga aacccgtcgt cgcttcgggc gaggagaccg tcaccgattt catcacgagg       420
agattcaacc gcgaaatagc ggagtatgtg ttcgaccctg ttctaagtgg gatctacgcc       480
gggaacccgg accaaatgag tattgctgag gtgttgcctg ccttgcctag gtgggaaagg       540
gagtacggat cagtgaccaa gggccttatg aaggataagg gtgcgatggg aggtcgaaag       600
atcatcagct ttaagggtgg caaccagcta cttacaaacc gcttacagca gctactcact       660
actccggtga gattcaattg caaggtgaca gggattacag ccagcaatgg cgggtacatc       720
gtgagcgctg ttgaggacgg cgtatctgag agctacaccg catctcgtgt gatcttgacc       780
acacccgctt actcagcagc ggctaccata actaaccttg atgcagccac tgcggcactg       840
ttgaacgaaa tccattatcc acgtatgggc gtgttacact gggctttga tgcaactgcc       900 ttgccacagc cgctggacgg gttcggattt ctagtgccga acgcggagaa catgcacttc       960
ctgggagcca tctgcaatgc agccatcttc cggacaaggg ctccgcccgg caagatcctg      1020
tttacagtgt tcctcggagg cgcacgccag gagtcgctct tcgatcagat gactcctgag      1080
```

-continued

| | |
|---|---|
| gctcttcagc agcaagtcgt tagtgaggtg atgagcttgt tgcacttgtc agctccaccg | 1140 |
| gtgatgcagc acttctcctc ctggaacaag gccatccctc aattgaacgt cgggcacgtg | 1200 |
| aagttgcggc gcgcggtaga ggcgttcgag aagaaatacc ctggaatcca tctctcgggc | 1260 |
| aactacctcc agggagttgc aataccagct ttactccagc acgccgcagc tttagctgct | 1320 |
| tctcttaaga agaac | 1335 |

<210> SEQ ID NO 186
<211> LENGTH: 1413
<212> TYPE: DNA
<213> ORGANISM: Bacillus subtilis

<400> SEQUENCE: 186

| | |
|---|---|
| atgagtgacg gcaaaaaaca tgtagtcatc atcggcggcg gcattaccgg tttagccgcc | 60 |
| gccttctata tggaaaaaga aatcaaagaa aagaatctgc cgcttgaact gacgcttgtt | 120 |
| gaggcaagtc cgagagtcgg cggaaaaatc cagactgtca agaaggacgg ctatatcatc | 180 |
| gaaagagggc cagactcatt tctggaacga agaaaagcg ccccgcagct tgttaaagac | 240 |
| ttaggtcttg agcatttgct tgtcaacaat gcgaccggac aatcctatgt gcttgtaaac | 300 |
| cgcactctgc atccaatgcc gaagggcgct gtaatgggga taccgacaaa aattgcgccg | 360 |
| tttgttccta cgggtctgtt ttctttgtct gggaaggcga gagctgctat ggatttcatc | 420 |
| ctgcctgcta gcaaaacaaa ggatgatcag tcattgggga aattcttccg cagacgtgtc | 480 |
| ggagatgaag tggtcgagaa cttaatcgag ccgcttctat cagggatcta cgcaggcgac | 540 |
| attgacaagc tcagcctgat gtcgacattc ccgcaatttt atcagacgga acaaaagcat | 600 |
| agaagcctga ttctcggcat gaaaaaaaca aggcctcaag gctcaggcca gcagctgacg | 660 |
| gcaaaaaaac aagggcagtt ccagactctg tcaaccggtt tgcagaccct tgtagaagag | 720 |
| atcgaaaagc agttaaagct gacgaaggtg tataaaggca caaaagtgac caaactcagc | 780 |
| catagcggct ctggctattc gctcgaactg gataacggcg tcacacttga tgctgattca | 840 |
| gtaattgtga ctgctccgca taaagcggct gcgggaatgc tttctgagct tcctgccatt | 900 |
| tctcatttga aaaatatgca ctccacatcc gtggcaaacg tcgctttagg tttccctgaa | 960 |
| ggctccgtcc aaatggagca tgagggcacg ggttttgtca tttcaagaaa cagtgacttt | 1020 |
| gcgatcacag cctgtacgtg gacgaataaa aaatggccgc acgcagcgcc ggaaggcaaa | 1080 |
| acgctgcttc gggcatatgt cggaaaagct ggagacgaat ccattgtcga tctatcagat | 1140 |
| aatgacatta tcaacattgt gttagaagac ttaaagaaag tcatgaacat aaacggcgag | 1200 |
| ccggaaatga catgtgtcac ccgatggcat gaaagcatgc cgcagtacca tgtcggccat | 1260 |
| aagcagcgta tcaaggagct gcgtgaagca cttgcatctg cgtatccggg tgtttatatg | 1320 |
| acaggcgctt ctttcgaagg tgtcggcatt cccgactgca ttgatcaagg aaaagctgcc | 1380 |
| gtgtctgacg cgcttaccta tttattcagc taa | 1413 |

<210> SEQ ID NO 187
<211> LENGTH: 1413
<212> TYPE: DNA
<213> ORGANISM: Bacillus pumilus

<400> SEQUENCE: 187

| | |
|---|---|
| atgcatgaca atcaaaaaca ccttgtcatc attggcggtg gcatcactgg tttagccgcc | 60 |
| gccttctatt tggaaaagga agtcgaggaa aaggtcttc cgattcaaat atcacttatt | 120 |
| gaagcgagcc ctaggctagg tggaaaaata caaacattat ataagacgg ctacatcatt | 180 |

```
gaacgtggac ctgattcatt tttagaaaga aaggtcagtg ggccgcagct tgcaaaagat    240
gtcggtctgt ccgatcagct cgtcaataat gaaactgggc aagcgtatgt actggtcaat    300
gaaaagcttc acccgatgcc aaaaggtgct gttatgggga ttccaactca aatcagccca    360
tttattacaa ctggtctttt ttcagttgcg ggaaaagcaa gagcggcgat ggatttcgtg    420
ttgccaaaaa gcaagcagac ggaagaccag tcgcttggtg aatttttag aagacgtgtg     480 ggtgatgagg tcgttgagaa tttaattgag ccgcttctat caggcattta tgcaggggat    540
attgaccgtc tgagcttaat gtcgaccttc ccgcaatttt atcaaacaga acagcagcat    600
cgaagtttga ttcttgggat gaaaaaatca cagcagcatg cgaaagcgca gcaagtgact    660
gcgaaaaaac aaggacagtt ccaaacgatc aatcaaggat tgcagtcgct tgtggaagca    720
gtagaaggta agctcaagct gacaacggtc tataaaggga caaagtcaa acaaattgaa     780 aaaacggatg gaggctatgg cttacaatta gacagcggtc aaacgctttt tgccgattca    840
gccattgtca cgactccgca tcaatcgatt tattccatgt ttcctaaaga agcagggcta    900
gagtatttgc atgacatgac ctctacttct gttgcaacag tagcactcgg ttttaaagat    960
gaggatgttc ataatgaata tgacggcact ggatttgtca tctcaagaaa cagtgatttc   1020
tctattacgg cctgtacatg gacaaacaaa aaatggccgc atactgctcc gaaaggaaaa   1080
acgctattgc gtgcgtatgt agggaaggct ggcgacgaat caattgtcga gcagtcagac   1140
agtcaaatcg tcagcattgt gctagaagat ttaaagaaaa tcatggatat taaagcagat   1200
ccagaattga cgacagtgac tcgctggaag acaagtatgc cgcaatatca cgtcggtcat   1260
cagaaagcca tttcgaacat gcgagaaacg tttaagcaat catatcctgg tgtttatatt   1320
acaggtgctg cttttgaagg tgtcggaatc cctgattgta ttgatcaagg aaaagccgcc   1380
atctcagagg ctgtatcgta tctattttca taa                                1413
```

<210> SEQ ID NO 188
<211> LENGTH: 1413
<212> TYPE: DNA
<213> ORGANISM: Bacillus pumilus

<400> SEQUENCE: 188

```
atgcatgaca atcaaaaaca ccttgtcatc attggcggtg gcatcactgg tttagccgcc     60
gccttctatt tggaaaagga agtcgaagaa aaaggtcttc ccattcaaat atctcttatt    120
gaagcgagcc ctaggctagg tggaaaaatc caaacattat ataaagacgg ctacatcatt    180
gaacgtgggc ctgattcatt tttagaaaga aaggtcagtg gaccgcagct ggcgaaagat    240
gtaggtctat ccgatcagct cgtcaataat gaaacagggc aggcgtatgt actagtcaat    300
gaaacccttc acccgatgcc aaaaggcgct gtcatggta ttccaactca aatcagccca     360
ttcatcacaa ccggtctttt ttcagttgca ggaaaagcga gagccgcaat ggatttcgtc    420
ttgccaaaaa gcaagcaaac agaagatcag tcgctcggtg aatttttag aagacgtgtc     480 ggtgatgaag tagttgagaa tttaatcgaa cctcttctat caggcattta tgcaggtgac    540
attgaccgtc tcagcttaat gtccaccttc ccgcagtttt atcaaacaga acaaaagcat    600
cgcagtttga ttcttgggat gaaaaaatca cagcagcatg cgaaagcgca gcaagtgaca    660
gcgaaaaaac aagggcagtt ccaaacgatc aatcaaggac ttcaagcgct tgttgaagca    720
gtagaaagca agctcaagct gacaacgatt tataaaggga caaagtgaa gcagattgaa     780 aaaacagatg ggggctacgg tgtgcagtta gacagcggtc aaacgctttt ggctgattca    840
```

```
gccattgtga caactccgca tcaatcgatc tattccatgt ttccaaaaga agcggggctt      900
gagtacttgc atgatatgac atctacttct gttgcaacgg ttgcactcgg ttttaaagaa      960
gaggatgttc ataatgaata tgacggtact ggttttgtca tctcaagaaa cagtgatttc     1020
tctattacag cttgtacgtg gacgaacaaa aaatggccgc atacagctcc taaaggaaaa     1080
acattattgc gtgcttatgt agggaaggct ggcgacgaat caattgtcga acagtcagac     1140
catcaaatcg tcagcattgt actgaggat  ttgaagaaaa ttatggatat taaagcagat     1200
ccagaactga caacagtgac tcgctggaag acgagcatgc cgcaatatca cgtcggtcat     1260
caaaaagcca tttcgaacat gcgagaaacg tttaagcaat catatcctgg tgtttatatc     1320
acaggtgctg cttttgaagg tgtcggaatc cctgattgta ttgatcaagg aaaagctgcc     1380
atttcagagg ctgtatctta tctattttca taa                                  1413
```

```
<210> SEQ ID NO 189
<211> LENGTH: 1329
<212> TYPE: DNA
<213> ORGANISM: Artificial Sequence
<220> FEATURE:
<223> OTHER INFORMATION: Recombinant

<400> SEQUENCE: 189
atgcaaactc agcccgtcat aatagcgggc gctggcattg cgggcctttc tatcgcatac       60
gagctgcaac agaagggcat tccttacgaa attatgaag cctcgtccta cgccggaggc      120
gtggtcaagt cccttcacat tgatggctac gaactagacg ccggacctaa ttcacttgcc      180
gcgtccgctg ccttcatggc ctacatcgac caactcggac tccaagatca agtgcttgaa      240
gccgccgcag catccaagaa ccgcttcctc gtaagaaacg acaagctcca tgcagtctcg      300
ccgcacccgt ttaagatcct ccagtcggcc tacatcagtg gcggcgctaa gtggagattg      360
tttaccgaaa ggttccgcaa agctgcggct ccagagggtg aggagacagt gagcagcttc      420
gtgacgagga ggtttggcaa ggagatcaac gactacctgt ttgaacccgt cttgtccggg      480
atctacgcgg gcaacccgga tttgatgagt gttggcgagg ttctgccgat gcttcctcaa      540
tgggagcaga agtacggcag cgttacacaa ggcttgttga agaataaggg cgcaatgggc      600
ggccgaaaga taatcgcttt caagggcggg aatgccacac tgaccaaccg tcttcagtca      660
ctgctctcag gaaagatccg cttcaattgc gccgtgacgg tgtcacacg aggcgcagac      720 gactacattg ttcagtacac tgagaatggc aataccgcaa tgttgaatgc aagccgcgtg      780
atcttcacaa caccgctta ctcaactgct gttgccatcc aggcgttgga cgccagcttg      840
gccactcacc tctctgatgt acctatcct cgcatgggtg tgttgcactt gggcttcggt      900
gctgaggcaa ggcagaaggc tcctgcgggc tttgggttct tggtcccaca cgcagccgga      960
aagcacttcc tgggagcaat ctgtaactcc gctatcttcc cttcgcgggt gcccactggc     1020
aaggtgttat tcaccgtgtt cttgggcggt gccagacagg agcaactgtt tgaccagcta     1080
ggccctgaga agttacaaca gacagtggtg aaggagctta tggaattgct gggcctaact     1140
acgccgccgg agatgcaacg attctctgag tggaatcgcg caataccgca acttaatgtt     1200
ggctacgccc agactcgtca gcagattggc gtattcgagc agcgctaccc tggcatccgc     1260
ttggccggga actatgtaac tggagtggcg gtgcccgcca ttatccaagc tgcaaagggc     1320
tattgctaa                                                             1329
```

```
<210> SEQ ID NO 190
<211> LENGTH: 1320
```

<212> TYPE: DNA
<213> ORGANISM: Artificial Sequence
<220> FEATURE:
<223> OTHER INFORMATION: Recombinant

<400> SEQUENCE: 190

```
cagcccgtca taatagcggg cgctggcatt gcgggccttt ctatcgcata cgagctgcaa      60
cagaagggca ttccttacga aattatggaa gcctcgtcct acgccggagg cgtggtcaag     120
tcccttcaca ttgatggcta cgaactagac gccggaccta attcacttgc cgcgtccgct     180
gccttcatgg cctacatcga ccaactcgga ctccaagatc aagtgcttga agccgccgca     240
gcatccaaga accgcttcct cgtaagaaac gacaagctcc atgcagtctc gccgcacccg     300
tttaagatcc tccagtcggc ctacatcagt ggcggcgcta agtggagatt gtttaccgaa     360
aggttccgca agctgcggc tccagagggt gaggagacag tgagcagctt cgtgacgagg     420
aggtttggca aggagatcaa cgactacctg tttgaacccg tcttgtccgg gatctacgcg     480
ggcaacccgg atttgatgag tgttggcgag gttctgccga tgcttcctca atgggagcag     540
aagtacggca gcgttacaca aggcttgttg aagaataagg gcgcaatggg cggccgaaag     600
ataatcgctt tcaagggcgg gaatgccaca ctgaccaacc gtcttcagtc actgctctca     660
ggaaagatcc gcttcaattg cgccgtgacg ggtgtcacac gaggcgcaga cgactacatt     720
gttcagtaca ctgagaatgg caataccgca atgttgaatg caagccgcgt gatcttcaca     780
acaccgctt actcaactgc tgttgccatc caggcgttgg acgccagctt ggccactcac     840
ctctctgatg taccctatcc tcgcatgggt gtgttgcact gggcttcgg tgctgaggca     900
aggcagaagg ctcctgcggg cttgggttc ttggtcccac acgcagccgg aaagcacttc     960
ctgggagcaa tctgtaactc cgctatcttc ccttcgcggg tgcccactgg caaggtgtta    1020
ttcaccgtgt tcttgggcgg tgccagacag gagcaactgt ttgaccagct aggccctgag    1080
aagttacaac agacagtggt gaaggagctt atggaattgc tgggcctaac tacgccgccg    1140
gagatgcaac gattctctga gtggaatcgc gcaataccgc aacttaatgt tggctacgcc    1200
cagactcgtc agcagattgg cgtattcgag cagcgctacc ctggcatccg cttggccggg    1260
aactatgtaa ctggagtggc ggtgcccgcc attatccaag ctgcaaaggg ctattgctaa    1320
```

<210> SEQ ID NO 191
<211> LENGTH: 1347
<212> TYPE: DNA
<213> ORGANISM: Artificial Sequence
<220> FEATURE:
<223> OTHER INFORMATION: Recombinant

<400> SEQUENCE: 191

```
atgagcgacc agcccgtcct catcgttgga gctggtctct ccgggctctc aatcgcttac      60
gaactacaga agctgcaagt cccttaccaa gtgctggagg tttctggaca ttctggtgga     120
gtcatgaagt cactccggaa ggacggattt gaactgacg ctggtgccaa caccatagcc     180
gcgtctcccg agattcttgc gtactttacc tcactaggtc ttgagaatga gatcctccag     240
gcgactgctg cttctaaaca ccgcttcttg gtgcggcgaa ggcaactgca cgccgtgagc     300
ccgcacccgt tcaagatcat gtcatcgccg tacctcagcc gtggctccaa atggcggctc     360
tttactgagc ggtttcggaa gcccgtcgtc gcttcgggcg aggagaccgt caccgatttc     420
atcacgagga gattcaaccg cgaaatagcg gagtatgtgt tcgaccctgt tctaagcggg     480
atctacgccg ggaacccgga ccaaatgagt attgctgagg tgttgcctgc cttgcctagg     540
```

```
tgggaaaggg agtacggatc agtgaccaag ggccttatga aggataaggg tgcgatggga      600
ggtcgaaaga tcatcagctt taagggtggc aaccagctac ttacaaaccg cttacagcag      660
ctactcacta ctccggtgag attcaattgc aaggtgacag ggattacagc cagcaatggc      720
gggtacatcg tgagcgctgt tgaggacggc gtatctgaga gctacaccgc atctcgtgtg      780
atcttgacca cacccgctta ctcagcagcg gctaccataa ctaaccttga tgcagccact      840
gcggcactgt tgaacgaaat ccattatcca cgtatgggcg tgttacactt gggctttgat      900
gcaactgcct tgccacagcc gctggacggg ttcggatttc tagtgccgaa cgcggagaac      960
atgcacttcc tgggagccat ctgcaatgca gccatcttcc cggacaaggc tccgcccggc     1020
aagatcctgt ttacagtgtt cctcggaggc gcacgccagg agtcgctctt cgatcagatg     1080
actcctgagg ctcttcagca gcaagtcgtt agtgaggtga tgagcttgtt gcacttgtca     1140
gctccaccgg tgatgcagca cttctcctcc tggaacaagg ccatccctca attgaacgtc     1200
gggcacgtga agttgcggcg cgcggtagag gcgttcgaga agaaataccc tggaatccat     1260
ctctcgggca actacctcca gggagttgca ataccagctt tactccagca cgccgcagct     1320
ttagctgctt ctcttaagaa gaactga                                         1347

<210> SEQ ID NO 192
<211> LENGTH: 1413
<212> TYPE: DNA
<213> ORGANISM: Artificial Sequence
<220> FEATURE:
<223> OTHER INFORMATION: Recombinant

<400> SEQUENCE: 192
atgtcggatg caagaagca cgtcgtcatc ataggcggtg ggatcactgg cttggccgct       60
gcattctaca tggagaagga gattaaggag aagaacctcc cacttgagct gacgctagtt      120
gaggccagtc ccagggtcgg cggcaagatc cagacggtca agaaggacgg gtacataatt      180
gaacgcggcc ctgacagctt cttagagcgc aagaaatcgg ctccgcagct agttaaggac      240
ttgggacttg agcacctgct cgtcaacaac gcgaccggac agtcgtacgt gctcgtgaac      300
cggacgctcc acccgatgcc gaagggcgct gtgatgggca ttccgaccaa gatagcacca      360
tcgtgagta ccggcctatt cagccttttcc ggcaaggcaa gggctgcgat ggacttcatc      420
ttgcctgcct ctaagactaa ggacgatcag tccttgggcg agttcttccg ccgccgggtg      480
ggtgatgagg tggtggagaa cttaattgag ccgctcctat ctggaatcta cgctggtgac      540
atcgacaaac tgtctctgat gtccacctt ccgcagttct accaaactga gcagaagcac       600
cgttcactta tcttgggaat gaagaagact agacctcaag gttcgggtca gcaactgacg      660
gccaagaaac agggtcagtt ccagacgcta agcaccgggc ttcagacact cgtgaggag       720
attgagaaac agctcaaact tactaaggtg tacaagggca cgaaggtgac aaagttatcc      780
cactccggca gcgggtactc cctggagttg gacaatggcg taacgttgga cgccgactca      840
gttatcgtga cagcgccgca taaggctgct gccgggatgt tgtcagaact cccggcgatt      900
tcccatctca agaacatgca cagtacctcg gttgccaacg tcgccctcgg attcccggaa      960
ggaagtgttc aaatggagca cgaaggcacg ggtttcgtaa tttccaggaa ctccgacttt     1020
gccatcaccg cttgtacttg accaacaag aagtggcctc atgctgcgcc ggagggcaag      1080
acattgctca gagcttacgt cgggaaggcg ggcgacgagt caatcgtcga tcttagcgac     1140
aacgacatca ttaacattgt gctggaggac ttgaagaagg ttatgaacat caatggcgag     1200
ccagagatga cctgcgtgac ccgatggcac gagtctatgc cgcagtacca cgtcggtcac     1260
```

| | |
|---|---|
| aagcagcgca tcaaggagtt gcgcgaggca ctcgcctcag cttaccctgg cgtgtacatg | 1320 |
| actggcgctt cgtttgaggg cgttggtatt cctgactgca tcgaccaggg aaaggcggcc | 1380 |
| gtcagtgacg cgctcaccta cctcttcagt tga | 1413 |

<210> SEQ ID NO 193
<211> LENGTH: 1413
<212> TYPE: DNA
<213> ORGANISM: Artificial Sequence
<220> FEATURE:
<223> OTHER INFORMATION: Recombinant

<400> SEQUENCE: 193

| | |
|---|---|
| atgcacgaca accagaagca cctggtcata atcggaggcg gcataaccgg ccttgctgcg | 60 |
| gccttctacc tggagaagga ggtcgaggag aagggtctcc ctatccagat ttcattgatt | 120 |
| gaggcttcgc ctcggctggg agggaagatc cagacattgt acaaggacgg gtacatcatc | 180 |
| gagcgtggtc cagacagttt cctggagcgg aaggtcagcg gaccgcagct cgccaaggac | 240 |
| gtgggactta gcgaccaact ggtgaacaac gagacaggac aggcgtacgt cttggtgaat | 300 |
| gagaagttgc acccgatgcc taagggtgcc gtgatgggca tcccaacgca aatctcacct | 360 |
| ttcatcacca ccggactctt ctccgtggcc ggaaaggcac gagctgcaat ggacttcgtt | 420 |
| ctgcctaagt cgaaacagac cgaagaccag tctctaggcg agttcttccg ccgccgtgtg | 480 |
| ggtgacgagg ttgtggagaa cctcatcgag cctttgttgt ctgggatcta cgcgggcgac | 540 |
| atcgacagac ttagtctcat gagtaccttt ccgcaattct atcagacaga acagcagcat | 600 |
| cgaagtctca tactcgggat gaagaagtca caacaacatg caaaggccca gcaagttacc | 660 |
| gccaagaaac agggccagtt ccaaacgatc aaccagggcc tccagagctt ggtggaggca | 720 |
| gtggagggaa agttgaagct caccaccgtt tacaaaggga caaggttaa acagattgag | 780 |
| aagacggacg gcggttacgg gttacaattg gactccggac agactctctt cgctgattcc | 840 |
| gctatcgtaa ctactcctca ccagagcatc tactctatgt tcccgaagga ggcgggcctg | 900 |
| gagtacctgc acgacatgac ttcaacgtct gtcgccaccg tggctttggg cttcaaggac | 960 |
| gaggacgtcc acaatgagta tgacgggacg ggattcgtta tcagtaggaa ctccgacttc | 1020 |
| agcatcaccg cctgcacgtg gaccaacaag aagtggccac acaccgcgcc caaagggaag | 1080 |
| acccttctga gggcatacgt gggcaaggcg ggcgacgaga gcatcgtcga gcaatctgat | 1140 |
| tctcagattg tttcaatcgt cctcgaagac ctcaagaaga tcatggacat caaggcagac | 1200 |
| ccggaactta ccaccgttac tcgatggaag acctcgatgc ctcagtatca cgtcgggcac | 1260 |
| cagaaggcaa tcagcaacat gagggagaca ttcaagcagt cgtatcctgg cgtgtacatt | 1320 |
| accggagcag cattcgaagg cgtaggaatc cctgactgca ttgaccaggg caaggctgct | 1380 |
| atctcagagg ccgtgtccta tctcttctcg tga | 1413 |

<210> SEQ ID NO 194
<211> LENGTH: 1413
<212> TYPE: DNA
<213> ORGANISM: Artificial Sequence
<220> FEATURE:
<223> OTHER INFORMATION: Recombinant

<400> SEQUENCE: 194

| | |
|---|---|
| atgcacgaca accagaagca cctggtgata attggaggcg ggattaccgg cctagcagcc | 60 |
| gctttctatc tggagaagga ggtggaggag aagggcctcc cgatacagat ttcgctgatt | 120 |

| | |
|---|---|
| gaagcctctc cgcgcctggg cggcaagatc cagacattgt acaaggacgg gtacatcatt | 180 |
| gagcgcgggc ctgactcgtt cctggagcgg aaggtctccg gtcctcaact ggccaaagac | 240 |
| gtgggtcttt ccgatcagct tgtgaacaat gagaccggtc aggcttacgt cttggtcaac | 300 |
| gaaactctgc atcccatgcc taagggagcc gttatgggca ttccaacgca aatctctccg | 360 |
| ttcataacga ctgggctgtt cagcgttgcg ggcaaagcaa gggctgctat ggacttcgtg | 420 |
| ctgccaaaga gtaagcagac cgaggaccag tccctcggcg agttcttccg ccgccgagtg | 480 |
| ggcgatgagg tggttgagaa tctaatcgaa ccgctgttgt cgggcatcta tgcgggcgac | 540 |
| atcgacaggc taagtcttat gtccactttc cctcagttct accagacaga gcagaaacac | 600 |
| aggagtctca tccttggaat gaagaagtcc cagcagcacg cgaaggctca gcaagtgacc | 660 |
| gccaagaagc aaggacagtt ccagaccatc aaccagggcc tacaggccct tgtcgaagcc | 720 |
| gttgagtcga gttaaagtt gacgacgatc tacaagggca ccaaggtgaa gcagattgag | 780 |
| aagactgacg gtggctatgg tgtgcaactc gattcgggcc aaacattgct cgctgactcc | 840 |
| gctatcgtca cgacgccaca ccagtcgatc tactcgatgt tcccgaagga ggcgggccta | 900 |
| gagtaccttc acgacatgac ctccacttcg gtcgccaccg ttgcactcgg ctttaaggag | 960 |
| gaggacgttc acaacgagta cgatggcacc ggattcgtga tctccaggaa ctcggacttc | 1020 |
| tcgattaccg cgtgcacgtg gacaaataag aagtggccgc acacagcgcc aaagggcaag | 1080 |
| acccttctgc gggcgtatgt gggcaaggcc ggtgacgaga gcattgtcga acaatctgac | 1140 |
| catcagatcg tttctattgt tcttgaggat ctcaagaaga taatggacat taaggccgac | 1200 |
| cctgagctta ccacagtgac gaggtggaag acctcgatgc cgcagtatca cgtagggcac | 1260 |
| cagaaggcca tctccaacat gcgggagaca ttcaagcagt cgtaccctgg cgtgtacatt | 1320 |
| actggcgctc ctttcgaggg cgttggcatc ccggactgca tcgaccaggg caaggccgca | 1380 |
| atctcagagg cagtgtcgta cctgttcagc tag | 1413 |

<210> SEQ ID NO 195
<211> LENGTH: 1329
<212> TYPE: DNA
<213> ORGANISM: Artificial Sequence
<220> FEATURE:
<223> OTHER INFORMATION: Recombinant

<400> SEQUENCE: 195

| | |
|---|---|
| atgcaaacgc aaccagtgat aatcgcgggc gctggcatcg ccggactttc cattgcgtac | 60 |
| gagctccagc agaagggtat cccgtacgag atcatggagg caagttccta tgccggcggc | 120 |
| gtcgtcaagt cactgcacat cgacgggtac gagctggacg cgggacccaa cagcctagcc | 180 |
| gcttccgctg ccttcatggc gtacatcgac cagctgggc tccaagacca agtcctcgag | 240 |
| gctgccgcgg cgagtaaaaa tcgctttctc gtgaggaacg acaagcttca cgctgtgtca | 300 |
| ccgcaccctt tcaaaatact tcaaagcgcc tacatctcgg gcggtgctaa gtggcggtta | 360 |
| ttcacgagc gttttaggaa ggccgccgct cccgaaggtg aggagactgt tcctctcttc | 420 |
| gtcacacgca ggttcggaaa ggagatcaac gattatctct tgagcctgt tctcagcgga | 480 |
| atatacgccg gcaacccaga ccttatgagc gtcgagagg ttctccctat gctgccgcaa | 540 |
| tgggagcaaa agtatggttc tgtgacccaa ggcctactga agaataaggg ggcgatgggc | 600 |
| ggaagaaaga taattgcatt caagggggggt aatgccaccc ttacaaatcg cctgcaaagc | 660 |
| cttttgtcgg gaaaaatccg tttcaattgt gccgtcaccg tgttacaag aggcgcagat | 720 |
| gattacatcg ttcagtacac cgagaacggt aataccgcca tgctaaacgc atctagggtg | 780 |

```
attttcacaa ccccggccta ctcaactgcc gtcgccatcc aagccctcga cgccagcctg      840
gccactcatc tcagtgatgt gccttaccct cgtatggggg tattacatct tggcttcggg      900
gccgaagcgc gacagaaagc ccccgctgga tttggcttcc tagtccctca cgccgccggt      960
aaacattttc ttggcgccat ctgtaactcc gcaatcttcc catccagagt gcctactggc     1020
aaggttctgt ttactgtgtt cctgggcggt gcccgccagg agcagctatt cgaccaatta     1080
ggcccagaaa agctccaaca aaccgttgtg aaggaactaa tggagttgct cggactgacg     1140
acaccacccg agatgcagag gttttctgag tggaaccgcg cgattccaca actcaacgtc     1200
gggtacgccc agacccggca acagataggg gttttcgagc agcgctatcc aggcattcga     1260
cttgctggta attacgtcac aggagtcgct gtgccagcca aatacaagc tgcaaagggg     1320 tattgctga                                                             1329
```

<210> SEQ ID NO 196
<211> LENGTH: 1347
<212> TYPE: DNA
<213> ORGANISM: Artificial Sequence
<220> FEATURE:
<223> OTHER INFORMATION: Recombinant

<400> SEQUENCE: 196

```
atgtcagacc aaccagtctt gattgttggg gccggcctct ctggcctgtc gattgcctac       60
gaactgcaga agctccaggt gccgtaccaa gtcctggagg tgtcgggcca tagcggcggt      120
gtcatgaaat cgctgcgtaa ggacggcttc gagttggacg cgggcgcgaa cacaatcgcg      180
gctagcccag aaatacttgc ttactttaca agtctgggtc tggagaatga gatcctccag      240
gctacagccg ctagcaaaca tcgattcctg gtgcgcaggc gacaactgca cgccgtcagt      300
ccacatccat tcaagataat gtcgagcccc tatttaagcc gcgggtccaa gtggaggctc      360
tttactgaaa gatttcgaaa accggtcgtc gctagcggag aagaaactgt tacagatttt      420
attactcgca ggttcaacag ggagattgca gaatatgtct tcgatccagt tctctcagga      480
atttacgcgg gcaacccaga ccagatgagc atcgctgaag tcctgcccgc gctccctcgg      540
tgggaacgag aatatggaag cgtcaccaaa ggtctcatga aggacaaggg ggccatgggc      600
ggtcggaaga tcatatcgtt taaaggcggg aaccagcttc tgactaaccg gctgcaacag      660
ctgctcacta caccagtgcg gtttaattgc aaagtcacag gtataacggc tagtaatggc      720
ggctacattg tttcagcggt cgaagatggt gtgagcgagt catacaccgc ctcccgcgtg      780
atccttacca caccggccta ctcggcggca gctacaatca ccaatcttga cgcggctaca      840
gccgcattac tcaacgagat tcattatccc aggatggggg tcctccatct gggcttcgac      900
gcgacagctc ttccccagcc cttggatggc ttcgggtttc tggtcccgaa cgccgaaaac      960
atgcattttc tcggcgccat ttgcaacgcc gcgatcttcc cggataaggc cccgcctgga     1020
aaaatattgt tcactgtctt tcttggcggc gcacgccagg agtccctgtt cgaccaaatg     1080 acccagagg ctctgcagca gcaggtggtc tctgaggtga tgtcacttct gcacctttct     1140
gcacctccag tgatgcagca cttctcaagc tggaataaag ctatccccca gttgaacgtc     1200
ggccacgtga agcttcgtag ggcggtcgaa gcgttcgaaa agaagtatcc aggcattcac     1260
ctgtccggca actatctgca gggcgtcgca atcccggcgc tactccagca cgccgctgcg     1320
ctagccgcgt ctcttaagaa gaattag                                         1347
```

<210> SEQ ID NO 197

```
<211> LENGTH: 1413
<212> TYPE: DNA
<213> ORGANISM: Artificial Sequence
<220> FEATURE:
<223> OTHER INFORMATION: Recombinant

<400> SEQUENCE: 197
atgagtgacg ggaagaagca cgttgtgata atcggaggcg ggataaccgg cctcgccgcc      60
gccttctata tggagaagga aattaaggag aaaaacctcc cgctagagct gacgttggtg     120
gaagcgtcac caagggtcgg cggtaagatc cagaccgtca aaaggatgg ctacatcatc      180 gagcgcggcc cggacagctt cctcgagcgg aagaagtccg cacccagtt agtcaaagac      240 ctcggcttgg aacaccttt ggtcaacaac gcgacaggtc agtcctatgt gcttgtgaat      300
cggacgctgc acccgatgcc taagggcgct gtcatgggta tccccacgaa gatcgcgccg      360
ttcgtatcga ccggcctgtt ctccctatca ggtaaggccc gcgctgccat ggactttatc      420
ctccctgcct cgaaaactaa agacgatcag tcactaggcg agttcttcg gcggcgagtg      480 ggtgacgagg tggtggagaa cctcatagaa ccctgctgt ccgggatcta cgctggagac      540
atcgacaagc tgagcctcat gtctacttt ccgcaatttt atcagaccga gcagaaacac      600
agatctctta tccttggcat gaagaagacc aggcctcagg gtcgggtca acagctcaca      660 gcaaagaagc aagggcagtt ccaaaccctg agcacaggct tgcagaccct ggtcgaagaa      720
attgagaagc agctgaaatt aacgaaggtt tacaagggaa ccaaggtcac caaacttagt      780
cacagcggct cgggctacag cctagagctt gacaacggag tgactctgga cgcagacagc      840
gtgatcgtga cggcgcccca caaggctgcg gcgggaatgc tgagtgagct ccccgccata      900
agtcatctca agaacatgca ctcgacgtcg gtagccaatg tcgcgttggg gtttcccgag      960
ggtagcgtcc aaatggaaca cgaaggaact ggtttcgtca tatcccggaa ctctgacttc     1020
gcgatcacag cgtgcacttg gacgaataaa aagtggccgc acgcagcgcc tgaggggaag     1080
acccttcttc gagcgtatgt gggcaaagcg ggcgatgaaa gcattgtgga tttatcggac     1140
aacgacatta tcaacatcgt actggaagac ctaaagaaag tcatgaacat aaacggcgaa     1200
ccggagatga catgcgtcac taggtggcac gagagcatgc cgcagtacca cgtggggcac     1260
aagcagcgca tcaaggaatt gagggaggcc ctcgctagcg cgtaccctgg agtttacatg     1320
accggcgcca gttttgaggg tgtcggtatc cctgactgta tcgaccaggg taaggccgcg     1380
gtaagcgacg cattgacgta cctgttctca tga                                1413

<210> SEQ ID NO 198
<211> LENGTH: 1413
<212> TYPE: DNA
<213> ORGANISM: Artificial Sequence
<220> FEATURE:
<223> OTHER INFORMATION: Recombinant

<400> SEQUENCE: 198
atgcacgaca accagaagca tctggtcatc attggcgggg gcatcacggg cttggcagcc      60
gccttctacc tggagaagga ggtcgaggag aagggccttc cgattcaaat atctctgatt     120
gaggcgtctc ccgactcgg cggaagatc cagaccctct ataaagacgg ctatataatt       180
gagcggggac cagattcttt cctggagcga aaggtctcgg cccacagtt ggcgaaagat      240 gtcggcctct ccgatcaact cgtgaacaac gagaccgggc aggcctatgt tctggtgaac      300
gagaaattgc atcctatgcc taagggggcc gtcatgggaa taccaaccca atatctcccc      360
ttcataacaa ccggactgtt ctcggttgcc ggtaaggcca gggccgcgat ggacttcgtc      420
```

```
ctgccaaagt ctaagcagac ggaggaccag tccctcgggg aattttttccg ccgccgggtc      480 ggcgacgagg ttgtggaaaa cctgattgag ccgttgctgt ctggcatcta cgcaggcgat      540
atcgacaggc tgagccttat gtctacgttc ccgcaatttt atcagaccga gcagcagcac      600
cggtctctga tacttggcat gaagaaatca aacagcacg ccaaagcaca acaggttact       660
gctaagaagc aaggacaatt ccagacaatc aaccaagggt tgcagtccct cgtggaggcg      720
gtagaaggca aattgaaact caccaccgtc tacaagggca cgaaagttaa gcagatcgag      780
aaaacggatg gcgggtacgg tctccagctc gatagcggcc agacactgtt cgccgactca      840
gcgatcgtca ccacccccca ccagtccatc tacagcatgt tccctaagga ggcggggtta      900
gaatacttac atgacatgac ctccacctcc gtcgccacag tagctctcgg cttcaaggac      960
gaggacgtgc acaacgaata cgacggtacc gggttcgtga tctcgcggaa ttcggacttc     1020
agtattactg cctgcacctg gacgaacaag aagtggccac acacagcacc caaaggtaag     1080
accttgctga gggcttatgt gggtaaggcg ggggacgaga gcatagtgga gcagtctgac     1140
tcgcagatcg tcagcatcgt actggaagac ctgaagaaga tcatggacat caaggccgac     1200
ccggagttga ccaccgtcac acggtggaaa acctcaatgc cacaatatca tgtcggacat     1260
cagaaggcca tctccaacat gcgcgagacc ttcaagcagt cttacccggg cgtgtatatc     1320
accggagcgg ctttcgaggg ggtcggcatc cctgactgca tagaccaggg gaaggcggcc     1380
atcagcgagg ctgtgtcgta cctttttctcg tga                                  1413

<210> SEQ ID NO 199
<211> LENGTH: 1413
<212> TYPE: DNA
<213> ORGANISM: Artificial Sequence
<220> FEATURE:
<223> OTHER INFORMATION: Recombinant

<400> SEQUENCE: 199
atgcatgaca accagaaagca cctggttatc attggcggtg gcataaccgg gctcgccgcc       60
gccttttacc tggagaagga ggtggaggaa aaaggcctcc caatccagat cagtttgata      120
gaggcgagtc cgcgcttggg gggcaagatc cagactctgt ataaagatgg atacattatc      180
gagaggggtc cagacagctt cctggagcgc aaggtctccg ggcctcagtt ggcgaaggat      240
gttgggttgt cagatcagct cgtgaacaac gaaacgggcc aggcgtatgt gttagtcaat      300
gaaactctgc accccatgcc caagggcgcg gtgatgggga tacccaccca gatcagtccc      360
ttcatcacaa ccggtctgtt ctcggtcgca gggaaggccc gagcggcgat ggattttgtc      420
ctgcccaagt cgaagcagac cgaggaccag agcctcgggg agttttttcag gcgcagagtt      480 ggcgatgagg tcgtcgagaa cctcattgag ccgcttctca gcgggattta tgcgggagac      540
atcgacaggc tctccctgat gtcaactttt ccgcagttct accagacgga gcaaaagcac      600
aggagcctga ttctgggaat gaagaagtca aacaacatg ctaaagccca gcaggtaact       660
gcaaagaagc agggtcagtt ccaaacaatc aatcaaggtc tccaggcact cgtcgaggcc      720
gtggagtcaa agctaaagct gaccaccata tacaagggta ccaaagtgaa acaaatcgag      780
aagacagacg gcggttacgg agtgcagctt gactccggcc agaccctcct cgccgactct      840
gcgatcgtga ccacgccgca ccagtccatc tactctatgt tccccaagga ggccgggctc      900
gaatatttgc acgatatgac cagcaccagc gtcgctacgg tagcactcgg gttcaaggag      960
gaggacgtcc acaacgagta cgatggcact ggcttcgtga tcagccgtaa ctctgatttc     1020
```

| | |
|---|---|
| agcatcactg catgcacatg gactaataag aaatggcccc acactgcacc caagggcaag | 1080 |
| acgctgctgc gagcctacgt cgggaaggcc ggggacgagt ctattgtaga gcagagcgat | 1140 |
| caccagattg tgagtatcgt actggaggac ctgaaaaaga tcatggatat aaaggcggac | 1200 |
| ccagagctga ctaccgtgac ccgctggaaa acatccatgc cgcaatacca tgtgggccac | 1260 |
| caaaaagcga tctccaacat gcgggagacg ttcaagcaat cttatcccgg cgtgtacatc | 1320 |
| acggagccg cgttcgaggg cgtgggcatc ccggattgca tcgatcaggg taaggctgcg | 1380 |
| atatcggagg ctgtcagtta cctgttttct tag | 1413 |

<210> SEQ ID NO 200
<211> LENGTH: 1434
<212> TYPE: DNA
<213> ORGANISM: Paenibacillus macerans

<400> SEQUENCE: 200

| | |
|---|---|
| gtgagcaaaa aaatcgccgt catcggcgga ggcataaccg ggttaagcgt ggcttattac | 60 |
| gtgcgtaaat tgctgcgtga acaggggta acgctggggg ttaccctcgt ggaacagtcc | 120 |
| gatcggctgg gcggcaaaat ccgttcccta cgacgtgacg gctttacgat agaacagggc | 180 |
| ccggattcaa tgatcgcgcg caagcccgcc gcgctggaat tgatccggga actcgggctg | 240 |
| gaggataagc tggcgggaac gaatccgcag gcgaagcgaa gttatatatt gcatcgcggc | 300 |
| aaattccatc ccatgccgcc ggggctgatg ctcggcatac cgacgcaaat gtggccgatg | 360 |
| gtcaagacgg ggctgctctc tccggccggc aagctgcggg ccgcgatgga tctgctgctt | 420 |
| cccgcgcggc gcggcggcgg cgacgaatcg ctcggcggct tcatccgccg ccggctcggc | 480 |
| agagaagtgc tggagcagat gacggagccg cttctagccg gcatatatgc cggggacacc | 540 |
| gaacagctta gcttgaaagc gacgtttccg cagtttatgg agatggagcg caagcaccgc | 600 |
| agcctgatcc ttgggctgct ggccggcaaa aagcagccgc gcggccgggg ggaagccag | 660 |
| gtcccgctgc cgaaggccgc gcaaaccagc atgtttctga cgttgacggg cggtttggag | 720 |
| ggactgacgg aagcgctgga ggaatcgcta agcgaagaga aataattac cggccaggcg | 780 |
| gtaaccggac tgtcgcagca agaggcgggt tatgagctta acttaagcgg gggcgagcgt | 840 |
| ttgaacgcgg acggagtcat tttggcagtt cctgcttttg ctgcggcccg gctattggat | 900 |
| ggcgttcccg aagccgctta cctggagcgg atccgttatg tgtccgtggc caatttagcc | 960 |
| ttcgcctacc ggcgggaaga cgttccgcac gatttgaacg gctccggcgt gcttatcccg | 1020 |
| cgcggggagg ggcgaatgat tacgccatt acctgggttt cttcgaaatg gctgcattcg | 1080 |
| gctcccggcg ataaagcgct gctgcgagcc tatatcggcc gcctgggcga cgaggcatgg | 1140 |
| accgcgatgt gcagggccga catcgagcgc cgggtggccg ccgagctgcg cgatttgctg | 1200 |
| ggcatcgccg ccagcccgct gttttgcgag ctcgccgctt tgccggagtc gatgccccaa | 1260 |
| tatccggtcg gcatgtcga gcggcttgag gcgctgcgcg gggcattgtg ccgggcgaag | 1320 |
| ccggggctgc tgctgtgcgg cgcgggatat gccggcgtag gcattcccga ctgcatccgg | 1380 |
| cagggcaagg aagccgctga agcatggcg gcttatttga gggatggacg gtga | 1434 |

<210> SEQ ID NO 201
<211> LENGTH: 1482
<212> TYPE: DNA
<213> ORGANISM: Paenibacillus thiaminolyticus

<400> SEQUENCE: 201

| | |
|---|---|
| atgaaagctc tgcggaaact tgtcgttatc ggtggcggaa ttacgggatt gagcgcggcg | 60 |

```
ttctatgcgc tgaagcaggc ggatgaagag gggcagccca tctccgttac catcatagag      120
caatcggacc gtctcggcgg aagatacag  accctgcgga aggaagggtg tgtcattgag      180
aaaggcccgg actccttcct cgcccggaag ctgccgatga tcgatttggc gcgcgacctc      240
ggaatggatt ctgaattggt cgccacgaat ccgcatgcca aaaaaacata tatattgcgc      300
cggggcaagc tgtaccggat gccgcccggc ctcgtgctgg gcatcccgac ggagctgggg      360
ccgttcgcga agacagggct catctccccg tggggaagc  tgcgcgcggc tatggatctg      420
ttcatcaagc cgcatccggc ggatgaagat gaatccgttg gcgcgttcct ggacagacgg      480
ctcggacgcg aagtgacgga gcatattgcc gagccgctgc ttgccggcat ttatgccgga      540
gatttgcagg cgctgagcct gcaggccacc ttcccgcagt tcgcgcaggt ggagcggaag      600
cacggtggcc tgatacgcgg aatgaaggcg agccgccaag caggccaatc ggtaccgggg      660
ctgccggatg tcgccaaagg aacgatgttc ctgacattcc gcaacggctt gacctcgctc      720
gtcgaacggc tggaggagac gctgcgggac cgggccgaat tgtgccttgg catcggcgcg      780
gaaggattcg agaagcggga ggacggaacg tatctggtgc gcttgagcga tgggagcagg      840
ctgcaggcga tgccgtcat  cgtgacgacg ccttcgtatc atgcggcatc cttgctcgag      900
gagcatgtcg atgcgagcgc cttgcaggcg atccgtcatg tatccgtcgc gaatgtcgtc      960
agcgtgttcg atcgcaagca ggtcaataat cagttcgacg gcacagggtt cgtcatctcg      1020
cgccgggaag gccgggcgat tacggcctgc acgtggacct cggtgaagtg gccgcatacg      1080
agccgcgggg acaagcttat tatccgctgc tacattggcc gggccggtga cgaggaacgg      1140
gtggactggc cggacgaggc gctcaagcgg acggtgcgca gcgagctgcg ggagctgctt      1200
gatatcgata tcgacccgga gttcgtcgag attacgcgcc ttcgccactc gatgccccag      1260
tatccggtcg gccatgtgca ggcgatccgc tcgctgaggg acgaggtggg gcgcacgctc      1320
ccaggcgtgt tcctggcagg acagccgtac gaagggggtcg gcatgcccga ttgcgttcgc      1380
agcggccgcg atgcggcgga agccgcggtt agcgcgatga aggccatgag tacggagcca      1440
gaggcgccag ccgaggatgc cgctactgga acggcggggt aa                        1482
```

<210> SEQ ID NO 202
<211> LENGTH: 1425
<212> TYPE: DNA
<213> ORGANISM: Paenibacillus polymyxa

<400> SEQUENCE: 202

```
atgggtgata agaaacgccg tgttgttgtt gtcggcggtg ccttaccgg  cctcagcgcg       60 gcatttttata tccgcaagca ttaccgggaa gcaggagttg aacctgtgat tactttggtc      120
gagaaaagct cgtccatggg aggcatgatt gagacactgc accgggatgg atttgtgatt      180
gaaaaagggc ccgattcgtt cctggctcgc aaaacggcaa tgattgatct ggccaaagaa      240
ttggagatcg atcatgagct ggtaagtcag aatccggagt cgaagaaaac gtatatcatg      300
cagcgtggca agcttcatcc tatgccagca ggacttgttc tcggtattcc gacagaacta      360
agaccattct tgagaagtgg tttggttcct ccggcaggca aactgcgggc gttgatggat      420
tttgtcatcc cgccgcgtcg tacaacagag gatgaatcgc tcggttatat gattgaacgc      480
cgtcttggag cagaagtgct ggagaacttg acggaaccac tgctcgcagg aatctatgca      540
ggtgatatgc ggcgattgag cctccaggct accttcccgc agttcggaga agtagagcgc      600
gattacggca gcttgatccg gggcatgatg acggggcgca aaccggctga gacgcatacc      660
```

| | |
|---|---:|
| ggaacaaaac ggagcgcttt tttgaacttt cgccagggac ttcagagcct tgttcatgca | 720 |
| ctcgtccatg agttgcagga tgtggatcaa cgtctgaaca ctgcggtgaa atcgctgcaa | 780 |
| cgccttgatg gagcgcagac cagataccgt gttgaacttg gtaatggcga aatgcttgaa | 840 |
| gccgatgatg tagtggttac tgtgccgaca tatgtcgcgt cggagctgtt gaagcctcac | 900 |
| gtggacacag cggcactgga tgcgattaac tatgtgtctg tagccaatgt agtgctcgct | 960 |
| tttgagaaaa aagaggtgga gcatgtattc gacggatcgg gtttcctcgt tccgcggaaa | 1020 |
| gagggtcgga atattacggc ttgcacgtgg acatcgacga aatggctgca taccagcccg | 1080 |
| gatgataaag tactgcttcg ctgttatgtt ggtcgctccg gtgacgaaca gaacgtagag | 1140 |
| cttccggatg aagcgctgac gaatctcgtt ctcaaagatc tgagagagac gatgggtatt | 1200 |
| gaagcagtgc cgatcttctc cgagattaca aggcttcgta atccatgcc acagtatccg | 1260 |
| gtgggacacc ttcaacatat tgccgctctc cgtgaggagc ttggcagcaa attaccgggt | 1320 |
| gtgtacattg caggtgcagg ttatgagggc gtaggcttgc ctgattgcat cagacaagcg | 1380 |
| aaggaaatgt ctgttcaggc tacacaagag cttgcagcag attaa | 1425 |

<210> SEQ ID NO 203
<211> LENGTH: 1413
<212> TYPE: DNA
<213> ORGANISM: Bacillus atrophaeus

<400> SEQUENCE: 203

| | |
|---|---:|
| atgagtgacg gcaaaaagca tcttgtcatc atcggcggcg gcatcacggg attggcctcc | 60 |
| gccttctata tggaaaaaga aatcagagag aaaaatttgc ctctttctgt gacgttagtc | 120 |
| gaagcaagcc cgagagttgg cgggaaaatt caaacggccc gcaaggacgg ttatattatt | 180 |
| gaaagagggc cggactcatt tttagaaaga aaaaaaagcg caccggagct tgtcgaagat | 240 |
| ttaggccttg agcatttgct tgtcaacaat gcgacggggc agtcttatgt gctggttaac | 300 |
| gaaacgcttc acccgatgcc aaagggcgct gttatgggca tacctactaa aatagcgcca | 360 |
| tttatgtcta ccggcttatt ttcattttcc ggcaaagcgc gcgcggctat ggatttcgtt | 420 |
| ttgcccgcaa gcaagccgaa ggaagatcag tccctgggtg aattcttccg caggcgtgtc | 480 |
| ggtgacgaag ttgttgaaaa tttgattgag ccgctattat ccggcattta tgcgggtgac | 540 |
| attgacaggc tcagcctgat gtcgacgttc ccgcagtttt atcagaccga acaaaagcac | 600 |
| agaagcttga tcctcggcat gaaaaaaaca aggcctcagg gctccggaca gcggttaacg | 660 |
| gctaaaaaac aagggcaatt ccaaaaccta aagaccggct tgcagacact cgtcgaagag | 720 |
| ctggaaaacc agctgaagct gacgaaggta tacaagggta caaaagtaac caatatcagc | 780 |
| cgcggggaaa agggctgctc catcgctctt gataacggga tgacgctgga tgccgatgca | 840 |
| gcgattgtaa cctcaccgca caaatcggct gccggaatgt ttccggatct gccagctgtc | 900 |
| agtcagttaa aagacatgca ctctacctct gtggcgaatg tcgcgcttgg ctttccacaa | 960 |
| gaggctgtcc aaatggaaca tgaaggaacg ggttttgtca tctcaagaaa cagtgatttt | 1020 |
| tcaataacgg cctgtacttg gacgaataaa aaatggccgc actctgctcc ggaaggcaaa | 1080 |
| acgctcctca gggcttatgt cggaaaagcg ggtgatgaat caatcgtcga actgtctgat | 1140 |
| aatgagatta tcaaaattgt attagaagac ctaaagaaag tcatgaaaat caaaggcgaa | 1200 |
| cctgaaatga cgtgcgtcac acgctggaat gagagtatgc cccaatatca tgtcggccac | 1260 |
| aaacagcgta taaaaaaagt gcgcgaagca ctggctgctt cctatccggg agtttacatg | 1320 |
| acgggcgctt cattcgaagg cgttgggatt ccggactgta tcgatcaagg gaaaagcgcc | 1380 |

<210> SEQ ID NO 204
<211> LENGTH: 1413
<212> TYPE: DNA
<213> ORGANISM: Bacillus atrophaeus

<400> SEQUENCE: 204

| | | | | | |
|---|---|---|---|---|---|
| atgagtgacg | gcaaaaagca | tcttgtcatc | atcggcggcg | gcatcacggg | attggcctcc | 60 |
| gccttctata | tggaaaaaga | aatcagagag | aaaaatttgc | ctctttctgt | gacgttagtc | 120 |
| gaagcaagcc | cgagagttgg | cgggaaaatt | caaacggccc | gcaaggacgg | ttatattatt | 180 |
| gaaagagggc | cggactcatt | tttagaaaga | aaaaaaagcg | caccggagct | tgtcgaagat | 240 |
| ttaggacttg | agcatttgct | tgtcaacaat | gcgacggggc | agtcttatgt | gctggttaac | 300 |
| gaaacgcttc | acccgatgcc | aaagggcgct | gttatgggca | tacctactaa | aatagcgcca | 360 |
| tttatgtcta | cccgcttatt | ttcattttcc | ggcaaagcgc | gcgcggctat | ggatttcgtt | 420 |
| ttgcccgcaa | gcaagccgaa | ggaagatcag | tccctgggtg | aattcttccg | caggcgtgtc | 480 |
| ggtgacgaag | ttgttgaaaa | tttgattgag | ccgctattat | ccggcattta | tgcgggtgac | 540 |
| attgacagac | tcagcctgat | gtcgacgttc | ccgcagtttt | atcagaccga | acaaaagcac | 600 |
| agaagcttga | tcctcggcat | gaaaaaaaca | aggcctcagg | gctccggaca | gcagttaacg | 660 |
| gctaaaaaac | aagggcaatt | ccaaacctta | agaccggct | tgcagacact | cgtcgaagag | 720 |
| ctggaaaacc | agctgaaact | gacgaaggta | tacaagggta | caaagtaac | caatatcagc | 780 |
| cgcggggaaa | agggctgctc | catcgctctt | gataacggga | tgacgctgga | tgccgatgcc | 840 |
| gcgattgtga | cctcaccgca | caaatcggct | gccggaatgt | ttccggatct | gccagctgtc | 900 |
| agccagttaa | aagacatgca | ctctacctct | gtggcgaatg | tcgcgcttgg | ctttccacaa | 960 |
| gaggctgtcc | aaatggaaca | tgaaggaacg | gttttgtca | tctcaagaaa | cagtgatttt | 1020 |
| tcaataacgg | cctgtacttg | gacgaataaa | aaatggccgc | actctgctcc | ggaaggcaaa | 1080 |
| acgctcctca | gggcttatgt | cggaaaagcg | ggtgatgaat | caatcgtcga | actgtctgat | 1140 |
| aatgagatta | tcaaaattgt | attagaagac | ctaaagaaag | tcatgaaaat | caaggcgaa | 1200 |
| cctgaaatga | cgtgcgtcac | acgctggaat | gagagtatgc | cccaatatca | tgtcggccac | 1260 |
| aaacagcgta | taaaaaaagt | gcgcgaagca | ctggctgctt | cctatccggg | agtttacatg | 1320 |
| acgggcgctt | cattcgaagg | cgttgggatt | ccggactgta | tcgaccaagg | gaaaagcgcc | 1380 |
| gtttcagacg | tacttgctta | tttattcgaa | tga | | | 1413 |

<210> SEQ ID NO 205
<211> LENGTH: 1434
<212> TYPE: DNA
<213> ORGANISM: Artificial Sequence
<220> FEATURE:
<223> OTHER INFORMATION: Recombinant

<400> SEQUENCE: 205

| | | | | | |
|---|---|---|---|---|---|
| atgtcaaaga | agattgcagt | cattggtggt | gggataacag | ggttgtccgt | ggcctactac | 60 |
| gtgaggaagc | tgcttcggga | gcaaggcgtt | aatgcgggcg | ttaccctcgt | cgagcaatcc | 120 |
| gaccgcctcg | gcgggaagat | tagatccttg | agacgagacg | gctttaccat | tgagcaaggc | 180 |
| cctgactcta | tgattgcacg | taagcccgca | gctctcgaac | ttatccgtga | gcttggtctg | 240 |
| gaggacaagt | tggcgggcac | aaaccctcaa | gccaaacgct | cctacatact | gcaccgtggc | 300 |

| | |
|---|---|
| aagtttcatc cgatgccacc tgggctgatg ctcgggattc ccactcaaat gtggccaatg | 360 |
| gtcaagaccg ggctgctatc tccggccgga agctacggg ctgcgatgga cctacttctt | 420 |
| cctgcaaggc gcggaggcgg cgacgaatca cttggtgggt ttatccggag gcggcttgga | 480 |
| cgtgaggtgt tggagcagat gaccgaacca ctccttgctg gaatctatgc tggcgacaca | 540 |
| gaacagcttt cacttaaagc gacctttcct caattcatgg agatggaaag gaaacatcgc | 600 |
| agtctcatcc ttggactatt ggctgggaag aaacagccac cgcgtcccgg tggtagccaa | 660 |
| gtgccgctcc caaaggccgc tcagaccagt atgttcttga cactcaccgg cgggttggaa | 720 |
| ggtctgaccg aagcactaga ggaaagccta tcagaggaga agataattac tggccaagca | 780 |
| gttaccggac tttcgcagca agaggccggg tatgagttaa atctctctgg cggagagaga | 840 |
| cttaatgcag acgagtgat cctcgcagtc ccagcgttcg ctgccgcccg acttcttgac | 900 |
| ggcgtgcctg aggccgccta cctagagcgc atccgctatg tcagtgttgc taatttggcg | 960 |
| ttcgcttaca ggcgtgagga cgtgcctcat gatctgaatg ggtccggcgt gttaatccct | 1020 |
| agaggtgaag ggaggatgat tacgccata acttgggttt cgtccaaatg gttgcattca | 1080 |
| gcacccggtg acaaggcact gctgagagcg tacattgggc gactaggtga tgaggcttgg | 1140 |
| acagccatgt gtagggccga catcgagcgt agagtcgccg ctgaactccg cgatctacta | 1200 |
| ggaattgccg ctagtccttt gttctgtgaa ctagccgcac tcccagaatc tatgccgcag | 1260 |
| tatccagtgg gtcacgtcga acgactcgaa gccttgcgag gagcattgtg tcgcgctaaa | 1320 |
| ccagggttgt tgttgtgtgg tgccgggtac gctggcgttg gcattccaga ctgcattcgg | 1380 |
| caaggcaaag aagccgctga gtcgatggcg gcttatttga gggacggacg ctag | 1434 |

<210> SEQ ID NO 206
<211> LENGTH: 1482
<212> TYPE: DNA
<213> ORGANISM: Artificial Sequence
<220> FEATURE:
<223> OTHER INFORMATION: Recombinant

<400> SEQUENCE: 206

| | |
|---|---|
| atgaaggctc tgaggaaact tgtggtcatc ggcggaggga tcactgggct ttcggccgcc | 60 |
| ttctatgcac taaagcaagc cgatgaggaa gggcagccca tctcggtcac cataattgaa | 120 |
| cagagcgata ggctcggcgg aaagatccag acactccgca aggagggctg cgtaattgag | 180 |
| aagggcccgg attccttcct cgctaggaag ttgccgatga ttgatctagc tcgggatctt | 240 |
| ggcatggact ccgaattggt ggcgactaat ccgcacgcaa agaagactta catcttgagg | 300 |
| cgcggaaagc tctaccggat gcctccaggc ttagtgcttg catacctac ggaactagga | 360 |
| ccattcgcta agacagggct cattagccct tggggcaaac tccgcgccgc tatggatttg | 420 |
| ttcattaagc ctcatccagc cgatgaagac gaaagtgttg gcgctttcct ggacagacgt | 480 |
| ctcggtaggg aagtgaccga gcacattgcg gaacctttat tggcgggcat ctacgcgggc | 540 |
| gacttgcaag ccttaagcct tcaagccact ttcccacagt ttgcacaagt agagcgcaag | 600 |
| cacggagggc tgatacgcgg tatgaaggcc agcagacagg ccggtcagtc cgtgcctggg | 660 |
| ctgccggacg tcgccaaggg tacgatgttc cttacctttc gcaacgggct taccagctta | 720 |
| gttgaaaggt tggaggaaac tctcagagac agggctgaac tctgtctggg catcggcgca | 780 |
| gaagggtttg agaaacgtga agatggaaca taccttgttc gactaagcga tggttcgagg | 840 |
| ctccaggccg acgcagtaat tgtcactacg ccgagctatc atgcggcatc cctgttggag | 900 |
| gagcatgtgg atgcttcggc cctccaggcc attcgtcatg taagcgttgc aaatgtcgtt | 960 |

| | |
|---|---|
| agcgtcttcg accgaaagca agtgaataac cagttcgacg gcacagggtt tgttatctca | 1020 |
| cggcgagaag gtcgcgcaat caccgcctgt acctggacat ccgtgaaatg ccgcatact | 1080 |
| tcgcgcggcg acaaactgat tatccggtgc tacatcggta gggctggcga cgaggagcga | 1140 |
| gtggattggc ccgatgaagc tctcaagcgt actgtaagat cagaactgcg tgagttgctg | 1200 |
| gacattgaca ttgatccgga atttgtggag attacacgac tcaggcactc tatgcctcaa | 1260 |
| tacccagtcg gccacgtcca ggctatccgc tctttgaggg acgaggtcgg taggacttta | 1320 |
| ccgggcgtgt tccttgctgg gcaaccctac gaaggtgtgg aatgcctga ctgtgtgagg | 1380 |
| tccggccggg atgccgccga agcagcagta agtgctatgc aagcaatgag tacagaacca | 1440 |
| gaagcaccgg cagaggacgc cgctactgga acggcgggtt ga | 1482 |

<210> SEQ ID NO 207
<211> LENGTH: 1425
<212> TYPE: DNA
<213> ORGANISM: Artificial Sequence
<220> FEATURE:
<223> OTHER INFORMATION: Recombinant

<400> SEQUENCE: 207

| | |
|---|---|
| atgggagaca agaagcggag agttgttgtt gttggcggcg gcttgactgg cctaagcgcc | 60 |
| gccttctaca tccggaaaca ttatcgagaa gctggagttg agcccgtcat cacgcttgtt | 120 |
| gagaaatcta gctcgatggg agggatgatt gagacccttc atagggacgg gtttgtcatc | 180 |
| gagaagggcc cggacagttt cttggcacgg aagaccgcaa tgattgatct ggcgaaagag | 240 |
| ctggagattg accacgagtt ggtcagccag aatccagaat cgaagaagac ctacataatg | 300 |
| caacgtggaa agctgcaccc tatgccagcg ggacttgttc tgggcattcc caccgaattg | 360 |
| cgtccctttc tccggagcgg gcttgtctca cccgctggga agttgcgggc gctgatggac | 420 |
| ttcgtaatac cgccacgaag gacgaccgaa gatgagtcac tcgggtacat gatcgagcgc | 480 |
| cgactgggtg ccgaggtgtt ggagaacctc acagagccgt tgctcgctgg aatctacgct | 540 |
| ggcgacatga aagattgtc cctccaggct acgtttccgc agttcggtga ggtggagcgc | 600 |
| gactacggct ccttaatcag aggaatgatg accgacgta agcctgcgga cacacaca | 660 |
| gggaccaaga ggtctgcctt tctcaatttc agacagggtc tgcaatcact ggttcacgcc | 720 |
| ttagtccatg aactccagga tgtagatcag aggttaaata ctgcggtgaa gtcgcttcag | 780 |
| aggcttgacg gcgcacaaac ccgttatcgc gttgaactcg gcaatggcga aatgcttgag | 840 |
| gctgacgacg tggtggttac tgtaccaacc tacgtggcga gcgagcttct taagccgcac | 900 |
| gtggacacgg cggcgttaga cgctattaac tatgtgtcgg tggctaatgt agttcttgca | 960 |
| tcgagaaga aggaagtaga gcacgtcttc gatggatcgg gcttcttggt gcctcggaag | 1020 |
| gagggaagga acataaccgc ctgcacctgg acttcgacca agtggctcca cacatcacca | 1080 |
| gatgacaagg ttctgttacg ttgttacgtg ggcagaagtg gagatgagca gaatgtggaa | 1140 |
| ctcccggatg aggcactcac taatctggtg cttaaggatc tgagagagac gatgggcatc | 1200 |
| gaggcggttc caatcttctc agagattacc cggctccgca gtcaatgcc gcagtaccca | 1260 |
| gtaggacatc tccagcacat cgccgcattg cgcgaggaac tcggctctaa gctaccagga | 1320 |
| gtgtacatcg ccggagcggg ctacgagggc gttggtcttc cggattgcat tcgccaggcc | 1380 |
| aaagaaatgt cagtccaggc aacgcaagaa ctcgctgccg actga | 1425 |

<210> SEQ ID NO 208

<211> LENGTH: 1413
<212> TYPE: DNA
<213> ORGANISM: Artificial Sequence
<220> FEATURE:
<223> OTHER INFORMATION: Recombinant

<400> SEQUENCE: 208

| | | | | | |
|---|---|---|---|---|---|
| atgagtgacg | ggaagaagca | cttggttata | atcggggggg | gaataaccgg | cctggccagc | 60 |
| gctttctata | tggagaagga | gatccgggag | aagaacttac | ctctcagcgt | gaccttggtg | 120 |
| gaggcatccc | cgcgggtagg | ggggaagatc | cagactgctc | gaaaggacgg | ctatatcata | 180 |
| gagcggggcc | cggacagctt | cctggagcgc | aagaagtcgg | cgcccgagtt | agtcgaggac | 240 |
| ctcggtctcg | agcacttact | cgtaaacaac | gctacagggc | agtcttacgt | cctcgtcaac | 300 |
| gaaacactgc | acccgatgcc | caaaggcgcg | gtgatgggaa | tccccactaa | gattgcacct | 360 |
| ttcatgtcga | ctggcctttt | cagcttcagt | gggaaggcga | gggcggcaat | ggacttcgtc | 420 |
| ctgcccgcgt | ccaagccgaa | ggaggatcag | agcctcggcg | agttttttccg | caggcgagtt | 480 |
| ggggatgagg | tcgtggaaaa | cctcattgag | cccttgctat | ccggaatcta | tgccggagac | 540 |
| atcgacaggc | tcagcctttat | gtctactttc | ccccagttct | accagacaga | gcaaaagcac | 600 |
| cgaagtttga | tcctcgggat | gaagaagacg | cgtcctcagg | gttctggtca | gaggctaaca | 660 |
| gcaaagaagc | agggtcaatt | ccagacgctt | aaaacagggc | ttcaaacact | tgtggaggaa | 720 |
| ctcgagaatc | agcttaaact | aaccaaagtg | tacaaggggc | cgaaggtaac | taacatcagc | 780 |
| cgcggtgaaa | agggctgcag | catcgcactt | gacaacggga | tgacactgga | cgcggacgca | 840 |
| gcaatcgtca | cgagccccca | caaatcagcg | gcgggaatgt | tccccgacct | tccggcggtc | 900 |
| agccagctga | agacatgca | ctccaccttc | gtcgcaaacg | tcgcgctcgg | cttcccgcag | 960 |
| gaggctgtcc | agatggagca | tgaggggact | ggcttcgtta | tcagcagaaa | ttcggacttc | 1020 |
| agtatcacag | cgtgcacttg | gacaaacaag | aaatggcctc | acagcgcacc | tgaggggaag | 1080 |
| acactttttgc | gagcgtacgt | ggggaaagct | ggggacgagt | ccatagttga | actaagcgac | 1140 |
| aacgagataa | ttaagatcgt | gcttgaggac | cttaagaaag | tgatgaagat | aaagggcgag | 1200 |
| cccgaaatga | catgcgtaac | tagatggaat | gagtccatgc | cacagtacca | cgtcgggcac | 1260 |
| aagcagcgta | tcaaaaaggt | cagggaggct | ttggcggcct | catacccggg | cgtatacatg | 1320 |
| accggtgcat | ccttcgaggg | ggtggggata | ccagactgca | tcgaccaagg | caaatccgca | 1380 |
| gtctcagacg | ttttggcata | cttgttcggc | tag | | | 1413 |

<210> SEQ ID NO 209
<211> LENGTH: 1413
<212> TYPE: DNA
<213> ORGANISM: Artificial Sequence
<220> FEATURE:
<223> OTHER INFORMATION: Recombinant

<400> SEQUENCE: 209

| | | | | | |
|---|---|---|---|---|---|
| atgtcggatg | gcaagaagca | cctcgtcatc | atcggcgggg | gtatcaccgg | acttgcgtcc | 60 |
| gcgttctaca | tggagaagga | gatcagggag | aagaacttgc | ccctctcagt | gaccctggtg | 120 |
| gaggcctcgc | ccgtgttgg | tggtaagatc | cagacagcgc | gaaaagacgg | ctacattatc | 180 |
| gagcggggc | ccgactcctt | cctcgagagg | aagaagtctg | cccccgagct | tgtggaggac | 240 |
| ttggggcttg | agcacctcct | cgtgaacaat | gcgaccgggc | agagctacgt | tttggtgaac | 300 |
| gagaccctgc | acccgatgcc | caagggagcc | gtgatgggaa | tccctaccaa | gatcgcgcct | 360 |
| ttcatgagca | ctcgactttt | ttcattcagc | ggcaaggcca | gagccgctat | ggactttgtt | 420 |

-continued

```
ctcccggctt ctaagcctaa ggaagaccag agtctaggcg aattcttcag gcgaagagtc      480
ggcgatgagg ttgttgagaa ccttatagag ccattattgt caggtatata cgcaggagac      540
attgacaggc tgtctctcat gagtaccttc cctcaattct accagacgga gcagaaacac      600
aggagcctca tattggggat gaagaagacg cgtcctcaag gaagcggaca gcagttgacg      660
gccaagaagc agggccagtt ccaaacgctc aagaccggac ttcagaccct cgtcgaggag      720
cttgagaacc agctaaagtt gacgaaggtt tacaagggca ctaaggtcac aaacatctcg      780
aggggcgaga agggatgcag catcgcgtta gacaacggga tgaccctaga cgctgacgca      840
gctattgtga ctagccccca taagtccgca gccggcatgt ttccagactt gccggccgtt      900
agccagttga aggacatgca ctcgaccagc gtggcaaacg tcgcattggg cttcccacag      960
gaggcggtgc agatggagca tgaggggacc ggattcgtga tctcaaggaa ttccgatttc     1020
tccattacgg catgtacctg acaaacaaa aaatggcccc acagcgcccc agaagggaaa     1080
acactcctac gcgcttatgt tggcaaggcc ggcgatgagt caattgtgga gctctccgac     1140
aatgagatca tcaaaatcgt tcttgaagat cttaagaagg taatgaagat taaggggaa     1200 ccggaaatga cgtgtgtgac aaggtggaac gagagtatgc cccaatatca cgtgggccac     1260
aagcagagga taaagaaggt gagggaggcg ttggcggcgt cttacccccgg cgtgtacatg     1320 acggggctt cattcgaggg ggtgggcatc cccgactgca ttgaccaagg caaaagcgcg     1380
gtgtctgacg tgctcgcgta cctgttcgag tag                                 1413
```

<210> SEQ ID NO 210
<211> LENGTH: 1413
<212> TYPE: DNA
<213> ORGANISM: Artificial Sequence
<220> FEATURE:
<223> OTHER INFORMATION: Recombinant

<400> SEQUENCE: 210

```
atgtccgacg ggaagaagca cctggtaatc atcggtggtg ggatcaccgg tctggcttca       60
gcgttctaca tggaaaagga gatccggag aagaacttgc cccttcggt gactctagtg      120 gaggcctctc cacgggtggg gggcaagatt cagaccgcgc gcaaggatgg ctacatcata      180
gagcgaggac cagactcatt cctagagcgt aagaagtccg ccccagagct cgtcgaggat      240
ctcggtctag agcacttgct agtgaataac gctacaggac agtcctacgt gctcgtgaac      300
gagacactac acccgatgcc taagggggct gtcatgggta taccgaccaa gatcgccccg      360
ttcatgtcca ctcgcctttt ctcgttctcg ggcaaagctc gggccgctat ggatttcgtc      420
ttgcctgcct cgaaaccgaa ggaggaccag tccttaggag agttcttccg ccggagggtc      480
ggcgacgagg tggtggagaa cttaatcgaa cccttgctct cggggatcta cgctggagac      540
attgatcgac tatcgcttat gtctacgttt cctcaatttt accagacgga gcagaagcac      600
cgtagcctca ttttgggtat gaagaagaca cggcctcaag gttcggggca gcagcttact      660
gccaagaagc agggccaatt ccagacactc aagaccggct gcagactct agtggaggag      720 ctggagaatc aattgaagct gacaaaggtc tacaagggta ccaaggtgac aaacatatcg      780
cgtggcgaaa agggatgctc cattgccctc gacaacggta tgaccctcga cgccgacgca      840
gcgattgtga cgagcccaca caagagcgcg gcgggcatgt tcccggactt gcctgcagtg      900
tcacagctga agacatgca ttctacatcc gtcgccaacg tcgccctggg cttcccag      960 gaggctgtgc agatggagca cgaggggacg ggcttcgtta tcagccgcaa ctccgacttt     1020
```

```
tctattaccg cgtgcacatg gaccaacaag aagtggccgc acagcgctcc ggaggggaaa      1080
acacttctcc gagcatacgt aggcaaggcc gggacgagt caattgttga gctctccgac       1140
aatgaaatca ttaaaatagt tctggaggat cttaagaagg taatgaagat aaaggggaa       1200 cctgaaatga cgtgtgttac ccgctggaat gagtcaatgc cccagtacca tgtgggacac     1260
aagcagagga taaagaaggt gagggaggcg ctcgctgcgt cctacccagg ggtctacatg      1320
acaggagcga gttttgaggg ggtgggtatt cccgactgta tcgaccaggg taagtcggca     1380
gtgtctgacg tgctcgctta cctattcgag tag                                   1413

<210> SEQ ID NO 211
<211> LENGTH: 1434
<212> TYPE: DNA
<213> ORGANISM: Artificial Sequence
<220> FEATURE:
<223> OTHER INFORMATION: Recombinant

<400> SEQUENCE: 211
atgtcgaaga agatcgccgt tatcggtgga ggcattacag ggctctcggt cgcctactac       60
gtgcgtaagc tgcttcgtga gcaaggcgtc aacgctggtg tgacgctggt tgagcagtct      120
gatcgcctcg gtggaaaaat ccgtagcctt cgcagagacg ggttcacgat tgaacaagga      180
ccagattcca tgatcgcgcg caaacccgcg gcgttggagc taattcgaga actcggactc      240
gaggacaagc tcgccggcac taacccacag gcaaagcgt cgtacatcct tcaccgcggg       300
aagttccacc cgatgccccc aggcctgatg ctcggcatcc cgacccagat gtggccgatg      360
gtcaagaccg gctcctgtc tcccgcgggg aaactaaggg ccgctatgga cctcctcctc      420
cctgctcgga ggggcggcgg tgatgagagt ctcgggggat ttatcaggcg gagattaggc     480
cgcgaggtac ttgagcaaat gaccgaacca ctgctcgcag gtatctatgc aggcgatacg     540
gaacaactgt ccttgaaagc aacatttcca caattcatgg agatggaaag aaaacatagg    600
tccctcatac tcggtcttct tgctggaaaa aagcaacctc cgagacccgg tggttcacaa    660
gtgcctctgc ctaaagcggc gcaaacttca atgttcctga ctctgacagg cgggctcgaa    720
ggccttaccg aagctctaga ggaatccttg tctgaggaaa aaataatcac cggccaggct    780
gttaccgggc ttagccaaca ggaagccggt tatgaactga cctttcagg tggagagagg    840 ttgaacgccg atgggggtcat attggctgta ccggcgttcg ccgcggctcg cctgctggac   900
ggcgtccctg aggccgcgta tttggagcgc atacgctatg tttctgttgc gaacctcgct    960
tttgcatata gacgggaaga tgtgccccat gatcttaatg gttccggagt gttgatccca   1020
cgcggggagg gtcgaatgat aacggcaatt acttgggttt ccagcaagtg gttacattcg   1080
gctcctgggg ataaagctct tttgcgggca tacatcggac gtctcggcga cgaagcctgg   1140
acggccatgt gcagagccga cattgagcga cgggtcgctg cagagctgag agacttgttg    1200
ggcatagctg catctccatt gttctgcgag ctggctgcat tgcctgaaag catgccgcaa    1260
tatccagtag ggcatgtgga gcgcctcgaa gctctccgag gcgcgttgtg tagggcgaaa    1320
cctggactgc tgctctgcgg tgccggctat gcaggtgtgg gaattcctga ctgtatcagg    1380
caaggtaaag aagcggcaga gtccatggcc gcttacctta gggatgggcg ctag         1434

<210> SEQ ID NO 212
<211> LENGTH: 1482
<212> TYPE: DNA
<213> ORGANISM: Artificial Sequence
<220> FEATURE:
<223> OTHER INFORMATION: Recombinant
```

<400> SEQUENCE: 212

```
atgaaggcgc tgcggaagct ggtggtaatc gggggggga tcacgggct gtcggccgcg        60
ttctacgcac tcaagcaggc cgacgaagag ggtcagccaa tttccgtaac gattatcgag       120
caatccgatc gacttggcgg caagatacag accctgagaa aggagggatg cgtcattgaa       180
aagggaccag attcatttct ggcgaggaag ctccccatga tcgatctggc gagagactta       240
ggcatggact cggagctggt ggccacaaat cctcatgcaa aaaagactta catcctacgg       300
cgcggtaagt tgtaccgcat gccaccgggc ctggtgttgg ggattcctac cgagttagga       360
cccttcgcga aaaccggact catcagcccc tggggaaaac ttcgagccgc gatggacctt       420
ttcatcaaac cacatccagc cgatgaagat gagtctgtgg gagcttttt agatagacgt        480
ttaggtcgcg aggtgacgga gcacatcgca gagccgctgc tcgccgggat atacgcaggc       540
gatcttcaag ctttgtcctt gcaagctacg ttccctcagt tcgcgcaagt ggaacgcaaa       600
cacgaggtc tcatcagagg tatgaaagcg tctcgccaag ctggacagtc agtcccaggg       660
ctcccagatg tggccaaggg taccatgttt cttactttca gaaatggttt gactagcctg       720
gtggagcgtc tcgaagaaac ccttcgagat agagccgagc tctgtctggg tatcggtgca       780
gaggggtttg aaaaacggga agacggcacg taccttgttc gattatctga tggctccaga       840
ttgcaagccg acgccgttat agttaccaca ccatcatacc atgccgcctc cctactggag       900
gagcacgtcg acgccagcgc gttacaggct atccgccacg tatctgtagc caacgtggtg       960
agcgttttcg ataggaagca ggttaacaat cagtttgatg ggacaggttt tgttatctca      1020
agacgcgaag gcagggctat cactgcttgc acttggacct cagttaagtg gccgcatacc      1080
agccggggg ataagttgat aatccggtgt tacattggtc gtgcaggaga tgaggagcgc       1140
gtggattggc cagacgaagc gctaaagcgg accgtgagaa gtgagcttcg cgagctgtta      1200
gacatagaca tagatcccga attcgtggaa attacgggt tgaggcactc tatgccacaa       1260
taccctgttg gtcatgtgca agctatacgg tccctgcgcg acgaagtagg ccggaccttg      1320
ccgggcgtgt ttcttgcggg tcagccgtat gaggggttg ggatgccaga ttgtgtgcgt       1380
tctgccgcg acgcggcaga ggctgccgta tcagccatgc aagccatgtc gacagaaccc       1440
gaagccccgg cggaagatgc agcgacagga actgcaggtt ag                        1482
```

<210> SEQ ID NO 213
<211> LENGTH: 1425
<212> TYPE: DNA
<213> ORGANISM: Artificial Sequence
<220> FEATURE:
<223> OTHER INFORMATION: Recombinant

<400> SEQUENCE: 213

```
atgggggata agaagaggag ggtcgttgtc gtgggtgggg gactgaccgg actatcagcc        60
gcgttctaca ttagaaagca ctaccgagag gccggcgtgg agccggtgat cacgctggtc       120
gagaagtcga gttcgatggg cggaatgatc gagaccctac acagggacgg ctttgtgatt       180
gagaagggac cagatagctt ccttgcacgc aagacagcca tgatcgatct cgcaaaagag       240
ctcgagatag accacgaact ggtgtctcag aacccggagt ccaagaagac atatatcatg       300
cagagaggta aactcacccc catgccagcc gggttggttc taggaatacc taccgagctc       360
cgcccgtttt tgcgtagcgg tctcgtgagc ccgccggga agctgcgtgc gctaatggac       420
ttcgtgatcc cgcctcggcg aacgaccgaa gacgaatcgc tgggatacat gattgaacgg       480
```

| | |
|---|---|
| cgattgggcg ctgaggtgct tgaaaatctt acggagcctc tgcttgcagg gatttatgcg | 540 |
| ggtgatatga ggcggttgtc tctccaggca acgttccac agttcggtga ggtagaacgc | 600 |
| gattacggct cactgatacg gggcatgatg accggtcgca agcctgccga gacacacacc | 660 |
| ggtacaaaaa ggtcagcctt tcttaatttc cggcaagggt tacagtcact tgttcatgca | 720 |
| cttgtacacg aattgcagga cgtcgatcaa agacttaata ccgcagtgaa gagcctgcag | 780 |
| cgcctggatg gggcccaaac taggtaccgt gtggaattag caatggaga gatgctggag | 840 |
| gccgatgacg tggtggtcac cgtcccaacg tacgtagctt ctgagctcct caagccccac | 900 |
| gttgacaccg cagctctgga tgcaatcaat tatgtgagcg tggctaatgt cgtcctggcc | 960 |
| tttgagaaga aggaagtgga gcatgtgttc gacggatcag ggttcttggt tccgagaaaa | 1020 |
| gagggcagga atatcacggc gtgcacttgg acttcgacaa aatggctcca cacctccccg | 1080 |
| gatgacaaag tacttctgcg atgctatgtg ggccgaagtg gtgatgagca aatgtagag | 1140 |
| ctccccgacg aggcactgac caacctcgtc ctcaaggacc taaggagac tatgggcatt | 1200 |
| gaggccgtgc caattttctc tgaaataaca cgcctgcgca agtccatgcc ccaataccct | 1260 |
| gtgggccatc ttcaacacat tgcggccctg cgggaagaac ttgggtctaa gctgccgggc | 1320 |
| gtgtacatag cgggcgccgg ttacgagggt gtcgggttgc ctgactgtat tagacaggca | 1380 |
| aaggaaatgt ccgtgcaagc aacccaagaa cttgctgctg actga | 1425 |

<210> SEQ ID NO 214
<211> LENGTH: 1413
<212> TYPE: DNA
<213> ORGANISM: Artificial Sequence
<220> FEATURE:
<223> OTHER INFORMATION: Recombinant

<400> SEQUENCE: 214

| | |
|---|---|
| atgagtgacg gtaagaagca tttggtcatc atcggcggcg gcatcaccgg cttagcctcc | 60 |
| gccttctaca tggaaaagga gattcgggag aagaaccttc ccttgtcagt taccctggtg | 120 |
| gaggcctcgc cacgggtcgg gggtaaaatc cagacggccc ggaaggatgg ttatattatc | 180 |
| gagcgcggac ccgactcgtt cctcgagcgc aagaagagcg caccgaact cgttgaggac | 240 |
| cttggcctcg aacatctcct cgttaacaat gcaactggtc agtcgtacgt cctggtcaac | 300 |
| gagacactcc atcccatgcc caagggcgcg gtgatgggca ttccgacgaa gattgccct | 360 |
| tttatgtcga ctggccttt cagcttctcg ggaaaggccc gtgccgctat ggacttcgtc | 420 |
| ctccctgcct cgaaaccgaa ggaggaccag tctcttggag aattttttag gcgcagagtg | 480 |
| ggggacgagg ttgtggagaa tctgatcgaa ccgcttctga gcggaatcta tgcgggcgac | 540 |
| attgaccgcc tctcactcat gagcaccttc ccacaattct accagacgga gcagaagcat | 600 |
| cggtcactca tcctggggat gaaaaaaacc cggcctcaag gatcaggaca aaggcttaca | 660 |
| gctaaaaagc aggggcagtt tcaaactctc aagacgggcc tgcagactct agtcgaggag | 720 |
| ttagaaaacc agttgaagtt gaccaaggtg tacaagggca cgaaagtgac aaacatcagc | 780 |
| cggggcgaaa agggttgttc aatcgcgttg acaacggca tgaccctgga cgcagacgca | 840 |
| gcaatcgtga catcgcccca caagagtgct gcgggcatgt tccctgatct gccggcggtc | 900 |
| agccagctta aggatatgca ctcaacctcg gtggctaacg tggccttggg cttccctcag | 960 |
| gaggccgtcc aaatggagca cgaaggaacc ggctttgtta tcagccgtaa cagtgacttc | 1020 |
| tcgattaccg cttgtacctg gacgaacaag aagtggcctc acagcgcgcc agaagggaag | 1080 |
| accctcctgc gagcctacgt cggcaaggct ggtgacgagt cgatcgttga gttgtctgac | 1140 |

```
aacgagatta tcaagatcgt acttgaagat ctcaagaagg tcatgaagat aaagggtgaa    1200
cccgagatga cttgcgttac tagatggaac gagtctatgc ctcagtatca cgtggggcac    1260
aagcagagga tcaagaaggt ccgggaggcc ttggctgcct cgtatccggg agtctacatg    1320
accggggcct catttgaggg agtcggtatc cccgactgca tcgaccaagg aaagtccgcc    1380
gtctctgacg tgttggctta tctattcggc tag                                 1413
```

<210> SEQ ID NO 215
<211> LENGTH: 1413
<212> TYPE: DNA
<213> ORGANISM: Artificial Sequence
<220> FEATURE:
<223> OTHER INFORMATION: Recombinant

<400> SEQUENCE: 215

```
atgagcgacg gaaagaaaca tctcgtgatc atcgggggcg aataacagg cctagcctcg     60 gcattctaca tggagaagga gatcagagag aaaaacctcc cgctctctgt gaccctggtg    120
gaggcttcac cgagagtggg cggaagata cagacggcgc gcaaggatgg ctacataata    180
gagcggggcc cagattcttt cctggagaga aaaaaaagcg ccccggaatt ggtggaggac    240
ctcggcctcg aacacctcct ggtgaataac gcaacagggc aaagctacgt actcgttaat    300
gagactctcc accccatgcc aaaaggggcc gtgatgggaa tccccacaaa gatcgctcca    360
ttcatgagca ccaggttatt ctctttctct ggtaaagcta gggcagccat ggacttcgtc    420
ctgccagcct ccaaaccgaa agaagaccaa agcctcgggg aattcttccg ccggagggtg    480
ggcgacgagg tggttgagaa tttaattgaa cctctcctct caggtatata cgcaggggac    540
atcgaccgct tgtcgctgat gagcaccttt ccgcagttct accagacgga gcagaagcat    600
cgctcactca ttcttggtat gaagaagact cgtccgcaag gtctggcca gcagctgaca    660 gccaagaaac aggggcagtt ccaaactctt aagaccggcc tacagactct ggtggaggag    720
ctcgagaacc agctgaagct cacaaaggtt tacaagggca caaggtgac aaacatctca    780 aggggggaga agggttgctc catcgcgctc gataacggca tgacactcga tgctgatgcg    840
gcgatagtaa ctagcccgca caagtcggcc gcgggaatgt tccccgacct ccccgcggtc    900
tcgcaactga aggacatgca ttccaccagc gtcgccaacg tagctctagg ctttcctcag    960
gaggcagtcc aaatggaaca cgagggcacg ggtttcgtaa tctcccgcaa cagcgacttc   1020
tcaatcactg cttgcacgtg gactaacaag aagtggccgc attcggcccc cgagggcaag   1080
acgcttcttc gagcatacgt gggtaaggct ggtgatgaga gtatcgtcga gctctcggac   1140
aacgagatca ttaagatcgt gttggaggac ttgaagaagg tgatgaaaat caaggggag   1200 ccggaaatga cttgcgtgac tcgctggaac gagagcatgc cgcagtacca cgttgggcat   1260
aagcagagga taaagaaagt tcgcgaagcg ctggccgcgt cttaccctgg agtgtatatg   1320
acgggagcct cctttgaggg tgtggggatc ccggactgca tcgaccaggg aaagtcagct   1380
gtctccgacg tgctggccta cttattcgag tga                                1413
```

<210> SEQ ID NO 216
<211> LENGTH: 1428
<212> TYPE: DNA
<213> ORGANISM: Artificial Sequence
<220> FEATURE:
<223> OTHER INFORMATION: Recombinant

<400> SEQUENCE: 216

| | |
|---|---|
| aagaagattg cagtcattgg tggtgggata acagggttgt ccgtggccta ctacgtgagg | 60 |
| aagctgcttc gggagcaagg cgttaatgcg ggcgttaccc tcgtcgagca atccgaccgc | 120 |
| ctcggcggga agattagatc cttgagacga dacggcttta ccattgagca aggccctgac | 180 |
| tctatgattg cacgtaagcc cgcagctctc gaacttatcc gtgagcttgg tctggaggac | 240 |
| aagttggcgg gcacaaaccc tcaagccaaa cgctcctaca tactgcaccg tggcaagttt | 300 |
| catccgatgc cacctgggct gatgctcggg attcccactc aaatgtggcc aatggtcaag | 360 |
| accgggctgc tatctccggc cggaaagcta cgggctgcga tggacctact tcttcctgca | 420 |
| aggcgcggag gcggcgacga atcacttggt gggtttatcc ggaggcggct tggacgtgag | 480 |
| gtgttggagc agatgaccga accactcctt gctggaatct atgctggcga cacagaacag | 540 |
| cttcactta aagcgacctt tcctcaattc atggagatgg aaaggaaaca tcgcagtctc | 600 |
| atccttggac tattggctgg gaagaaacag ccaccgcgtc ccggtggtag ccaagtgccg | 660 |
| ctcccaaagg ccgctcagac cagtatgttc ttgacactca ccggcgggtt ggaaggtctg | 720 |
| accgaagcac tagaggaaag cctatcagag gagaagataa ttactggcca agcagttacc | 780 |
| ggactttcgc agcaagaggc cgggtatgag ttaaatctct ctggcggaga gagacttaat | 840 |
| gcagacggag tgatcctcgc agtcccagcg ttcgctgccg cccgacttct tgacggcgtg | 900 |
| cctgaggccg cctacctaga gcgcatccgc tatgtcagtg ttgctaattt ggcgttcgct | 960 |
| tacaggcgtg aggacgtgcc tcatgatctg aatgggtccg gcgtgttaat ccctagaggt | 1020 |
| gaagggagga tgattacggc cataacttgg gtttcgtcca aatggttgca ttcagcaccc | 1080 |
| ggtgacaagg cactgctgag agcgtacatt gggcgactag gtgatgaggc ttggacagcc | 1140 |
| atgtgtaggg ccgacatcga gcgtagagtc gccgctgaac tccgcgatct actaggaatt | 1200 |
| gccgctagtc ctttgttctg tgaactagcc gcactccag aatctatgcc gcagtatcca | 1260 |
| gtgggtcacg tcgaacgact cgaagccttg cgaggagcat tgtgtcgcgc taaaccaggg | 1320 |
| ttgttgttgt gtggtgccgg gtacgctggc gttggcattc cagactgcat tcggcaaggc | 1380 |
| aaagaagccg ctgagtcgat ggcggcttat ttgagggacg gacgctag | 1428 |

<210> SEQ ID NO 217
<211> LENGTH: 1470
<212> TYPE: DNA
<213> ORGANISM: Artificial Sequence
<220> FEATURE:
<223> OTHER INFORMATION: Recombinant

<400> SEQUENCE: 217

| | |
|---|---|
| aggaaacttg tggtcatcgg cggagggatc actgggcttt cggccgcctt ctatgcacta | 60 |
| aagcaagccg atgaggaagg gcagcccatc tcggtcacca taattgaaca gagcgatagg | 120 |
| ctcggcggaa agatccagac actccgcaag gagggctgcg taattgagaa gggcccggat | 180 |
| tccttcctcg ctaggaagtt gccgatgatt gatctagctc gggatcttgg catggactcc | 240 |
| gaattggtgg cgactaatcc gcacgcaaag aagacttaca tcttgaggcg cggaaagctc | 300 |
| taccggatgc ctccaggctt agtgcttggc ataccctacgg aactaggacc attcgctaag | 360 |
| acagggctca ttagcccttg gggcaaactc cgcgccgcta tggatttgtt cattaagcct | 420 |
| catccagccg atgaagacga aagtgttggc gctttcctgg acagacgtct cggtagggaa | 480 |
| gtgaccgagc acattgcgga acctttattg gcgggcatct acgcgggcga cttgcaagcc | 540 |
| ttaagccttc aagccacttt cccacagttt gcacaagtag agcgcaagca cggagggctg | 600 |
| atacgcggta tgaaggccag cagacaggcc ggtcagtccg tgcctgggct gccggacgtc | 660 |

```
gccaagggta cgatgttcct tacctttcgc aacgggctta ccagcttagt tgaaaggttg      720
gaggaaactc tcagagacag ggctgaactc tgtctgggca tcggcgcaga agggtttgag      780
aaacgtgaag atggaacata ccttgttcga ctaagcgatg gttcgaggct ccaggccgac      840
gcagtaattg tcactacgcc gagctatcat gcggcatccc tgttggagga gcatgtggat      900
gcttcggccc tccaggccat tcgtcatgta agcgttgcaa atgtcgttag cgtcttcgac      960
cgaaagcaag tgaataacca gttcgacggc acagggtttg ttatctcacg gcgagaaggt     1020
cgcgcaatca ccgcctgtac ctggacatcc gtgaaatggc cgcatacttc gcgcggcgac     1080
aaactgatta tccggtgcta catcggtagg gctggcgacg aggagcgagt ggattggccc     1140
gatgaagctc tcaagcgtac tgtaagatca gaactgcgtg agttgctgga cattgacatt     1200
gatccggaat ttgtggagat tacacgactc aggcactcta tgcctcaata cccagtcggc     1260
cacgtccagg ctatccgctc tttgagggac gaggtcggta ggactttacc gggcgtgttc     1320
cttgctgggc aaccctacga aggtgtggga atgcctgact gtgtgaggtc cggccgggat     1380
gccgccgaag cagcagtaag tgctatgcaa gcaatgagta cagaaccaga agcaccggca     1440
gaggacgccg ctactggaac ggcgggttga                                      1470

<210> SEQ ID NO 218
<211> LENGTH: 1410
<212> TYPE: DNA
<213> ORGANISM: Artificial Sequence
<220> FEATURE:
<223> OTHER INFORMATION: Recombinant

<400> SEQUENCE: 218
cggagagttg ttgttgttgg cggcggcttg actggcctaa gcgccgcctt ctacatccgg       60
aaacattatc gagaagctgg agttgagccc gtcatcacgc ttgttgagaa atctagctcg      120
atgggaggga tgattgagac ccttcatagg gacgggtttg tcatcgagaa gggcccggac      180
agtttcttgg cacggaagac cgcaatgatt gatctggcga aagagctgga gattgaccac      240
gagttggtca gccagaatcc agaatcgaag aagacctaca taatgcaacg tggaaagctg      300
caccctatgc cagcgggact tgttctgggc attcccaccg aattgcgtcc ctttctccgg      360
agcgggcttg tctcacccgc tgggaagttg cgggcgctga tggacttcgt aataccgcca      420
cgaaggacga ccgaagatga gtcactcggg tacatgatcg agcgccgact gggtgccgag      480
gtgttggaga acctcacaga gccgttgctc gctggaatct acgctggcga catgagaaga      540
ttgtccctcc aggctacgtt tccgcagttc ggtgaggtgg agcgcgacta cggctcctta      600
atcagaggaa tgatgaccgg acgtaagcct gcggagacac acacagggac caagaggtct      660
gcctttctca atttcagaca gggtctgcaa tcactggttc acgccttagt ccatgaactc      720
caggatgtag atcagaggtt aaatactgcg gtgaagtcgc ttcagaggct tgacggcgca      780
caaacccgtt atcgcgttga actcggcaat ggcgaaatgc ttgaggctga cgacgtggtg      840
gttactgtac caacctacgt ggcgagcgag cttcttaagc cgcacgtgga cacggcggcg      900
ttagacgcta ttaactatgt gtcggtggct aatgtagttc ttgcattcga aagaaggaa       960 gtagagcacg tcttcgatgg atcgggcttc ttggtgcctc ggaaggaggg aaggaacata     1020
accgcctgca cctggacttc gaccaagtgg ctccacacat caccagatga caaggttctg     1080
ttacgttgtt acgtgggcag aagtggagat gagcagaatg tggaactccc ggatgaggca     1140
ctcactaatc tggtgcttaa ggatctgaga gagacgatgg gcatcgaggc ggttccaatc     1200
```

```
ttctcagaga ttacccggct ccgcaagtca atgccgcagt acccagtagg acatctccag   1260
cacatcgccg cattgcgcga ggaactcggc tctaagctac caggagtgta catcgccgga   1320
gcgggctacg agggcgttgg tcttccggat tgcattcgcc aggccaaaga aatgtcagtc   1380
caggcaacgc aagaactcgc tgccgactga                                   1410
```

<210> SEQ ID NO 219
<211> LENGTH: 1398
<212> TYPE: DNA
<213> ORGANISM: Artificial Sequence
<220> FEATURE:
<223> OTHER INFORMATION: Recombinant

<400> SEQUENCE: 219

```
aagcacctgg taatcatcgg tggtgggatc accggtctgg cttcagcgtt ctacatggaa     60
aaggagatcc gggagaagaa cttgcccctt tcggtgactc tagtggaggc ctctccacgg    120 gtgggggggca agattcagac cgcgcgcaag gatggctaca tcatagagcg aggaccagac   180
tcattcctag agcgtaagaa gtccgcccca gagctcgtcg aggatctcgg tctagagcac    240
ttgctagtga ataacgctac aggacagtcc tacgtgctcg tgaacgagac actcacccccg   300 atgcctaagg gggctgtcat gggtataccg accaagatcg ccccgttcat gtccactcgc    360
cttttctcgt tctcgggcaa agctcgggcc gctatggatt tcgtcttgcc tgcctcgaaa    420
ccgaaggagg accagtcctt aggagagttc ttccgccgga gggtcggcga cgaggtggtg    480
gagaacttaa tcgaacccctt gctctcgggg atctacgctg agacattga tcgactatcg    540 cttatgtcta cgtttcctca attttaccag acggagcaga agcaccgtag cctcattttg    600
ggtatgaaga agacacggcc tcaaggttcg gggcagcagc ttactgccaa gaagcagggc    660
caattccaga cactcaagac cggcttgcag actctagtgg aggagctgga gaatcaattg    720
aagctgacaa aggtctacaa gggtaccaag gtgacaaaca tatcgcgtgg cgaaaaggga    780
tgctccattg ccctcgacaa cggtatgacc ctcgacgccg acgcagcgat tgtgacgagc    840
ccacacaaga gcgccgcggg catgttcccg gacttgcctg cagtgtcaca gctgaaagac    900
atgcattcta catccgtcgc caacgtcgcc ctgggctttc cccaggaggc tgtgcagatg    960
gagcacgagg ggacgggctt cgttatcagc cgcaactccg acttttctat taccgcgtgc   1020
acatggacca acaagaagtg gccgcacagc gctccggagg ggaaaacact tctccgagca   1080
tacgtaggca aggccgggga cgagtcaatt gttgagctct ccgacaatga aatcattaaa   1140
atagttctgg aggatcttaa gaaggtaatg aagataaagg gggaacctga aatgacgtgt   1200
gttacccgct ggaatgagtc aatgccccag taccatgtgg gacacaagca gaggataaag   1260
aaggtgaggg aggcgctcgc tgcgtcctac ccagggtgtct acatgacagg agcgagtttt   1320 gaggggggtgg gtattcccga ctgtatcgac cagggtaagt cggcagtgtc tgacgtgctc   1380
gcttacctat tcgagtag                                                1398
```

<210> SEQ ID NO 220
<211> LENGTH: 1422
<212> TYPE: DNA
<213> ORGANISM: Artificial Sequence
<220> FEATURE:
<223> OTHER INFORMATION: Recombinant

<400> SEQUENCE: 220

```
attgcagtca ttggtggtgg gataacaggg ttgtccgtgg cctactacgt gaggaagctg     60
cttcgggagc aaggcgttaa tgcgggcgtt accctcgtcg agcaatccga ccgcctcggc    120
```

-continued

```
gggaagatta gatccttgag acgagacggc tttaccattg agcaaggccc tgactctatg      180
attgcacgta agcccgcagc tctcgaactt atccgtgagc ttggtctgga ggacaagttg      240
gcgggcacaa accctcaagc caaacgctcc tacatactgc accgtggcaa gtttcatccg      300
atgccacctg ggctgatgct cgggattccc actcaaatgt ggccaatggt caagaccggg      360
ctgctatctc cggccggaaa gctacgggct gcgatggacc tacttcttcc tgcaaggcgc      420
ggaggcggcg acgaatcact tggtgggttt atccggaggc ggcttggacg tgaggtgttg      480
gagcagatga ccgaaccact ccttgctgga atctatgctg gcgacacaga acagctttca      540
cttaaagcga cctttcctca attcatggag atggaaagga acatcgcag tctcatcctt       600 ggactattgg ctgggaagaa acagccaccg cgtcccggtg gtagccaagt gccgctccca      660
aaggccgctc agaccagtat gttcttgaca ctcaccggcg ggttggaagg tctgaccgaa      720
gcactagagg aaagcctatc agaggagaag ataattactg gccaagcagt taccggactt      780
tcgcagcaag aggccgggta tgagttaaat ctctctggcg agagagact taatgcagac       840 ggagtgatcc tcgcagtccc agcgttcgct gccgcccgac ttcttgacgg cgtgcctgag      900
gccgcctacc tagagcgcat ccgctatgtc agtgttgcta atttggcgtt cgcttacagg      960
cgtgaggacg tgcctcatga tctgaatggg tccggcgtgt taatccctag aggtgaaggg     1020
aggatgatta cggccataac ttgggttccg tccaaatggt tgcattcagc acccggtgac     1080
aaggcactgc tgagagcgta cattgggcga ctaggtgatg aggcttggac agccatgtgt     1140
agggccgaca tcgagcgtag agtcgccgct gaactccgcg atctactagg aattgccgct     1200
agtcctttgt tctgtgaact agccgcactc ccagaatcta tgccgcagta tccagtgggt     1260
cacgtcgaac gactcgaagc cttgcgagga gcattgtgtc gcgctaaacc agggttgttg     1320
ttgtgtggtg ccgggtacgc tggcgttggc attccagact gcattcggca aggcaaagaa     1380
gccgctgagt cgatggcggc ttatttgagg gacggacgct ag                        1422
```

<210> SEQ ID NO 221
<211> LENGTH: 1464
<212> TYPE: DNA
<213> ORGANISM: Artificial Sequence
<220> FEATURE:
<223> OTHER INFORMATION: Recombinant

<400> SEQUENCE: 221

```
cttgtggtca tcggcggagg gatcactggg ctttcggccg ccttctatgc actaaagcaa       60
gccgatgagg aagggcagcc catctcggtc accataattg aacagagcga taggctcggc      120
ggaaagatcc agacactccg caaggagggc tgcgtaattg agaagggccc ggattccttc      180
ctcgctagga agttgccgat gattgatcta gctcggatc ttggcatgga ctccgaattg       240
gtggcgacta atccgcacgc aaagaagact tacatcttga ggcgcggaaa gctctaccgg      300
atgcctccag gctagtgct tggcataccct acggaactag gaccattcgc taagacaggg      360
ctcattagcc cttggggcaa actccgcgcc gctatggatt tgttcattaa gcctcatcca      420
gccgatgaag acgaaagtgt tggcgctttc ctggacagac gtctcggtag ggaagtgacc      480
gagcacattg cggaaccttt attggcgggc atctacgcgg gcgacttgca agccttaagc      540
cttcaagcca ctttcccaca gtttgcacaa gtagagcgca agcacggagg gctgatacgc      600
ggtatgaagg ccagcagaca ggccggtcag tccgtgcctg ggctgccgga cgtcgccaag      660
ggtacgatgt tccttacctt tcgcaacggg cttaccagct tagttgaaag gttggaggaa      720
```

```
actctcagag acagggctga actctgtctg ggcatcggcg cagaagggtt tgagaaacgt      780
gaagatggaa cataccttgt tcgactaagc gatggttcga ggctccaggc cgacgcagta      840
attgtcacta cgccgagcta tcatgcggca tccctgttgg aggagcatgt ggatgcttcg      900
gccctccagg ccattcgtca tgtaagcgtt gcaaatgtcg ttagcgtctt cgaccgaaag      960
caagtgaata accagttcga cggcacaggg tttgttatct cacggcgaga aggtcgcgca     1020
atcaccgcct gtacctggac atccgtgaaa tggccgcata cttcgcgcgg cgacaaactg     1080
attatccggt gctacatcgg tagggctggc gacgaggagc gagtggattg gcccgatgaa     1140
gctctcaagc gtactgtaag atcagaactg cgtgagttgc tggacattga cattgatccg     1200
gaatttgtgg agattacacg actcaggcac tctatgcctc aatacccagt cggccacgtc     1260
caggctatcc gctctttgag ggacgaggtc ggtaggactt taccgggcgt gttccttgct     1320
gggcaaccct acgaaggtgt gggaatgcct gactgtgtga ggtccggccg ggatgccgcc     1380
gaagcagcag taagtgctat gcaagcaatg agtacagaac cagaagcacc ggcagaggac     1440
gccgctactg gaacggcggg ttga                                           1464
```

```
<210> SEQ ID NO 222
<211> LENGTH: 1404
<212> TYPE: DNA
<213> ORGANISM: Artificial Sequence
<220> FEATURE:
<223> OTHER INFORMATION: Recombinant

<400> SEQUENCE: 222
gttgttgttg ttggcggcgg cttgactggc ctaagcgccg ccttctacat ccggaaacat       60
tatcgagaag ctggagttga gcccgtcatc acgcttgttg agaaatctag ctcgatggga      120
gggatgattg agacccttca tagggacggg tttgtcatcg agaagggccc ggacagtttc      180
ttggcacgga agaccgcaat gattgatctg gcgaaagagc tggagattga ccacgagttg      240
gtcagccaga atccagaatc gaagaagacc tacataatgc aacgtggaaa gctgcaccct      300
atgccagcgg gacttgttct gggcattccc accgaattgc gtcccttttct ccggagcggg      360 cttgtctcac ccgctgggaa gttgcgggcg ctgatggact tcgtaatacc gccacgaagg      420
acgaccgaag atgagtcact cgggtacatg atcgagcgcc gactgggtgc cgaggtgttg      480
gagaacctca cagagccgtt gctcgctgga atctacgctg cgacatgag aagattgtcc      540 ctccaggcta cgtttccgca gttcggtgag gtggagcgcg actacggctc cttaatcaga      600
ggaatgatga ccggacgtaa gcctgcggag acacacacag ggaccaagag gtctgccttt      660
ctcaatttca gacagggtct gcaatcactg gttcacgcct tagtccatga actccaggat      720
gtagatcaga ggttaaatac tgcggtgaag tcgcttcaga ggcttgacgg cgcacaaacc      780
cgttatcgcg ttgaactcgg caatggcgaa atgcttgagg ctgacgacgt ggtggttact      840
gtaccaacct acgtggcgag cgagcttctt aagccgcacg tggacacggc ggcgttagac      900
gctattaact atgtgtcggt ggctaatgta gttcttgcat tcgagaagaa ggaagtagag      960
cacgtcttcg atggatcggg cttcttggtg cctcggaagg agggaaggaa cataaccgcc     1020
tgcacctgga cttcgaccaa gtggctccac acatcaccag atgacaaggt tctgttacgt     1080
tgttacgtgg gcagaagtgg agatgagcag aatgtggaac tcccggatga ggcactcact     1140
aatctggtgc ttaaggatct gagagagacg atgggcatca aggcggttcc aatcttctca     1200
gagattaccc ggctccgcaa gtcaatgccg cagtacccag taggacatct ccagcacatc     1260
gccgcattgc gcgaggaact cggctctaag ctaccaggag tgtacatcgc cggagcgggc     1320
```

```
tacgagggcg ttggtcttcc ggattgcatt cgccaggcca agaaatgtca gtccaggca      1380 acgcaagaac tcgctgccga ctga                                            1404

<210> SEQ ID NO 223
<211> LENGTH: 1398
<212> TYPE: DNA
<213> ORGANISM: Artificial Sequence
<220> FEATURE:
<223> OTHER INFORMATION: Recombinant

<400> SEQUENCE: 223
aagcacctgg taatcatcgg tgtgggatc accggtctgg cttcagcgtt ctacatggaa        60
aaggagatcc gggagaagaa cttgcccctt tcggtgactc tagtggaggc ctctccacgg     120
gtggggggca agattcagac cgcgcgcaag gatggctaca tcatagagcg aggaccagac     180
tcattcctag agcgtaagaa gtccgcccca gagctcgtcg aggatctcgg tctagagcac     240
ttgctagtga ataacgctac aggacagtcc tacgtgctcg tgaacgagac actacacccg     300
atgcctaagg gggctgtcat gggtataccg accaagatcg ccccgttcat gtccactcgc     360 ctttttctcgt tctcgggcaa agctcgggcc gctatggatt tcgtcttgcc tgcctcgaaa     420
ccgaaggagg accagtcctt aggagagttc ttccgccgga gggtcggcga cgaggtggtg     480
gagaacttaa tcgaaccctt gctctcgggg atctacgctg agacattga tcgactatcg     540 cttatgtcta cgtttcctca attttaccag acggagcaga agcaccgtag cctcattttg     600
ggtatgaaga agacacggcc tcaaggttcg gggcagcagc ttactgccaa gaagcagggc     660
caattccaga cactcaagac cggcttgcag actctagtgg aggagctgga gaatcaattg     720
aagctgacaa aggtctacaa gggtaccaag gtgacaaaca tcgcgtgg cgaaaaggga      780 tgctccattg ccctcgacaa cggtatgacc ctcgacgccg acgcagcgat gtgacgagc      840 ccacacaaga gcgccgcggg catgttcccg gacttgcctg cagtgtcaca gctgaaagac     900
atgcattcta catccgtcgc caacgtcgcc ctgggctttc cccaggaggc tgtgcagatg     960
gagcacgagg ggacgggctt cgttatcagc cgcaactccg acttttctat taccgcgtgc    1020
acatggacca acaagaagtg gccgcacagc gctccggagg ggaaaacact tctccgagca    1080
tacgtaggca aggccgggga cgagtcaatt gttgagctct ccgacaatga aatcattaaa    1140
atagttctgg aggatcttaa gaaggtaatg aagataaagg gggaacctga atgacgtgt     1200 gttacccgct ggaatgagtc aatgccccag taccatgtgg acacaagca gaggataaag     1260 aaggtgaggg aggcgctcgc tgcgtcctac ccaggggtct acatgacagg agcgagtttt     1320 gaggggtgg gtattcccga ctgtatcgac cagggtaagt cggcagtgtc tgacgtgctc     1380
gcttacctat tcgagtag                                                   1398

<210> SEQ ID NO 224
<211> LENGTH: 445
<212> TYPE: PRT
<213> ORGANISM: Artificial Sequence
<220> FEATURE:
<223> OTHER INFORMATION: Recombinant

<400> SEQUENCE: 224

Gln Pro Val Leu Ile Val Gly Ala Gly Leu Ser Gly Leu Ser Ile Ala
1               5                   10                  15

Tyr Glu Leu Gln Lys Leu Gln Val Pro Tyr Gln Val Leu Glu Val Ser
            20                  25                  30
```

Gly His Ser Gly Gly Val Met Lys Ser Leu Arg Lys Asp Gly Phe Glu
        35                  40                  45

Leu Asp Ala Gly Ala Asn Thr Ile Ala Ala Ser Pro Glu Ile Leu Ala
 50                  55                  60

Tyr Phe Thr Ser Leu Gly Leu Glu Asn Glu Ile Leu Gln Ala Thr Ala
 65                  70                  75                  80

Ala Ser Lys His Arg Phe Leu Val Arg Arg Arg Gln Leu His Ala Val
                 85                  90                  95

Ser Pro His Pro Phe Lys Ile Met Ser Ser Pro Tyr Leu Ser Arg Gly
            100                 105                 110

Ser Lys Trp Arg Leu Phe Thr Glu Arg Phe Lys Pro Val Val Ala
        115                 120                 125

Ser Gly Glu Glu Thr Val Thr Asp Phe Ile Thr Arg Arg Phe Asn Arg
130                 135                 140

Glu Ile Ala Glu Tyr Val Phe Asp Pro Val Leu Ser Gly Ile Tyr Ala
145                 150                 155                 160

Gly Asn Pro Asp Gln Met Ser Ile Ala Glu Val Leu Pro Ala Leu Pro
                165                 170                 175

Arg Trp Glu Arg Glu Tyr Gly Ser Val Thr Lys Gly Leu Met Lys Asp
            180                 185                 190

Lys Gly Ala Met Gly Gly Arg Lys Ile Ile Ser Phe Lys Gly Gly Asn
        195                 200                 205

Gln Leu Leu Thr Asn Arg Leu Gln Gln Leu Leu Thr Thr Pro Val Arg
        210                 215                 220

Phe Asn Cys Lys Val Thr Gly Ile Thr Ala Ser Asn Gly Gly Tyr Ile
225                 230                 235                 240

Val Ser Ala Val Glu Asp Gly Val Ser Glu Ser Tyr Thr Ala Ser Arg
                245                 250                 255

Val Ile Leu Thr Thr Pro Ala Tyr Ser Ala Ala Thr Ile Thr Asn
            260                 265                 270

Leu Asp Ala Ala Thr Ala Ala Leu Leu Asn Glu Ile His Tyr Pro Arg
        275                 280                 285

Met Gly Val Leu His Leu Gly Phe Asp Ala Thr Ala Leu Pro Gln Pro
290                 295                 300

Leu Asp Gly Phe Gly Phe Leu Val Pro Asn Ala Glu Asn Met His Phe
305                 310                 315                 320

Leu Gly Ala Ile Cys Asn Ala Ala Ile Phe Pro Asp Lys Ala Pro Pro
                325                 330                 335

Gly Lys Ile Leu Phe Thr Val Phe Leu Gly Gly Ala Arg Gln Glu Ser
            340                 345                 350

Leu Phe Asp Gln Met Thr Pro Glu Ala Leu Gln Gln Val Val Ser
        355                 360                 365

Glu Val Met Ser Leu Leu His Leu Ser Ala Pro Val Met Gln His
370                 375                 380

Phe Ser Ser Trp Asn Lys Ala Ile Pro Gln Leu Asn Val Gly His Val
385                 390                 395                 400

Lys Leu Arg Arg Ala Val Glu Ala Phe Glu Lys Lys Tyr Pro Gly Ile
                405                 410                 415

His Leu Ser Gly Asn Tyr Leu Gln Gly Val Ala Ile Pro Ala Leu Leu
            420                 425                 430

Gln His Ala Ala Ala Leu Ala Ala Ser Leu Lys Lys Asn
        435                 440                 445

```
<210> SEQ ID NO 225
<211> LENGTH: 448
<212> TYPE: PRT
<213> ORGANISM: Artificial Sequence
<220> FEATURE:
<223> OTHER INFORMATION: Recombinant

<400> SEQUENCE: 225

Met Ser Asp Gln Pro Val Leu Ile Val Gly Ala Gly Leu Ser Gly Leu
1               5                   10                  15

Ser Ile Ala Tyr Glu Leu Gln Lys Leu Gln Val Pro Tyr Gln Val Leu
            20                  25                  30

Glu Val Ser Gly His Ser Gly Val Met Lys Ser Leu Arg Lys Asp
        35                  40                  45

Gly Phe Glu Leu Asp Ala Gly Ala Asn Thr Ile Ala Thr Ser Pro Glu
    50                  55                  60

Ile Leu Ala Tyr Phe Thr Ser Leu Gly Leu Glu Asn Glu Ile Leu Gln
65                  70                  75                  80

Ala Thr Ala Thr Ser Lys His Arg Phe Leu Val Arg Arg Arg Gln Leu
                85                  90                  95

His Ala Val Ser Pro His Pro Phe Lys Ile Met Ser Ser Pro Tyr Leu
            100                 105                 110

Cys Arg Gly Ser Lys Trp Arg Leu Phe Thr Glu Arg Phe Arg Lys Pro
        115                 120                 125

Val Val Ala Ser Gly Glu Glu Thr Val Thr Asp Phe Ile Thr Arg Arg
    130                 135                 140

Phe Asn Arg Glu Ile Ala Glu Tyr Val Phe Asp Pro Val Leu Ser Gly
145                 150                 155                 160

Ile Tyr Ala Gly Asn Pro Asp Gln Met Ser Ile Ala Glu Val Leu Pro
                165                 170                 175

Ala Leu Pro Arg Trp Glu Arg Glu Tyr Gly Ser Val Thr Lys Gly Leu
            180                 185                 190

Met Lys Asp Lys Gly Ala Met Gly Gly Arg Lys Ile Ile Ser Phe Lys
        195                 200                 205

Gly Gly Asn Gln Leu Leu Thr Asn Arg Leu Gln Gln Leu Leu Thr Thr
    210                 215                 220

Pro Val Arg Phe Asn Cys Lys Val Thr Gly Ile Thr Ala Ser Asn Gly
225                 230                 235                 240

Gly Tyr Ile Val Ser Ala Val Glu Asp Gly Val Ser Glu Ser Tyr Thr
                245                 250                 255

Ala Ser Arg Val Ile Leu Thr Thr Pro Ala Tyr Ser Ala Ala Ala Thr
            260                 265                 270

Ile Thr Asn Leu Asp Ala Ala Thr Ala Ala Leu Leu Asn Glu Ile His
        275                 280                 285

Tyr Pro Arg Met Gly Val Leu His Leu Gly Phe Asp Ala Thr Ala Leu
    290                 295                 300

Pro Gln Pro Leu Asp Gly Phe Gly Phe Leu Val Pro Asn Ala Glu Asn
305                 310                 315                 320

Met His Phe Leu Gly Ala Ile Cys Asn Ala Ala Ile Phe Pro Asp Lys
                325                 330                 335

Ala Pro Pro Gly Lys Ile Leu Phe Thr Val Phe Leu Gly Gly Ala Arg
            340                 345                 350

Gln Glu Ser Leu Phe Asp Gln Met Thr Pro Glu Ala Leu Gln Gln Gln
        355                 360                 365

Val Val Ser Glu Val Met Ser Leu Leu His Leu Ser Ala Pro Pro Val
```

```
            370                 375                 380
Met Gln His Phe Ser Ser Trp Asn Lys Ala Ile Pro Gln Leu Asn Val
385                 390                 395                 400

Gly His Val Lys Leu Arg Arg Ala Val Glu Ala Phe Glu Lys Lys Tyr
                405                 410                 415

Pro Gly Ile His Leu Ser Gly Asn Tyr Leu Gln Gly Val Ala Ile Pro
                420                 425                 430

Ala Leu Leu Gln His Ala Ala Ala Leu Ala Ala Ser Leu Lys Lys Asn
                435                 440                 445
```

<210> SEQ ID NO 226
<211> LENGTH: 466
<212> TYPE: PRT
<213> ORGANISM: Artificial Sequence
<220> FEATURE:
<223> OTHER INFORMATION: Recombinant

<400> SEQUENCE: 226

```
Lys Lys His Val Val Ile Ile Gly Gly Gly Ile Thr Gly Leu Ala Ala
1               5                   10                  15

Ala Phe Tyr Met Glu Lys Glu Ile Lys Glu Lys Asn Leu Pro Leu Glu
                20                  25                  30

Leu Thr Leu Val Glu Ala Ser Pro Arg Val Gly Gly Lys Ile Gln Thr
                35                  40                  45

Val Lys Lys Asp Gly Tyr Ile Ile Glu Arg Gly Pro Asp Ser Phe Leu
            50                  55                  60

Glu Arg Lys Lys Ser Ala Pro Gln Leu Val Lys Asp Leu Gly Leu Glu
65                  70                  75                  80

His Leu Leu Val Asn Asn Ala Thr Gly Gln Ser Tyr Val Leu Val Asn
                85                  90                  95

Arg Thr Leu His Pro Met Pro Lys Gly Ala Val Met Gly Ile Pro Thr
                100                 105                 110

Lys Ile Ala Pro Phe Val Ser Thr Gly Leu Phe Ser Leu Ser Gly Lys
                115                 120                 125

Ala Arg Ala Ala Met Asp Phe Ile Leu Pro Ala Ser Lys Thr Lys Asp
            130                 135                 140

Asp Gln Ser Leu Gly Glu Phe Phe Arg Arg Val Gly Asp Glu Val
145                 150                 155                 160

Val Glu Asn Leu Ile Glu Pro Leu Leu Ser Gly Ile Tyr Ala Gly Asp
                165                 170                 175

Ile Asp Lys Leu Ser Leu Met Ser Thr Phe Pro Gln Phe Tyr Gln Thr
                180                 185                 190

Glu Gln Lys His Arg Ser Leu Ile Leu Gly Met Lys Lys Thr Arg Pro
                195                 200                 205

Gln Gly Ser Gly Gln Gln Leu Thr Ala Lys Lys Gln Gly Gln Phe Gln
            210                 215                 220

Thr Leu Ser Thr Gly Leu Gln Thr Leu Val Glu Glu Ile Glu Lys Gln
225                 230                 235                 240

Leu Lys Leu Thr Lys Val Tyr Lys Gly Thr Lys Val Thr Lys Leu Ser
                245                 250                 255

His Ser Gly Ser Gly Tyr Ser Leu Glu Leu Asp Asn Gly Val Thr Leu
                260                 265                 270

Asp Ala Asp Ser Val Ile Val Thr Ala Pro His Lys Ala Ala Ala Gly
                275                 280                 285

Met Leu Ser Glu Leu Pro Ala Ile Ser His Leu Lys Asn Met His Ser
```

```
            290                 295                 300
Thr Ser Val Ala Asn Val Ala Leu Gly Phe Pro Glu Gly Ser Val Gln
305                 310                 315                 320

Met Glu His Glu Gly Thr Gly Phe Val Ile Ser Arg Asn Ser Asp Phe
                325                 330                 335

Ala Ile Thr Ala Cys Thr Trp Thr Asn Lys Lys Trp Pro His Ala Ala
            340                 345                 350

Pro Glu Gly Lys Thr Leu Leu Arg Ala Tyr Val Gly Lys Ala Gly Asp
        355                 360                 365

Glu Ser Ile Val Asp Leu Ser Asp Asn Asp Ile Ile Asn Ile Val Leu
    370                 375                 380

Glu Asp Leu Lys Lys Val Met Asn Ile Asn Gly Glu Pro Glu Met Thr
385                 390                 395                 400

Cys Val Thr Arg Trp His Glu Ser Met Pro Gln Tyr His Val Gly His
                405                 410                 415

Lys Gln Arg Ile Lys Glu Leu Arg Glu Ala Leu Ala Ser Ala Tyr Pro
            420                 425                 430

Gly Val Tyr Met Thr Gly Ala Ser Phe Glu Gly Val Gly Ile Pro Asp
        435                 440                 445

Cys Ile Asp Gln Gly Lys Ala Ala Val Ser Asp Ala Leu Thr Tyr Leu
    450                 455                 460

Phe Ser
465

<210> SEQ ID NO 227
<211> LENGTH: 465
<212> TYPE: PRT
<213> ORGANISM: Artificial Sequence
<220> FEATURE:
<223> OTHER INFORMATION: Recombinant

<400> SEQUENCE: 227

Lys His Leu Val Ile Ile Gly Gly Gly Ile Thr Gly Leu Ala Ala Ala
1               5                   10                  15

Phe Tyr Leu Glu Lys Glu Val Glu Glu Lys Gly Leu Pro Ile Gln Ile
            20                  25                  30

Ser Leu Ile Glu Ala Ser Pro Arg Leu Gly Gly Lys Ile Gln Thr Leu
        35                  40                  45

Tyr Lys Asp Gly Tyr Ile Ile Glu Arg Gly Pro Asp Ser Phe Leu Glu
    50                  55                  60

Arg Lys Val Ser Gly Pro Gln Leu Ala Lys Asp Val Gly Leu Ser Asp
65                  70                  75                  80

Gln Leu Val Asn Asn Glu Thr Gly Gln Ala Tyr Val Leu Val Asn Glu
                85                  90                  95

Lys Leu His Pro Met Pro Lys Gly Ala Val Met Gly Ile Pro Thr Gln
            100                 105                 110

Ile Ser Pro Phe Ile Thr Thr Gly Leu Phe Ser Val Ala Gly Lys Ala
        115                 120                 125

Arg Ala Ala Met Asp Phe Val Leu Pro Lys Ser Lys Gln Thr Glu Asp
    130                 135                 140

Gln Ser Leu Gly Glu Phe Phe Arg Arg Val Gly Asp Glu Val Val
145                 150                 155                 160

Glu Asn Leu Ile Glu Pro Leu Leu Ser Gly Ile Tyr Ala Gly Asp Ile
                165                 170                 175

Asp Arg Leu Ser Leu Met Ser Thr Phe Pro Gln Phe Tyr Gln Thr Glu
```

```
                180             185             190
    Gln Gln His Arg Ser Leu Ile Leu Gly Met Lys Lys Ser Gln Gln His
                195                 200                 205
    Ala Lys Ala Gln Gln Val Thr Ala Lys Lys Gln Gly Gln Phe Gln Thr
            210                 215                 220
    Ile Asn Gln Gly Leu Gln Ser Leu Val Glu Ala Val Glu Gly Lys Leu
    225                 230                 235                 240
    Lys Leu Thr Thr Val Tyr Lys Gly Thr Val Lys Gln Ile Glu Lys
                    245                 250                 255
    Thr Asp Gly Gly Tyr Gly Leu Gln Leu Asp Ser Gly Gln Thr Leu Phe
                    260                 265                 270
    Ala Asp Ser Ala Ile Val Thr Thr Pro His Gln Ser Ile Tyr Ser Met
                275                 280                 285
    Phe Pro Lys Glu Ala Gly Leu Glu Tyr Leu His Asp Met Thr Ser Thr
                290                 295                 300
    Ser Val Ala Thr Val Ala Leu Gly Phe Lys Asp Glu Asp Val His Asn
    305                 310                 315                 320
    Glu Tyr Asp Gly Thr Gly Phe Val Ile Ser Arg Asn Ser Asp Phe Ser
                        325                 330                 335
    Ile Thr Ala Cys Thr Trp Thr Asn Lys Lys Trp Pro His Thr Ala Pro
                    340                 345                 350
    Lys Gly Lys Thr Leu Leu Arg Ala Tyr Val Gly Lys Ala Gly Asp Glu
                    355                 360                 365
    Ser Ile Val Glu Gln Ser Asp Ser Gln Ile Val Ser Ile Val Leu Glu
                370                 375                 380
    Asp Leu Lys Lys Ile Met Asp Ile Lys Ala Asp Pro Glu Leu Thr Thr
    385                 390                 395                 400
    Val Thr Arg Trp Lys Thr Ser Met Pro Gln Tyr His Val Gly His Gln
                        405                 410                 415
    Lys Ala Ile Ser Asn Met Arg Glu Thr Phe Lys Gln Ser Tyr Pro Gly
                    420                 425                 430
    Val Tyr Ile Thr Gly Ala Ala Phe Glu Gly Val Gly Ile Pro Asp Cys
                    435                 440                 445
    Ile Asp Gln Gly Lys Ala Ala Ile Ser Glu Ala Val Ser Tyr Leu Phe
                450                 455                 460
    Ser
    465

<210> SEQ ID NO 228
<211> LENGTH: 465
<212> TYPE: PRT
<213> ORGANISM: Artificial Sequence
<220> FEATURE:
<223> OTHER INFORMATION: Recombinant

<400> SEQUENCE: 228

Lys His Leu Val Ile Ile Gly Gly Gly Ile Thr Gly Leu Ala Ala Ala
    1               5                   10                  15
    Phe Tyr Leu Glu Lys Glu Val Glu Glu Lys Gly Leu Pro Ile Gln Ile
                    20                  25                  30
    Ser Leu Ile Glu Ala Ser Pro Arg Leu Gly Gly Lys Ile Gln Thr Leu
                    35                  40                  45
    Tyr Lys Asp Gly Tyr Ile Ile Glu Arg Gly Pro Asp Ser Phe Leu Glu
                50                  55                  60
    Arg Lys Val Ser Gly Pro Gln Leu Ala Lys Asp Val Gly Leu Ser Asp
```

```
                65                  70                  75                  80
        Gln Leu Val Asn Asn Glu Thr Gly Gln Ala Tyr Val Leu Val Asn Glu
                        85                  90                  95
        Thr Leu His Pro Met Pro Lys Gly Ala Val Met Gly Ile Pro Thr Gln
                        100                 105                 110
        Ile Ser Pro Phe Ile Thr Thr Gly Leu Phe Ser Val Ala Gly Lys Ala
                        115                 120                 125
        Arg Ala Ala Met Asp Phe Val Leu Pro Lys Ser Lys Gln Thr Glu Asp
                        130                 135                 140
        Gln Ser Leu Gly Glu Phe Phe Arg Arg Val Gly Asp Glu Val Val
        145                 150                 155                 160
        Glu Asn Leu Ile Glu Pro Leu Leu Ser Gly Ile Tyr Ala Gly Asp Ile
                        165                 170                 175
        Asp Arg Leu Ser Leu Met Ser Thr Phe Pro Gln Phe Tyr Gln Thr Glu
                        180                 185                 190
        Gln Lys His Arg Ser Leu Ile Leu Gly Met Lys Lys Ser Gln His
                        195                 200                 205
        Ala Lys Ala Gln Gln Val Thr Ala Lys Lys Gln Gly Gln Phe Gln Thr
                        210                 215                 220
        Ile Asn Gln Gly Leu Gln Ala Leu Val Glu Ala Val Glu Ser Lys Leu
        225                 230                 235                 240
        Lys Leu Thr Thr Ile Tyr Lys Gly Thr Lys Val Lys Gln Ile Glu Lys
                        245                 250                 255
        Thr Asp Gly Gly Tyr Gly Val Gln Leu Asp Ser Gly Gln Thr Leu Leu
                        260                 265                 270
        Ala Asp Ser Ala Ile Val Thr Thr Pro His Gln Ser Ile Tyr Ser Met
                        275                 280                 285
        Phe Pro Lys Glu Ala Gly Leu Glu Tyr Leu His Asp Met Thr Ser Thr
                        290                 295                 300
        Ser Val Ala Thr Val Ala Leu Gly Phe Lys Glu Glu Asp Val His Asn
        305                 310                 315                 320
        Glu Tyr Asp Gly Thr Gly Phe Val Ile Ser Arg Asn Ser Asp Phe Ser
                        325                 330                 335
        Ile Thr Ala Cys Thr Trp Thr Asn Lys Lys Trp Pro His Thr Ala Pro
                        340                 345                 350
        Lys Gly Lys Thr Leu Leu Arg Ala Tyr Val Gly Lys Ala Gly Asp Glu
                        355                 360                 365
        Ser Ile Val Glu Gln Ser Asp His Gln Ile Val Ser Ile Val Leu Glu
                        370                 375                 380
        Asp Leu Lys Lys Ile Met Asp Ile Lys Ala Asp Pro Glu Leu Thr Thr
        385                 390                 395                 400
        Val Thr Arg Trp Lys Thr Ser Met Pro Gln Tyr His Val Gly His Gln
                        405                 410                 415
        Lys Ala Ile Ser Asn Met Arg Glu Thr Phe Lys Gln Ser Tyr Pro Gly
                        420                 425                 430
        Val Tyr Ile Thr Gly Ala Ala Phe Glu Gly Val Gly Ile Pro Asp Cys
                        435                 440                 445
        Ile Asp Gln Gly Lys Ala Ala Ile Ser Glu Ala Val Ser Tyr Leu Phe
                        450                 455                 460
        Ser
        465

<210> SEQ ID NO 229
```

<211> LENGTH: 537
<212> TYPE: DNA
<213> ORGANISM: Artificial Sequence
<220> FEATURE:
<223> OTHER INFORMATION: Recombinant

<400> SEQUENCE: 229

```
aaggccttgg tactgtactc gacgcgggac ggccagaccc acgcaattgc ttcatacatc      60
gcctcctgca tgaaggagaa ggccgaatgc gacgtgatcg acctcaccca cggggagcac     120
gtgaacctca cccaatacga tcaggtgcta atcggtgcga gtattcgtta cggccacttc     180
aacgccgtgc ttgacaagtt catcaagaga acgtggatc aactgaacaa catgccaagc     240
gcgttcttct gcgtaaacct cacagcaagg aagcccgaga agcgtactcc ccagacaaac     300
ccttatgtcc gaaaattctt gcttgctacc ccctggcagc ccgcgttgtg cggagtgttc     360
gcaggggccc ttcggtaccc gcgataccgg tggatcgaca aggtgatgat ccagctaata     420
atgcggatga ctgggggaga gacagacacg agcaaggagg tcgagtacac ggattgggag     480
caggttaaga agttcgcgga ggattttgca aagctatcgt acaagaaggc cctctag       537
```

<210> SEQ ID NO 230
<211> LENGTH: 1338
<212> TYPE: DNA
<213> ORGANISM: Artificial Sequence
<220> FEATURE:
<223> OTHER INFORMATION: Recombinant

<400> SEQUENCE: 230

```
cagcccgtcc tcatcgttgg agctggtctc tccgggctct caatcgctta cgaactacag      60
aagctgcaag tcccttacca agtgctggag gtttctggac attctggtgg agtcatgaag     120
tcactccgga aggacggatt tgaactcgac gctggtgcca acaccatagc cgcgtctccc     180
gagattcttg cgtactttac ctcactaggt cttgagaatg agatcctcca ggcgactgct     240
gcttctaaac accgcttctt ggtgcggcga aggcaactgc acgccgtgag cccgcacccg     300
ttcaagatca tgtcatcgcc gtacctcagc cgtggctcca aatggcggct ctttactgag     360
cggtttcgga agcccgtcgt cgcttcgggc gaggagaccg tcaccgattt catcacgagg     420
agattcaacc gcgaaatagc ggagtatgtg ttcgaccctg ttctaagcgg gatctacgcc     480
gggaacccgg accaaatgag tattgctgag gtgttgcctg ccttgcctag gtgggaaagg     540
gagtacggat cagtgaccaa gggccttatg aaggataagg gtgcgatggg aggtcgaaag     600
atcatcagct ttaagggtgg caaccagcta cttacaaacc gcttacagca gctactcact     660
actccggtga gattcaattg caaggtgaca gggattacag ccagcaatgg cgggtacatc     720
gtgagcgctg ttgaggacgg cgtatctgag agctacaccg catctcgtgt gatcttgacc     780
acacccgctt actcagcagc ggctaccata actaaccttg atgcagccac tgcggcactg     840
ttgaacgaaa tccattatcc acgtatgggc gtgttacact gggctttga tgcaactgcc     900
ttgccacagc cgctggacgg gttcggattt ctagtgccga acgcggagaa catgcacttc     960
ctgggagcca tctgcaatgc agccatcttc ccggacaagg ctccgcccgg caagatcctg    1020
tttacagtgt tcctcggagg cgcacgccag gagtcgctct cgatcagat gactcctgag    1080
gctcttcagc agcaagtcgt tagtgaggtg atgagcttgt tgcacttgtc agctccaccg    1140
gtgatgcagc acttctcctc ctggaacaag gccatccctc aattgaacgt cgggcacgtg    1200
aagttgcggc gcgcggtaga ggcgttcgag aagaaatacc ctggaatcca tctctcgggc    1260
aactacctcc agggagttgc aataccagct ttactccagc acgccgcagc tttagctgct    1320
```
tctcttaaga agaactga 1338

<210> SEQ ID NO 231
<211> LENGTH: 1344
<212> TYPE: DNA
<213> ORGANISM: Artificial Sequence
<220> FEATURE:
<223> OTHER INFORMATION: Recombinant

<400> SEQUENCE: 231

| | | | | | |
|---|---|---|---|---|---|
| atgagcgacc | aacccgtcct | catcgttgga | gctggtctct | ccgggctctc | aatcgcttac | 60 |
| gaactacaga | agctgcaagt | cccttaccaa | gtgctggagg | tttctggaca | ttctggtgga | 120 |
| gtcatgaagt | cactccggaa | ggacggattt | gaactcgacg | ctggtgccaa | caccatagcc | 180 |
| acgtctcccg | agattcttgc | gtactttacc | tcactaggtc | ttgagaatga | gatcctccag | 240 |
| gcgactgcta | cttctaaaca | ccgcttcttg | gtgcggcgaa | ggcaactgca | cgccgtgagc | 300 |
| ccgcacccgt | tcaagatcat | gtcatcgccg | tacctctgcc | gtggctccaa | atggaggctc | 360 |
| tttactgagc | ggtttcggaa | acccgtcgtc | gcttcgggcg | aggagaccgt | caccgatttc | 420 |
| atcacgagga | gattcaaccg | cgaaatagcg | gagtatgtgt | tcgaccctgt | tctaagtggg | 480 |
| atctacgccg | ggaacccgga | ccaaatgagt | attgctgagg | tgttgcctgc | cttgcctagg | 540 |
| tgggaaaggg | agtacggatc | agtgaccaag | ggccttatga | aggataaggg | tgcgatggga | 600 |
| ggtcgaaaga | tcatcagctt | taagggtggc | aaccagctac | ttacaaaccg | cttacagcag | 660 |
| ctactcacta | ctccggtgag | attcaattgc | aaggtgacag | ggattacagc | cagcaatggc | 720 |
| gggtacatcg | tgagcgctgt | tgaggacggc | gtatctgaga | gctacaccgc | atctcgtgtg | 780 |
| atcttgacca | cacccgctta | ctcagcagcg | gctaccataa | ctaaccttga | tgcagccact | 840 |
| gcggcactgt | tgaacgaaat | ccattatcca | cgtatgggcg | tgttacactt | gggctttgat | 900 |
| gcaactgcct | tgccacagcc | gctggacggg | ttcggatttc | tagtgccgaa | cgcggagaac | 960 |
| atgcacttcc | tgggagccat | ctgcaatgca | gccatcttcc | cggacaaggc | tccgcccggc | 1020 |
| aagatcctgt | ttacagtgtt | cctcggaggc | gcacgccagg | agtcgctctt | cgatcagatg | 1080 |
| actcctgagg | ctcttcagca | gcaagtcgtt | agtgaggtga | tgagcttgtt | gcacttgtca | 1140 |
| gctccaccgg | tgatgcagca | cttctcctcc | tggaacaagg | ccatccctca | attgaacgtc | 1200 |
| gggcacgtga | agttgcggcg | cgcggtagag | gcgttcgaga | agaaataccc | tggaatccat | 1260 |
| ctctcgggca | actacctcca | gggagttgca | ataccagctt | tactccagca | cgccgcagct | 1320 |
| ttagctgctt | ctcttaagaa | gaac | | | | 1344 |

<210> SEQ ID NO 232
<211> LENGTH: 1338
<212> TYPE: DNA
<213> ORGANISM: Artificial Sequence
<220> FEATURE:
<223> OTHER INFORMATION: Recombinant

<400> SEQUENCE: 232

| | | | | | |
|---|---|---|---|---|---|
| cagcccgtcc | tcatcgttgg | agctggtctc | tccgggctct | caatcgctta | cgaactacag | 60 |
| aagctgcaag | tcccttacca | agtgctggag | gtttctggac | attctggtgg | agtcatgaag | 120 |
| tcactccgga | aggacggatt | tgaactcgac | gctggtgcca | acaccatagc | cacgtctccc | 180 |
| gagattcttg | cgtactttac | ctcactaggt | cttgagaatg | agatcctcca | ggcgactgct | 240 |
| acttctaaac | accgcttctt | ggtgcggcga | aggcaactgc | acgccgtgag | cccgcacccg | 300 |

| | |
|---|---|
| ttcaagatca tgtcatcgcc gtacctctgc cgtggctcca atggaggct ctttactgag | 360 |
| cggtttcgga aacccgtcgt cgcttcgggc gaggagaccg tcaccgattt catcacgagg | 420 |
| agattcaacc gcgaaatagc ggagtatgtg ttcgaccctg ttctaagtgg gatctacgcc | 480 |
| gggaacccgg accaaatgag tattgctgag gtgttgcctg ccttgcctag gtgggaaagg | 540 |
| gagtacggat cagtgaccaa gggccttatg aaggataagg gtgcgatggg aggtcgaaag | 600 |
| atcatcagct ttaagggtgg caaccagcta cttacaaacc gcttacagca gctactcact | 660 |
| actccggtga gattcaattg caaggtgaca gggattacag ccagcaatgg cgggtacatc | 720 |
| gtgagcgctg ttgaggacgg cgtatctgag agctacaccg catctcgtgt gatcttgacc | 780 |
| acaccgctt actcagcagc ggctaccata actaaccttg atgcagccac tgcggcactg | 840 |
| ttgaacgaaa tccattatcc acgtatgggc gtgttacact tgggctttga tgcaactgcc | 900 |
| ttgccacagc cgctggacgg gttcggattt ctagtgccga acgcggagaa catgcacttc | 960 |
| ctgggagcca tctgcaatgc agccatcttc ccggacaagg ctccgcccgg caagatcctg | 1020 |
| tttacagtgt tcctcggagg cgcacgccag gagtcgctct tcgatcagat gactcctgag | 1080 |
| gctcttcagc agcaagtcgt tagtgaggtg atgagcttgt tgcacttgtc agctccaccg | 1140 |
| gtgatgcagc acttctcctc ctggaacaag gccatccctc aattgaacgt cgggcacgtg | 1200 |
| aagttgcggc gcgcggtaga ggcgttcgag aagaaatacc ctggaatcca tctctcgggc | 1260 |
| aactacctcc agggagttgc aataccagct ttactccagc acgccgcagc tttagctgct | 1320 |
| tctcttaaga agaactga | 1338 |

<210> SEQ ID NO 233
<211> LENGTH: 1401
<212> TYPE: DNA
<213> ORGANISM: Artificial Sequence
<220> FEATURE:
<223> OTHER INFORMATION: Recombinant

<400> SEQUENCE: 233

| | |
|---|---|
| aagaagcacg tcgtcatcat aggcggtggg atcactggct tggccgctgc attctacatg | 60 |
| gagaaggaga ttaaggagaa gaacctccca cttgagctga cgctagttga ggccagtccc | 120 |
| agggtcggcg gcaagatcca gacggtcaag aaggacgggt acataattga acgcggccct | 180 |
| gacagcttct tagagcgcaa gaaatcggct ccgcagctag ttaaggactt gggacttgag | 240 |
| cacctgctcg tcaacaacgc gaccggacag tcgtacgtgc tcgtgaaccg gacgctccac | 300 |
| ccgatgccga agggcgctgt gatgggcatt ccgaccaaga tagcaccatt cgtgagtacc | 360 |
| ggcctattca gcctttccgg caaggcaagg gctgcgatgg acttcatctt gcctgcctct | 420 |
| aagactaagg acgatcagtc cttgggcgag ttcttccgcc gccgggtggg tgatgaggtg | 480 |
| gtggagaact taattgagcc gctcctatct ggaatctacg ctggtgacat cgacaaactg | 540 |
| tctctgatgt ccacctttcc gcagttctac caaactgagc agaagcaccg ttcacttatc | 600 |
| ttgggaatga agaagactag acctcaaggt tcgggtcagc aactgacggc caagaaacag | 660 |
| ggtcagttcc agacgctaag caccgggctt cagacactcg tggaggagat tgagaaacag | 720 |
| ctcaaactta ctaaggtgta caagggcacg aaggtgacaa agttatccca ctccggcagc | 780 |
| gggtactccc tggagttgga caatggcgta acgttggacg ccgactcagt tatcgtgaca | 840 |
| gcgccgcata aggctgctgc cgggatgttg tcagaactcc cggcgatttc ccatctcaag | 900 |
| aacatgcaca gtacctcggt tgccaacgtc gccctcggat tccggaagg aagtgttcaa | 960 |
| atggagcacg aaggcacggg tttcgtaatt tccaggaact ccgactttgc catcaccgct | 1020 |

```
tgtacttgga ccaacaagaa gtggcctcat gctgcgccgg agggcaagac attgctcaga    1080
gcttacgtcg ggaaggcggg cgacgagtca atcgtcgatc ttagcgacaa cgacatcatt    1140
aacattgtgc tggaggactt gaagaaggtt atgaacatca atggcgagcc agagatgacc    1200
tgcgtgaccc gatggcacga gtctatgccg cagtaccacg tcggtcacaa gcagcgcatc    1260
aaggagttgc gcgaggcact cgcctcagct taccctggcg tgtacatgac tggcgcttcg    1320
tttgagggcg ttggtattcc tgactgcatc gaccagggaa aggcggccgt cagtgacgcg    1380
ctcacctacc tcttcagttg a                                              1401
```

<210> SEQ ID NO 234
<211> LENGTH: 1398
<212> TYPE: DNA
<213> ORGANISM: Artificial Sequence
<220> FEATURE:
<223> OTHER INFORMATION: Recombinant

<400> SEQUENCE: 234

```
aagcacctgg tcataatcgg aggcggcata accggccttg ctgcggcctt ctacctggag     60
aaggaggtcg aggagaaggg tctccctatc cagatttcat tgattgaggc ttcgcctcgg    120
ctgggaggga agatccagac attgtacaag gacgggtaca tcatcgagcg tggtccagac    180
agtttcctgg agcggaaggt cagcggaccg cagctcgcca aggacgtggg acttagcgac    240
caactggtga acaacgagac aggacaggcg tacgtcttgg tgaatgagaa gttgcacccg    300
atgcctaagg gtgccgtgat gggcatccca acgcaaatct cacctttcat caccaccgga    360
ctcttctccg tggccggaaa ggcacgagct gcaatggact tcgttctgcc taagtcgaaa    420
cagaccgaag accagtctct aggcgagttc ttccgccgcc gtgtgggtga cgaggttgtg    480
gagaacctca tcgagccttt gttgtctggg atctacgcgg gcgacatcga cagacttagt    540
ctcatgagta cctttccgca attctatcag acagaacagc agcatcgaag tctcatactc    600
gggatgaaga agtcacaaca acatgcaaag gcccagcaag ttaccgccaa gaaacagggc    660
cagttccaaa cgatcaacca gggcctccag agcttggtgg aggcagtgga gggaaagttg    720
aagctcacca ccgtttacaa agggacaaag gttaaacaga ttgagaagac ggacggcggt    780
tacgggttac aattggactc cggacagact ctcttcgctg attccgctat cgtaactact    840
cctcaccaga gcatctactc tatgttcccg aaggaggcgg gcctggagta cctgcacgac    900
atgacttcaa cgtctgtcgc caccgtggct ttgggcttca aggacgagga cgtccacaat    960
gagtatgacg gacgggatt cgttatcagt aggaactccg acttcagcat caccgcctgc   1020
acgtggacca acaagaagtg gccacacacc gcgcccaaag ggaagaccct tctgagggca   1080
tacgtgggca aggcggcga cgagagcatc gtcgagcaat ctgattctca gattgtttca   1140
atcgtcctcg aagacctcaa gaagatcatg gacatcaagg cagacccgga acttaccacc   1200
gttactcgat ggaagacctc gatgcctcag tatcacgtcg gcaccagaa ggcaatcagc   1260 aacatgaggg agacattcaa gcagtcgtat cctggcgtgt acattaccgg agcagcattc   1320
gaaggcgtag gaatccctga ctgcattgac cagggcaagg ctgctatctc agaggccgtg   1380
tcctatctct ctctcgtga                                                 1398
```

<210> SEQ ID NO 235
<211> LENGTH: 1398
<212> TYPE: DNA
<213> ORGANISM: Artificial Sequence
<220> FEATURE:

<223> OTHER INFORMATION: Recombinant

<400> SEQUENCE: 235

| | | | |
|---|---|---|---|
| aagcacctgg tgataattgg aggcgggatt accggcctag cagccgcttt ctatctggag | 60 |
| aaggaggtgg aggagaaggg cctcccgata cagatttcgc tgattgaagc ctctccgcgc | 120 |
| ctgggcggca agatccagac attgtacaag gacgggtaca tcattgagcg cgggcctgac | 180 |
| tcgttcctgg agcggaaggt ctccggtcct caactggcca agacgtggg tctttccgat | 240 |
| cagcttgtga acaatgagac cggtcaggct tacgtcttgg tcaacgaaac tctgcatccc | 300 |
| atgcctaagg gagccgttat gggcattcca acgcaaatct ctccgttcat aacgactggg | 360 |
| ctgttcagcg ttgcgggcaa agcaagggct gctatggact tcgtgctgcc aaagagtaag | 420 |
| cagaccgagg accagtccct cggcgagttc ttccgccgcc gagtgggcga tgaggtggtt | 480 |
| gagaatctaa tcgaaccgct gttgtcgggc atctatgcgg gcgacatcga caggctaagt | 540 |
| cttatgtcca ctttccctca gttctaccag acagagcaga acacaggag tctcatcctt | 600 |
| ggaatgaaga agtcccagca gcacgcgaag gctcagcaag tgaccgccaa gaagcaagga | 660 |
| cagttccaga ccatcaacca gggcctacag gcccttgtcg aagccgttga gtcgaagtta | 720 |
| aagttgacga cgatctacaa gggcaccaag gtgaagcaga ttgagaagac tgacggtggc | 780 |
| tatggtgtgc aactcgattc gggccaaaca ttgctcgctg actccgctat cgtcacgacg | 840 |
| ccacaccagt cgatctactc gatgttcccg aaggaggcgg gcctagagta ccttcacgac | 900 |
| atgacctcca cttcggtcgc caccgttgca ctcggctta aggaggagga cgttcacaac | 960 |
| gagtacgatg caccggatt cgtgatctcc aggaactcgg acttctcgat taccgcgtgc | 1020 |
| acgtggacaa ataagaagtg gccgcacaca cgccaaagg gcaagaccct tctgcgggcg | 1080 |
| tatgtgggca aggccggtga cgagagcatt gtcgaacaat ctgaccatca gatcgtttct | 1140 |
| attgttcttg aggatctcaa gaagataatg gacattaagg ccgaccctga gcttaccaca | 1200 |
| gtgacgaggt ggaagacctc gatgccgcag tatcacgtag gcaccagaa ggccatctcc | 1260 |
| aacatgcggg agacattcaa gcagtcgtac cctggcgtgt acattactgg cgctgctttc | 1320 |
| gagggcgttg gcatcccgga ctgcatcgac cagggcaagg ccgcaatctc agaggcagtg | 1380 |
| tcgtacctgt tcagctag | 1398 |

<210> SEQ ID NO 236
<211> LENGTH: 68
<212> TYPE: PRT
<213> ORGANISM: Glycine max

<400> SEQUENCE: 236

Met Ala Thr Ala Thr Thr Thr Ala Thr Ala Ala Phe Ser Gly Val Val
1               5                   10                  15

Ser Val Gly Thr Glu Thr Arg Arg Ile Tyr Ser Phe Ser His Leu Gln
            20                  25                  30

Pro Ser Ala Ala Phe Pro Ala Lys Pro Ser Ser Phe Lys Ser Leu Lys
        35                  40                  45

Leu Lys Gln Ser Ala Arg Leu Thr Arg Arg Leu Asp His Arg Pro Phe
    50                  55                  60

Val Val Arg Cys
65

<210> SEQ ID NO 237
<211> LENGTH: 56
<212> TYPE: PRT

<213> ORGANISM: Artificial Sequence
<220> FEATURE:
<223> OTHER INFORMATION: Recombinant

<400> SEQUENCE: 237

Met Ala Thr Thr Thr Ala Ala Ala Val Thr Ile Ser Ile Pro Lys
1               5                   10                  15

Lys Pro Val Phe Ile Arg Arg Pro Arg Leu Arg Gly Pro Val Asp Cys
            20                  25                  30

Arg Gly Leu His Ala Ser Asp Ala Ile Ile Ser Asn Glu Ala Pro Thr
            35                  40                  45

Gly Thr Thr Ile Ser Ala Asp Cys
    50                  55

<210> SEQ ID NO 238
<211> LENGTH: 76
<212> TYPE: PRT
<213> ORGANISM: Eragrostis tef

<400> SEQUENCE: 238

Met Ala Ala Ala Pro Pro Leu Ala Ala Asp Met Val Leu Pro Ser Pro
1               5                   10                  15

Cys Pro Ala Ala Val Ala Pro Thr Pro Val Val Ala Ala Ala Trp Gly
            20                  25                  30

Ala Ala Arg Ala Gly Ser Val Arg Cys Lys Ala Thr Gln Leu Arg Met
            35                  40                  45

Met Arg Thr Gly Gly Pro Val Ala Pro Val Ala Gly Arg Arg Arg Arg
    50                  55                  60

Ala Pro Leu Ser Val Arg Cys Asp Ala Ser Ser Arg
65                  70                  75

<210> SEQ ID NO 239
<211> LENGTH: 80
<212> TYPE: PRT
<213> ORGANISM: Setaria italica

<400> SEQUENCE: 239

Met Ala Ala Ala Pro Pro Leu Ser Ala Asp Ala Leu Ser Phe Leu Pro
1               5                   10                  15

Ser Ala Ala Ala Pro Ala Ala Ala Pro Thr Pro Val Val Ala Ala
            20                  25                  30

Ala Trp Gly Ala Ala Arg Ala Ala Gly Ser Val Arg Gly Lys Ala Ala
            35                  40                  45

Leu Arg Met Ala Arg Arg Gly Ser Gly Leu Ala Pro Val Val Gly Arg
    50                  55                  60

Arg Pro Arg Pro Pro Leu Ser Val Arg Cys Asp Ala Thr Ser Arg
65                  70                  75                  80

<210> SEQ ID NO 240
<211> LENGTH: 84
<212> TYPE: PRT
<213> ORGANISM: Acalypha ostryifolia

<400> SEQUENCE: 240

Met Ala Thr Thr Thr Ala Thr Thr Ser Phe Ser Gly Val Ser Ile Cys
1               5                   10                  15

Pro Pro His Gln Thr Asn Arg Thr Ser Leu Phe Pro Pro Gln Ser Leu
            20                  25                  30

Ser Phe Pro Ser Ser Lys His Gly Ser Leu Val Asn Ser Val Gln Phe

```
            35                  40                  45
Asn Arg Ser Arg Arg Ala Arg Arg Asn His Phe Ser Leu Thr Ser Ile
 50                  55                  60
Thr Asn Ala Pro Arg Arg Lys Arg Leu Leu Ser Val Arg Cys Asp Ala
 65                  70                  75                  80
Ser Ala Thr Ser

<210> SEQ ID NO 241
<211> LENGTH: 78
<212> TYPE: PRT
<213> ORGANISM: Adansonia digitata

<400> SEQUENCE: 241

Met Ala Ala Ser Ser Ser Val Val Ser Phe Ser Gly Ile Ser Leu
  1               5                  10                  15

Cys Ser Thr His Ser Ile Ser Asn Lys Thr Tyr Leu Phe Ser Ala His
                 20                  25                  30

Pro Arg Ile Ser Val Ser Phe Pro Ser Lys Pro Asn Ser Leu Lys Ser
            35                  40                  45

Phe Lys Gln Leu Gln Leu Lys Lys Asn Gly Leu Phe Glu Lys Phe Ser
 50                  55                  60

Arg Thr Ser Ser Arg Ser Phe Val Val Arg Cys Asp Ala Ser
 65                  70                  75

<210> SEQ ID NO 242
<211> LENGTH: 82
<212> TYPE: PRT
<213> ORGANISM: Taraxacum officinale

<400> SEQUENCE: 242

Met Ala Thr Thr Ala Ser Phe Ser Gly Val Arg Ile His Ala Pro Ser
  1               5                  10                  15

Ser Thr Cys Ile Asp Arg Thr Thr Leu Phe Ala Gln Pro Ser Val Ser
                 20                  25                  30

Phe Ser Ser Phe Ser Lys Pro Arg Arg Thr Thr Leu Arg Ser Leu Lys
            35                  40                  45

Leu Arg Ser Arg Ser Asn Asp Val Leu Leu Arg Thr Arg Thr Gly Asp
 50                  55                  60

Arg Phe Gly Gly Lys Ser Ser Arg Ser Phe Val Val Arg Cys Asp Ala
 65                  70                  75                  80

Ser Ser

<210> SEQ ID NO 243
<211> LENGTH: 77
<212> TYPE: PRT
<213> ORGANISM: Amaranthus cruentus

<400> SEQUENCE: 243

Met Ala Thr Ala Thr Thr Ser Phe Pro Gly Ala Tyr Leu Arg Val Pro
  1               5                  10                  15

Pro Lys Asn Gly Val Arg Asn Ala Leu Phe Ser Gln Ser Ile Val Ser
                 20                  25                  30

Ile Ala Arg Asn Ser Arg Lys Pro Lys Ser Leu Lys Ser Leu Lys Leu
            35                  40                  45

Ser Thr Asn Ser Phe Asn Phe Gly Leu His Lys Ser Cys Arg Lys Gly
 50                  55                  60

Ser Lys Ser Gly Ser Phe Val Val Arg Cys Asp Ala Ala
```

-continued

```
             65                  70                  75

<210> SEQ ID NO 244
<211> LENGTH: 80
<212> TYPE: PRT
<213> ORGANISM: Amaranthus cruentus

<400> SEQUENCE: 244

Met Ala Ile Ala Thr Thr Ser Phe Pro Gly Thr Tyr Leu Arg Val Pro
1               5                   10                  15

Pro Lys Asn Gly Val Arg Asn Ala Leu Phe Ser Arg Ser Val Val Ser
                20                  25                  30

Asn Gly Val Asn Ser Arg Lys Pro Asn Ser Leu Glu Ser Leu Lys Ser
            35                  40                  45

Ser Arg Asn Ser Ser Asn Val Cys Leu Ser Thr Ser Phe Gly His Tyr
        50                  55                  60

Arg Lys Ser Ser Lys Ser Gly Ser Phe Phe Val Arg Cys Asn Ala Ala
65                  70                  75                  80

<210> SEQ ID NO 245
<211> LENGTH: 80
<212> TYPE: PRT
<213> ORGANISM: Amaranthus hypochondriacus

<400> SEQUENCE: 245

Met Ala Ile Ala Thr Thr Ser Phe Pro Gly Thr Tyr Leu Arg Val Pro
1               5                   10                  15

Pro Lys Asn Gly Val Arg Asn Ala Leu Phe Ser Arg Ser Val Val Ser
                20                  25                  30

Asn Gly Val Asn Ser Arg Lys Pro Asn Ser Leu Glu Ser Leu Lys Ser
            35                  40                  45

Ser Arg Asn Ser Ser Asn Val Cys Leu Ser Thr Ser Phe Gly His Tyr
        50                  55                  60

Arg Lys Ser Ser Lys Ser Gly Ser Phe Phe Val Arg Cys Asn Ala Ala
65                  70                  75                  80

<210> SEQ ID NO 246
<211> LENGTH: 77
<212> TYPE: PRT
<213> ORGANISM: Amaranthus palmeri

<400> SEQUENCE: 246

Met Ala Thr Ala Thr Thr Ser Phe Pro Gly Ala Tyr Leu Arg Val Pro
1               5                   10                  15

Pro Lys Asn Gly Val Arg Asn Ala Leu Phe Ser Gln Ser Ile Val Ser
                20                  25                  30

Ile Ala Leu Asn Ser Arg Lys Pro Lys Ser Phe Lys Ser Leu Lys Ser
            35                  40                  45

Ser Ala Asn Ser Cys Asn Phe Gly Leu His Lys Ser Tyr Arg Lys Gly
        50                  55                  60

Ser Lys Ser Gly Ser Phe Val Val Arg Cys Asp Ala Ala
65                  70                  75

<210> SEQ ID NO 247
<211> LENGTH: 80
<212> TYPE: PRT
<213> ORGANISM: Amaranthus palmeri

<400> SEQUENCE: 247
```

Met Ala Thr Ala Thr Thr Ser Phe Pro Gly Thr Tyr Leu Arg Val Pro
1               5                   10                  15

Pro Lys Asn Gly Val Arg Asn Ala Leu Phe Ser Arg Ser Val Val Ser
                20                  25                  30

Asn Gly Val Asn Ser Arg Lys Pro Asn Ser Leu Lys Ser Leu Lys Leu
            35                  40                  45

Ser Arg Asn Ser Ser Asn Val Cys Leu Tyr Thr Ser Phe Gly His Tyr
    50                  55                  60

Arg Lys Ser Ser Lys Ser Gly Ser Phe Ile Ile Arg Cys Asn Ala Ala
65              70                  75                  80

<210> SEQ ID NO 248
<211> LENGTH: 77
<212> TYPE: PRT
<213> ORGANISM: Amaranthus palmeri

<400> SEQUENCE: 248

Met Ala Thr Ala Thr Thr Ser Phe Pro Gly Ala Tyr Leu Arg Val Pro
1               5                   10                  15

Pro Lys Asn Gly Val Arg Asn Ala Leu Phe Ser Gln Ser Ile Val Ser
                20                  25                  30

Ile Ala Leu Asn Ser Arg Lys Pro Lys Ser Phe Lys Ser Leu Lys Ser
            35                  40                  45

Ser Ala Asn Ser Cys Asn Phe Gly Leu His Lys Ser Tyr Arg Lys Gly
    50                  55                  60

Ser Lys Ser Gly Ser Phe Val Val Arg Cys Asp Ala Ala
65              70                  75

<210> SEQ ID NO 249
<211> LENGTH: 77
<212> TYPE: PRT
<213> ORGANISM: Amaranthus palmeri

<400> SEQUENCE: 249

Met Ala Thr Ala Thr Thr Ser Phe Pro Gly Ala Tyr Leu Arg Val Pro
1               5                   10                  15

Pro Lys Asn Gly Val Arg Asn Ala Leu Phe Ser Gln Ser Ile Val Ser
                20                  25                  30

Ile Ala Leu Asn Ser Arg Lys Pro Lys Ser Phe Lys Ser Leu Lys Ser
            35                  40                  45

Ser Ala Asn Ser Cys Asn Phe Gly Leu His Lys Ser Tyr Arg Lys Gly
    50                  55                  60

Ser Lys Ser Gly Ser Phe Val Val Arg Cys Asp Ala Ala
65              70                  75

<210> SEQ ID NO 250
<211> LENGTH: 80
<212> TYPE: PRT
<213> ORGANISM: Amaranthus palmeri

<400> SEQUENCE: 250

Met Ala Thr Ala Thr Thr Ser Phe Pro Gly Thr Tyr Leu Arg Val Pro
1               5                   10                  15

Pro Lys Asn Gly Val Arg Asn Ala Leu Phe Ser Arg Ser Val Val Ser
                20                  25                  30

Asn Gly Val Asn Ser Arg Lys Pro Lys Ser Leu Lys Ser Leu Lys Ser
            35                  40                  45

Ser Arg Asn Ser Ser Asn Val Cys Leu Tyr Thr Ser Phe Gly His Tyr

```
                 50                  55                  60
Arg Lys Ser Ser Lys Ser Gly Ser Phe Ile Ile Arg Cys Asn Ala Ala
 65                  70                  75                  80

<210> SEQ ID NO 251
<211> LENGTH: 80
<212> TYPE: PRT
<213> ORGANISM: Amaranthus rudis

<400> SEQUENCE: 251

Met Ala Thr Ala Thr Thr Ser Phe Pro Gly Thr Tyr Leu Arg Val Pro
  1               5                  10                  15

Pro Lys Asn Gly Val Arg Asn Ala Leu Phe Ser Arg Ser Val Val Ser
                 20                  25                  30

Asn Gly Val Asp Ser Arg Lys Pro Asn Ser Leu Lys Ser Met Lys Leu
             35                  40                  45

Ser Arg Asn Ser Ser Asn Val Cys Leu Tyr Thr Ser Phe Gly His Tyr
         50                  55                  60

Arg Lys Ser Ser Lys Ser Gly Ser Phe Ile Val Arg Cys Asn Ala Ala
 65                  70                  75                  80

<210> SEQ ID NO 252
<211> LENGTH: 80
<212> TYPE: PRT
<213> ORGANISM: Amaranthus rudis

<400> SEQUENCE: 252

Met Ala Thr Ala Thr Thr Ser Phe Pro Gly Thr Tyr Leu Arg Val Pro
  1               5                  10                  15

Pro Lys Asn Gly Val Arg Asn Ala Leu Phe Ser Arg Ser Val Val Ser
                 20                  25                  30

Asn Gly Val Asp Ser Arg Lys Pro Asn Ser Leu Lys Ser Met Lys Leu
             35                  40                  45

Ser Arg Asn Ser Ser Asn Val Cys Leu Tyr Thr Ser Phe Gly His Tyr
         50                  55                  60

Arg Lys Ser Ser Lys Ser Gly Ser Phe Ile Val Arg Cys Asn Ala Ala
 65                  70                  75                  80

<210> SEQ ID NO 253
<211> LENGTH: 80
<212> TYPE: PRT
<213> ORGANISM: Amaranthus rudis

<400> SEQUENCE: 253

Met Ala Thr Ala Thr Thr Ser Phe Pro Gly Thr Tyr Leu Arg Val Pro
  1               5                  10                  15

Pro Lys Asn Gly Val Arg Asn Ala Leu Phe Ser Arg Ser Val Val Ser
                 20                  25                  30

Asn Gly Val Asp Ser Arg Lys Pro Asn Ser Leu Lys Ser Met Lys Leu
             35                  40                  45

Ser Arg Asn Ser Ser Asn Val Cys Leu Tyr Thr Ser Phe Gly His Tyr
         50                  55                  60

Arg Lys Ser Ser Lys Ser Gly Ser Phe Ile Val Arg Cys Asn Ala Ala
 65                  70                  75                  80

<210> SEQ ID NO 254
<211> LENGTH: 80
<212> TYPE: PRT
<213> ORGANISM: Amaranthus viridis
```

<400> SEQUENCE: 254

Met Ala Ile Ala Thr Thr Ser Phe Pro Gly Thr Tyr Leu Arg Val Pro
1               5                   10                  15

Pro Lys Asn Gly Val Arg Asn Ala Leu Phe Ser Arg Ser Val Val Ser
            20                  25                  30

Asn Gly Val Asn Ser Arg Lys Pro Asn Ser Leu Glu Ser Leu Lys Ser
        35                  40                  45

Ser Arg Asn Ser Ser Asn Val Cys Leu Ser Thr Ser Phe Gly His Tyr
    50                  55                  60

Arg Lys Gly Ser Lys Ser Gly Ser Phe Val Val Arg Cys Asp Ala Ala
65                  70                  75                  80

<210> SEQ ID NO 255
<211> LENGTH: 77
<212> TYPE: PRT
<213> ORGANISM: Amaranthus viridis

<400> SEQUENCE: 255

Met Ala Thr Ala Thr Thr Ser Phe Pro Gly Ala Tyr Leu Arg Val Pro
1               5                   10                  15

Pro Lys Asn Gly Val Arg Asn Ala Leu Phe Ser Gln Ser Ile Val Ser
            20                  25                  30

Ile Ala Arg Asn Ser Arg Lys Pro Lys Ser Leu Lys Ser Leu Lys Leu
        35                  40                  45

Ser Thr Asn Ser Phe Asn Phe Gly Leu His Lys Ser Cys Arg Lys Gly
    50                  55                  60

Ser Lys Ser Gly Ser Phe Val Val Arg Cys Asp Ala Ala
65                  70                  75

<210> SEQ ID NO 256
<211> LENGTH: 71
<212> TYPE: PRT
<213> ORGANISM: Ambrosia trifida

<400> SEQUENCE: 256

Met Ser Thr Met Ser Thr Leu Phe His Leu Pro Ser Ser Leu Cys Thr
1               5                   10                  15

Asp Arg Thr Ile Thr Ser Ser Phe Ala Gln Pro Ser Val Ser Val Asn
            20                  25                  30

Ser Phe Ser Lys Pro Arg Arg Val Ala Leu Arg Ser Leu Lys Leu Lys
        35                  40                  45

Thr Arg Ser Asn Asp Val Leu Leu Arg Lys Ser Ser Arg Ser Leu Val
    50                  55                  60

Val Arg Cys Asp Ala Ser Ser
65                  70

<210> SEQ ID NO 257
<211> LENGTH: 87
<212> TYPE: PRT
<213> ORGANISM: Conyza canadensis

<400> SEQUENCE: 257

Met Ala Thr Ala Ala Phe Ser Gly Val Pro Cys Ile Asp Arg Thr Ser
1               5                   10                  15

Leu Leu Ser Ala Gln Pro Ser Ser Ser Ser Ser Ser Val Val Val
            20                  25                  30

Cys Tyr Ser Ser Phe Ser Lys Pro Gly Thr Thr Leu Leu Pro Ser Leu

```
                35                  40                  45
Lys Leu Lys Ser Ser Arg Asn Asn Asn Ser Asn Val Phe Leu Phe
 50                  55                  60
Gly Asn Thr Arg Lys Thr Ser Arg Leu Ser Phe Leu Val Arg Cys Asp
 65                  70                  75                  80
Ser Ser Ser Ser Ser Ser Ser
                 85

<210> SEQ ID NO 258
<211> LENGTH: 71
<212> TYPE: PRT
<213> ORGANISM: Cucumis melo

<400> SEQUENCE: 258

Met Ala Phe Ser Thr Ala Pro Phe Tyr Ala Ile Gly Ile Arg Phe Pro
 1               5                  10                  15
Ser His Ser Ser Ile Ser Ser Thr Thr Asn Ala Leu Ile Leu Lys
                20                  25                  30
Ser Pro Leu Ala Leu Ala Leu Thr Ala Lys Pro Lys Ser Pro Leu Leu
                35                  40                  45
Leu Lys Arg Asn Val Gly Cys Gln Arg Phe Gly Arg Asn Ser Arg Phe
 50                  55                  60
Val Val Arg Cys Asp Ala Ser
 65                  70

<210> SEQ ID NO 259
<211> LENGTH: 78
<212> TYPE: PRT
<213> ORGANISM: Kochia Scoparia

<400> SEQUENCE: 259

Met Ala Thr Ala Thr Thr Ser Phe Pro Gly Ala Tyr Leu His Leu Pro
 1               5                  10                  15
Pro Lys Asn Gly Val Arg Asn Ala Leu Phe Ser Gln Pro Ile Cys Ser
                20                  25                  30
Ser Asn Leu Asn Leu Lys Lys Pro Asn Ser Leu Lys Ser Val Lys Leu
                35                  40                  45
Ser Arg Ser Ser Gly Asn Ala Leu Phe Tyr Lys Asn Ala Lys Lys Asn
 50                  55                  60
Ser Lys Phe Gly Ser Leu Val Val Arg Cys Asp Ala Ala Gly
 65                  70                  75

<210> SEQ ID NO 260
<211> LENGTH: 78
<212> TYPE: PRT
<213> ORGANISM: Kochia Scoparia

<400> SEQUENCE: 260

Met Ala Thr Ala Thr Thr Ser Phe Pro Gly Ala Tyr Leu His Leu Pro
 1               5                  10                  15
Pro Lys Asn Gly Val Arg Asn Ala Leu Phe Ser Gln Pro Ile Cys Ser
                20                  25                  30
Ser Asn Leu Asn Leu Lys Lys Pro Asn Ser Leu Lys Ser Val Lys Leu
                35                  40                  45
Ser Arg Ser Ser Gly Asn Ala Leu Phe Tyr Lys Asn Ala Lys Lys Asn
 50                  55                  60
Ser Lys Phe Gly Ser Leu Val Val Arg Cys Asp Ala Ala Gly
 65                  70                  75
```

<210> SEQ ID NO 261
<211> LENGTH: 78
<212> TYPE: PRT
<213> ORGANISM: Kochia Scoparia

<400> SEQUENCE: 261

Met Ala Thr Ala Thr Thr Ser Phe Pro Gly Ala Tyr Leu His Leu Pro
1               5                   10                  15

Pro Lys Asn Gly Val Arg Asn Ala Leu Phe Ser Gln Pro Ile Cys Ser
            20                  25                  30

Ser Asn Leu Asn Leu Lys Lys Pro Asn Ser Leu Lys Ser Val Lys Leu
        35                  40                  45

Ser Arg Ser Ser Gly Asn Ala Leu Phe Tyr Lys Asn Ala Lys Lys Asn
    50                  55                  60

Ser Lys Phe Gly Ser Leu Val Val Arg Cys Asp Ala Ala Gly
65                  70                  75

<210> SEQ ID NO 262
<211> LENGTH: 84
<212> TYPE: PRT
<213> ORGANISM: Rosa hybrid cultivar

<400> SEQUENCE: 262

Met Ala Ser Ser Thr Thr Ser Phe Ala Ala Ser Gly Val Gly Leu Arg
1               5                   10                  15

Leu Pro Gln Ser Val Ser Thr Lys Cys Cys Ser Lys Ala Ser Leu Phe
            20                  25                  30

Pro His Pro Thr Leu Ser Leu Thr Phe His Ala Arg Pro Gln Phe Phe
        35                  40                  45

Arg Gly Leu Ala Ser Arg Gln Phe Asn Pro Asn Gly Ala Phe Gly Thr
    50                  55                  60

Gly Ser Gly Arg Leu Gly Arg Thr Pro Asn Pro Phe Val Val Arg Ser
65                  70                  75                  80

Glu Ala Ser Ser

<210> SEQ ID NO 263
<211> LENGTH: 80
<212> TYPE: PRT
<213> ORGANISM: Sedum album

<400> SEQUENCE: 263

Met Ala Ala Ser Ala Ala Thr Ile Thr Ser Ile Ser Ala Ile Thr
1               5                   10                  15

Pro Lys Pro Ser Ser Phe Ser Ser Pro Ser Val Thr Val Pro Arg
            20                  25                  30

Phe Ser Val Ser Cys Ser Ala Ile Pro Arg Pro His Lys Asn Pro Cys
        35                  40                  45

Ser Leu Lys Phe Arg Val Lys Asp Ser Arg Phe Asn Gly Ile Val Lys
    50                  55                  60

Lys Arg Ser Asn Ser Asn Ser Phe Val Val Arg Cys Asp Thr Ser Ser
65                  70                  75                  80

<210> SEQ ID NO 264
<211> LENGTH: 79
<212> TYPE: PRT
<213> ORGANISM: Sedum album

<400> SEQUENCE: 264

Met Ala Asp Ala Ala Thr Ile Thr Ala Gly Ile Thr Leu Thr Thr
1               5                   10                  15

Ala Arg Arg Ser Ser Ser Ile Ala Pro Gln Phe Ser Val Cys Cys
            20                  25                  30

Ser Ala Ile Thr Asn Thr Gln Lys Asn Leu Ser Phe Leu Lys Leu Arg
        35                  40                  45

Val Lys Asp Ala Thr Leu Thr Thr Arg Ile Glu Gly Ile Gln Lys Lys
    50                  55                  60

Arg Tyr Asn Ser Ala Ser Phe Val Val Arg Cys Asp Ala Ser Ser
65                  70                  75

<210> SEQ ID NO 265
<211> LENGTH: 81
<212> TYPE: PRT
<213> ORGANISM: Spinacia oleracea

<400> SEQUENCE: 265

Met Ala Thr Ala Thr Thr Ser Phe Leu Gly Ala Tyr Leu Arg Val Pro
1               5                   10                  15

Pro Asn Asn Gly Val Arg Asn Ala Leu Phe Ser Gln Pro Phe Leu Ser
            20                  25                  30

Leu Arg Ile Lys Ser Lys Arg Thr Lys Ser Leu Asn Ser Leu Lys Phe
        35                  40                  45

Thr Gly Asp Ser Ser Lys Ile Leu Leu Phe Lys Cys Ser Arg Pro Phe
    50                  55                  60

Glu Lys Gly Leu Lys Ser Gly Ser Phe Val Val Arg Cys Asp Ala Ala
65                  70                  75                  80

Gly

<210> SEQ ID NO 266
<211> LENGTH: 79
<212> TYPE: PRT
<213> ORGANISM: Allium cepa

<400> SEQUENCE: 266

Met Ala Ala Thr Ser Ser Ala Thr Thr His Leu Pro Phe Phe Ser Pro
1               5                   10                  15

His Thr Lys His Ala Lys Thr Asn Ser Phe Phe Ala Ser Leu Pro Val
            20                  25                  30

Ser Ala Tyr Ser Thr Lys Asn Ser Ile Ser Phe Lys Ala Leu Lys Ala
        35                  40                  45

Val Arg Trp Ser Glu Thr Phe Gly Gln Ser Lys Lys Ala Asn Gly Phe
    50                  55                  60

Ala Lys Arg Lys Gln Phe Ala Val Val Arg Cys Asp Ala Ser Ser
65                  70                  75

<210> SEQ ID NO 267
<211> LENGTH: 204
<212> TYPE: DNA
<213> ORGANISM: Glycine max

<400> SEQUENCE: 267
atggctactg ctactaccac agctaccgct gcattctctg gtgttgtgag tgttggaacc      60
gagacacgta gaatttactc tttctcacac ttgcaaccta gcgcagcctt ccctgccaag     120
ccatcatcct ttaagtcctt gaagctgaaa cagtcggcga ggcttacgag gcgcctcgat     180
catagaccct tgtggtccg atgc                                             204

<210> SEQ ID NO 268
<211> LENGTH: 168
<212> TYPE: DNA
<213> ORGANISM: Artificial Sequence
<220> FEATURE:
<223> OTHER INFORMATION: Recombinant

<400> SEQUENCE: 268

```
atggccacta ccacagcagc cgcggcggtc accatcagca ttcctaaaaa gcctgttttt      60
atccgccgcc cacgacttcg tgggcccgtc gactgcagag gcctgcatgc atccgacgca     120
atcatctcca acgaggcccc tacagggacg acaatctcgg ctgactgt                  168
```

<210> SEQ ID NO 269
<211> LENGTH: 228
<212> TYPE: DNA
<213> ORGANISM: Eragrostis tef

<400> SEQUENCE: 269

```
atggcagccg cacctcccct agcagccgac atggtgttac catccccatg ccctgccgcg      60
gttgcaccta ccccagtggt tgcagctgct tggggtgcag cccgagctgg atctgttaga     120
tgtaaagcga cccaacttcg aatgatgaga actgggggcc ctgttgctcc agttgccggt     180
agacgacgac gagctccatt gagtgtacgt tgtgatgctt cctccaga                  228
```

<210> SEQ ID NO 270
<211> LENGTH: 240
<212> TYPE: DNA
<213> ORGANISM: Setaria italica

<400> SEQUENCE: 270

```
atggctgccg ctcctccoct ctctgcagat gcactatcat tcctaccatc cgccgccgct      60
ccggcagccg ctgcaccaac acctgttgta gctgcggcat ggggagccgc acgagctgca     120
gggtcagtta gaggtaaagc tgctttgcgt atggctcgaa ggggtagtgg actggctcca     180
gtggttggaa gaagacctcg acgacctcct ctttcagtta gatgtgacgc aacatctcgt     240
```

<210> SEQ ID NO 271
<211> LENGTH: 252
<212> TYPE: DNA
<213> ORGANISM: Acalypha ostryifolia

<400> SEQUENCE: 271

```
atggctacaa ccaccgcgac gacgtctttc tcgggcgtct cgatctgccc acctcaccag      60
acgaatcgca cctctttgtt tccgccccag tccttgtctt tcccctccag taagcatggc     120
agtcttgtga actctgtgca attcaaccgt tcgcgacgcg ctagacgtaa tcacttcagc     180
ctcacttcca ttaccaatgc accgaggcgc aaaaggttac tatctgtccg gtgcgacgcg     240
agtgccacat ct                                                        252
```

<210> SEQ ID NO 272
<211> LENGTH: 234
<212> TYPE: DNA
<213> ORGANISM: Adansonia digitata

<400> SEQUENCE: 272

```
atggcggcgt catcttcgtc cgtcgtgagc ttctcgggca tctcgttgtg cagtactcac      60
tcgatctcca acaagaccta tctattctcc gcccaccgc gcatttcggt gtcgttcccc      120
```

```
agtaagccca atagtttgaa gtccttcaag cagctccagc tgaagaagaa cggactcttt    180
gagaagttct ctcgtacctc cagtcggagc ttcgtggtga ggtgcgacgc gtcg          234
```

<210> SEQ ID NO 273
<211> LENGTH: 246
<212> TYPE: DNA
<213> ORGANISM: Taraxacum officinale

<400> SEQUENCE: 273

```
atggctacaa ccgcgagctt ctcgggtgtt cgtattcacg cgccttcctc cacatgtatc    60
gaccggacca cttattcgc ccagccttcg gtgagctttt cttcctttc caagccgagg     120 cgaacgacct tgaggtcgct gaagctaagg tcgaggtcca acgatgtgtt gcttcgcacc    180
cgcacaggtg acagattcgg cggaaagagc tcacgttcat tgttgtgcg ctgcgacgca    240 tcttct                                                               246
```

<210> SEQ ID NO 274
<211> LENGTH: 231
<212> TYPE: DNA
<213> ORGANISM: Amaranthus cruentus

<400> SEQUENCE: 274

```
atggcgaccg cgacgacctc gtttcccggc gcgtacctgc gcgtgccgcc caagaacggg    60
gttcgtaacg ccctctttag ccagtctatc gtgtcaatag cgcgcaactc tcggaaaccc    120
aaatcgctca aatcccttaa actatctacc aactccttta acttcggtct gcacaagtct    180
tgtcgaaagg gaagcaaatc cgggtcgttc gtagtgcgtt gtgacgcggc c             231
```

<210> SEQ ID NO 275
<211> LENGTH: 240
<212> TYPE: DNA
<213> ORGANISM: Amaranthus cruentus

<400> SEQUENCE: 275

```
atggccatcg ccaccacgag ctttccggga acgtacctcc gggtgccgcc caagaacggc    60
gtccgaaacg ccctattcag tcgctccgtc gtgtctaatg gggtgaactc aaggaagccg    120
aactcgctgg agtcgcttaa atcgtcgagg aatagctcga acgtctgctt gagtacgtcg    180
ttcgggcatt accggaaatc gagtaagtcg ggctcgttct tcgttcggtg taacgccgcc    240
```

<210> SEQ ID NO 276
<211> LENGTH: 240
<212> TYPE: DNA
<213> ORGANISM: Amaranthus hypochondriacus

<400> SEQUENCE: 276

```
atggccatcg ccacgacctc gttccccggc acgtacctgc gagtgccgcc caagaacggg    60
gtccggaacg cgctgttctc tcggtccgtg gtcagcaatg gtgttaattc acgaaagccg    120
aacagtctgg aatctctcaa gagcagtcga aactcctcca acgtctgcct ttcgaccagc    180
ttcggtcact accggaagtc tagtaagagc gggtcgttct tgtccggtg taatgctgcc    240
```

<210> SEQ ID NO 277
<211> LENGTH: 231
<212> TYPE: DNA
<213> ORGANISM: Amaranthus palmeri

<400> SEQUENCE: 277

```
atggcgacgg ccaccaccct cgttcccggc gcatacctcc gcgtgccgcc caagaacggc    60
```

```
gtccgcaacg cactctttag ccagagcatc gtcagtatcg cccttaacag tcgcaagcct    120
aaatcgttca agtcactaaa gtcaagcgct aattcgtgca actttggact tcacaagtcc    180
taccggaaag gcagcaagtc tggcagcttc gtcgttcgtt gtgatgccgc c             231
```

<210> SEQ ID NO 278
<211> LENGTH: 240
<212> TYPE: DNA
<213> ORGANISM: Amaranthus palmeri

<400> SEQUENCE: 278

```
atggccaccg ccaccacctc gttccccggc acgtacctgc gcgtgccgcc caagaacggc    60
gtcaggaacg cgctgtttag tcgctcagtc gtgtccaacg gggtgaactc acgaaagccc    120
aacagtttaa agagcttaaa actgtcgagg aactctagta atgtctgcct ctacacctcc    180
ttcggacact atcgaaagtc cagtaagtcg ggctcattca tcatccggtg caatgcggcc    240
```

<210> SEQ ID NO 279
<211> LENGTH: 231
<212> TYPE: DNA
<213> ORGANISM: Amaranthus palmeri

<400> SEQUENCE: 279

```
atggccaccg caacaaccag cttccctggc gcgtaccttc gtgtgccgcc caagaacggc    60
gtccgcaatg cgctgtttag tcagtccatc gtgagtatcg ctctcaattc ccggaaacct    120
aagagcttta agagcctaaa gtcgagcgct aattcttgca acttcgggct tcacaagagc    180
tatcggaaag ggtctaagag cgggtcattc gtcgtgcggt gcgacgcggc c             231
```

<210> SEQ ID NO 280
<211> LENGTH: 231
<212> TYPE: DNA
<213> ORGANISM: Amaranthus palmeri

<400> SEQUENCE: 280

```
atggccacgg ccacgacctc gtttccgggt gcgtacctgc gagttccgcc caagaacggt    60
gtacggaacg ccttgttctc ccaatccatc gtgagcatcg ccctcaacag tcgcaaaccg    120
aagtcattca aatccctgaa aagttcggcc aatagctgta acttcgggct gcataagagt    180
taccgcaagg ggtcgaaatc cgggtcgttc gtcgtccggt gcgacgctgc g             231
```

<210> SEQ ID NO 281
<211> LENGTH: 240
<212> TYPE: DNA
<213> ORGANISM: Amaranthus palmeri

<400> SEQUENCE: 281

```
atggcaactg ccacgacgtc ctttccggga acgtatctcc gcgtgccgcc caagaacggc    60
gtccgcaacg ccctgttctc acgatccgtc gttagcaatg gcgtcaatag ccgcaagcct    120
aagtccctga aatcgctcaa gtcgtcgcgc aactctagta atgtctgtct ctacacatcg    180
ttcggacatt accgcaaatc atccaaatcc ggctcgttca taatccggtg caatgcggct    240
```

<210> SEQ ID NO 282
<211> LENGTH: 240
<212> TYPE: DNA
<213> ORGANISM: Amaranthus rudis

<400> SEQUENCE: 282

```
atggcgacag cgaccacatc cttccctggc acttacctga gagtgccgcc caagaatggg    60
gtgagaaacg ccttgttcag ccgcagcgta gtctctaatg gggtggatag tcgcaaaccg   120
aatagcctca agagtatgaa gctcagccgc aacagctcaa atgtctgcct ctacacgagc   180
tttggccact accgaaagtc ctccaagtct gggtcgttca tcgtgcgctg taacgccgcg   240
```

<210> SEQ ID NO 283
<211> LENGTH: 240
<212> TYPE: DNA
<213> ORGANISM: Amaranthus rudis

<400> SEQUENCE: 283

```
atggccacgg ccaccacctc ctttcctggc acatacctcc gcgtccctcc caagaatggg    60
gtgcgaaacg cactctttag tagatcggtc gtttccaatg tgtcgattc ccgcaagccg    120 aactccctca agtcgatgaa gctgtcccgc aactcatcga acgtttgcct ctatacctcg   180
tttgggcact accgcaagtc gagcaaatcg ggctcgttca ttgtccggtg taatgcagcc   240
```

<210> SEQ ID NO 284
<211> LENGTH: 240
<212> TYPE: DNA
<213> ORGANISM: Amaranthus rudis

<400> SEQUENCE: 284

```
atggcgacgg cgacaacctc gtttccggga acgtacctgc gcgtgccgcc caagaacggg    60
gtgcggaacg ccctgttcag ccgctccgtc gtgtccaatg gcgtcgattc gaggaagcct   120
aactcattga aatctatgaa gttgtctcgt aattccagca acgtttgcct ctacacctcg   180
ttcgggcatt accgcaagtc aagcaagtcc ggatcgttta tcgtgcggtg caacgctgcg   240
```

<210> SEQ ID NO 285
<211> LENGTH: 240
<212> TYPE: DNA
<213> ORGANISM: Amaranthus viridis

<400> SEQUENCE: 285

```
atggccattg ccaccacgtc gtttcccggc acgtacctga gggttccgcc caagaacgga    60
gtccgcaacg cactgtttag tcgctccgtg gtgagtaacg gggtcaactc cagaaaacct   120
aattcgctgg agtcccttaa atcgagccgg aacagctcga acgtctgctt gtcaacctcc   180
tttggccact accggaaggg ctccaagtcg ggctcattcg tcgtgcggtg cgatgcggcg   240
```

<210> SEQ ID NO 286
<211> LENGTH: 231
<212> TYPE: DNA
<213> ORGANISM: Amaranthus viridis

<400> SEQUENCE: 286

```
atggccaccg ccacgacgtc ctttcccggt gcgtatctgc gagtgcctcc caagaacggc    60
gtccggaacg cgctgttcag ccagtccatc gtgagcatcg cgcggaatag tcggaaacct   120
aagtcgctca aatccttgaa actgtcaacg aactctttca atttcgggtt gcataagtcc   180
tgccgaaagg gtagcaaatc cgggtctttc gttgtgcggt gcgacgcggc c             231
```

<210> SEQ ID NO 287
<211> LENGTH: 213
<212> TYPE: DNA
<213> ORGANISM: Ambrosia trifida

<400> SEQUENCE: 287

```
atgagtacga tgtcaaccct atttcacctc ccgtctagcc tgtgtaccga caggacgatc    60
accagcagct tcgcacaacc gagcgtttcg gtcaactcgt tctcgaagcc gcgccgcgtc   120
gcgctccggt ccttaaagct caaaacgcga gtaatgacg tcctgctgcg gaaatcttca    180
cgttcgctag tcgtgcgttg cgacgccagc agc                                 213
```

<210> SEQ ID NO 288
<211> LENGTH: 261
<212> TYPE: DNA
<213> ORGANISM: Conyza canadensis

<400> SEQUENCE: 288

```
atggcgacgg ccgccttctc gggcgttccg tgcattgacc ggacatcact cctctccgcc    60
cagccatcgt cctcctcttc cagtagcgtc gtggtctgct actcctcctt tagcaagccg   120
ggcacgaccc tattgccgtc gttgaagctc aaaagcagcc gcaacaacaa caattcaaac   180
gtattcctct cgggaacac caggaaaaca tcccgtctgt cattcctagt gcgctgcgat    240
tcctcatctt caagctctag c                                              261
```

<210> SEQ ID NO 289
<211> LENGTH: 213
<212> TYPE: DNA
<213> ORGANISM: Cucumis melo

<400> SEQUENCE: 289

```
atggcgttta gcaccgcacc cttctacgca attggtatca gatttcccag ccatagctca    60
tcaatctcaa gcaccactaa cgccctcatc cttaaaagtc cactggcgtt agccctaacc   120
gctaagccga gtctcccct actcctcaag cgcaacgttg ctgccagcg attcgggcga    180 aactcccgct tcgtcgtgcg ctgcgatgcg tcc                                 213
```

<210> SEQ ID NO 290
<211> LENGTH: 234
<212> TYPE: DNA
<213> ORGANISM: Kochia Scoparia

<400> SEQUENCE: 290

```
atggcgaccg ccacgacctc cttccccggc gcgtacctcc atctcccgcc caagaacggg    60
gtccgcaacg ccttgttctc tcaacccatc tgttcatcca acctcaacct caagaaacct   120
aactctctca atcggtgaa gctgtcccgc agttccggca atgccctatt ctacaagaac    180
gccaagaaga atagtaagtt cggcagtctg gtcgtgcggt gcgacgcggc ggga          234
```

<210> SEQ ID NO 291
<211> LENGTH: 234
<212> TYPE: DNA
<213> ORGANISM: Kochia Scoparia

<400> SEQUENCE: 291

```
atggccaccg cgacgaccag ctttcccggc gcgtatctgc acctcccgcc caagaacggc    60
gtgagaaacg cgctgttcag tcaaccgata tgctcgtcca atctcaacct caagaaaccc   120
aattctctga aaagcgtcaa actgtcgcgt agtagcggca atgcgctgtt ctacaagaac   180
gccaagaaga atagcaagtt cgggtcgctc gtggtgcgct gcgacgcggc gggc          234
```

<210> SEQ ID NO 292
<211> LENGTH: 234
<212> TYPE: DNA

<213> ORGANISM: Kochia Scoparia

<400> SEQUENCE: 292

| | |
|---|---|
| atggccacag ccaccacgtc cttccctggg gcctacctac atctcccgcc caagaatggc | 60 |
| gtgcgaaacg cgctgttcag tcagcctata tgcagcagta atcttaacct caagaagcct | 120 |
| aattccctca gtcagtgaa actgagccgg tctagcggga acgcgctgtt ctacaagaac | 180 |
| gccaaaaaga atagcaagtt cggctcgctc gtggtccggt gcgacgcggc gggc | 234 |

<210> SEQ ID NO 293
<211> LENGTH: 252
<212> TYPE: DNA
<213> ORGANISM: Rosa hybrid cultivar

<400> SEQUENCE: 293

| | |
|---|---|
| atggcgtcat cgaccacttc gttcgccgcc agtggagttg gattgcggct ccctcagtcc | 60 |
| gtgagcacga agtgctgctc taaagcgtca ttgttcccac accccacact atcgttgacc | 120 |
| ttccacgcta ggccacagtt ctttagaggc ttggcgtctc gccagttcaa tccaaacgga | 180 |
| gcgtttggga cgggctccgg acggctgggc cggacaccaa atccgtttgt cgtcagaagc | 240 |
| gaagcgagtt ct | 252 |

<210> SEQ ID NO 294
<211> LENGTH: 240
<212> TYPE: DNA
<213> ORGANISM: Sedum album

<400> SEQUENCE: 294

| | |
|---|---|
| atggcggcga gcgcggctac gatcaccctcc agcatatcgg cgattacccc gaagccgtcg | 60 |
| tccttctcaa gcagcccttc ggtcaccgtg ccccgattct ctgtgtcgtg cagcgcgata | 120 |
| ccgcgtccac acaagaatcc ctgctcgttg aagttccggg tgaaggactc acggtttaac | 180 |
| ggaattgtca agaagcgcag taacagcaac tcattcgtag tacgttgtga cacttcctcg | 240 |

<210> SEQ ID NO 295
<211> LENGTH: 237
<212> TYPE: DNA
<213> ORGANISM: Sedum album

<400> SEQUENCE: 295

| | |
|---|---|
| atggccgccg acgcagctac cattacggcg ggtatcactc tcacgacggc ccgccgctcc | 60 |
| tcctccagta ttgcgccgca gttctcggtg tgttgctcag cgattaccaa cacgcaaaaa | 120 |
| aatctgagct tcctcaagtt gcgcgtgaaa acgccacct tgactacacg gattgagggt | 180 |
| attcagaaga agcggtacaa ctccgcgtcc ttcgtcgtca gatgcgacgc gagcagc | 237 |

<210> SEQ ID NO 296
<211> LENGTH: 243
<212> TYPE: DNA
<213> ORGANISM: Spinacia oleracea

<400> SEQUENCE: 296

| | |
|---|---|
| atggccactg ccacgacgtc ctttctcggc gcttacttgc gggtgccgcc caacaatggc | 60 |
| gtgaggaatg cgctgttcag tcaaccgttc ctgtcgcttc gcattaagtc caaacgcact | 120 |
| aagagcctca actcgttgaa attcacagga gactcaagta agattctgct gtttaagtgc | 180 |
| tcccggccgt ttgagaaggg gcttaaatcc ggctcgttcg tggtgcgctg cgacgcggcc | 240 |
| ggt | 243 |

-continued

```
<210> SEQ ID NO 297
<211> LENGTH: 237
<212> TYPE: DNA
<213> ORGANISM: Allium cepa

<400> SEQUENCE: 297
atggcggcaa cgagctccgc gaccactcac ctcccttttt tcagcccgca caccaaacac      60
gcaaagacaa actctttctt cgcgtccctt ccggtcagcg cctactccac gaaaaactct     120
atcagtttca aggcgctcaa ggccgtgcga tggagcgaga ccttcgggca atcgaagaag     180
gccaatggtt ttgccaaaag gaagcaattt gccgtcgtgc ggtgcgatgc gagttca        237
```